US007598051B2

(12) United States Patent
Fanger et al.

(10) Patent No.: US 7,598,051 B2
(45) Date of Patent: Oct. 6, 2009

(54) COMPOSITIONS AND METHODS FOR THE THERAPY AND DIAGNOSIS OF OVARIAN CANCER

(75) Inventors: Gary R Fanger, Mill Creek, WA (US); Steven P Fling, Bainbridge Island, WA (US)

(73) Assignee: Corixa Corporation, Wilmington, DE (US)

( * ) Notice: Subject to any disclaimer, the term of this patent is extended or adjusted under 35 U.S.C. 154(b) by 182 days.

(21) Appl. No.: 11/250,759

(22) Filed: Oct. 14, 2005

(65) Prior Publication Data

US 2006/0057141 A1 Mar. 16, 2006

Related U.S. Application Data

(63) Continuation of application No. 10/369,186, filed on Feb. 14, 2003, now abandoned, which is a continuation-in-part of application No. 10/361,811, filed on Feb. 5, 2003, now abandoned, which is a continuation-in-part of application No. 10/212,677, filed on Aug. 2, 2002, now abandoned, which is a continuation-in-part of application No. 09/970,966, filed on Oct. 2, 2001, now Pat. No. 6,720,146, which is a continuation-in-part of application No. 09/825,294, filed on Apr. 3, 2001, now Pat. No. 6,710,170, which is a continuation-in-part of application No. 09/713,550, filed on Nov. 14, 2000, now Pat. No. 6,617,109, which is a continuation-in-part of application No. 09/656,668, filed on Sep. 7, 2000, now abandoned, which is a continuation-in-part of application No. 09/640,173, filed on Aug. 15, 2000, now Pat. No. 6,613,515, which is a continuation-in-part of application No. 09/561,778, filed on May 1, 2000, now abandoned, which is a continuation-in-part of application No. 09/394,374, filed on Sep. 10, 1999, now abandoned.

(51) Int. Cl.
*G01N 1/00* (2006.01)
*G01N 1/18* (2006.01)
*G01N 33/48* (2006.01)
*G01N 33/53* (2006.01)
*G01N 33/537* (2006.01)
*G01N 33/543* (2006.01)
*G01N 33/574* (2006.01)

(52) U.S. Cl. .............................. 435/7.23; 435/4; 435/7.1; 435/7.2; 435/7.21; 435/7.92; 436/63; 436/64; 436/174; 436/175; 436/177; 436/178; 436/501; 436/512; 530/350; 530/380; 530/386; 530/387.1

(58) Field of Classification Search .................. 435/4, 435/7.1, 7.2, 7.21, 7.23, 7.92; 436/63, 64, 436/174, 175, 177, 178, 501, 512; 530/350, 530/380, 386, 387.1

See application file for complete search history.

(56) References Cited

U.S. PATENT DOCUMENTS

| 5,279,966 | A | 1/1994 | Jessell et al. ............. 435/320.1 |
| 5,585,232 | A | 12/1996 | Farr .............................. 435/6 |
| 5,589,337 | A | 12/1996 | Farr .............................. 435/6 |
| 5,849,480 | A | 12/1998 | Cros et al. ...................... 435/6 |
| 6,525,023 | B1 | 2/2003 | Yamasaki et al. ............. 514/12 |

FOREIGN PATENT DOCUMENTS

| DE | 20103510 U1 | 8/1998 |
| EP | 1067182 A2 | 1/2001 |
| JP | 6-303997 | 11/1994 |
| WO | WO 93/17715 | 9/1993 |
| WO | WO 94/12881 | 6/1994 |
| WO | WO 95/14772 | 6/1995 |
| WO | WO 98/37418 | 8/1998 |
| WO | WO 99/04265 | 1/1999 |
| WO | WO 00/52044 | 9/2000 |
| WO | WO 00/61629 | 10/2000 |
| WO | WO 00/77026 | 12/2000 |
| WO | WO 01/36685 | 5/2001 |
| WO | WO 01/47944 | 7/2001 |
| WO | WO 01/81634 | 11/2001 |
| WO | WO 02/08288 | 1/2002 |

OTHER PUBLICATIONS

Tascilar et al. (Annals of Oncology 10,Suppl. 4:S107-S110, 1999).*
Tockman et al. (Cancer Research 52:2711s-2718s, 1992).*
Chen, L. et al., "Increased expression of cerulopladmin in the retina following photic injury," *Molecular Vision 9*: 151-158, 2003.
Curti, B.D., "Physical barriers to drug delivery in tumors," *Critical Reviews in Oncology/Hematology 14*: 29-39, 1993.
Database EMBL Acccession No. AA536804, Jul. 31, 1997.
Database EMBL Accession No. AC016957, Dec. 14, 1999.
Database EMBL, Accession No. AF060226, May 6, 1998.
Database EMBL, Accession No. AX001326, Mar. 10, 2000.
Database EMBL, Accession No. X02662, May 7, 1999.
EMBL-EBI Database, Accession No. BE385990, Jul. 29, 2000.
GenBank Accession No. AA173383, Sep. 30, 1997.
GenBank Accession No. AA173739, Sep. 30, 1997.
GenBank Database, Acccession No. NM_001508, Dec. 15, 1997.
GenBank Database, Acccession No. NP_001499, Dec. 15, 1997.
GenBank Database, Accession No. AA223587, Feb. 19, 1997.

(Continued)

*Primary Examiner*—Alana M. Harris
(74) *Attorney, Agent, or Firm*—Seed IP Law Group PLLC

(57) ABSTRACT

Compositions and methods for the therapy and diagnosis of cancer, particularly ovarian cancer, are disclosed. Illustrative compositions comprise one or more ovarian tumor polypeptides, immunogenic portions thereof, polynucleotides that encode such polypeptides, antigen presenting cell that expresses such polypeptides, and T cells that are specific for cells expressing such polypeptides. The disclosed compositions are useful, for example, in the diagnosis, prevention and/or treatment of diseases, particularly ovarian cancer.

9 Claims, No Drawings

OTHER PUBLICATIONS

GenBank Database, Accession No. AA281245, Jan. 14, 1998.
GenBank Database, Accession No. AB041649, Jun. 30, 2000.
GenBank Database, Accession No. AF161511, Jun. 23, 1999.
GenBank Database, Accession No. AI023799, Aug. 28, 1998.
GenBank Database, Accession No. AI307373, Apr. 8, 1999.
GenBank Database, Accession No. AI360254, Feb. 16, 1999.
GenBank Database, Accession No. AI936826, Mar. 8, 2000.
GenBank Database, Accession No. AW149665, Nov. 3, 1999.
GenBank Database, Accession No. AW150789, Nov. 3, 1999.
GenBank Database, Accession No. AW377176, Apr. 7, 1998.
GenBank Database, Accession No. AW406327, Oct. 30, 1998.
GenBank Database, Accession No. AX136281, May 30, 2001.
Genbank Database, Accession No. H06756, Jun. 21, 1995.
GenBank Database, Accession No. L19184, Oct. 13, 1994.
GenBank Database, Accession No. Q9JJ96, Oct. 1, 2000.
GenBank Database, Accession No. R60095, Apr. 14, 1993.
GenBank Database, Accession No. Z95125, Sep. 27, 1997.
Genseq (Derwent) Database, Accession No. AAK54063, Nov. 16, 2001.
Genseq (Derwent) Database, Accession No. AAL27277, Jan. 24, 2002.
Genseq (Derwent) Database, Accession No. AAL33984, Jan. 24, 2002.
Genseq (Derwent) Database, Accession No. AAL33985, Jan. 24, 2002.
Genseq (Derwent) Database, Accession No. AAL33986, Jan. 24, 2002.
Genseq (Derwent) Database, Accession No. AAU83599, May 8, 2002.
Gerhold, D. et al., "It's the genes! EST access to human genome content," *BioEssays* 18(12): 973-981, 1996.
Gibson et al., "Novel method for real time quantitative RT-PCR," *Genome Research* 6:995-1001, Oct. 1996.
Gura, T., "Systems for Identifying New Drugs Are Often Faulty,"*Science* 278: 1041-1042, Nov. 7, 1997.
Hartwell, L.H. et al., "Integrating Genetic Approaches into the Discovery of Anticancer Drugs," *Science* 278: 1064-1068, Nov. 7, 1997.
Haynes, P.A. et al., "Proteome analysis: Biological assay or data archive?," *Electrophoresis* 19: 1862-1871, 1998.
Heid et al., "Real time quantitative PCR," *Genome Research* 6:986-994, Oct. 1996.
Houghton, A.N. et al., "Monoclonal Antibodies: Potential Applications to the Treatment of Cancer," *Seminars in Oncology* 13(2): 166-179, Jun. 1986.
Hu, Y. et al., "Analysis of Genomic and Proteomic Data Using Advanced Literature Mining," *Journal of Proteome Research 2*: 405-412, 2003.
Jain, R.K., "Barriers to Drug Delivery in Solid Tumors," *Scientific American 271*: 58-65, Jul. 1994.
McKee, K.K. et al., "Cloning and characterization of two human G protein-coupled receptor genes (GPR38 and GPR39) related to the growth hormone secretagogue and neurotensin receptors," *Genomics* 46(3): 426-434, 1997.
Meden and Kuhn, "Overexpression of the oncogene c-erbB-2 (HER2/neu) in ovarian cancer: a new prognostic factor," *European Journal of Obstetrics & Gynecology and Reproductive Biology* 71:173-179, 1997.
Nagase et al, "Prediction of the coding sequences of unidentified human genes. XI. The complete sequences of 100 new cDNA clones from brain which code for large proteins in vitro," *DNA Research* 5(5): 277-286, 1998.
Novocastra Laboratories Ltd., Data Sheet, Mesothelin, NCL-L-MESO, Feb. 2004.
Prydz, K. et al., "Cholesterol depletion deduces apical transport capacity in epithelial Madin-Darby canine kidney cells," *Biochemical Journal 357*: 11-15, 2001.
Russell, R.B. et al., "Structural Features can be Unconserved in Proteins with Similar Folds," *J. Mol. Biol. 244*: 332-350, 1994.
Schena et al., "Quantitative monitoring of gene expression patterns with a complementary DNA microarray," *Science 270*:467-470, Oct. 20, 1995.
Wells, T.N.C. et al., "The chemokine information source: identification and characterization of novel chemokines using the WorldWideWeb and Expressed Sequence Tag Databases," *Journal of Leukocyte Biology 61*(5): 545-550, May 1997.
Winter, G. et al., "Humanized antibodies," *Trends in Protein Sciences 14*: 139-143, May 1993.
EMBL-EBI Database, Accession No. BE395581, Jul. 29, 2000.
EMBL-EBI Database, Accession No. BE378674, Jul. 29, 2000.
EMBL-EBI Database, Accession No. BE746601, Sep. 20, 2000.
EMBL-EBI Database, Accession No. BE395797, Jul. 29, 2000.
EMBL-EBI Database, Accession No. BF345141, Nov. 27, 2000.
EMBL-EBI Database, Accession No. BF125134, Oct. 26, 2000.
GenBank Database, Accession No. BC017318, Oct. 4, 2003.
GenBank Database, Accession No. BC011449, Aug. 19, 2003.
GenBank Database, Accession No. AAH17318, Oct. 4, 2003.
GenBank Database, Accession No. AK012406, Sep. 2, 2005.
GenBank Database, Accession No. BAA95101, Jun. 30, 2000.

* cited by examiner

COMPOSITIONS AND METHODS FOR THE THERAPY AND DIAGNOSIS OF OVARIAN CANCER

CROSS-REFERENCE TO RELATED APPLICATIONS

This application is a continuation of U.S. application Ser. No. 10/369,186, filed on Feb. 14, 2003; which is a continuation-in-part of U.S. application Ser. No. 10/361,811, filed on Feb. 5, 2003; which is a continuation-in-part of U.S. application Ser. No. 10/212,677, filed on Aug. 2, 2002; which is a continuation-in-part of U.S. application Ser. No. 09/970,966, filed on Oct. 2, 2001, now U.S. Pat. No. 6,720,146; which is a continuation-in-part of U.S. application Ser. No. 09/825,294, filed on Apr. 3, 2001, now U.S. Pat. No. 6,710,170; which is a continuation-in-part of U.S. application Ser. No. 09/713,550, filed on Nov. 14, 2000, now U.S. Pat. No. 6,617,109; which is a continuation-in-part of U.S. Pat. No. 09/656,668, filed on Sep. 7, 2000, now abandoned; which is a continuation-in-part of U.S. application Ser. No. 09/640,173, filed on Aug. 15, 2000, now U.S. Pat. No. 6,613,515; which is a continuation-in-part of U.S. application Ser. No. 09/561,778, filed on May 1, 2000, now abandoned; which is a continuation-in-part of U.S. application Ser. No. 09/394,374, filed on Sep. 10, 1999, now abandoned.

STATEMENT REGARDING SEQUENCE LISTING SUBMITTED ON CD-ROM

The Sequence Listing associated with this application is provided on CD-ROM in lieu of a paper copy, and is hereby incorporated by reference into the specification. Three CD-ROMs are provided, containing identical copies of the sequence listing: CD-ROM No. 1 is labeled COPY 1, contains the file 484c10.app.txt which is 450 KB and created on Oct. 14, 2005; CD-ROM No. 2 is labeled COPY 2, contains the file 484c10.app.txt which is 450 KB and created on Oct. 14, 2005; CD-ROM No. 3 is labeled CRF (Computer Readable Form), contains the file 484c10.app.txt which is 450 KB and created on Oct. 14, 2005.

BACKGROUND OF THE INVENTION

1. Field of the Invention

The present invention relates generally to ovarian cancer therapy. The invention is more specifically related to polypeptides comprising at least a portion of an ovarian carcinoma protein, and to polynucleotides encoding such polypeptides, as well as antibodies and immune system cells that specifically recognize such polypeptides. Such polypeptides, polynucleotides, antibodies and cells may be used in vaccines and pharmaceutical compositions for treatment of ovarian cancer.

2. Description of Related Art

Ovarian cancer is a significant health problem for women in the United States and throughout the world. Although advances have been made in detection and therapy of this cancer, no vaccine or other universally successful method for prevention or treatment is currently available. Management of the disease currently relies on a combination of early diagnosis and aggressive treatment, which may include one or more of a variety of treatments such as surgery, radiotherapy, chemotherapy and hormone therapy. The course of treatment for a particular cancer is often selected based on a variety of prognostic parameters, including an analysis of specific tumor markers. However, the use of established markers often leads to a result that is difficult to interpret, and high mortality continues to be observed in many cancer patients.

Immunotherapies have the potential to substantially improve cancer treatment and survival. Such therapies may involve the generation or enhancement of an immune response to an ovarian carcinoma antigen. However, to date, relatively few ovarian carcinoma antigens are known and the generation of an immune response against such antigens has not been shown to be therapeutically beneficial.

Accordingly, there is a need in the art for improved methods for identifying ovarian tumor antigens and for using such antigens in the therapy of ovarian cancer. The present invention fulfills these needs and further provides other related advantages.

BRIEF SUMMARY OF THE INVENTION

Briefly stated, this invention provides compositions and methods for the therapy of cancer, such as ovarian cancer.

In one aspect, the present invention provides polynucleotide compositions comprising a sequence selected from the group consisting of:

(a) sequences provided in SEQ ID NO: 1-185, 187-199, 203-206, 208, 210-214, 216-246, 250-256, 262-268, 273-277, 283, 285, and 287-288;

(b) complements of the sequences provided in SEQ ID NO: 1-185, 187-199, 203-206, 208, 210-214, 216-246, 250-256, 262-268, 273-277, 283, 285, and 287-288;

(c) sequences consisting of at least 20 contiguous residues of a sequence provided in SEQ ID NO: 1-185, 187-199, 203-206, 208, 210-214, 216-246, 250-256, 262-268, 273-277, 283, 285, and 287-288;

(d) sequences that hybridize to a sequence provided in SEQ ID NO: 1-185, 187-199, 203-206, 208, 210-214, 216-246, 250-256, 262-268, 273-277, 283, 285, and 287-288, under moderately stringent conditions;

(e) sequences having at least 75% identity to a sequence provided in SEQ ID NO: 1-185, 187-199, 203-206, 208, 210-214, 216-246, 250-256, 262-268, 273-277, 283, 285, and 287-288;

(f) sequences having at least 90% identity to a sequence provided in SEQ ID NO: 1-185, 187-199, 203-206, 208, 210-214, 216-246, 250-256, 262-268, 273-277, 283, 285, and 287-288; and (g) degenerate variants of a sequence provided in SEQ ID NO: 1-185, 187-199, 203-206, 208, 210-214, 216-246, 250-256, 262-268, 273-277, 283, 285, and 287-288.

In one preferred embodiment, the polynucleotide compositions of the invention are expressed in at least about 20%, more preferably in at least about 30%, and most preferably in at least about 50% of ovarian tumors samples tested, at a level that is at least about 2-fold, preferably at least about 5-fold, and most preferably at least about 10-fold higher than that for normal tissues.

In one aspect, the present invention provides polypeptides comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished. Within certain embodiments, the ovarian carcinoma protein comprises a sequence that is encoded by a polynucleotide sequence selected from the group consisting of SEQ ID NO: 1-185, 187-199, 203-206, 208, 210-214, 216-246, 250-256, 262-268, 273-277, 283, 285, and 287-288, and complements of such polynucleotides.

The present invention further provides polynucleotides that encode a polypeptide as described above or a portion thereof, expression vectors comprising such polynucleotides and host cells transformed or transfected with such expression vectors.

The present invention further provides polypeptide compositions comprising an amino acid sequence selected from the group consisting of sequences recited in SEQ ID NO:186, 200-202, 207, 209, 215, 247-249, 257-261, 269-272, 278-282, 284, 286 and 289-293.

In certain preferred embodiments, the polypeptides of the present invention are immunogenic, i.e., they are capable of eliciting an immune response, particularly a humoral and/or cellular immune response, as further described herein.

The present invention further provides fragments, variants and/or derivatives of the disclosed polypeptide sequences, wherein the fragments, variants and/or derivatives preferably have a level of immunogenic activity of at least about 50%, preferably at least about 70% and more preferably at least about 90% of the level of immunogenic activity of the ovarian carcinoma protein comprises an amino acid sequence encoded by a polynucleotide that comprises a sequence recited in any one of SEQ ID NO: 1-185, 187-199, 203-206, 208, 210-214, 216-246, 250-256, 262-268, 273-277, 283, 285, and 287-288.

Within other aspects, the present invention provides pharmaceutical compositions comprising a polypeptide and/or polynucleotide as described above and a physiologically acceptable carrier.

Within a related aspect of the present invention, the pharmaceutical compositions, e.g., vaccine compositions, are provided for prophylactic or therapeutic applications. Such compositions generally comprise an immunogenic polypeptide or polynucleotide of the invention and an immunostimulant, such as an adjuvant.

The present invention further provides pharmaceutical compositions that comprise: (a) an antibody or antigen-binding fragment thereof that specifically binds to a polypeptide of the present invention, or a fragment thereof; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Illustrative antigen presenting cells include dendritic cells, macrophages, monocytes, fibroblasts and B cells.

Within related aspects, pharmaceutical compositions are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins, typically in the form of pharmaceutical compositions, e.g., vaccine compositions, comprising a physiologically acceptable carrier and/or an immunostimulant. The fusions proteins may comprise multiple immunogenic polypeptides or portions/variants thereof, as described herein, and may further comprise one or more polypeptide segments for facilitating the expression, purification and/or immunogenicity of the polypeptide(s).

Within further aspects, the present invention provides methods for stimulating an immune response in a patient, preferably a T cell response in a human patient, comprising administering a pharmaceutical composition described herein. The patient may be afflicted with ovarian cancer, in which case the methods provide treatment for the disease, or patient considered at risk for such a disease may be treated prophylactically.

Within further aspects, the present invention provides methods for inhibiting the development of a cancer in a patient, comprising administering to a patient a pharmaceutical composition as recited above. The patient may be afflicted with ovarian cancer, in which case the methods provide treatment for the disease, or patient considered at risk for such a disease may be treated prophylactically.

The present invention further provides, within other aspects, methods for removing tumor cells from a biological sample, comprising contacting a biological sample with T cells that specifically react with a polypeptide of the present invention, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a polypeptide of the present invention, comprising contacting T cells with one or more of: (i) an ovarian carcinoma polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating CD4$^+$ and/or CD8$^+$ T cells isolated from a patient with one or more of: (i) a polypeptide comprising at least an immunogenic portion of polypeptide disclosed herein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer, preferably an ovarian cancer, in a patient comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a polypeptide of the present invention; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a polypeptide of the present invention; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description. All references disclosed herein are hereby incorporated by reference in their entirety as if each was incorporated individually.

BRIEF DESCRIPTION OF THE SEQUENCE IDENTIFIERS

SEQ ID NO:1, 2, 5, 9, 10, 13, 16, 19, 23, 27, 28, 32, 33, 35, 38, 41-50, 52, 53, 56, 57, 63, 65, 69-72, 75, 78, 80-82, 84, 86, 89-93, 95, 97-100, 103, 107, 111, 114, 117, 120, 121, 125, 128, 132-134, 136, 137, 140, 143-146, 148-151, 156, 158, 160-162, 166-168, 171, 174-183, 185, and 193-199 are described in Tables III-VII below.

SEQ ID NO:200 is the amino acid sequence of a polypeptide encoded by the polynucleotide recited in SEQ ID NO:182;

SEQ ID NO:201 is the amino acid sequence of a polypeptide encoded by the polynucleotide recited in SEQ ID NO:182;

SEQ ID NO:202 is the amino acid sequence of a polypeptide encoded by the polynucleotide recited in SEQ ID NO:182.

SEQ ID NO:203 is the determined extended cDNA sequence for SEQ ID NO:197.

SEQ ID NO:204 is the determined extended cDNA sequence for SEQ ID NO:198.

SEQ ID NO:205 is the determined extended cDNA sequence for SEQ ID NO:199.

SEQ ID NO:206 is the determined cDNA sequence for the coding region of O568S fused to an N-terminal His tag.

SEQ ID NO:207 is the amino acid sequence of the polypeptide encoded by the polynucleotide recited in SEQ ID NO:206.

SEQ ID NO:208 is the determined cDNA sequence for the coding region of GPR39 as downloaded from the High Throughput Genomics Database.

SEQ ID NO:209 is the amino acid sequence encoded by the cDNA sequence recited in SEQ ID NO:208.

SEQ ID NO:210 is the nucleotide sequence of O1034C an ovary specific EST clone discovered using electronic subtraction.

SEQ ID NO:211 is the full length nucleotide sequence of O591S.

SEQ ID NO:212 is the sequence BF345141 which shows sequence homology with O1034C/O591S allowing for the extension of O591S.

SEQ ID NO:213 is the sequence BE336607 which shows sequence homology with O1034C/O591S allowing for the extension of O591S.

SEQ ID NO:214 is the consensus nucleotide sequence of O1034C/O591S containing 1897 base pairs.

SEQ ID NO:215 is the predicted translation of the open reading frame identified within SEQ ID NO:214 (nucleotides 260-682).

SEQ ID NO:216 is a determined 5' DNA sequence of clone number 91226.5.

SEQ ID NO:217 is a determined 5' DNA sequence of clone number 91227.2.

SEQ ID NO:218 is a determined 5' DNA sequence of clone number 91230.2.

SEQ ID NO:219 is a determined 5' DNA sequence of clone number 91231.2.

SEQ ID NO:220 is a determined 5' DNA sequence of clone number 91238.3.

SEQ ID NO:221 is a determined 5' DNA sequence of clone number 91239.6.

SEQ ID NO:222 is a determined 5' DNA sequence of clone number 91240.2.

SEQ ID NO:223 is a determined 5' DNA sequence of clone number 91241.2.

SEQ ID NO:224 is a determined 5' DNA sequence of clone number 91242.5.

SEQ ID NO:225 is a determined 5' DNA sequence of clone number 91243.6.

SEQ ID NO:226 is a determined 5' DNA sequence of clone number 91245.2.

SEQ ID NO:227 is a determined 5' DNA sequence of clone number 91246.4.

SEQ ID NO:228 is a determined 3' DNA sequence of clone number 91247.3.

SEQ ID NO:229 is a determined 5' DNA sequence of clone number 91247.4.

SEQ ID NO:230 is a determined 5' DNA sequence of clone number 91249.2.

SEQ ID NO:231 is a determined 5' DNA sequence of clone number 91253.2.

SEQ ID NO:232 is a determined 5' DNA sequence of clone number 91254.2.

SEQ ID NO:233 is a determined 5' DNA sequence of clone number 91259.2.

SEQ ID NO:234 is a determined 3' DNA sequence of clone number 91261.3.

SEQ ID NO:235 is a determined 5' DNA sequence of clone number 91261.4.

SEQ ID NO:236 is a determined 5' DNA sequence of clone number 91262.2.

SEQ ID NO:237 is a determined 5' DNA sequence of clone number 91263.2.

SEQ ID NO:238 is a determined 5' DNA sequence of clone number 91264.2.

SEQ ID NO:239 is a determined 5' DNA sequence of clone number 91268.2.

SEQ ID NO:240 is a determined 5' DNA sequence of clone number 91269.5.

SEQ ID NO:241 is a determined 5' DNA sequence of clone number 91271.5.

SEQ ID NO:242 is a determined 3' DNA sequence of clone number 91273.3.

SEQ ID NO:243 is a determined 5' DNA sequence of clone number 91274.6.

SEQ ID NO:244 is the DNA sequence of GenBank Accession Number 18549403, which shares homology to SEQ ID NO:246.

SEQ ID NO:245 is the DNA sequence of GenBank Accession Number 10436393_FLJ14035, which shares homology to SEQ ID NO:246.

SEQ ID NO:246, also referred to as O646SgenomicContig, is a DNA (contig) sequence assembled based on a search of the publicly available databases using SEQ ID NO:243 as a query.

SEQ ID NO:247 is a amino acid sequence corresponding to the DNA sequence of GenBank Accession Number 18549403, SEQ ID NO:244.

SEQ ID NO:248 is a amino acid sequence corresponding to the DNA sequence of GenBank Accession Number 10436393_FLJ 14035, SEQ ID NO:245.

SEQ ID NO:249 is a amino acid sequence corresponding to a polypeptide encoded by SEQ ID NO:246, also referred to as O646GenomicContig_MajorORF.

SEQ ID NO:250 is the DNA sequence of GenBank Accession Number 3980529, which shares homology to SEQ ID NO:262.

SEQ ID NO:251 is the DNA sequence of GenBank Accession Number 13629915, which shares homology to SEQ ID NO:262.

SEQ ID NO:252 is the DNA sequence of GenBank Accession Number 9789986, which shares homology to SEQ ID NO:262.

SEQ ID NO:253 is the DNA sequence of GenBank Accession Number 6006516, which shares homology to SEQ ID NO:262.

SEQ ID NO:254 is the DNA sequence of GenBank Accession Number 5689424, which shares homology to SEQ ID NO:262.

SEQ ID NO:255 is the DNA sequence of GenBank Accession Number 15638833, which shares homology to SEQ ID NO:262.

SEQ ID NO:256, also referred to as O646SGenomicContig, is a DNA (contig) sequence assembled based on a search of the publicly available databases using SEQ ID NO:243 as a query.

SEQ ID NO:257 is an amino acid sequence corresponding to the DNA sequence of GenBank Accession Number 13629915, SEQ ID NO:251.

SEQ ID NO:258 is an amino acid sequence corresponding to the DNA sequence of GenBank Accession Number 9789986, SEQ ID NO:252.

SEQ ID NO:259 is an amino acid sequence corresponding to the DNA sequence of GenBank Accession Number 6006516, SEQ ID NO:253.

SEQ ID NO:260 is an amino acid sequence corresponding to the DNA sequence of GenBank Accession Number 5689424, SEQ ID NO:254.

SEQ ID NO:261, also referred to as O648S_GenomicContig_ORF, is a amino acid sequence corresponding to a polypeptide encoded by SEQ ID NO:262.

SEQ ID NO:262 is the DNA sequence of GenBank Accession Number 16933560, which shares homology to SEQ ID NO:268.

SEQ ID NO:263 is the DNA sequence of GenBank Accession Number 12053028, which shares homology to SEQ ID NO:268.

SEQ ID NO:264 is the DNA sequence of GenBank Accession Number 7638812, which shares homology to SEQ ID NO:268.

SEQ ID NO:265 is the DNA sequence of GenBank Accession Number 939922, which shares homology to SEQ ID NO:268.

SEQ ID NO:266 is the DNA sequence of GenBank Accession Number 6093230, which shares homology to SEQ ID NO:268.

SEQ ID NO:267 is the DNA sequence of GenBank Accession Number 11465000, which shares homology to SEQ ID NO:268.

SEQ ID NO:268 also referred to as O647SgenomicContig3, is a DNA (contig) sequence assembled based on a search of the publicly available databases using SEQ ID NO:234 as a query.

SEQ ID NO:269 is an amino acid sequence corresponding to the DNA sequence of GenBank Accession Number 16933560, SEQ ID NO:262.

SEQ ID NO:270 is an amino acid sequence corresponding to the DNA sequence of GenBank Accession Number 12053028, SEQ ID NO:263.

SEQ ID NO:271 is an amino acid sequence corresponding to the DNA sequence of GenBank Accession Number 7638812, SEQ ID NO:264.

SEQ ID NO:272 is an amino acid sequence corresponding to the DNA sequence of GenBank Accession Number 939922, SEQ ID NO:265.

SEQ ID NO:273 also referred to as O645SgenomicContig2, is a DNA (contig) sequence assembled based on a search of the publicly available databases using SEQ ID NO:238 as a query.

SEQ ID NO:274 is the DNA sequence of GenBank Accession Number NM006580, also referred to as Claudin16, which shares homology to SEQ ID NO:277.

SEQ ID NO:275 is the DNA sequence of GenBank Accession Number AF152101.1, also referred to as Paracellin-1, which shares homology to SEQ ID NO:277.

SEQ IN NO:276 is the DNA sequence of GenBank Accession Number 18425237, which shares homology to SEQ ID NO:277.

SEQ ID NO:277 also referred to as O644SgenomicContig2, is a DNA (contig) sequence assembled based on a search of the publicly available databases using SEQ ID NO:240 as a query.

SEQ ID NO:278 is an amino acid sequence corresponding to the DNA sequence of GenBank Accession Number NM006580, SEQ ID NO:277.

SEQ ID NO:279 is an amino acid sequence corresponding to the DNA sequence of GenBank Accession Number AF152101.1, SEQ ID NO:275.

SEQ ID NO:280 also referred to as O644S_GenomicContig2_ORF1, is a amino acid sequence corresponding to an open reading frame of SEQ ID NO:277.

SEQ ID NO:281 also referred to as O644S_GenomicContig2_ORF2, is a amino acid sequence corresponding to an open reading frame of SEQ ID NO:277.

SEQ ID NO:282 also referred to as O644S_GenomicContig2_ORF3, is a amino acid sequence corresponding to an open reading frame of SEQ ID NO:277.

SEQ ID NO:283 is a DNA sequence of a signal peptide minus O591S fusion protein containing a N-terminal histidine tag.

SEQ ID NO:284 is a corresponding amino acid sequence of a signal peptide minus O591S fusion protein containing a N-terminal histidine tag.

SEQ ID NO:285 is a 1740 bp DNA sequence identified by BlastN search of a LifeSeq Gold database using SEQ ID NO:198 as a query.

SEQ ID NO:286 is an amino acid sequence encode by the DNA sequence set forth in SEQ ID NO:285.

SEQ ID NO:287 is the sequence for the forward primer, CBH-005, used in the amplification of O591S-A.

SEQ ID NO:288 is the sequence for the reverse primer, CBH-003, used in the amplification of O591S-A.

SEQ ID NO:289 corresponds to the amino acid sequence corresponding to residue 1-114 of SEQ ID NO:215.

SEQ ID NO:290 corresponds to the amino acid sequence corresponding to residue 1-115 of SEQ ID NO:215 (O591S).

SEQ ID NO:291 corresponds to amino acid residues 26-55 of SEQ ID NO:215 (O591S).

SEQ ID NO:292 corresponds to amino acid residues 53-78 of SEQ ID NO:215 (O591S).

SEQ ID NO:293 corresponds to amino acid residues 103-129 of SEQ ID NO:215 (O591S).

DETAILED DESCRIPTION OF THE INVENTION

U.S. patents, U.S. patent application publications, U.S. patent applications, foreign patents, foreign patent applications and non-patent publications referred to in this specification and/or listed in the Application Data Sheet, are incorporated herein by reference, in their entirety.

The present invention is directed generally to compositions and their use in the therapy and diagnosis of cancer, particularly ovarian cancer. As described further below, illustrative compositions of the present invention include, but are not restricted to, polypeptides, particularly immunogenic polypeptides, polynucleotides encoding such polypeptides, antibodies and other binding agents, antigen presenting cells (APCs) and immune system cells (e.g., T cells).

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

Polypeptide Compositions

As used herein, the term "polypeptide" is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising epitopes, i.e., antigenic determinants substantially responsible for the immunogenic properties of a polypeptide and being capable of evoking an immune response.

Particularly illustrative polypeptides of the present invention comprise those encoded by a polynucleotide sequence set forth in any one of SEQ ID NO: 1-185, 187-199, 203-206, 208, 210-214, 216-246, 250-256, 262-268, 273-277, 283, 285, and 287-288; or a sequence that hybridizes under moderately stringent conditions, or, alternatively, under highly stringent conditions, to a polynucleotide sequence identified above. Certain other illustrative polypeptides of the invention comprise amino acid sequences as set forth in any one of SEQ ID NO:186, 200-202, 207, 209, 215, 247-249, 257-261, 269-272, 278-282, 284, 286, and 289-293.

The polypeptides of the present invention are sometimes herein referred to as ovarian tumor proteins or ovarian tumor polypeptides, as an indication that their identification has been based at least in part upon their increased levels of expression in ovarian tumor samples. Thus, a "ovarian tumor polypeptide" or "ovarian tumor protein," refers generally to a polypeptide sequence of the present invention, or a polynucleotide sequence encoding such a polypeptide, that is expressed in a substantial proportion of ovarian tumor samples, for example preferably greater than about 20%, more preferably greater than about 30%, and most preferably greater than about 50% or more of ovarian tumor samples tested, at a level that is at least two fold, and preferably at least five fold, greater than the level of expression in normal tissues, as determined using a representative assay provided herein. An ovarian tumor polypeptide sequence of the invention, based upon its increased level of expression in tumor cells, has particular utility both as a diagnostic marker as well as a therapeutic target, as further described below.

In certain preferred embodiments, the polypeptides of the invention are immunogenic, i.e., they react detectably within an immunoassay (such as an ELISA or T-cell stimulation assay) with antisera and/or T-cells from a patient with ovarian cancer. Screening for immunogenic activity can be performed using techniques well known to the skilled artisan. For example, such screens can be performed using methods such as those described in Harlow and Lane, Antibodies: A Laboratory Manual, Cold Spring Harbor Laboratory, 1988. In one illustrative example, a polypeptide may be immobilized on a solid support and contacted with patient sera to allow binding of antibodies within the sera to the immobilized polypeptide.

Unbound sera may then be removed and bound antibodies detected using, for example, $^{125}$I-labeled Protein A.

As would be recognized by the skilled artisan, immunogenic portions of the polypeptides disclosed herein are also encompassed by the present invention. An "immunogenic portion," as used herein, is a fragment of an immunogenic polypeptide of the invention that itself is immunologically reactive (i.e., specifically binds) with the B-cells and/or T-cell surface antigen receptors that recognize the polypeptide. Immunogenic portions may generally be identified using well known techniques, such as those summarized in Paul, *Fundamental Immunology*, 3rd ed., 243-247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well-known techniques.

In one preferred embodiment, an immunogenic portion of a polypeptide of the present invention is a portion that reacts with antisera and/or T-cells at a level that is not substantially less than the reactivity of the full-length polypeptide (e.g., in an ELISA and/or T-cell reactivity assay). Preferably, the level of immunogenic activity of the immunogenic portion is at least about 50%, preferably at least about 70% and most preferably greater than about 90% of the immunogenicity for the full-length polypeptide. In some instances, preferred immunogenic portions will be identified that have a level of immunogenic activity greater than that of the corresponding full-length polypeptide, e.g., having greater than about 100% or 150% or more immunogenic activity.

In certain other embodiments, illustrative immunogenic portions may include peptides in which an N-terminal leader sequence and/or transmembrane domain have been deleted. Other illustrative immunogenic portions will contain a small N- and/or C-terminal deletion (e.g., 1-30 amino acids, preferably 5-15 amino acids), relative to the mature protein.

In another embodiment, a polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof.

In another embodiment of the invention, polypeptides are provided that comprise one or more polypeptides that are capable of eliciting T cells and/or antibodies that are immunologically reactive with one or more polypeptides described herein, or one or more polypeptides encoded by contiguous nucleic acid sequences contained in the polynucleotide sequences disclosed herein, or immunogenic fragments or variants thereof, or to one or more nucleic acid sequences which hybridize to one or more of these sequences under conditions of moderate to high stringency.

The present invention, in another aspect, provides polypeptide fragments comprising at least about 5, 10, 15, 20, 25, 50, or 100 contiguous amino acids, or more, including all intermediate lengths, of a polypeptide compositions set forth herein, such as those set forth in SEQ ID NO:186, 200-202, 207, 209, 215, 247-249, 257-261, 269-272, 278-282, 284, 286, and 289-293 or those encoded by a polynucleotide sequence set forth in any one of SEQ ID NO: 1-185, 187-199, 203-206, 208, 210-214, 216-246, 250-256, 262-268, 273-277, 283, 285, and 287-288.

In another aspect, the present invention provides variants of the polypeptide compositions described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

In one preferred embodiment, the polypeptide fragments and variants provide by the present invention are immunologically reactive with an antibody and/or T-cell that reacts with a full-length polypeptide specifically set for the herein.

In another preferred embodiment, the polypeptide fragments and variants provided by the present invention exhibit a level of immunogenic activity of at least about 50%, preferably at least about 70%, and most preferably at least about 90% or more of that exhibited by a full-length polypeptide sequence specifically set forth herein.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating their immunogenic activity as described herein and/or using any of a number of techniques well known in the art.

For example, certain illustrative variants of the polypeptides of the invention include those in which one or more portions, such as an N-terminal leader sequence or transmembrane domain, have been removed. Other illustrative variants include variants in which a small portion (e.g., 1-30 amino acids, preferably 5-15 amino acids) has been removed from the N- and/or C-terminal of the mature protein.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE I

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Within other illustrative embodiments, a polypeptide may be a fusion polypeptide that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. *New Engl. J. Med.,* 336:86-91, 1997).

In one preferred embodiment, the immunological fusion partner is derived from a *Mycobacterium* sp., such as a *Mycobacterium tuberculosis*-derived Ra12 fragment. Ra12 compositions and methods for their use in enhancing the expression and/or immunogenicity of heterologous polynucleotide/polypeptide sequences is described in U.S. Patent Application No. 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. Patent Application No. 60/158,585; see also, Skeiky et al., *Infection and Immun.* (1999) 67:3998-4007, incorporated herein by reference). C-terminal fragments of the MTB32A coding sequence express at high levels and remain as a soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from *influenzae* virus, NS1 (hemaglutinin).

Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798, 1992). Within a preferred embodiment, a repeat portion of LYTA may be incorporated into a fusion polypeptide. A repeat portion is found in the C-terminal region starting at residue 178. A particularly preferred repeat portion incorporates residues 188-305.

Yet another illustrative embodiment involves fusion polypeptides, and the polynucleotides encoding them, wherein the fusion partner comprises a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of $CD4^+$ T-cells specific for the polypeptide.

Polypeptides of the invention are prepared using any of a variety of well known synthetic and/or recombinant techniques, the latter of which are further described below. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

In general, polypeptide compositions (including fusion polypeptides) of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

Polynucleotide Compositions

The present invention, in other aspects, provides polynucleotide compositions. The terms "DNA" and "polynucleotide" are used essentially interchangeably herein to refer to a DNA molecule that has been isolated free of total genomic DNA of a particular species. "Isolated," as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

As will be understood by those skilled in the art, the polynucleotide compositions of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be also recognized by the skilled artisan, polynucleotides of the invention may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide/protein of the invention or a portion thereof) or may comprise a sequence that encodes a variant or derivative, preferably and immunogenic variant or derivative, of such a sequence.

Therefore, according to another aspect of the present invention, polynucleotide compositions are provided that comprise some or all of a polynucleotide sequence set forth in any one of SEQ ID NO:1-185, 187-199, 203-206, 208, 210-214, 216-246, 250-256, 262-268, 273-277, 283, 285, and 287-288, complements of a polynucleotide sequence set forth as described above, and degenerate variants of a polynucleotide sequence set forth as described above. In certain preferred embodiments, the polynucleotide sequences set forth herein encode immunogenic polypeptides, as described above.

In other related embodiments, the present invention provides polynucleotide variants having substantial identity to the sequences disclosed herein in SEQ ID NO:1-185, 187-199, 203-206, 208, 210-214, 216-246, 250-256, 262-268, 273-277, 283, 285, and 287-288, for example those comprising at least 70% sequence identity, preferably at least 75%, 80%, 85%, 90%, 95%, 96%, 97%, 98%, or 99% or higher, sequence identity compared to a polynucleotide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the immunogenicity of the polypeptide encoded by the variant polynucleotide is not substantially diminished relative to a polypeptide encoded by a polynucleotide sequence specifically set forth herein). The term "variants" should also be understood to encompasses homologous genes of xenogenic origin.

In additional embodiments, the present invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In certain preferred embodiments, the polynucleotides described above, e.g., polynucleotide variants, fragments and hybridizing sequences, encode polypeptides that are immunologically cross-reactive with a polypeptide sequence specifically set forth herein. In other preferred embodiments, such polynucleotides encode polypeptides that have a level of immunogenic activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in protein—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Therefore, in another embodiment of the invention, a mutagenesis approach, such as site-specific mutagenesis, is employed for the preparation of immunogenic variants and/or derivatives of the polypeptides described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the immunogenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis etal., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants of the present invention, recursive sequence recombination, as described in U.S. Pat. No. 5,837,458, may be employed. In this approach, iterative cycles of recombination and screening or selection are performed to "evolve" individual polynucleotide variants of the invention having, for example, enhanced immunogenic activity.

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10-14, 15-20, 30, 50, or even of 100-200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch(es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15-25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequences set forth herein, or to any continuous portion of the sequences, from about 15-25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

According to another embodiment of the present invention, polynucleotide compositions comprising antisense oligonucleotides are provided. Antisense oligonucleotides have been demonstrated to be effective and targeted inhibitors of protein synthesis, and, consequently, provide a therapeutic approach by which a disease can be treated by inhibiting the synthesis of proteins that contribute to the disease. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. Nos. 5,739, 119 and 5,759,829). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., Science. 1988 Jun. 10; 240(4858):1544-6; Vasanthakumar and Ahmed, Cancer Commun. 1989; 1 (4):225-32; Peris et al., Brain Res Mol Brain Res. 1998 Jun. 15; 57(2):310-20; U.S. Pat. Nos. 5,801,154; 5,789,573; 5,718,709 and 5,610, 288). Antisense constructs have also been described that inhibit and can be used to treat a variety of abnormal cellular proliferations, e.g., cancer (U.S. Pat. Nos. 5,747,470; 5,591, 317 and 5,783,683).

Therefore, in certain embodiments, the present invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein. Selection of antisense compositions specific for a given gene sequence is based upon analysis of the chosen target sequence and determination of secondary structure, $T_m$, binding energy, and relative stability. Antisense compositions may be selected based upon their relative inability to form dimers, hairpins, or other secondary structures that would reduce or prohibit specific binding to the target mRNA in a host cell. Highly preferred target regions of the mRNA, are those which are at or near the AUG translation initiation codon, and those sequences which are substantially complementary to 5' regions of the mRNA. These secondary structure analyses and target site selection considerations can be performed, for example, using v.4 of the OLIGO primer analysis software and/or the BLASTN 2.0.5 algorithm software (Altschul et al., Nucleic Acids Res. 1997, 25(17):3389-402).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., Nucleic Acids Res. 1997 Jul. 15; 25(14):2730-6). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane.

According to another embodiment of the invention, the polynucleotide compositions described herein are used in the design and preparation of ribozyme molecules for inhibiting expression of the tumor polypeptides and proteins of the present invention in tumor cells. Ribozymes are RNA-protein complexes that cleave nucleic acids in a site-specific fashion. Ribozymes have specific catalytic domains that possess endonuclease activity (Kim and Cech, Proc Natl. Acad Sci USA. 1987 December; 84(24):8788-92; Forster and Symons, Cell. 1987 Apr. 24; 49(2):211-20). For example, a large number of ribozymes accelerate phosphoester transfer reactions with a high degree of specificity, often cleaving only one of several phosphoesters in an oligonucleotide substrate (Cech et al., Cell. 1981 December; 27(3 Pt 2):487-96; Michel and Westhof, J Mol Biol. 1990 Dec. 5; 216(3):585-610; Reinhold-Hurek and Shub, Nature. 1992 May 14; 357(6374):173-6). This specificity has been attributed to the requirement that the substrate bind via specific base-pairing interactions to the internal guide sequence ("IGS") of the ribozyme prior to chemical reaction.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., Proc Natl. Acad Sci USA. 1992 Aug. 15; 89(16): 7305-9). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. Nucleic Acids Res. 1992 Sep. 11; 20(17):4559-65. Examples of hairpin motifs are described by Hampel et al. (Eur. Pat. Appl. Publ. No. EP 0360257), Hampel and Tritz, Biochemistry 1989 Jun. 13; 28(12):4929-33; Hampel et al., Nucleic Acids Res. 1990 Jan. 25; 18(2):299-304 and U.S. Pat. No. 5,631,359. An example of the hepatitis δ virus motif is described by Perrotta and Been, Biochemistry. 1992 Dec. 1; 31(47):11843-52; an example of the RNaseP motif is described by Guerrier-Takada et al., Cell. 1983 December; 35(3 Pt 2):849-57; Neurospora VS RNA ribozyme motif is described by Collins (Saville and Collins, Cell. 1990 May 18; 61(4):685-96; Saville and Collins, Proc Natl Acad Sci USA. 1991 Oct. 1; 88(19):8826-30; Collins and Olive, Biochemistry. 1993 Mar. 23; 32(11):2795-9); and an example of the Group I intron is described in (U.S. Pat. No. 4,987,071). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Ribozyme activity can be optimized by altering the length of the ribozyme binding arms, or chemically synthesizing ribozymes with modifications that prevent their degradation by serum ribonucleases (see, e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells Ribozymes expressed from such promoters have been shown to function in mammalian cells. Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

In another embodiment of the invention, peptide nucleic acids (PNAs) compositions are provided. PNA is a DNA mimic in which the nucleobases are attached to a pseudopeptide backbone (Good and Nielsen, Antisense Nucleic Acid Drug Dev. 1997 7(4) 431-37). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (*Trends Biotechnol* 1997 June; 15(6): 224-9). As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., *Science* 1991 Dec. 6; 254(5037):1497-500; Hanvey et al., Science. 1992 Nov. 27; 258(5087):1481-5; Hyrup and Nielsen, Bioorg Med Chem. 1996 January; 4(1):5-23). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc or Fmoc protocols for solid-phase peptide synthesis, although other methods, including a modified Merrifield method, have been used.

PNA monomers or ready-made oligomers are commercially available from PerSeptive Biosystems (Framingham, Mass.). PNA syntheses by either Boc or Fmoc protocols are straightforward using manual or automated protocols (Norton et al., Bioorg Med Chem. 1995 April; 3(4):437-45). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography, providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (for example, Norton et al., Bioorg Med Chem. 1995 April; 3(4):437-45; Petersen et al., J Pept Sci. 1995 May-June; 1(3):175-83; Orum et al., Biotechniques. 1995 September; 19(3):472-80; Footer et al., Biochemistry. 1996 Aug. 20; 35(33):10673-9; Griffith et al., Nucleic Acids Res. 1995 Aug. 11; 23(15):3003-8; Pardridge et al., Proc Natl Acad Sci USA. 1995 Jun. 6; 92(12):5592-6; Boffa et al., Proc Natl Acad Sci USA. 1995 Mar. 14; 92(6):1901-5; Gambacorti-Passerini et al., Blood. 1996 Aug. 15; 88(4): 1411-7; Armitage et al., Proc Natl Acad Sci USA. 1997 Nov. 11; 94(23):12320-5; Seeger et al., Biotechniques. 1997 September; 23(3):512-7). U.S. Pat. No. 5,700,922 discusses PNA-DNA-PNA chimeric molecules and their uses in diagnostics, modulating protein in organisms, and treatment of conditions susceptible to therapeutics.

Methods of characterizing the antisense binding properties of PNAs are discussed in Rose (Anal Chem. 1993 Dec. 15; 65(24):3545-9) and Jensen et al. (Biochemistry. 1997 Apr. 22; 36(16):5072-7). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs that have been described and will be apparent to the skilled artisan include use in DNA strand invasion, antisense inhibition, mutational analysis, enhancers of transcription, nucleic acid purification, isolation of transcriptionally active genes, blocking of transcription factor binding, genome cleavage, biosensors, in situ hybridization, and the like.

Polynucleotide Identification, Characterization and Expression

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989, and other like references). For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using the microarray technology of Affymetrix, Inc. (Santa Clara, Calif.) according to the manufacturer's instructions (and essentially as described by Schena et al., *Proc. Natl. Acad. Sci. USA* 93:10614-10619, 1996 and Heller et al., *Proc. Natl. Acad. Sci. USA* 94:2150-2155, 1997). Alternatively, polynucleotides may be amplified from cDNA prepared from cells expressing the proteins described herein, such as tumor cells.

Many template dependent processes are available to amplify a target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Any of a number of other template dependent processes, many of which are variations of the PCR™ amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well-known to those of skill in the art.

An amplified portion of a polynucleotide of the present invention may be used to isolate a full length gene from a suitable library (e.g., a tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}$P) using well known techniques. A bacterial or bacteriophage library is then generally screened by hybridizing filters containing denatured bacterial colonies (or lawns containing phage plaques) with the labeled probe (see Sambrook et al.,

*Molecular Cloning: A Laboratory Manual,* Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, amplification techniques, such as those described above, can be useful for obtaining a full length coding sequence from a partial cDNA sequence. One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111-19, 1991) and walking PCR (Parker et al., *Nucl. Acids. Res.* 19:3055-60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215-223, Horn, T. et al. (1980) *Nucl. Acids Res. Symp. Ser.* 225-232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202-204) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, WH Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, any of a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem.* 264:5503-5509); and the like pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) *Methods Enzymol.* 153:516-544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307-311. Alternatively, plant promoters such as the small subunit of RUBISCO or heat shock promoters may be used (Coruzzi, G. et al. (1984) *EMBO J.* 3:1671-1680; Broglie, R. et al. (1984) *Science* 224:838-843; and Winter, J. et al. (1991) *Results Probl. Cell Differ.* 17:85-105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191-196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia larvae*. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard, E. K. et al. (1994) *Proc. Natl. Acad. Sci.* 91:3224-3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, COS, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223-32) and adenine phosphoribosyltransferase (Lowy, I. et al. (1990) Cell 22:817-23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567-70); npt, which confers resistance to the aminoglycosides, neomycin and G-418 (Colbere-Garapin, F. et al (1981) J. Mol. Biol. 150:1-14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121-131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211-1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3:263-281) while the enterokinase cleavage site provides a means for purifying the desired polypeptide from the fusion protein. A discussion of vectors which contain fusion proteins is provided in Kroll, D. J. et al. (1993; DNA Cell Biol. 12:441-453).

In addition to recombinant production methods, polypeptides of the invention, and fragments thereof, may be produced by direct peptide synthesis using solid-phase techniques (Merrifield J. (1963) J. Am. Chem. Soc. 85:2149-2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

Antibody Compositions, Fragments Thereof and Other Binding Agents

According to another aspect, the present invention further provides binding agents, such as antibodies and antigen-binding fragments thereof, that exhibit immunological binding to a tumor polypeptide disclosed herein, or to a portion, variant or derivative thereof. An antibody, or antigen-binding fragment thereof, is said to "specifically bind," "immunogically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) Annual Rev. Biochem. 59:439-473.

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Binding agents may be further capable of differentiating between patients with and without a cancer, such as ovarian cancer, using the representative assays provided herein. For example, antibodies or other binding agents that bind to a tumor protein will preferably generate a signal indicating the presence of a cancer in at least about 20% of patients with the disease, more preferably at least about 30% of patients. Alternatively, or in addition, the antibody will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. Preferably, a statistically significant number of samples with and without the disease will be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) Proc. Nat. Acad. Sci. USA 69:2659-2662; Hochman et al. (1976) Biochem 15:2706-2710; and Ehrlich et al. (1980) Biochem 19:4091-4096.

A single chain Fv ("sFv") polypeptide is a covalently linked $V_H$::$V_L$ heterodimer which is expressed from a gene fusion including $V_H$- and $V_L$-encoding genes linked by a peptide-encoding linker. Huston et al. (1988) Proc. Nat. Acad. Sci. USA 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349: 293-299; Lobuglio et al. (1989) Proc. Nat. Acad. Sci. USA 86:4220-4224; Shaw et al. (1987) J Immunol. 138:4534-4538; and Brown et al. (1987) Cancer Res. 47:3577-3583), rodent CDRs grafted into a human supporting FR prior to fusion with an appropriate human antibody constant domain (Riechmann et al. (1988) Nature 332:323-327; Verhoeyen et al. (1988) Science 239:1534-1536; and Jones et al. (1986) Nature 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) Ann. Rev. Biochem. 59:439-473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in Sequences of Proteins of Immunological Interest, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

In another embodiment of the invention, monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

T Cell Compositions

The present invention, in another aspect, provides T cells specific for a tumor polypeptide disclosed herein, or for a variant or derivative thereof. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. Nos. 5,240,856; 5,215,926; WO 89/06280; WO 91/16116 and WO 92/07243). Alternatively, T cells may be derived from related or unrelated humans, non-human mammals, cell lines or cultures.

T cells may be stimulated with a polypeptide, polynucleotide encoding a polypeptide and/or an antigen presenting cell (APC) that expresses such a polypeptide. Such stimulation is performed under conditions and for a time sufficient to permit the generation of T cells that are specific for the polypeptide of interest. Preferably, a tumor polypeptide or polynucleotide of the invention is present within a delivery vehicle, such as a microsphere, to facilitate the generation of specific T cells.

T cells are considered to be specific for a polypeptide of the present invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065-1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a tumor polypeptide (100 ng/ml-100 µg/ml, preferably 200 ng/ml-25 µg/ml) for 3-7 days will typically result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a tumor polypeptide, polynucleotide or polypeptide-expressing APC may be $CD4^+$ and/or $CD8^+$. Tumor polypeptide-specific T cells may be expanded using standard techniques. Within preferred embodiments, the T cells are derived from a patient, a related donor or an unrelated donor, and are administered to the patient following stimulation and expansion.

For therapeutic purposes, $CD4^+$ or $CD8^+$ T cells that proliferate in response to a tumor polypeptide, polynucleotide or APC can be expanded in number either in vitro or in vivo. Proliferation of such T cells in vitro may be accomplished in a variety of ways. For example, the T cells can be re-exposed to a tumor polypeptide, or a short peptide corresponding to an immunogenic portion of such a polypeptide, with or without the addition of T cell growth factors, such as interleukin-2, and/or stimulator cells that synthesize a tumor polypeptide. Alternatively, one or more T cells that proliferate in the presence of the tumor polypeptide can be expanded in number by cloning. Methods for cloning cells are well known in the art, and include limiting dilution.

Pharmaceutical Compositions

In additional embodiments, the present invention concerns formulation of one or more of the polynucleotide, polypeptide, T-cell and/or antibody compositions disclosed herein in pharmaceutically-acceptable carriers for administration to a cell or an animal, either alone, or in combination with one or more other modalities of therapy.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Therefore, in another aspect of the present invention, pharmaceutical compositions are provided comprising one or more of the polynucleotide, polypeptide, antibody, and/or T-cell compositions described herein in combination with a physiologically acceptable carrier. In certain preferred embodiments, the pharmaceutical compositions of the invention comprise immunogenic polynucleotide and/or polypeptide compositions of the invention for use in prophylactic and therapeutic vaccine applications. Vaccine preparation is generally described in, for example, M. F. Powell and M. J. Newman, eds., "Vaccine Design (the subunit and adjuvant approach)," Plenum Press (NY, 1995). Generally, such compositions will comprise one or more polynucleotide and/or polypeptide compositions of the present invention in combination with one or more immunostimulants.

It will be apparent that any of the pharmaceutical compositions described herein can contain pharmaceutically acceptable salts of the polynucleotides and polypeptides of the invention. Such salts can be prepared, for example, from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

In another embodiment, illustrative immunogenic compositions, e.g., vaccine compositions, of the present invention comprise DNA encoding one or more of the polypeptides as described above, such that the polypeptide is generated in situ. As noted above, the polynucleotide may be administered within any of a variety of delivery systems known to those of ordinary skill in the art. Indeed, numerous gene delivery techniques are well known in the art, such as those described by Rolland, Crit. Rev. Therap. Drug Carrier Systems 15:143-198, 1998, and references cited therein. Appropriate polynucleotide expression systems will, of course, contain the necessary regulatory DNA regulatory sequences for expression in a patient (such as a suitable promoter and terminating signal). Alternatively, bacterial delivery systems may involve the administration of a bacterium (such as Bacillus-Calmette-Guerrin) that expresses an immunogenic portion of the polypeptide on its cell surface or secretes such an epitope.

Therefore, in certain embodiments, polynucleotides encoding immunogenic polypeptides described herein are introduced into suitable mammalian host cells for expression using any of a number of known viral-based systems. In one illustrative embodiment, retroviruses provide a convenient and effective platform for gene delivery systems. A selected nucleotide sequence encoding a polypeptide of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) J. Virol. 57:267-274; Bett et al. (1993) J. Virol. 67:5911-5921; Mittereder et al. (1994) Human Gene Therapy 5:717-729; Seth et al. (1994) J. Virol. 68:933-940; Barr et al. (1994) Gene Therapy 1:51-58; Berkner, K. L. (1988) BioTechniques 6:616-629; and Rich et al. (1993) Human Gene Therapy 4:461-476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179:1867-1875.

Additional viral vectors useful for delivering the polynucleotides encoding polypeptides of the present invention by gene transfer include those derived from the pox family of viruses, such as vaccinia virus and avian poxvirus. By way of example, vaccinia virus recombinants expressing the novel molecules can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the polypeptide of interest into the viral genome. The resulting TK.sup.(−) recombinant can be selected by culturing the cells in the presence of 5-bromodeoxyuridine and picking viral plaques resistant thereto.

A vaccinia-based infection/transfection system can be conveniently used to provide for inducible, transient expression or coexpression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al. Proc. Natl. Acad. Sci. USA (1986) 83:8122-8126.

Alternatively, avipoxviruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions of the present invention, such as those vectors described in U.S. Pat. Nos. 5,843,723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. J. Biol. Chem. (1993) 268:6866-6869 and Wagner et al. Proc. Natl. Acad. Sci. USA (1992) 89:6099-6103, can also be used for gene delivery under the invention.

Additional illustrative information on these and other known viral-based delivery systems can be found, for example, in Fisher-Hoch et al., *Proc. Natl. Acad. Sci. USA* 86:317-321, 1989; Flexner et al., *Ann. N.Y. Acad. Sci.* 569: 86-103, 1989; Flexner et al., *Vaccine* 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627,1988; Rosenfeld et al., *Science* 252:431-434, 1991; Kolls et al., *Proc. Natl. Acad. Sci. USA* 91:215-219, 1994; Kass-Eisler et al., *Proc. Natl. Acad. Sci. USA* 90:11498-11502, 1993; Guzman et al., *Circulation* 88:2838-2848, 1993; and Guzman et al., *Cir. Res.* 73:1202-1207, 1993.

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In another embodiment of the invention, a polynucleotide is administered/delivered as "naked" DNA, for example as described in Ulmer et al., *Science* 259:1745-1749, 1993 and reviewed by Cohen, *Science* 259:1691-1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

According to another embodiment, the pharmaceutical compositions described herein will comprise one or more immunostimulants in addition to the immunogenic polynucleotide, polypeptide, antibody, T-cell and/or APC compositions of this invention. An immunostimulant refers to essentially any substance that enhances or potentiates an immune response (antibody and/or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Within certain embodiments of the invention, the adjuvant composition is preferably one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145-173, 1989.

Certain preferred adjuvants for eliciting a predominantly Th1-type response include, for example, a combination of monophosphoryl lipid A, preferably 3-de-O-acylated monophosphoryl lipid A, together with an aluminum salt. MPL® adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol® to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Preferably the formulation additionally comprises an oil in water emulsion and tocopherol.

Additional illustrative adjuvants for use in the pharmaceutical compositions of the invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Enhanzyn®) (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Other preferred adjuvants include adjuvant molecules of the general formula $$HO(CH_2CH_2O)_n\text{-A-R}, \qquad (I)$$

wherein, n is 1-50, A is a bond or —C(O)—, R is $C_{1-50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4-24, most preferably 9; the R component is $C_{1-50}$, preferably $C_4$-$C_{20}$ alkyl and most preferably $C_{12}$ alkyl, and A is a bond. The concentration of the polyoxyethylene ethers should be in the range 0.1-20%, preferably from 0.1-10%, and most preferably in the range 0.1-1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

According to another embodiment of this invention, an immunogenic composition described herein is delivered to a host via antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245-251, 1998) and have been shown to be effective as a physiological adjuvant for eliciting prophylactic or therapeutic antitumor immunity (see Timmerman and Levy, *Ann. Rev. Med.* 50:507-529, 1999). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594-600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide of the invention (or portion or other variant thereof) such that the encoded polypeptide, or an immunogenic portion thereof, is expressed on the cell surface. Such transfection may take place ex vivo, and a pharmaceutical composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456-460, 1997. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature 1997 Mar. 27; 386(6623):410-4; Hwang et al., Crit Rev Ther Drug Carrier Syst 1998; 15(3):243-84; U.S. Pat. Nos. 5,641,515; 5,580,579 and 5,792,451). Tablets, troches, pills, capsules and the like may also contain any of a variety of additional components, for example, a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Of course, any material used in preparing any dosage unit form should be pharmaceutically pure and substantially non-toxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. Nos. 5,543,158; 5,641,515 and 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. Nos. 5,756,353 and 5,804,212. Likewise, the delivery of drugs using intranasal microparticle resins (Takenaga et al., J Controlled Release 1998 Mar. 2; 52(1-2):81-7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol 1998 July; 16(7):307-21; Takakura, Nippon Rinsho 1998 March; 56(3):691-5; Chandran et al., Indian J Exp Biol. 1997 August; 35(8):801-9; Margalit, Crit Rev Ther Drug Carrier Syst. 1995; 12(2-3):233-61; U.S. Pat. Nos. 5,567,434; 5,552,157; 5,565,213; 5,738,868 and 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., J Biol Chem. 1990 Sep. 25; 265(27):16337-42; Muller et al., DNA Cell Biol. 1990 April; 9(3):221-9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, he use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 December; 24(12):1113-28). To avoid side effects due to intracellular polymeric overloading, such ultrafine particles (sized around 0.1 µm) may be designed using polymers able to be degraded in vivo. Such particles can be made as described, for example, by Couvreur et al., Crit Rev Ther Drug Carrier Syst. 1988; 5(1):1-20; zur Muhlen et al., Eur J Pharm Biopharm. 1998 March; 45(2): 149-55; Zambaux et al. J Controlled Release. 1998 Jan. 2; 50(1-3):31-40; and U.S. Pat. No. 5,145,684.

Cancer Therapeutic Methods

In further aspects of the present invention, the pharmaceutical compositions described herein may be used for the treatment of cancer, particularly for the immunotherapy of ovarian cancer. Within such methods, the pharmaceutical compositions described herein are administered to a patient, typically a warm-blooded animal, preferably a human. A patient may or may not be afflicted with cancer. Accordingly, the above pharmaceutical compositions may be used to prevent the development of a cancer or to treat a patient afflicted with a cancer. Pharmaceutical compositions and vaccines may be administered either prior to or following surgical removal of primary tumors and/or treatment such as administration of radiotherapy or conventional chemotherapeutic drugs. As discussed above, administration of the pharmaceutical compositions may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10-50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 μg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

Cancer Detection and Diagnostic Compositions, Methods and Kits

In general, a cancer may be detected in a patient based on the presence of one or more ovarian tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as ovarian cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding an ovarian tumor protein, which is also indicative of the presence or absence of a cancer. In general, a ovarian tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length ovarian tumor proteins and polypeptide portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with ovarian cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as ovarian cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106-7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 μg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use tumor polypeptides to detect antibodies that bind to such polypeptides in a biological sample. The detection of such tumor protein specific antibodies may correlate with the presence of a cancer.

A cancer may also, or alternatively, be detected based on the presence of T cells that specifically react with a tumor protein in a biological sample. Within certain methods, a biological sample comprising $CD4^+$ and/or $CD8^+$ T cells isolated from a patient is incubated with a tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2-9 days (typically 4 days) at 37° C. with polypeptide (e.g., 5-25 μg/ml). It may be desirable to incubate another aliquot of a T cell sample in the absence of tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a tumor protein in a biological sample. For example, at least two oligonucleotide primers may be employed in a polymerase chain reaction (PCR) based assay to amplify a portion of a tumor cDNA derived from a biological sample, wherein at least one of the oligonucleotide primers is specific for (i.e., hybridizes to) a polynucleotide encoding the tumor protein. The amplified cDNA is then separated and detected using techniques well known in the art, such as gel electrophoresis. Similarly, oligonucleotide probes that specifically hybridize to a polynucleotide encoding a tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a tumor protein of the invention that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10-40 nucleotides in length. In a preferred embodiment, the oligonucleotide primers comprise at least 10 contiguous nucleotides, more preferably at least 15 contiguous nucleotides, of a DNA molecule having a sequence as disclosed herein. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the compositions described herein may be used as markers for the progression of cancer. In this embodiment, assays as described above for the diagnosis of a cancer may be performed over time, and the change in the level of reactive polypeptide(s) or polynucleotide(s) evaluated. For example, the assays may be performed every 24-72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a tumor protein in a biological sample. Such kits generally comprise at least one oligonucleotide probe or primer, as described above, that hybridizes to a polynucleotide encoding a tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a tumor protein.

The following Examples are offered by way of illustration and not by way of limitation.

EXAMPLES

Example 1

Identification of Representative Ovarian Carcinoma cDNA Sequences

Primary ovarian tumor and metastatic ovarian tumor cDNA libraries were each constructed in kanamycin resistant pZErO™-2 vector (Invitrogen) from pools of three different ovarian tumor RNA samples. For the primary ovarian tumor library, the following RNA samples were used: (1) a moderately differentiated papillary serous carcinoma of a 41 year old, (2) a stage IIIC ovarian tumor and (3) a papillary serous adenocarcinoma for a 50 year old Caucasian. For the metastatic ovarian tumor library, the RNA samples used were omentum tissue from: (1) a metastatic poorly differentiated papillary adenocarcinoma with psammoma bodies in a 73 year old, (2) a metastatic poorly differentiated adenocarcinoma in a 74 year old and (3) a metastatic poorly differentiated papillary adenocarcinoma in a 68 year old.

The number of clones in each library was estimated by plating serial dilutions of unamplified libraries. Insert data were determined from 32 primary ovarian tumor clones and 32 metastatic ovarian tumor clones. The library characterization results are shown in Table II.

TABLE II

CHARACTERIZATION OF cDNA LIBRARIES

| Library | # Clones in Library | Clones with Insert (%) | Insert Size Range (bp) | Ave. Insert Size (bp) |
|---|---|---|---|---|
| Primary Ovarian Tumor | 1,258,000 | 97 | 175-8000 | 2356 |
| Metastatic Ovarian Tumor | 1,788,000 | 100 | 150-4300 | 1755 |

Four subtraction libraries were constructed in ampicillin resistant pcDNA3.1 vector (Invitrogen). Two of the libraries were from primary ovarian tumors and two were from metastatic ovarian tumors. In each case, the number of restriction enzyme cuts within inserts was minimized to generate full length subtraction libraries. The subtractions were each done with slightly different protocols, as described in more detail below.

A. POTS 2 Library: Primary Ovarian Tumor Subtraction Library

Tracer: 10 µg primary ovarian tumor library, digested with Not I
Driver: 35 µg normal pancreas in pcDNA3.1(+)
20 µg normal PBMC in pcDNA3.1(+)
10 µg normal skin in pcDNA3.1(+)
35 µg normal bone marrow in pZErO™-2
Digested with Bam HI/Xho I/Sca I Two hybridizations were performed, and Not I-cut pcDNA3.1(+) was the cloning vector for the subtracted library. Sequence results for previously unidentified clones that were randomly picked from the subtracted library are presented in Table III.

TABLE III

OVARIAN CARCINOMA SEQUENCES

| Sequence | SEQ ID NO |
|---|---|
| 21907 | 1 |
| 21909 | 2 |
| 21911 | 5 |
| 21920 | 9 |
| 21921 | 10 |
| 25099 | 143 |
| 25101 | 144 |
| 25103 | 145 |
| 25107 | 146 |
| 25111 | 148 |
| 25113 | 149 |
| 25115 | 150 |
| 25116 | 151 |
| 25752 | 156 |
| 25757 | 158 |
| 25763 | 160 |
| 25769 | 161 |
| 25770 | 162 |

B. POTS 7 Library: Primary Ovarian Tumor Subtraction Library

Tracer: 10 µg primary ovarian tumor library, digested with Not I
Driver 35 µg normal pancreas in pcDNA3.1(+)
20 µg normal PBMC in pcDNA3.1(+)
10 µg normal skin in pcDNA3.1(+)
35 µg normal bone marrow in pZErO™-2 Digested with Bam HI/Xho I/Sca I
~25 µg pZErO™-2, digested with Bam HI and Xho I Two hybridizations were performed, and Not I-cut pcDNA3.1(+) was the cloning vector for the subtracted library. Sequence results for previously unidentified clones that were randomly picked from the subtracted library are presented in Table IV.

TABLE IV

OVARIAN CARCINOMA SEQUENCES

| Sequence | SEQ ID NO |
|---|---|
| 24937 | 125 |
| 24940 | 128 |
| 24946 | 132 |
| 24950 | 133 |
| 24951 | 134 |
| 24955 | 136 |
| 24956 | 137 |
| 25791 | 166 |
| 25796 | 167 |
| 25797 | 168 |
| 25804 | 171 |

C. OS1D Library: Metastatic Ovarian Tumor Subtraction Library

Tracer: 10 µg metastatic ovarian library in pZErO™-2, digested with Not I
Driver: 24.5 µg normal pancreas in pcDNA3.1
14 µg normal PBMC in pcDNA3.1
14 µg normal skin in pcDNA3.1
24.5 µg normal bone marrow in pZErO™-2
50 µg pZErO™-2, digested with Bam HI/Xho I/Sfu I Three hybridizations were performed, and the last two hybridizations were done with an additional 15 µg of biotinylated pZErO™-2 to remove contaminating pZErO™-2 vectors. The cloning vector for the subtracted library was pcDNA3.1/Not I cut. Sequence results for previously unidentified clones that were randomly picked from the subtracted library are presented in Table V.

TABLE V

Ovarian Carcinoma Sequences

| Sequence | SEQ ID NO |
|---|---|
| 23645.1 | 13 |
| 23660.1 | 16 |
| 23666.1 | 19 |
| 23679.1 | 23 |
| 24635 | 57 |
| 24647 | 63 |
| 24651 | 65 |
| 24661 | 69 |
| 24663 | 70 |
| 24664 | 71 |
| 24670 | 72 |
| 24675 | 75 |
| 24683 | 78 |

D. OS1F Library: Metastic Ovarian Tumor Subtraction Library

Tracer: 10 μg metastatic ovarian tumor library, digested with Not I
Driver: 12.8 μg normal pancreas in pcDNA3.1
  7.3 μg normal PBMC in pcDNA3.1
  7.3 μg normal skin in pcDNA3.1
  12.8 μg normal bone marrow in pZErO™-2
  25 μg pZErO™-2, digested with Bam HI/Xho I/Sfu I One hybridization was performed. The cloning vector for the subtracted library was pcDNA3.1/Not I cut. Sequence results for previously unidentified clones that were randomly picked from the subtracted library are presented in Table VI.

TABLE VI

OVARIAN CARCINOMA SEQUENCES

| Sequence | | SEQ ID NO |
|---|---|---|
| 24336 | (79% with *H. sapiens* mitochondrial genome (consensus sequence)) | 27 |
| 24337 | | 28 |
| 24341 | (91% *Homo sapiens* chromosome 5, BAC clone 249h5 (LBNL H149) | 32 |
| 24344 | | 33 |
| 24348 | | 35 |
| 24351 | | 38 |
| 24355 | (91% *Homo sapiens* chromosome 17, clone hCIT.91_J_4) | 41 |
| 24356 | | 42 |
| 24357 | (87% *S. scrofa* mRNA for UDP glucose pyrophosphorylase) | 43 |
| 24358 | | 44 |
| 24359 | (78% Human mRNA for KIAA0111 gene, complete cds) | 45 |
| 24360 | | 46 |
| 24361 | | 47 |
| 24362 | (88% *Homo sapiens* Chromosome 16 BAC clone CIT987SK-A-233A7) | 48 |
| 24363 | (87% *Homo sapiens* eukaryotic translation elongation factor 1 alpha 1 (EEF1A1) | 49 |
| 24364 | (89% Human DNA sequence from PAC 27K14 on chromosome Xp11.3-Xp11.4) | 50 |
| 24367 | (89% *Homo sapiens* 12p13.3 BAC RCPI11-935C2) | 52 |
| 24368 | | 53 |
| 24690 | | 81 |
| 24692 | | 82 |
| 24694 | | 84 |
| 24696 | | 86 |
| 24699 | | 89 |
| 24701 | | 90 |
| 24703 | | 91 |
| 24704 | (88% *Homo sapiens* chromosome 9, clone hRPK.401_G_18) | 92 |
| 24705 | | 93 |
| 24707 | | 95 |
| 24709 | | 97 |
| 24711 | | 98 |
| 24713 | | 99 |
| 24714 | (91% Human DNA sequence from clone 125N5 on chromosome 6q26-27) | 100 |
| 24717 | (89% *Homo sapiens* proliferation-associated gene A (natural killer-enhancing factor A) (PAGA) | 103 |
| 24727 | | 107 |
| 24732 | | 111 |
| 24737 | (84% Human ADP/ATP translocase mRNA) | 114 |
| 24741 | | 117 |
| 24745 | | 120 |
| 24746 | | 121 |

The sequences in Table VII, which correspond to known sequences, were also identified in the above libraries.

TABLE VII

OVARIAN CARCINOMA SEQUENCES

| Identity | SEQ ID NO | Sequence | Library |
|---|---|---|---|
| *H. sapiens* DNA for muscle nicotinic acetylcholine receptor gene promotor, clone ICRFc105F02104 | 3 | 21910 | POTS2 |
| *Homo sapiens* complement component 3 (C3) gene, exons 1-30. | 4 | 21913 | POTS2 |
| *Homo sapiens* SWI/SNF related, matrix associated, actin dependent regulator of chromatin, subfamily a, member 4 (SMARCA4) | 6 | 21914 | POTS2 |
| Human ferritin Heavy subunit mRNA, complete cds. | 7 | 21915 | POTS2 |
| *Homo sapiens* CGI-151 protein mRNA, complete cds | 8 | 21916 | POTS2 |
| Human BAC clone GS055K18 from 7p15-p21 | 11 | 23636.1 | OS1D |

TABLE VII-continued

OVARIAN CARCINOMA SEQUENCES

| Identity | SEQ ID NO | Sequence | Library |
|---|---|---|---|
| HUMGFIBPA Human growth hormone-dependent insulin-like growth factor-binding protein | 12 | 23637.1 | OS1D |
| *Homo sapiens* ribosomal protein, large, P0 (RPLP0) mRNA | 14 | 23647.1 | OS1D |
| HUMTRPM2A Human TRPM-2 mRNA | 15 | 23657.1 | OS1D |
| HUMMTA *Homo sapiens* mitochondrial DNA | 17 | 23661.1 | OS1D |
| HSU78095 *Homo sapiens* placental bikunin mRNA | 18 | 23662.1 | OS1D |
| HUMTI227HC Human mRNA for TI-227H | 20 | 23669.1 | OS1D |
| HUMMTCG Human mitochondrion | 21 | 23673.1 | OS1D |
| *Homo sapiens* FK506-binding protein 1A (12 kD) (FKBP1A) mRNA | 22 | 23677.1 | OS1D |
| *Homo sapiens* mRNA for zinc-finger DNA-binding protein, complete cds | 24 | 24333 | OS1F |
| *Homo sapiens* mRNA; cDNA DKFZp564E1962 (from clone DKFZp564E1962) | 25 | 24334 | OS1F |
| *Homo sapiens* tumor protein, translationally-controlled 1 (TPT1) mRNA. | 26 | 24335 | OS1F |
| *Homo sapiens* interleukin 1 receptor accessory protein (IL1RAP) mRNA. | 29 | 24338 | OS1F |
| Human mRNA for KIAA0026 gene | 30 | 24339 | OS1F |
| *Homo sapiens* K—Cl cotransporter KCC4 mRNA, complete cds | 31 | 24340 | OS1F |
| *Homo sapiens* nuclear chloride ion channel protein (NCC27) mRNA | 34 | 24345 | OS1F |
| *Homo sapiens* mRNA for DEPP (decidual protein induced by progesterone) | 36 | 24349 | OS1F |
| *Homo sapiens* atrophin-1 interacting protein 4 (AIP4) mRNA | 37 | 24350 | OS1F |
| Human collagenase type IV mRNA, 3' end. | 39 | 24352 | OS1F |
| Human mRNA for T-cell cyclophilin | 40 | 24354 | OS1F |
| *Homo sapiens* tumor suppressing subtransferable candidate 1 (TSSC1) | 51 | 24366 | OS1F |
| *Homo sapiens* clone 24452 mRNA sequence | 54 | 24374 | OS1F |
| *Homo sapiens* eukaryotic translation elongation factor 1 alpha 1 (EEF1A1) | 55 | 24627 | OS1D |
| Genomic sequence from Human 9q34 | 56 | 24634 | OS1D |
| Human insulin-like growth factor-binding protein-3 gene | 58 | 24636 | OS1D |
| Human ribosomal protein L3 mRNA, 3' end | 59 | 24638 | OS1D |
| *Homo sapiens* annexin II (lipocortin II) (ANX2) mRNA | 60 | 24640 | OS1D |
| *Homo sapiens* tubulin, alpha, ubiquitous (K-ALPHA-1) | 61 | 24642 | OS1D |
| Human non-histone chromosomal protein HMG-14 mRNA | 62 | 24645 | OS1D |
| *Homo sapiens* ferritin, heavy polypeptide 1 (FTH1) | 64 | 24648 | OS1D |
| *Homo sapiens* 12p13.3 PAC RPCI1-96H9 (Roswell Park Cancer Institute Human PACLibrary) | 66 | 24653 | OS1D |
| *Homo sapiens* T cell-specific tyrosine kinase mRNA | 67 | 24655 | OS1D |
| *Homo sapiens* keratin 18 (KRT18) mRNA | 68 | 24657 | OS1D |
| *Homo sapiens* growth arrest specific transcript 5 gene | 73 | 24671 | OS1D |
| *Homo sapiens* ribosomal protein S7 (RPS7) | 74 | 24673 | OS1D |
| *Homo sapiens* mRNA; cDNA DKFZp564H182 | 76 | 24677 | OS1D |
| Human TSC-22 protein mRNA | 77 | 24679 | OS1D |
| Human mRNA for ribosomal protein | 79 | 24687 | OS1D |
| Genomic sequence from Human 13 | 80 | 24689 | OS1F |
| *Homo sapiens* clone IMAGE 286356 | 83 | 24693 | OS1F |
| *Homo sapiens* v-fos FBJ murine osteosarcoma viral oncogene homolog(FOS) mRNA | 85 | 24695 | OS1F |
| *Homo sapiens* hypothetical 43.2 Kd protein mRNA | 87 | 24697 | OS1F |
| Human heat shock protein 27 (HSPB1) gene exons 1-3 | 88 | 24698 | OS1F |
| *Homo sapiens* senescence-associated epithelial membrane protein (SEMP1) | 94 | 24706 | OS1F |
| Human ferritin H chain mRNA | 96 | 24708 | OS1F |
| *Homo sapiens* mRNA for KIAA0287 gene | 101 | 24715 | OS1F |
| *Homo sapiens* CGI-08 protein mRNA | 102 | 24716 | OS1F |

TABLE VII-continued

OVARIAN CARCINOMA SEQUENCES

| Identity | SEQ ID NO | Sequence | Library |
|---|---|---|---|
| *H. sapiens* CpG island DNA genomic Mse1 fragment, clone 84a5 | 104 | 24719 | OS1F |
| Human clone 23722 mRNA | 105 | 24721 | OS1F |
| *Homo sapiens* zinc finger protein slug (SLUG) gene | 106 | 24722 | OS1F |
| *Homo sapiens* (clone L6) E-cadherin (CDH1) gene | 108 | 24728 | OS1F |
| *Homo sapiens* ribosomal protein L13 (RPL13) | 109 | 24729 | OS1F |
| *H. sapiens* RNA for snRNP protein B | 110 | 24730 | OS1F |
| *Homo sapiens* mRNA; cDNA DKFZp434K114 | 112 | 24734 | OS1F |
| *Homo sapiens* cornichon protein mRNA | 113 | 24735 | OS1F |
| *Homo sapiens* keratin 8 (KRT8) mRNA | 115 | 24739 | OS1F |
| Human DNA sequence from PAC 29K1 on chromosome 6p21.3-22.2. | 116 | 24740 | OS1F |
| *Homo sapiens* mRNA for KIAA0762 protein | 118 | 24742 | OS1F |
| Human clones 23667 and 23775 zinc finger protein mRNA | 119 | 24744 | OS1F |
| Human H19 RNA gene, complete cds. | 122 | 24933 | POTS7 |
| Human triosephosphate isomerase mRNA, complete cds. | 123 | 24934 | POTS7 |
| Human cyclooxygenase-1 (PTSG1) mRNA, partial cds | 124 | 24935 | POTS7 |
| *Homo sapiens* megakaryocyte potentiating factor (MPF) mRNA. | 126 | 24938 | POTS7 |
| Human mRNA for Apo1__Human (MER5(Aop1-Mouse)-like protein), complete cds | 127 | 24939 | POTS7 |
| *Homo sapiens* arylacetamide deacetylase (esterase) (AADAC) mRNA | 129 | 24942 | POTS7 |
| *Homo sapiens* echinoderm microtubule-associated protein-like EMAP2 mRNA, complete cds | 130 | 24943 | POTS7 |
| *Homo sapiens* podocalyxin-like (PODXL) mRNA. | 131 | 24944 | POTS7 |
| *Homo sapiens* synaptogyrin 2 (SYNGR2) mRNA. | 135 | 24952 | POTS7 |
| *Homo sapiens* amyloid beta precursor protein-binding protein 1, 59 kD (APPBP1) mRNA. | 138 | 24959 | POTS7 |
| Human aldose reductase mRNA, complete cds. | 139 | 24969 | POTS7 |
| Genomic sequence from Human 9q34, complete sequence [*Homo sapiens*] | 140 | 25092 | POTS2 |
| Human glyceraldehyde-3-phosphate dehydrogenase (GAPDH) mRNA, complete cds. | 141 | 25093 | POTS2 |
| *Homo sapiens* breast cancer suppressor candidate 1 (bcsc-1) mRNA, complete cds | 142 | 25098 | POTS2 |
| *Homo sapiens* SKB1 (*S. cerevisiae*) homolog (SKB1) mRNA. | 147 | 25110 | POTS2 |
| *Homo sapiens* prepro dipeptidyl peptidase I (DPP-I) gene, complete cds | 152 | 25117 | POTS2 |
| *Homo sapiens* preferentially expressed antigen of melanoma (PRAME) mRNA | 153 | 25745 | POTS2 |
| Human translocated t(8; 14) c-myc (MYC) oncogene, exon 3 and complete cds | 154 | 25746 | POTS2 |
| Human 12S RNA induced by poly(rI), poly(rC) and Newcastle disease virus | 155 | 25749 | POTS2 |
| Human mRNA for fibronectin (FN precursor) | 157 | 25755 | POTS2 |
| *Homo sapiens* mRNA for hepatocyte growth factor activator inhibitor type 2, complete cds | 159 | 25758 | POTS2 |
| *Homo sapiens* mRNA for KIAA0552 protein, complete cds | 163 | 25771 | POTS7 |
| *Homo sapiens* IMP (inosine monophosphate) dehydrogenase 2 (IMPDH2) mRNA | 164 | 25775 | POTS7 |
| *Homo sapiens* clone 23942 alpha enolase mRNA, partial cds | 165 | 25787 | POTS7 |
| *H. sapiens* vegf gene, 3'UTR | 169 | 25799 | POTS7 |
| *Homo sapiens* 30S ribosomal protein S7 homolog mRNA, complete cds | 170 | 25802 | POTS7 |
| *Homo sapiens* acetyl-Coenzyme A acetyltransferase 2 (acetoacetyl Coenzyme A thiolase) (ACAT2) mRNA | 172 | 25808 | POTS7 |
| *Homo sapiens* Norrie disease protein (NDP) mRNA | 173 | 25809 | POTS7 |

Still further ovarian carcinoma polynucleotide and/or polypeptide sequences identified from the above libraries are provided below in Table VIII. Sequences O574S (SEQ ID NO:183 & 185), O584S (SEQ ID NO:193) and O585S (SEQ ID NO:194) represent novel sequences. The remaining sequences exhibited at least some homology with known genomic and/or EST sequences.

TABLE VIII

| SEQ ID: | Sequence | Library |
|---|---|---|
| 174: | O565S_CRABP | OS1D |
| 175: | O566S_Ceruloplasmin | POTS2 |
| 176: | O567S_41191.SEQ(1 > 487) | POTS2 |
| 177: | O568S_KIAA0762.seq(1 > 3999) | POTS7 |
| 178: | O569S_41220.seq(1 > 1069) | POTS7 |
| 179: | O570S_41215.seq(1 > 1817) | POTS2 |
| 180: | O571S_41213.seq(1 > 2382) | POTS2 |
| 181: | O572S_41208.seq(1 > 2377) | POTS2 |
| 182: | O573S_41177.seq(1 > 1370) | OS1F |
| 183: | O574S_47807.seq(1 > 2060) | n/a |
| 184: | O568S/VSGF DNA seq | n/a |
| 185: | O574S_47807.seq(1 > 3000) | n/a |
| 186: | O568S/VSGF protein seq | n/a |
| 187: | 449H1(57581) | OS1D |
| 188: | 451E12(57582) | OS1D |
| 189: | 453C7_3'(57583.1)Osteonectin | OS1D |
| 190: | 453C7_5'(57583.2) | OS1D |
| 191: | 456G1_3'(57584.1)Neurotensin | OS1F |
| 192: | 456G1_5'(57584.2) | OS1F |
| 193: | O584S_465G5(57585) | OS1F |
| 194: | O585S_469B12(57586) | POTS2 |
| 195: | O569S_474C3(57587) | POTS7 |
| 196: | 483B1_3'(24934.1)Triosephosphate | POTS7 |
| 197: | 57885 Human preferentially expressed antigen of melanoma | POTS2 |
| 198: | 57886 Chromosome 22q12.1 clone CTA-723E4 | POTS2 |
| 199: | 57887 Homologous to mouse brain cDNA clone MNCb-0671 | POTS2 |

Further studies on the clone of SEQ ID NO:182 (also referred to as O573S) led to the identification of multiple open reading frames that encode the amino acid sequences of SEQ ID NO:200-202.

Example 2

Analysis of cDNA Expression Using Microarray Technology

In additional studies, sequences disclosed herein were found to be overexpressed in specific tumor tissues as determined by microarray analysis. Using this approach, cDNA sequences are PCR amplified and their mRNA expression profiles in tumor and normal tissues are examined using cDNA microarray technology essentially as described (Shena et al., 1995). In brief, the clones are arrayed onto glass slides as multiple replicas, with each location corresponding to a unique cDNA clone (as many as 5500 clones can be arrayed on a single slide or chip). Each chip is hybridized with a pair of cDNA probes that are fluorescence-labeled with Cy3 and Cy5 respectively. Typically, 1 µg of polyA$^+$ RNA is used to generate each cDNA probe. After hybridization, the chips are scanned and the fluorescence intensity recorded for both Cy3 and Cy5 channels. There are multiple built-in quality control steps. First, the probe quality is monitored using a panel of ubiquitously expressed genes. Secondly, the control plate also can include yeast DNA fragments of which complementary RNA may be spiked into the probe synthesis for measuring the quality of the probe and the sensitivity of the analysis. Currently, the technology offers a sensitivity of 1 in 100,000 copies of mRNA. Finally, the reproducitility of this technology can be ensured by including duplicated control cDNA elements at different locations.

The microarray results for clones 57885 (SEQ ID NO:197), 57886 (SEQ ID NO:198) and 57887 (SEQ ID NO:199) are as follows.

Clone 57885: 16/38 (42%) of ovarian tumors showed an expression signal value of >0.4. The mean value for all ovary tumors was 0.662 with a mean value of 0.187 for all normal tissues, which yields a 3.64 fold overexpression level in ovary tumor relative to essential normal tissues. Normal tissue expression was elevated (>0.4) in peritoneum, skin and thymus.

Clone 57886: 16/38 (42%) of ovarian tumors showed an expression signal value of >0.4. The mean value for all ovary tumors was 0.574 with a mean value of 0.166 for all normal tissues which yields a 3.46 fold overexpression level in ovary tumor relative to essential normal tissues. Normal tissue expression was elevated (>0.4) in heart, pancreas and small intestive.

Clone 57887: 17/38 (44%) of ovarian tumors showed an expression signal value of >0.4. The mean value for all ovary tumors is 0.744 with a mean value of 0.184 for all normal tissues which yields a 4.04 fold overexpression level in ovary tumor relative to essential normal tissues. Normal tissue expression was elevated (>0.4) in esophagus.

Example 3

Expression of Recombinant Antigen O568S in *E. Coli*

This example describes the expression of recombinant antigen O568S (SEQ ID NO:177) in *E. coli*. This sequence was identified in Example 1 from the POTS 7 subtraction library using primary ovarian tumor cDNA as the tracer. PCR primers specific for the open reading frame of O568S were designed and used in the specific amplification of O568S. The PCR product was enzymatically digested with EcoRI and ligated into pPDM, a modified pET28 vector which had been cut with the restriction enzymes EcoRI and Eco72I. The construct sequence and orientation was confirmed through sequence analysis, the sequence of which is shown in SEQ ID NO:206. The vector was then transformed into the expression hosts, BLR (DE3) and HMS 174 (DE3) pLys S. Protein expression was confirmed, the sequence of which is provided in SEQ ID NO:207.

Example 4

Additional Sequence Obtained for Clone O591S

The sequence of O591S (clone identifier 57887) was used to search public sequence databases. It was found that the reverse strand showed some degree of identity to the C-terminal end of GPR39. The cDNA for the coding region of GPR39 is disclosed in SEQ ID NO:208 and the corresponding amino acid sequence in SEQ ID NO:209. The GPR39 coding region contains two exons. Both O591S and GPR39, encoded by the complementary strand of O591S, are located on chromosome 2.

Example 5

Further Characterization of O591S and Identification of Extended Sequence

O1034C is an ovary specific gene identified by electronic subtraction. Briefly, electronic subtraction involves an analysis of EST database sequences to identify ovarian-specific genes. In the electronic subtraction method used to identify O1034C, sequences of EST clones derived from ovary libraries (normal and tumor) were obtained from the GenBank public human EST database. Each ovary sequence was used as a "seed" query in a BLASTN search of the total human EST database to identify other EST clones that share sequence with the seed sequence (clones that potentially originated from the same mRNA). EST clones with shared sequence were grouped into clusters, and clusters that shared sequence with other clusters were grouped into superclusters. The tissue source of each EST within each supercluster was noted, and superclusters were ranked based on the distribution of the tissues from which the ESTs originated. Superclusters that comprise primarily, or solely, EST clones from ovary libraries were considered to represent genes that were differentially expressed in ovary tissue, relative to all other normal adult tissue.

This clone was identified from the public EST databases as Integrated Molecular Analysis of Genomics and their Expression (IMAGE) clone number 595449 (the IMAGE consortium is a repository of EST clones and cDNA clones) and is disclosed as SEQ ID NO:210. Accession numbers AA173739 and AA173383 represents the sequence of the identified EST in Genebank. This clone is part of Unigene cluster HS.85339 (Unigene is an experimental system for automatically partitioning Genbank sequences into a non-redundant set of gene-orientated clusters) and was annotated as encoding a neurotensin-like G protein coupled receptor (GRP39). However, the inventors have discovered that IMAGE#595449 encodes a novel protein derived from the complementary strand to that which encodes the potential GPR39.

Microarray analysis of the clone using a series of ovary tumor specific probes indicated that this clone was over expressed 4.95-fold in a group of ovary tumor and normal ovary samples as compared to a group of essential normal tissue samples.

IMAGE#59449 was subjected to a Blast A search of the EST database and Genbank and an electronic full length clone contig (O1034C) was generated by extending IMAGE#595449 and its resulting contigs to completion. This process was repeated to completion when no further EST sequences were identified to extend the consensus sequence. This electronically derived clone was identified as coding a previously described clone, O591S, the sequence of which is disclosed in SEQ ID NO:211. The discovery of this ovary specific candidate is described in more detail in Example 4.

The consensus sequence for O1034C extended further 5' than O591S due to the additional sequences derived from two EST clones, accession numbers BF345141 and BE336607, the sequences for which are disclosed in SEQ ID NO:212 and 213 respectively. Although BF345141 diverges from the O1034C/O591S consensus at its 3'-end (possibly representing a different splice form), and from BE336607 at several bases at its 5'-end, the two ESTs were compared to the available matching chromosome sequence. They were found on human chromosome 2, clone RP11-159N20:htgs database accession number AC010974. These sequences were used to extend O1034C/O591S to form a final consensus sequence for O1034C/O591S of 1897 base pairs, disclosed in SEQ ID NO:214.

An open reading frame (ORF) was identified within the O1034C/O591S consensus sequence (nucleotides 260-682), the predicted translation of which is disclosed in SEQ ID NO:215. A BLASTx database search against the Genbank database indicated that this ORF had no identity (E value <1e-25) with any known human protein. The only match was with the G protein-coupled receptors, including GPR39, which the inventors have shown to be encoded at the 3'-end of O1034C/O591S on the complementary strand. However, the ORF did encode a protein that had 93% similarity (131/141 amino acids) and 91% identity (129/141 amino acids) with an un-named murine product (Accession #BAA95101), suggesting that this is a real translation product that represents a novel human ovary-specific antigen.

The novelty of O1034C/O591S was confirmed by Northern Blot analysis using single stranded probes that complement either GRP39 or O1034C/O591S. The strand-specific O1034C/O591S probe specifically hybridized to the ovary tumor samples probed on the Northern blot, whilst all samples were negative when probed with GPR39. In addition real-time PCR was performed using primers specific for either GPR39 or O1034C/O591S. These results further demonstrated the differential expression profiles of the two sequences. This protein is a putative membrane protein as determined from Corixa's Tmpred protein prediction algorithm.

Example 6

Expression Analysis and Further Characterization of Ovarian Sequence O568S

The ovarian sequence O568S was originally identified as cDNA clone 24742 (SEQ ID NO:118). Using clone 24742 as a query sequence to search public sequence databases, the sequence was found to have a high degree of homology with KIAA0762 (SEQ ID NO:177) and with VSGF. The DNA sequence for VSGF is provided in SEQ ID 184 and the VSGF protein sequence is provided in SEQ ID NO:186.

Real-time PCR (see Gibson et al., *Genome Research* 6:995-1001, 1996; Heid et al., *Genome Research* 6:986-994, 1996) is a technique that evaluates the level of PCR product accumulation during amplification. This technique permits quantitative evaluation of mRNA levels in multiple samples. Briefly, mRNA is extracted from tumor and normal tissue and cDNA is prepared using standard techniques. Real-time PCR is performed, for example, using a Perkin Elmer/Applied Biosystems (Foster City, Calif.) 7700 Prism instrument. Matching primers and fluorescent probes are designed for genes of interest using, for example, the primer express program provided by Perkin Elmer/Applied Biosystems (Foster City, Calif.). Optimal concentrations of primers and probes are initially determined by those of ordinary skill in the art, and control (e.g., β-actin) primers and probes are obtained commercially from, for example, Perkin Elmer/Applied Biosystems (Foster City, Calif.). To quantitate the amount of specific RNA in a sample, a standard curve is generated using a plasmid containing the gene of interest. Standard curves are generated using the Ct values determined in the real-time PCR, which are related to the initial cDNA concentration used in the assay. Standard dilutions ranging from $10-10^6$ copies of the gene of interest are generally sufficient. In addition, a standard curve is generated for the control sequence. This permits standardization of initial RNA content of a tissue sample to the amount of control for comparison purposes.

By RealTime PCR analysis, O568 was highly overexpressed in the majority of ovary tumors and ovary tumor metastases tested relative to normal ovary tissue and relative to an extensive normal tissue panel. Little or no expression was observed in normal esophagus, spinal cord, bladder, colon, liver, PBMC (activated or resting), lung, skin, small intestine, stomach, skeletal muscle, pancreas, dendritic cells, heart, spleen bone marrow, thyroid, trachea, thymus, bronchia, cerebellum, ureter, uterus and peritoneum epithelium. Some low level expression was observed in normal breast, brain, bone, kidney, adrenal gland and salivary gland, but the expression levels in these normal tissues were generally at least several fold less than the levels observed in ovary tumors overexpressing O568S.

Moreover, a series of Northern blots was performed which also demonstrated that the ORF region of O568S is specifically overexpressed in ovary tumors. The initial blot contained RNA from a series of normal tissues as well as from ovary tumors. This blot was probed using, as a labeled probe, DNA from O568S that corresponded to the 3'UTR of the VSGF sequence disclosed in SEQ ID NO:184. This blot revealed an ovary tumor-specific 5.0 Kb message as well as a potential 3.5 Kb brain specific message and a ubiquitously expressed 1.35 Kb message.

Another Northern blot was performed with RNAs from a number of different brain tissues and probed with the 3'UTR region as above. Five of eleven brain samples showed overexpression of the 3.5 Kb message. In order to determine whether the ORF region of O568S was specifically overexpressed in ovary tumors, a series of three blots was carried out using three separate probes designed from within the VSGF ORF of O568S. Results from these experiments clearly indicated that only the 5.0 Kb message is expressed in ovary tumor.

Example 7

Synthesis of Polypeptides

Polypeptides are synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence is attached to the amino terminus of the peptide to provide a method of conjugation, binding to an immobilized surface, or labeling of the peptide. Cleavage of the peptides from the solid support is carried out using the following cleavage mixture: trifluoroacetic acid:ethanedithiol:thioanisole:water:phenol (40:1:2:2:3). After cleaving for 2 hours, the peptides are precipitated in cold methyl-t-butyl-ether. The peptide pellets are then dissolved in water containing 0.1% trifluoroacetic acid (TFA) and lyophilized prior to purification by C18 reverse phase HPLC. A gradient of 0%-60% acetonitrile (containing 0.1% TFA) in water (containing 0.1% TFA) is used to elute the peptides. Following lyophilization of the pure fractions, the peptides are characterized using electrospray or other types of mass spectrometry and by amino acid analysis.

Example 8

O568S Northern Blot Analysis

As described in Example 6, Northern blot analysis demonstrated that the ORF region of O568S was specifically over expressed in ovarian tumors. The original probe used corresponded to the 3'UTR of the VSGF sequence disclosed in SEQ ID NO:184. The results from these Northern blots revealed an ovarian tumor-specific 5.0 Kb message as well as a potential 3.5 Kb brain specific message. To confirm that the entire region covered by the ORF yields a single 5.0 Kb ovarian tumor-specific message, two additional probes were designed. The probes were located at the 5' and 3' regions of the ORF. Northern blot analysis using these two probes demonstrated that both probes hybridized to a 5.0 Kb product present only in ovarian tumor samples. Both probes failed to hybridize with RNA derived from multiple brain samples.

Example 9

Real Time PCR and Northern Blot Analysis of O590S

Real time PCR analysis of ovarian tumor antigen O590S was performed essentially as described in Example 6. O590S specific primers and probe were designed and quantitative Real Time PCR was performed on a panel of cDNAs prepared from a variety of tissues including ovarian tumor samples and a panel of normal tissues. This analysis revealed that O590S-specific mRNA was over expressed in approximately 65% of ovarian tumor samples tested, 100% tumor samples derived from SCID mice, and 100% ovarian tumor cell lines tested, when compared to normal ovarian tissue. No detectable expression was observed in normal tissues.

In addition to Real Time PCR, Northern blot analysis was performed to determine to transcript size of O590S. The Northern blot was probed with a 537 bp PCR product specific for O590S, which was designed to avoid regions of repeat sequences. This probe revealed a smeared band that was approximately 9.0 Kb in size, which was present in the majority of ovarian tumor samples tested.

Example 10

Analysis of cDNA Expression Using Microarray Technology

This example describes microarray expression analysis of ovary tumor-and tissue-specific cDNAs identified from OTCLS4, POTS2 and POTS7 (Subtraction libraries described in Example 1). Microarray analysis was performed essentially as described in Example 2. Sequence expression was determined by probing with a number of ovarian tumor samples, including papillary serous cystic carcinoma, papillary serous adenocarcinoma, papillary serous neoplasm, papillary serous carcinoma, papillary serous cytstadenocarcinoma, and a panel of normal tissues including adrenal gland, pituitary gland, thymus, bronchus, stomach, pancreas, skin, spinal cord, kidney, spleen, brain, breast, small intestine, thyroid, trachea, colon, PBMC resting, PBMC activated, lung, aorta, bone marrow, mammary epithelial tissue, esophagus, heart, and liver.

Clones showing an ovarian tumor mean or median value that was at least two fold greater than the normal tissue value were selected for further analysis. Further selection criteria was imposed on mean and median values as follows:

Mean tumor value ≧0.2 and mean normal value of <0.4

Median tumor value ≧0.2 and median normal value of <0.3.

Based on the selection criteria above, 26 clones were selected from the OTCLS4, POTS2 and POTS7 for sequencing. These sequences are disclosed herein in SEQ ID NOs: 216-243. See Table IX for details.

TABLE IX

| SEQ ID NO | Clone ID | GenBank ID NO | GenBank Description | Ratio | Ratio 1/2 | Group 1 | Group 2 |
|---|---|---|---|---|---|---|---|
| 216 | 91226.5 | 15779016 | Homo sapiens, clone IMAGE: 4047062, mRNA | Mean | 2.09 | 0.722 | 0.346 |
| 217 | 91227.2 | 14760620 | Homo sapiens bHLH protein DEC2 (DEC2), mRNA | Mean | 2.45 | 0.62 | 0.153 |
| 218 | 91230.2 | 13543043 | Homo sapiens, hypothetical protein dJ473B4, clone MGC: 4987 IMAGE: 3450155, mRNA, complete cds | Mean | 2.17 | 0.434 | 0.2 |
| 219 | 91231 | 13277551 | Homo sapiens, coxsackie virus and adenovirus receptor, clone MGC: 5086 IMAGE: 3463613, mRNA, complete cds | Mean | 2.16 | 0.545 | 0.253 |
| 220 | 91238.3 | 12804424 | Homo sapiens, similar to phosphoserine aminotransferase, clone MGC: 1460 IMAGE: 3544564, mRNA, complete cds | Mean | 2.18 | 0.229 | 0.105 |
| 221 | 91239.6 | 14589888 | Homo sapiens cadherin 2, type 1, N-cadherin (neuronal) (CDH2), mRNA | Median | 2.22 | 0.581 | 0.262 |
| 222 | 91240.2 | 5729900 | Homo sapiens IGF-II mRNA-binding protein 3 (KOC1), mRNA | Mean | 2.08 | 0.236 | 0.114 |
| 223 | 91241.2 | 12653176 | Homo sapiens, MAD2 (mitotic arrest deficient, yeast, homolog)-like 1, clone MGC: 8662 IMAGE: 2964388, mRNA, complete cds | Median | 2.13 | 0.316 | 0.148 |
| 224 | 91242.5 | 12653176 | Homo sapiens, MAD2 (mitotic arrest deficient, yeast, homolog)-like 1, clone MGC: 8662 IMAGE: 2964388, mRNA, complete cds | Mean | 2.36 | 0.458 | 0.194 |
| 225 | 91243.6 | 15297244 | Homo sapiens laminin, gamma 2 (nicein (100 kD), kalinin (105 kD), BM600 (100 kD), Herlitz junctional epidermolysis bullosa)) (LAMC2), mRNA | Mean | 2.91 | 0.755 | 0.26 |
| 226 | 91245.2 | 7022574 | Homo sapiens cDNA FLJ10500 fis, clone NT2RP2000369 | Mean | 2.1 | 0.571 | 0.272 |
| 227 | 91246.4 | 1575533 | Human MAD2 (hsMAD2) mRNA, complete cds | Median | 2.51 | 0.292 | 0.116 |
| 228 | 91247.3 | 5912166 | Homo sapiens mRNA; cDNA DKFZp564H1663 (from clone DKFZp564H1663) | Mean | 2.03 | 0.369 | 0.182 |
| 229 | 91247.4 | 5912166 | Homo sapiens mRNA; cDNA DKFZp564H1663 (from clone DKFZp564H1663) | Mean | 2.03 | 0.369 | 0.182 |
| 230 | 91249.2 | 14711935 | Homo sapiens, hypothetical protein FLJ10461, clone IMAGE: 4102110, mRNA | Mean | 2.26 | 0.271 | 0.12 |
| 231 | 91253.2 | 14756011 | Homo sapiens similar to coxsackie virus and adenovirus receptor; 46 kD coxsackie and adenovirus receptor (CAR) protein (H. sapiens) (LOC93529), mRNA | Mean | 2.4 | 0.411 | 0.172 |
| 232 | 91254.2 | 11493240 | Human DNA sequence from clone RP11-124N19 on chromosome 13, complete sequence [Homo sapiens] | Mean | 5.15 | 1.396 | 0.271 |
| 233 | 91259.2 | 14771329 | Homo sapiens Wilms tumor (WT1), mRNA | Mean | 3.87 | 0.406 | 0.105 |
| 234 | 91261.3 | 11465000 | Homo sapiens 12 BAC RP11-283G6 (Roswell Park Cancer Institute Human BAC library) complete sequence | Mean | 2.57 | 0.34 | 0.132 |
| 235 | 91261.4 | 11465000 | Homo sapiens 12 BAC RP11-283G6 (Roswell Park Cancer Institute Human BAC library) complete sequence | Mean | 2.57 | 0.34 | 0.132 |
| 236 | 91262.2 | 4506070 | Homo sapiens protein kinase C, iota (PRKC1), mRNA | Mean | 2.46 | 0.695 | 0.282 |
| 237 | 91263.2 | 13647850 | Homo sapiens matrix metalloproteinase 11 (stromolysin 3) (MMP11), mRNA | Mean | 2.63 | 0.254 | 0.097 |
| 238 | 91264.2 | NA | NOVEL (no GENSEQ) | Mean | 15.6 | 2.058 | 0.132 |
| 239 | 91268.2 | 3980529 | Homo sapiens PAC clone RP4-797C5 from 7q31, complete sequence | Mean | 2.41 | 0.232 | 0.096 |
| 240 | 91269.5 | NA | NOVEL (no GENSEQ) | Mean | 3.04 | 0.226 | 0.074 |
| 241 | 91271.5 | 339440 | Homo sapiens transcriptional enhancer factor (TEF1) DNA, complete cds | Mean | 2.1 | 0.407 | 0.194 |
| 242 | 91273.3 | 15297244 | Homo sapiens laminin, gamma 2 (nicein (100 kD), kalinin (105 kD), BM600 (100 kD), Herlitz junctional epidermolysis bullosa)) (LAMC2), mRNA | Mean | 2.5 | 0.625 | 0.25 |
| 243 | 91274.6 | NA | NOVEL (GENSEQ"AAQ60336) | Mean | 2.58 | 0.204 | 0.079 |

Example 11

Expression Analysis and Further Characterization of Ovarian Sequence O646S

Ovarian tumor antigen O646S was originally described in Example 10 as clone 91274.6 (SEQ ID NO:243). Using SEQ ID NO:243 to search publicly available databases, a contig was generated, the DNA sequence of which is disclosed in SEQ ID NO:246, with a corresponding protein sequence disclosed in SEQ ID NO:249. This sequence was shown to share homology with Genbank Accession Number 18549403, the DNA and protein sequences of which are disclosed in SEQ ID NOs:244 and 247, respectively, and Genbank Accession Number FLJ14035, the DNA and protein sequences for which are disclosed in SEQ ID NOs:245 and 248, respectively.

Example 12

Further Characterization of Ovarian Sequence O648S

Ovarian tumor antigen O648S was originally described in Example 10 as clone 91268.2 (SEQ ID NO:239). Using SEQ ID NO:239 to search publicly available databases, a contig was generated, the DNA sequence of which is disclosed in SEQ ID NO:256, with a corresponding protein sequence disclosed in SEQ ID NO:261. This sequence was shown to share homology with several sequences including, Genbank Accession Number 3980529, the DNA sequence of which is disclosed in SEQ ID NOs:250, Genbank Accession Number 13629915, the DNA and protein sequences for which are disclosed in SEQ ID NOs:251 and 257, Genbank Accession Number 9789986, the DNA and protein sequences of which are disclosed in SEQ ID NOs:252 and 258, respectively, Genbank Accession Number 6006516, the DNA and protein sequences of which are disclosed in SEQ ID NOs:253 and 259, Genbank Accession Number 5689424, the DNA and protein sequences of which are disclosed in SEQ ID NOs:254 and 260, and Genbank Accession Number 15638833, the DNA sequence of which is disclosed in SEQ ID NO:255.

Example 13

Further Characterization of Ovarian Sequence O647S

Ovarian tumor antigen O647S was originally described in Example 10 as clone 91261.3 (SEQ ID NO:234). Using SEQ ID NO:234 to search publicly available databases, a contig was generated, the DNA sequence of which is disclosed in SEQ ID NO:268. This sequence was shown to share homology with several sequences, including Genbank Accession Number 16933560, the DNA and protein sequences of which are disclosed in SEQ ID NOs:262 and 269, Genbank Accession Number 12053028, the DNA and protein sequences for which are disclosed in SEQ ID NOs:263 and 270, Genbank Accession Number 7638812, the DNA and protein sequences of which are disclosed in SEQ ID NOs:264 and 271, Genbank Accession Number 939922, the DNA and protein sequences of which are disclosed in SEQ ID NOs:265 and 272, Genbank Accession Number 6093230, the DNA sequence of which are disclosed in SEQ ID NO:266 and Genbank Accession Number 11465000, the DNA sequence of which is disclosed in SEQ ID NO:267.

Example 14

Further Characterization of Ovarian Sequence O648S

Ovarian tumor antigen O645S was originally described in Example 10 as clone 91264.2 (SEQ ID NO:238). Using SEQ ID NO:238 to search publicly available databases, a contig was generated, the DNA sequence of which is disclosed in SEQ ID NO:273.

Example 15

Further Characterization of Ovarian Sequence O644S

Ovarian tumor antigen O644S was originally described in Example 10 as clone 91269.5 (SEQ ID NO:240). Using SEQ ID NO:240 to search publicly available databases, a contig was generated, the DNA sequence of which is disclosed in SEQ ID NO:277. This sequence was found to contain three open reading frames, the sequences of which are disclosed in SEQ ID NOs:280-282. These sequences were shown to share homology with Genbank Accession Number NM006580, the DNA and protein sequences of which are disclosed in SEQ ID NOs:274 and 278, Genbank Accession Number AF152101.1, the DNA and protein sequences for which are disclosed in SEQ ID NOs:275 and 279, and Genbank Accession Number 18425237, the DNA sequence of which is disclosed in SEQ ID NOs:276.

Example 16

O591S Expression in *E. Coli*

The identification and characterization of O591S (SEQ ID NO: 214, encoding the protein of SEQ ID NO: 215) was described above (Example 1 and 4). For production and purification of O591S protein used for antibody generation, a truncated form of O591S, lacking the signal peptide sequence, was expressed in *E. coli* using a modified pET 28 vector with an N-terminal histidine tag.

The truncated coding region of O591S-A was PCR amplified minus the signal sequence (amino acids 24-141) with the following primer pairs:

```
CBH-005
5'                                              (SEQ ID NO: 287)
cacttcttgcttccaggctttgcgctgcaaat
3'

CBH-003
5'actagctcgagtcagcagtgtgccgagaa 3' (SEQ ID NO: 288)
```

PCR amplification was performed under the following reaction conditions:
 10 µl 10× Pfu buffer
 1 µl 10 mM dNTPs
 2 µl 10 µM of each primer
 83 µl of sterile water
 1.5 µl Pfu DNA polymerase (Stratagene, La Jolla, Calif.)
 50 ηg DNA The reaction was amplified under the following conditions: 96° C. 2 minutes, followed by 40 cycles of 96° C. 20 seconds, 64° C. 15 seconds, and 72° C. 1 minute, With a final extension step of 72° C. for 4 minutes.

The PCR product was digested with Xho I and cloned into pPDM His (a modified pET28 vector with a histidine tag in frame on the 5' end) that has been digested with Eco72I and XhoI. Constructs were confirmed through nucleic acid sequence analysis, the corresponding DNA and protein sequence for which are disclosed in SEQ ID NOs:283 and 284, respectively. Following sequence analysis, the construct was then transformed into BLR(DE3) pLys S and HMS 174 (DE3) pLys S cells.

Example 17

The Generation of Rabbit Anti-O568S Polyclonal Antibodies and Expression Determination in Ovarian Tumors The over-expression of O568S in ovarian tumor samples and normal ovary was verified using affinity purified rabbit polyclonal antibodies to O568S in the immunohistorchemical (IHC) analysis of ovarian tumors and normal tissues.

Rabbits were immunized with purified recombinant O568S protein and polyclonal antibodies prepared. Briefly, production and purification of the O568S antigen used for antibody generation was as follows:

The ovarian tumor protein antigen O568S (amino acids 29-808) was expressed in an *E. coli* recombinant expression system and grown overnight at 37° C. in LB Broth with the appropriate antibiotics in a shaking incubator. The next morning, 10 ml of the overnight culture was added to 500 ml of 2×YT plus the appropriate antibiotics in a 2L-baffled Erlenmeyer flask. When the Optical Density (at 560 nanometers) of the culture reached 0.4-0.6 the cells were induced with IPTG (1 mM) for 4 hours, and then harvested by centrifugation, washed with phosphate buffered saline and centrifuged again. The supernatant was discarded and the cells were either processed immediately or frozen for future use. When processed immediately, in order to break open the *E. coli* cells, twenty milliliters of lysis buffer was added to the cell pellets, followed by vortex mixing and French Press disruption at a pressure of 16,000 psi. This lysed cell suspension was then centrifuged, the resulting supernatant and pellet fractions of which were examined by SDS-PAGE for the presence of recombinant protein.

The pellet prepared as described above was resuspended in 10 mM Tris pH 8.0, 1% CHAPS, washed and centrifuged again. This step was repeated an additional two times. The washed pellet containing inclusion bodies was then solubilized with either 8 M urea or 6 M guanidine HCl containing 10 mM Tris pH 8.0 plus 10 mM imidazole (solubilization buffer). The solubilized protein was added to 5 ml of nickel-chelate resin (Qiagen Inc.) and incubated for 45 min to 1 hour at room temperature with continuous agitation. After incubation, the resin and protein mixture was added to a disposable column and the flow through containing unbound proteins was collected. The column containing resin with bound protein was then washed with 10-20 column volumes of solubilization buffer, and eluted using an elution buffer solution containing 8M urea, 10 mM tris pH 8.0 and 300 mM imidazole. Column fractions (amounting to 3 ml of elution buffer each) were collected and examined by SDS-PAGE for the presence of O568S protein. Fractions containing the desired protein were pooled for further characterization. As an additional purification step, a strong anion exchange resin such as Hi-Prep Q (Biorad) was equilibrated with the appropriate buffer and the pooled fractions containing O568S protein were loaded onto this column and eluted using an increasing salt gradient. Fractions were collected and again evaluated by SDS-PAGE for the presence of O568S protein. The appropriate fractions were identified, combined and dialyzed against 10 mM Tris pH 8.0. Purity was determined by SDS-PAGE or HPLC, the concentration of purified protein was determined by Lowry assay or Amino Acid Analysis, the amino terminal protein sequence was determined to confirm authenticity, and the level of endotoxin was determined using a standard Limulus (LAL) assay. Fractions containing purified O568S were pooled, sterilized by filtration using a 0.22 micron filter, aliquoted and frozen until needed.

For the generation of polyclonal antiserum, rabbits were immunized with 400 micrograms of purified O568S protein combined with 100 micrograms of muramyldipeptide (MDP) and an equal volume of Incomplete Freund's Adjuvant (IFA). Every four weeks thereafter, animals were boosted with 100 micrograms of O568S antigen mixed with an equal volume of IFA. Seven days following each boost a blood sample from each immunized animal was taken and a serum fraction therefrom prepared by incubating the blood sample at 4° C. for 12-24 hours, clarified by centrifugation.

In order to characterize the above-mentioned rabbit polyclonal anti-O568S antiserum, 96 well plates were coated with the appropriate antigen in 50 µl (typically 1 µg of protein), incubated at 4C for 20 hours, after which 250µl of BSA blocking buffer was added followed by an additional 2 hours of incubation at room temperature (RT). Each well was then washed 6 times with PBS/0.01% tween. The rabbit anti-O568S antiserum to be tested was diluted in PBS, 50 µl of which was added to each well and incubated at RT for 30 minutes. Plates were washed as described above and then 50 µl of a 1:10000 dilution of goat anti-rabbit horse radish peroxidase (HRP) conjugated antibody was added and incubated at RT for 30 minutes. Next, plates were washed as described above and 100 µl of TMB containing microwell Peroxidase was added. Substrate was added to each well, incubated for 15 minutes in the dark at RT, the colorimetric reaction stopped with the addition of 100 µl of 1N H2SO4 and signal determined immediately at 450 nm.

For IHC analysis, paraffin embedded formalin-fixed tissue was sliced into 4 micron sections. Steam heat induced epitope retrieval (SHIER) in 0.1 M sodium citrate buffer (pH 6.0) was used for optimal staining conditions. Sections were incubated with 10% serum/PBS for 5 minutes. Primary antibody (0.5 µg/ml rabbit affinity purified anti-O568S polyclonal antibody) was added to each section for 25 minutes at varying concentrations, followed by a 25 minute incubation with an anti-rabbit biotinylated antibody. Rabbit IgG was also tested on all tissues and served as a negative control. Endogenous peroxidase activity was blocked by three 1.5 minute incubations with hydrogen peroxidase. The avidin biotin complex/horse radish peroxidase (ABC/HRP) system was used along with DAB chromogen to visualize antigen expression. Slides were counterstained with hematoxylin.

The tissues tested and their expression profiles are described in detail in Table X. Of the ovarian cancer metastases tested, six were adenocarcinomas, five of which tested positive and one was marginal. The majority of the tumor samples stained positive with a strong membrane localized signal, demonstrating that O568S is expressed on the surface of the tumor cells.

TABLE X

Tissue Expression of O568S

| TISSUE | O568S EXPRESSION |
| --- | --- |
| Ovarian cancer | 3/5 |
| Ovarian cancer metastases | 8/12 |
| Normal ovary | 3/4 |
| Normal lung (alveolar epithelium) | 0/1 |
| Normal lung (bronchiole epithelium) | 0/1 |
| Brain (cortex) | 6/6 (marginal staining of selected neuronal populations) |
| Brain (spinal cord) | 6/6 (marginal staining of purkinje cells) |
| Stomach | 5/5 (marginal staining of selected neuronal populations) |
| Skin | 0/1 |
| Heart | 0/1 |
| Kidney | 0/1 |
| Liver | 0/1 |
| Colon | 0/1 |
| Tonsil | 0/1 |
| Vagina | 1/1 (squamous epithelium) |

Example 18

Real-Time PCR Analysis of Ovarian Tumor Antigens Identified from the OTCLS4, POTS2 and POTS7 Libraries Clones identified as having a good expression profile by microarray analysis (as described in Example 10), were further analyzed by real-time PCR on an extended panel of ovarian tumor and normal tissue samples (including ovary, aorta, adrenal gland, bladder, bone, bronchus, brain, breast, CD34+ cells, dendritic cells, esophagus, heart, kidney, large intestine, liver, lung, lymph nodes, pancreas, peritoneum, bane marrow, skin, small intestine, spinal cord, spleen, stomach, thymus, thyroid, tonsil, trachea, ureter, uterus). Real time PCR was performed as described above in Example 6.

The first-strand cDNA used in the quantitative real-time PCR was synthesized from 20 μg of total RNA that was treated with DNase I (Amplification Grade, Gibco BRL Life Technology, Gaithersburg, Md.), using Superscript Reverse Transcriptase (RT) (Gibco BRL). Real-time PCR was performed with an ABIPRISM 7900 sequence detection system (PE Biosystems, Foster City, Calif.). The 7900 system uses SYBR™ green, a fluorescent dye that only intercalates into double stranded DNA, and a set of gene-specific forward and reverse primers. The increase in fluorescence was monitored during the whole amplification process. The optimal concentration of primers was determined using a checkerboard approach, and a pool of cDNAs from tumors was used in this process. The PCR reaction was performed in 12.5 μl volumes that included 2.5 μl of SYBR green buffer, 2 μl of cDNA template and 2.5 μl each of the forward and reverse primers for the gene of interest. The cDNAs used for RT reactions were diluted 1:10 for each gene of interest and 1:100 for the β-actin control. The expression of the gene of interest in various tissue samples was represented by comparative $C_T$ (threshold cycle) method. $C_T$ indicates the fractional cycle number at which the amount of amplified target reaches a fixed threshold. The $C_T$ value of normal aorta, skin, peritoneum, thyroid gland, dendritic cells, or CD34+ cells was used as a comparative reference in order to evaluate the overexpression levels seen with each of the genes.

The following clones have been evaluated on the extended ovarian real-time panel. In some cases where expression was fairly ubiquitous, mean real-time expression values were determined for ovarian tumor (not including ovarian tumor cell line and SCID samples), normal ovarian, and other normal tissues (not including normal ovary). All clones were found to be over-expressed in ovarian tumor to some degree, demonstrating their use as tumor immunotherapeutics and/or diagnostic targets.

Ovarian tumor antigen O644S (SEQ ID NO:240) was shown to be over-expressed in ovarian tumor tissue samples compared to normal tissues. Expression of O644S was similar in ovarian tumor samples compared to normal ovary. Mean expression ratios for O644S were as follows: ovarian tumor/normal ovary was 0.6 and ovarian tumor/other normal tissues was 5.8. These results indicate that O644S may be used in developing tumor immunotherapeutic and/or diagnostic agents.

Ovarian tumor antigen O645S (SEQ ID NO:238) was found to be over-expressed in over 70% of the ovarian tumors tested, and 100% of ovarian tumor SCID samples. No expression was detected in the normal tissues tested. This finding further supports the use of ovarian tumor antigen O645S in the diagnosis and treatment of ovarian cancer. Based on the excellent expression profile of this ovarian candidate, SEQ ID NO:238 was also run on an the Ovarian Metastatic Extended Panel, which included 14 primary ovarian tumors and 13 metastatic ovarian tumors. O645S was determined to be elevated in 10/14 (71%) of primary tumors and 11/13 (85%) metastatic tumors.

Ovarian tumor antigen O646S (SEQ ID NO:243) was found to be over-expressed in 100% of the ovarian tumors tested, 1/1 ovarian tumor cell lines (SKOV3-HTB77) and 100% of ovarian tumor SCID samples. Low-level expression was observed in 2/2 normal ovary samples tested, but no expression was detected in any other normal tissues tested. This finding further supports the use of ovarian tumor antigen O646S in the diagnosis and treatment of ovarian cancer, especially metastatic ovarian cancer. Based on the excellent expression profile of this ovarian candidate, SEQ ID NO:243 was also run on an the Ovarian Metastatic Extended Panel, which included 14 primary ovarian tumors and 13 metastatic ovarian tumors. O646S was determined to be elevated in 14/14 (100%) of primary tumors and 13/13 (100%) metastatic tumors.

Ovarian tumor antigen O647S (SEQ ID NO:234 and 235) was found to be over-expressed in over 80% of the ovarian tumors tested, and 100% of ovarian tumor SCID samples. O647S was also found to have low level expression in normal ovary, bronchus, brain/cerebellum, and heart. No expression was detected in any other normal tissues tested. This finding further supports the use of ovarian tumor antigen O647S in the diagnosis and treatment of ovarian cancer.

Ovarian tumor antigen O648S (SEQ ID NO:239) was found to be over-expressed in over 50% of the ovarian tumors tested. O648S was not expressed in normal ovary. Very low-level expression was seen in normal liver and pancreas. This finding further supports the use of ovarian tumor antigen O648S in the diagnosis and treatment of ovarian cancer.

Ovarian tumor antigen O651S (SEQ ID NO:232) was found to be over-expressed in over 60% of the ovarian tumors tested, 1/1 ovarian tumor cell lines (SKOV3-HTB77) and 100% of ovarian tumor SCID samples. No expression was detected in the normal tissues tested. This finding further supports the use of ovarian tumor antigen O651S in the diagnosis and treatment of ovarian cancer.

Ovarian tumor antigen O645S (SEQ ID NO:238) was found to be over-expressed in over 70% of the ovarian tumors tested, and 100% of ovarian tumor SCID samples. No expression was detected in the normal tissues tested. This finding further supports the use of ovarian tumor antigen O645S in the diagnosis and treatment of ovarian cancer.

Example 19

LifeSeq Analysis of Ovarian Tumor Antigen O590S

In Example 1 (Table VII) the DNA insert of clone 57886 was identified, and disclosed in SEQ ID NO:198 (606 bps in length), also referred to as O590S. Characterization of SEQ ID NO:198 by microarray analysis (Examples 2 and 9) indicated that corresponding mRNA was overexpressed in ovarian tumor tissue relative to normal tissues. Additional characterization by Northern blot analysis detected an mRNA transcript approximately 9.0 kb in size (Example 9). In this example, the DNA sequence for the ovarian tumor antigen O590S (SEQ ID NO:198) disclosed in Example 1 was used as a query to perform a BlastN search of the Incyte Genomics LifeSeq Gold database (LGtemplatesJan2001). This analysis identified an identical sequence match on template number 93744.1, corresponding to a 1740 base pair sequence, as is disclosed in SEQ ID NO:285. The gene bin, 93744, from which this match was identified contained 21 clones from various tumor libraries. Further analysis of the template 93744.1 sequence (SEQ ID NO:285), identified a −2 open reading frame that would translate a polypeptide with a predicted amino acid sequence disclosed in SEQ ID NO:286. In addition, this analysis confirmed that the open reading frame identified by SEQ ID NO:286 overlaps with and is contained within the nucleotide sequence of SEQ ID NO:198 corresponding to the ovarian tumor antigen O590S.

Example 20

Analysis of Ovarian Tumor Antigen O664S

O644S (initially described in example 10 as SEQ ID NO:240, with extended open reading frames disclosed in SEQ ID NOs:280-282) was previously identified as having a good expression profile by microarray (see Example 18 for details) and was further analyzed by real-time PCR.

The first strand cDNA used in the quantitative real-time PCR was synthesized from 20 µg of total RNA that was treated with DNase I (Amplification Grade, Gibco BRLLife Technology, Gaithersburg, MD0, using Superscript Reverse Transcriptase (RT) (Gibco BRL). Real-time PCR was performed with an ABIPRISM 7900 sequence detection system (PE Biosystems, Foster City, Calif.). The 7900 system uses SYBR™ green, a fluorescent dye that only intercalates into double stranded DNA, and a set of O644S specific forward and reverse primers. The increase in fluorescence was monitored during the whole amplification process. The optimal concentration of primers was determined using a checkerboard approach, and a pool of cDNAs from tumors was used in this process. The PCR was performed in 12.5 µl volumes that included 2.5 µl of SYBR green buffer, 2 µl of cDNA template and 2.5 µl each of the forward and reverse primer. The cDNAs used for the RT reactions were diluted 1:10 for O644S and 1:100 for the β-actin control. The expression of O644S in each of the tissue samples was represented by the comparative $C_T$ (threshold cycle) method. $C_T$ indicates the fractional cycle number at which the amount of amplified target reaches a fixed threshold. The $C_T$ value of normal skin was used as a comparative reference in order to evaluate the over-expression levels seen with O644S.

O644S did not show over-expression in ovarian tumor tissue compared to normal tissue, however it did show higher expression in ovarian tumor tissue than in other normal tissue. As O644S is over-expressed in ovarian tumor tissue compared to normal tissues, it is a useful ovarian tumor antigen for the development of immunotherapeutic and/or diagnostic reagents. The high expression of O644S in both ovary tumor and normal ovary demonstrates that it would be a useful marker in the detection of metastatic cancer.

Example 21

O591S is Over-Expressed in Ovarian Cancer

This example describes how the ovarian antigen O591S, and antibodies specific for O591S, represent important therapeutic and diagnostic reagents useful in the detection of various types of carcinomas. The identification and characterization of O591S (SEQ ID NO: 214, encoding the protein of SEQ ID NO: 215) was described above (Example 1 and 4). In order to further characterize O591S, antibodies were generated against amino acid 14-141 of SEQ ID NI:215.

To generate these antibodies, amino acids 14-141 of SEQ ID NO:215 were expressed in an *E. Coli* recombinant expression system and the cultures grown over-night in LB Broth, supplemented with the appropriate antibiotics, at 37° C. in a shaking incubator. Following the incubation, 10 mls of the over-night culture was added to 500 ml of 2×YT, supplemented with the appropriate antibiotics, in a two-liter baffled Erlenmeyer flask. When the optical density (at 560 nm) of the cultures reached 0.4-0.6, the cells were induced with IPTG (1 mM). Fours hours post-induction with IPTG, the cells were harvested by centrifugation, followed by washing with phosphate buffered saline (PBS). The supernatant was then discarded and the cells either frozen for future use, or immediately processed.

To process the cells, 20 µl of lysis buffer was added to the cell pellet and the mixture vortexed. To break open the *E. coli* cells, the mixture was run through a French Press at a pressure of 16,000 psi. The mixture was then centrifuged again and the supernatant and cell pellet checked by SDS-PAGE for the partitioning of the O591S-specific recombinant protein.

To isolate the O591S proteins localized to the cell pellet, the pellet was resuspended in 10 mM Tris pH 8.0, 1% CHAPS and the inclusion body pellet was washed and centrifuged. This procedure was repeated twice more. The washed inclusion body pellet was solubilized with either 8 M urea or 6 M guanidine HCl containing 10 mM Tris, pH 8.0 plus 10 mM imidazole. The solubilized protein was added to 5 ml of nickel-chelate resin (Qiagen) and incubated for 45 minutes to 1 hour at room temperature with continuous agitation. After incubation, the resin and protein mixture were poured through a disposable column and the flow through collected. The column was then washed with 10-20 column volumes of the solubilized buffer. The antigen was then eluted from the column using 8 M urea, 10 mM Tris, pH 8.0, and 300 mM imidazole and collected in 3 ml fractions.

A SDS-PAGE gel was run to determine which fractions to pool for further purification. As a final purification step, a strong anion resin, such as Hi-Prep Q (Biorad) was equilibrated with the appropriate buffer and the pooled fractions from above were loaded onto the column. Each antigen was eluted off the column with an increasing salt gradient. Fractions were collected as the column was run and second SDS-PAGE gel was run to determine which fractions from the column to pool. The pooled fractions were dialyzed against 10 mM Tris, pH 8.0.

In order to generate polyclonal anti-sera against O591S, 400 μg of O591S protein was combined with 100 μg of muramydipeptide (MDP). An equal volume of Incomplete Freund's Adjuvant (IFA) was added and the resulting solution mixed. Every four weeks, animals were boosted with 100 μg of antigen mixed with an equal volume of IFA. Seven days following each boost, the animal was bleed, and the sera isolated by incubating the blood at 4° C. for 12-24 hours followed by centrifugation.

In order to characterize the rabbit polyclonal anti-sera, 96 well plates were coated with antigen by incubating with 50 μl (typically 1 μg) at 4° C. for 20 hours. Following the incubation, 250 μl of BSA blocking buffer was added to the wells and incubated at room temperature for 2 hours. The plates were then washed 6 times with PBS/0.01% Tween.

Fifty microliters of the diluted sera was added to each well and incubated at room temperature for 30 minutes. Plates were washed as described above, before 50 μl of goat-anti-rabbit horse radish peroxidase (HRP) at a 1:10,000 dilution was added and incubated for 30 minutes. Plates were washed as described above and 100 μl of TMB microwell Peroxidase Substrate was added to each well. Following a 15-minute incubation in the dark at room temperature, the colorimatric reaction was stopped with 100 μl of $H_2SO_4$ and immediately read at 450 nm. All polyclonal antibodies tested demonstrated specific immunoreactivity to the appropriate antigen.

Immunohistochemical analysis (IHC) of O591S expression was then performed to determine the tissue specificity of O591S. For IHC, paraffin-embedded formalin fixed tissues were slice into 8-micron sections. Steam heat induced epitope retrieval (SHIER) in 0.1 M sodium citrate buffer (ph 6.0) was used for optimal staining conditions. Sections were incubated with 10% serum/PBS for 5 minutes. Primary antibody was added to each section for 25 minutes at a range of concentrations, followed by a 25-minute incubation with an anti-rabbit biotinylated antibody. Endogenous peroxidase activity was blocked by three 1.5-minute incubations with hydrogen peroxidase. The avidin biotin complex/horse radish peroxidase (ABC/HRP) system was used along with DAB chromogen to visualize antigen expression. The slides were then counterstained with hematoxylin.

Of the tissues tested, 4/5 primary ovarian cancers and 3/5 metastatic ovarian samples tested positive for O591S immunoreactivity. Of the normal tissue samples tested, 2/5 normal ovary samples were positive, and 1/1 normal bronchial epithelium was positive. Normal alveolar epithelium, kidney, colon, liver, and heart were all negative for O591S immunoreactivity.

These findings further validate the use of O591S in any of a variety of illustrative diagnostic and therapeutic embodiments described herein.

Example 22

Cell Surface Expression of the Ovarian Tumor Antigen, O591S

The identification and characterization of O591S (SEQ ID NO: 214, encoding the protein of SEQ ID NO: 215) was described above (Example 1 and 4). To characterize the cell surface expression of O591S, cell lines were either transfected with full-length O591S cDNA or infected with an adenoviral expression construct expressing O591S cDNAs. These cell lines were then stained using purified rabbit polyclonal anti-O591S antibodies raised against synthetic O591S peptides, and surface expression analyzed by FACS. The O591S polyclonal antibodies were raised against the following peptides; peptide 1 (SEQ ID NO:291) corresponding to amino acid positions 26-55 of the O591S protein sequence (SEQ ID NO:215), peptide 2 (SEQ ID NO:292) corresponding to amino acid positions 53-78 of the O591S protein sequence (SEQ ID NO:215), and peptide 3 (SEQ ID NO:293) corresponding to amino acid positions 103-129 of O591S protein sequence (SEQ ID NO:215). Polyclonal antibodies were generated essentially as described in Examples 17 and 21 of the present application.

Cell surface expression of O591S was determined as follows:

1. oNXA cells were transfected by $CaPO_4$ precipitation with (a) a negative control cDNA cloned into the expression vector pBIB, or (b) O591S cDNA cloned into the expression vector pBIB. Seventy-two hours post-transfection, the cells were harvested and stained with either (i) control rabbit polyclonal antibody, (ii) rabbit polyclonal anti-O591S antibody, or (iii) secondary antibody (anti-rabbit-FITC) alone. All cells transfected with an expression vector containing O591S stained using the O591S specific polyclonal antibodies, demonstrating surface expression of O591S.

2. oNXA cells were transfected by $CaPO_4$ precipitation with either; pBIB/O591S (O591S cDNA cloned into the expression vectors pBIB), pcDNA/O591S (O591S cDNA cloned into the expression vector, pcDNA3), or pCEP/O591S (O591S cDNA cloned into the expression vector pCEP4). Seventy-two hours post-transfection, cells were harvested and stained with either (i) control rabbit polyclonal antibody or (ii) rabbit polyclonal anti-O591S antibody. O591S was detected on the surface of all cells transfected with O591S specific sequences. O591S expression levels were shown to be highest with the episomal replicating vector pcDNA4.

3. oNXA and 293 cells were transfected by $CaPO_4$ precipitation with pcDNA/O591S (O591S cDNA cloned into the expression vector pc DNA3). Seventy-two hours post-transfection, the cells were harvested and stained with either (i) control rabbit polyclonal antibodies, or (ii) rabbit polyclonal anti-O519S antibody. The cells were than analyzed using FACS analysis. Both oNXA and 293 cells transfected with O591S demonstrated cell surface expression of O591S.

4. VA13 cells and oNXA cells were infected (MOI of 10:1) with O591S/adenovirus (O591S cDNA cloned into the adenoviral expression vector). Seventy-two hours post-infection, the cells were harvested and stained with either, (i) control rabbit polyclonal antibody, or (ii) rabbit polyclonal anti-O591S antibody. The cells were then analyzed using FACS. Cells infected with O591S/adenovirus demonstrated cell surface staining specific for O591S.

To further characterize that O591S was a surface expressed protein, oNXA cells were transfected by $CaPO_4$ precipitation with pBIB/O591S (O591S cDNA cloned into the expression vector PBIB). Seventy-two hours post-transfection the cells were harvested and incubated for an additional one hour in either the presence or absence of phoshatidylinositol phospholipae C (PI-PLC), an enzyme known to cleave glycosyl-phosphatidylinositol (GPI)-linked proteins. GPI-linked proteins are known to be surface expressed proteins. Following incubation with PI-PLC, the cells were washed and either stained with (i) rabbit polyclonal anti-O591S antibody, or (ii)

secondary antibody (anti-rabbit-FITC) alone, and analyzed by FACS for O591S cell surface expression. Analysis demonstrated that cells treated with PI-PLC were negative for the cell surface expression of O591S, further demonstrating that this protein is a surface expressed protein. Analysis of the O591S protein sequence (SEQ ID NO:215) revealed that the enzyme PI-PLC cleaved at either the Arg at position 114 of SEQ ID NO:215, resulting in the generation of a liberated 114 amino acid fragment, the sequence of which is disclosed in SEQ ID NO:289, and theoretically a 27 amino acid cell associated fragment (residues 115-141 of SEQ ID NO:215) or at the Gly at position 115 of SEQ ID NO:215, resulting in the generation of a 115 amino acid fragment, the sequence of which is disclosed in SEQ ID NO:290 and theoretically a 26 amino acid cell associated fragment (residues 116-141 of SEQ ID NO:215).

These data demonstrate that O591S is a surface expressed, GPI-linked protein, making the sequence a target for therapeutic antibodies.

From the foregoing it will be appreciated that, although specific embodiments of the invention have been described herein for purposes of illustration, various modifications may be made without deviating from the spirit and scope of the invention. Accordingly, the invention is not limited except as by the appended claims.

All of the above U.S. patents, U.S. patent application publications, U.S. patent applications, foreign patents, foreign patent applications and non-patent publications referred to in this specification and listed in the Application Data Sheet are incorporated herein by reference in their entirety.

What is claimed:

1. A method for detecting the presence of an ovarian cancer in a patient, comprising the steps of:
   (a) obtaining a biological sample from the patient;
   (b) contacting the biological sample with an antibody or antigen binding fragment thereof, that binds to a polypeptide comprising the amino acid sequence set forth in SEQ ID NO: 215;
   (c) detecting in the sample an amount of said polypeptide that binds to said antibody or antigen binding fragment thereof; and
   (d) comparing the amount of said polypeptide to a predetermined cut-off value and therefrom determining the presence of a cancer in the patient, wherein the detection of an amount of said polypeptide that is higher than the cut-off value is considered positive for the presence of ovarian cancer.

2. The method according to claim 1, wherein the sample is blood, sera, sputum, urine, or a tumor biopsy.

3. The method according to claim 1, wherein the antibody is monoclonal.

4. The method according to claim 1, wherein the antibody is humanized.

5. The method according to claim 1, wherein the antibody fragment is a single chain Fv, F(ab) fragment or F(ab')$_2$ fragment.

6. The method according to claim 1, wherein the antibody is polyclonal.

7. The method according to claim 1, conducted in a flow-through or strip test format.

8. The method of claim 1, wherein the antibody or antigen binding fragment thereof is immobilized on solid support.

9. The method of claim 8, wherein the solid support comprises nitrocellulose, glass, fiberglass, latex, plastic or a magnetic particle.

* * * * *

SEQUENCE LISTING

```
<160> NUMBER OF SEQ ID NOS: 293

<210> SEQ ID NO 1
<211> LENGTH: 396
<212> TYPE: DNA
<213> ORGANISM: Homo sapiens
<220> FEATURE:
<221> NAME/KEY: misc_feature
<222> LOCATION: 303, 370, 377, 382
<223> OTHER INFORMATION: n = A,T,C or G

<400> SEQUENCE: 1
caacctcact agtaaatgaa agaaatattg taatttgtat ttgatctgct gggtctttgg      60
agtcagaact ggttttatca gcagtttgat cttctgaggt ctggtatgta gtttgctggc     120
ccacagaacc ttcacgtgta ttcacagcct caatgccata aggaaactct tttagaagtt     180
ctgacagctg gtcatgtagg tataagacag gtgccttatc actgtggatt tcatttcttg     240
caggatcttg gggagtatag ttgctggatg catctatttc ctgagggtaa atatcctcct     300
ggncgacgcg gccgctcgag tctagagggc ccgtttaaac ccgctgatca gcctcgactg     360
tgccttctan ttgccancca tntgttgttt gccoct                               396

<210> SEQ ID NO 2
<211> LENGTH: 396
<212> TYPE: DNA
<213> ORGANISM: Homo sapiens

<400> SEQUENCE: 2
cgaccaaaaa gtaaactcca agtgaacatc aaatcaaatc taatcctttt ggccacatga      60
ctggttgttc tttatctcat agttacaatg aatcatataa actgtagact gccactacca     120
cgatacttct gtgacacaga aggaatgtcc tatttgccta tctatctgag gaatgttaaa     180
tagagaaaaa tagattataa aacaacctgg aggtcacagg attctgagat aatccctctg     240
ttaaaaaaca tctgaacagc aaatgtccaa tctgtaataa aatagttaaa ggtccaagtc     300
aagtccactt ctacttggct ggcccagcac aagaaatcta acagcacttt gtaatcattt     360
tgcttttcta attttcccgg aggacatggg ccattg                               396

<210> SEQ ID NO 3
<211> LENGTH: 396
<212> TYPE: DNA
<213> ORGANISM: Homo sapiens
<220> FEATURE:
```

```
<221> NAME/KEY: misc_feature
<222> LOCATION: 22, 28, 29, 30, 33, 36, 41, 43, 45, 46, 53, 56, 58, 61,
      64, 69, 70, 74, 75, 78, 83, 84, 85, 102, 143, 335
<223> OTHER INFORMATION: n = A,T,C or G

<400> SEQUENCE: 3 cgccctttt  ttttttttt  tnattggnnn  aantcncttt  nantnnaaaa  acntgnangg      60
naancccann  cccnnggnac  cannnccagg  agttgggtgg  anactgagtg  gggtttgtgt   120
gggtgagggg  gcatctactc  ctnttgcaac  aagccaaaag  tagaacagcc  taaggaaaag   180
tgacctgcct  tggagcctta  gtccctccct  tagggccccc  tcagcctacc  ctatccaagt   240
ctgaggctat  ggaagtctcc  ctcctagttc  actagcaggt  tccccatctt  ttccaggctg   300
cccctagcac  tccacgtttt  tctgaaaaaa  tctanacagg  cccttttgg   gtacctaaaa   360 cccagctgag  gttgtgagct  tgtaaggtaa  agcaag                               396

<210> SEQ ID NO 4
<211> LENGTH: 396
<212> TYPE: DNA
<213> ORGANISM: Homo sapiens
<220> FEATURE:
<221> NAME/KEY: misc_feature
<222> LOCATION: 13, 15, 21, 27, 34, 37, 41, 57, 58, 59, 63, 64, 71, 72,
      77, 78, 83, 87, 93, 170, 207, 210, 308, 379, 382, 389, 391,
      392, 393, 395
<223> OTHER INFORMATION: n = A,T,C or G

<400> SEQUENCE: 4
gaccaatcct  tgncncacta  ncaaaangac  cccnctnacc  nccaggaact  gaacctnnnt    60
gtnnacctcc  nnctgcnnag  ccntatntcc  aanatcaccc  accgtatcca  ctgggaatct   120
gccagcctct  tgcgatcaga  agagaccaat  cgaaaatgag  ggtttcacan  tcacagctga   180
aggaaaaggc  caaggcacct  tgtcggnggn  gacaatgtac  catgctaagg  ccaaagatca   240
actcacctgt  aataaattcg  acctcaaggt  caccataaaa  ccagcaccgg  aacagaaaaa   300
gaggcctnag  gatgcccaag  aaacacttt   gatcctttga  aaactgtacc  aaggtaccgg   360
ggggagaccc  aggaaaggnc  cnttatgtnt  nnntnt                                396

<210> SEQ ID NO 5
<211> LENGTH: 396
<212> TYPE: DNA
<213> ORGANISM: Homo sapiens
<220> FEATURE:
<221> NAME/KEY: misc_feature
<222> LOCATION: 135, 172, 343, 348, 354, 395
<223> OTHER INFORMATION: n = A,T,C or G

<400> SEQUENCE: 5
gacgccggag  ctgccgcgcc  agtcgcctag  caggtcctct  accggcttat  tcctgtgccg    60
gatcttcatc  ggcacagggg  ccactgagac  gtttctgcct  ccctctttct  tcctccgctc   120
tttctcttcc  ctctngttta  gtttgcctgg  gagcttgaaa  ggagaaagca  cngggtcgc    180 cccaaaccct  ttctgcttct  gcccatcaca  agtgccacta  ccgccatggg  cctcactatc   240
tcctccctct  tctcccgact  atttggcaag  aagcagatgc  gcattttgat  ggttggattg   300
gatgctgctg  gcaagacaac  cattcttgat  aaactgaaag  tangggganat  aagnaccacc  360 atttctacca  ttgggtttaa  tgggggaaac  agtana                               396

<210> SEQ ID NO 6
<211> LENGTH: 396
<212> TYPE: DNA
```

<213> ORGANISM: Homo sapiens
<220> FEATURE:
<221> NAME/KEY: misc_feature
<222> LOCATION: 212
<223> OTHER INFORMATION: n = A,T,C or G

<400> SEQUENCE: 6

| | | |
|---|---|---|
| acgggaggcg ccgggaagtc gacggcgccg gcggctcctg caggaggcca ctgtctgcag | 60 |
| ctcccgtgaa gatgtccact ccagacccac ccctgggcgg aactcctcgg ccaggtcctt | 120 |
| ccccgggccc tgcccttccc ctggagccat gctgggccct agcccgggtc cctcgccggg | 180 |
| ctccgcccac agcatgatgg ggcccagccc angggccgcc ctcagcagga cacccatcc | 240 |
| ccacccaggg gcctggaggg taccctcagg acaacatgca ccagatgcac aagcccatgg | 300 |
| agtccatgca tgagaagggc atgtcggacg acccgcgcta caaccagatg aaaggaatgg | 360 |
| ggatgcggtc aggggggccat gctgggatgg ggcccc | 396 |

<210> SEQ ID NO 7
<211> LENGTH: 396
<212> TYPE: DNA
<213> ORGANISM: Homo sapiens

<400> SEQUENCE: 7

| | | |
|---|---|---|
| acccgagagt cgtcggggtt tcctgcttca acagtgcttg gacggaaccc ggcgctcgtt | 60 |
| ccccaccccg gccggccgcc catagccagc cctccgtcac ctcttcaccg caccctcgga | 120 |
| ctgcccaag gccccgccg ccgctccagc gccgcgcagc caccgccgcc gccgccgcct | 180 |
| ctccttagtc gccgccatga cgaccgcgtc cacctcgcag gtgcgccaga actaccacca | 240 |
| ggactcagag gccgccatca accgccagat caacctggag ctctacgcct cctacgttta | 300 |
| cctgtccatg tcttactact ttgaccgcga tgatgtggct ttgaagaact ttgccaaata | 360 |
| ctttcttcac caatctcatg aggagaggga acatgc | 396 |

<210> SEQ ID NO 8
<211> LENGTH: 396
<212> TYPE: DNA
<213> ORGANISM: Homo sapiens

<400> SEQUENCE: 8

| | | |
|---|---|---|
| cgacaacaag gttaatacct tagttcttaa cattttttt ctttatgtgt agtgttttca | 60 |
| tgctaccttg gtaggaaact tatttacaaa ccatattaaa aggctaattt aaatataaat | 120 |
| aatataaagt gctctgaata aagcagaaat atattacagt tcattccaca gaaagcatcc | 180 |
| aaaccaccca aatgaccaag gcatatatag tatttggagg aatcagggt ttggaaggag | 240 |
| tagggaggag aatgaaggaa aatgcaacca gcatgattat agtgtgttca tttagataaa | 300 |
| agtagaaggc acaggagagg tagcaaaggc caggcttttc tttggttttc ttcaaacata | 360 |
| ggtgaaaaaa acactgccat tcacaagtca aggaac | 396 |

<210> SEQ ID NO 9
<211> LENGTH: 396
<212> TYPE: DNA
<213> ORGANISM: Homo sapiens
<220> FEATURE:
<221> NAME/KEY: misc_feature
<222> LOCATION: 321, 344
<223> OTHER INFORMATION: n = A,T,C or G

<400> SEQUENCE: 9

| | | |
|---|---|---|
| tcgacatcgc ggcaactttt tgcggattgt tcttgcttcc aggctttgcg ctgcaaatcc | 60 |

```
agtgctacca gtgtgaagaa ttccagctga acaacgactg ctcctccccc gagttcattg    120
tgaattgcac ggtgaacgtt caagacatgt gtcagaaaga agtgatggag caaagtgccg    180
ggatcatgta ccgcaagtcc tgtgcatcat cagcggcctg tctcatcgcc tctgccgggt    240
accagtcctt ctgctcccca gggaaactga actcagtttg catcagctgc tgcaacaccc    300
ctctttgtaa cgggccaagg nccaaaaaaa ggggaaagtt ctgncctcgg ccctcaggcc    360
agggctccgc accaccatcc tgttcctcaa attagc                              396
```

<210> SEQ ID NO 10
<211> LENGTH: 396
<212> TYPE: DNA
<213> ORGANISM: Homo sapiens
<220> FEATURE:
<221> NAME/KEY: misc_feature
<222> LOCATION: 115, 116, 117, 130, 138, 142, 143, 144, 145, 146, 153,
      157, 158, 159, 160, 164, 175, 176, 177, 178, 179, 183, 187, 197,
      198, 202, 203, 204, 205, 206, 211, 212, 213, 215, 216, 217,
      220, 221, 222, 226, 231, 234, 236, 237, 245, 246, 247
<223> OTHER INFORMATION: n = A,T,C or G
<220> FEATURE:
<221> NAME/KEY: misc_feature
<222> LOCATION: 250, 255, 264, 266, 267, 268, 269, 270, 271, 272, 279,
      284, 297, 303, 304, 305, 308, 315, 317, 318, 319, 320, 321, 322,
      323, 333, 334, 337, 338, 342, 343, 368, 372, 374, 380, 381,
      391, 395
<223> OTHER INFORMATION: n = A,T,C or G

<400> SEQUENCE: 10

```
ccttttttt tttttttttt tttttttttt tttttttttt tttttttttt tttttttttt    60
tttttttttt tttttttttt tttttttttt tttttttttt ttttaaaaaa aaaanntttt    120
tttttttttn aaaaaaangg gnnnntttt ttnccnnnn gggngggggg ggggnnnnnt    180
ttnaaanaaa aaaaccnnaa annnnngggg nnnannnaan nncccnccccc naancnntaa    240 aaaannnggn aaaanagggg gggnannnnn nnggggggna aaanttttt tttttttnaag    300 ggnnnggnaa aaaantnnnn nnntttttttt ttnnaanngg gnnaaaaaaa aaaaaaaaaa    360
attttttngg gntnaggggn nggggaaaa ncccna                              396
```

<210> SEQ ID NO 11
<211> LENGTH: 396
<212> TYPE: DNA
<213> ORGANISM: Homo sapiens

<400> SEQUENCE: 11

```
agaacacagg tgtcgtgaaa actacccta aaagccaaaa tgggaaagga aaagactcat    60
atcaacattg tcgtcattgg acacgtagat tcgggcaagt ccaccactac tggccatctg    120
atctataaat gcggtggcat cgacaaaaga accattgaaa aatttgagaa ggaggctgct    180
gagatgggaa agggctcctt caagtatgcc tgggtcttgg ataaactgaa agctgagcgt    240
gaacgtggta tcaccattga tatctccttg tggaaatttg agaccagcaa gtactatgtg    300
actatcattg atgccccagg acacagagac tttatcaaaa acatgattac agggacatct    360
caggctgact gtgctgtcct gattgttgct gctggt                              396
```

<210> SEQ ID NO 12
<211> LENGTH: 396
<212> TYPE: DNA
<213> ORGANISM: Homo sapiens

<400> SEQUENCE: 12

```
cgaaaaccttt taaacccgg tcatccggac atcccaacgc atgctcctgg agctcacagc    60
cttctgtggt gtcatttctg aaacaagggc gtggatccct caaccaagaa gaatgtttat   120
gtcttcaagt gacctgtact gcttgggac tattggagaa aataaggtgg agtcctactt   180
gtttaaaaaa tatgtatcta agaatgttct agggcactct gggaacctat aaaggcaggt   240
atttcgggcc ctcctcttca ggaatcttcc tgaagacatg cccagtcga aggcccagga   300 tggcttttgc tgcggccccg tggggtagga gggacagaga cagggagaa gtcagcctcc   360 acattcagag gcatcacaag taatggcaca attctt                              396
```

```
<210> SEQ ID NO 13
<211> LENGTH: 396
<212> TYPE: DNA
<213> ORGANISM: Homo sapiens

<400> SEQUENCE: 13
accacaggct ggccacaaga agcgctggag tgtgctggcg gctgcaggcc tacggggcct    60
ggtccggctg ctgcacgtgc gtgccggctt ctgctgcggg gtcatccgag cccacaagaa   120
ggccatcgcc accctgtgct tcagccccgc ccacgagacc catctcttca cggcctccta   180
tgacaagcgg atcatcctct gggacatcgg ggtgcccaac caggactacg aattccaggc   240
cagccagctg ctcacactgg acaccacctc tatccccctg cgcctctgcc ctgtcgcctc   300
ctgcccggac gcccgcctgc tggccggctg cgagggcggc tgctgctgct gggacgtgcg   360
gctggaccag ccccaaaaga ggagggtgtg tgaagt                              396
```

```
<210> SEQ ID NO 14
<211> LENGTH: 396
<212> TYPE: DNA
<213> ORGANISM: Homo sapiens

<400> SEQUENCE: 14
acggcgtcct cgtggaagtg acatcgtctt taaaccctgc gtggcaatcc ctgacgcacc    60
gccgtgatgc ccagggaaga cagggcgacc tggaagtcca actacttcct taagatcatc   120
caactattgg atgattatcc gaaatgtttc attgtgggag cagacaatgt gggctccaag   180
cagatgcagc agatccgcat gtcccttcgc gggaaggctg tggtgctgat gggcaagaac   240
accatgatgc gcaaggccat ccgagggcac ctggaaaaca cccagctct ggagaaactg   300 ctgcctcata tccgggggaa tgtgggcttt gtgttcacca aggaggacct cactgagatc   360
agggacatgt tgctggccaa taaggtgcca gctgct                              396
```

```
<210> SEQ ID NO 15
<211> LENGTH: 396
<212> TYPE: DNA
<213> ORGANISM: Homo sapiens
<220> FEATURE:
<221> NAME/KEY: misc_feature
<222> LOCATION: 333
<223> OTHER INFORMATION: n = A,T,C or G

<400> SEQUENCE: 15
accgcgcggg cacagggtgc cgctgaccga ggcgtgcaaa gactccagaa ttggaggcat    60
gatgaagact ctgctgctgt ttgtggggct gctgctgacc tgggagagtg ggcaggtcct   120
gggggaccag acggtctcag acaatgagct ccaggaaatg tccaatcagg gaagtaagta   180
cgtcaataag gaaattcaaa atgcttgtca acggggtgaa acagataaag actctcatag   240
aaaaaacaaa cgaagagcgc aagacactgc tcagcaacct agaagaagcc aagaagaaga   300
```
aagaggatgc cctaaatgag accagggaat canagacaaa gctgaaggag ctcccaggag    360
tgtgcaatga gaccatgatg gccctctggg aagagt    396

<210> SEQ ID NO 16
<211> LENGTH: 396
<212> TYPE: DNA
<213> ORGANISM: Homo sapiens
<220> FEATURE:
<221> NAME/KEY: misc_feature
<222> LOCATION: 114, 121, 122, 123, 127, 134, 136, 138, 140, 141, 142,
      143, 144, 148, 163, 166, 172, 173, 174, 176, 177, 183, 184, 185,
      187, 195, 196, 198, 199, 202, 203, 206, 213, 214, 215, 216,
      217, 218, 219, 223, 225, 226, 227, 229, 230, 236, 238
<223> OTHER INFORMATION: n = A,T,C or G
<220> FEATURE:
<221> NAME/KEY: misc_feature
<222> LOCATION: 239, 252, 256, 257, 261, 262, 268, 269, 273, 278, 280,
      288, 289, 290, 292, 293, 303, 312, 325, 327, 333, 335, 336, 341,
      342, 347, 354, 359, 365, 371, 383, 384, 386, 388, 391
<223> OTHER INFORMATION: n = A,T,C or G

<400> SEQUENCE: 16
tttttttttt tttttttttt tttttttttt tttttttttt tttttttttt tttttttttt    60
tttttttttt tttttttttt tttttttttt tttttttttt tttttttttt tttnggggggg   120 nnnaaanttt tttntnanan nnnngggnaa aaaaaaaaaa aanaangggg gnnntnnggc    180
ccnnnanaaa aaaanngnna annaancccc ccnnnnnnnc ccncnnntnn ggaaananna    240
aaaccccccc cngggnnggg nnaaaaannc ccngggggnan ttttatnnn annccccccc    300 ccngggggg gnggaaaaaa aaaantnccc ccnannaaaa nngggncccc cccntttnc      360 aaaangggggg nccgggcccc ccnnantntt nggggg                             396

<210> SEQ ID NO 17
<211> LENGTH: 396
<212> TYPE: DNA
<213> ORGANISM: Homo sapiens

<400> SEQUENCE: 17
accacactaa ccatatacca atgatggcgc gatgtaacac gagaaagcac ataccaaggc    60
caccacacac cacctgtcca aaaaggcctt cgatacggga taatcctatt tattacctca    120 gaagttttttt tcttcgcagg attttttctga gccttttacc actccagcct agcccctacc  180
ccccaactag gagggcactg gccccccaaca ggcatcaccc cgctaaatcc cctagaagtc   240
ccactcctaa acacatccgt attactcgca tcaggagtat caatcacctg agctcaccat    300
agtctaatag aaaacaaccg aaaccaaata attcaagcac tgcttattac aattttactg    360
ggtctctatt ttaccctcct acaagcctca gagtac                              396

<210> SEQ ID NO 18
<211> LENGTH: 396
<212> TYPE: DNA
<213> ORGANISM: Homo sapiens
<220> FEATURE:
<221> NAME/KEY: misc_feature
<222> LOCATION: 51, 54, 66, 81, 86, 98, 106, 111, 117, 124, 129, 133,
      135, 150, 151, 154, 159, 161, 172, 179, 181, 183, 185, 220, 223,
      229, 238, 258, 259, 264, 282, 289, 292, 294, 299, 303, 311,
      315, 329, 343, 349, 351, 353, 361, 369, 370, 389, 392
<223> OTHER INFORMATION: n = A,T,C or G
<220> FEATURE:
<221> NAME/KEY: misc_feature
<222> LOCATION: 396
<223> OTHER INFORMATION: n = A,T,C or G

```
<400> SEQUENCE: 18
tttttttttt tttttttttt tttttttttt tttttttttt ttttttttta ntcnaaaggg      60
gaaggnccct ttttattaaa nttggncatt ttactttnct tttttnaaaa ngctaanaaa     120 aaantttttnt ttntncttaa aaaaaccctn natntcacna ncaaaaaaaa cnattcccnc    180
ntncnttttg tgataaaaaa aaaggcaatg gaattcaacn tancctaana aaactttncc     240
tgggaggaaa aaaaattnnt ccgngggaaa cacttggggc tntccaaant gnanccatnc     300
tangaggacc ntctntaaga tttccaaang aaacccctttc ctnccaaang nantaccccg    360
ntgcctacnn cccataaaaa aaacctcanc cntaan                               396

<210> SEQ ID NO 19
<211> LENGTH: 396
<212> TYPE: DNA
<213> ORGANISM: Homo sapiens
<220> FEATURE:
<221> NAME/KEY: misc_feature
<222> LOCATION: 47, 69, 75, 80, 83, 87, 88, 90, 92, 102, 104, 108, 116,
      121, 130, 138, 139, 142, 153, 156, 158, 162, 165, 166, 180, 192,
      193, 195, 201, 224, 226, 232, 235, 237, 241, 248, 251, 253,
      256, 269, 272, 274, 277, 284, 287, 290, 292, 297
<223> OTHER INFORMATION: n = A,T,C or G
<220> FEATURE:
<221> NAME/KEY: misc_feature
<222> LOCATION: 299, 305, 306, 315, 323, 324, 326, 332, 351, 368, 377,
      380, 383, 387, 392
<223> OTHER INFORMATION: n = A,T,C or G

<400> SEQUENCE: 19
tttttttttt tttttttttt tttttttttt tttttttttt ttttttntgg tctgggcttt      60
tattttacna aaaanctaan ggnaaanntn cnttaaacta antngaaanac aaagtnttaa    120 ngaaaaaggn ctgggggnnt cntttacaaa aanggncngg gncannnttg ggcttaaaan    180
ttcaaaaagg gnncntcaaa ngggtttgca tttgcatgtt tcancnctaa ancgnangaa     240
naaacccngg ngnccnctgg gaaaagttnt tnanctncca aaanatnaan tntttgnanc     300
agggnntttt tgggnaaaaa aannanttcc anaaactttc catccctggg ntttgggttc    360
ggccttgngt tttcggnatn atntccntta angggg                               396

<210> SEQ ID NO 20
<211> LENGTH: 396
<212> TYPE: DNA
<213> ORGANISM: Homo sapiens
<220> FEATURE:
<221> NAME/KEY: misc_feature
<222> LOCATION: 29, 43, 49, 53, 55, 75, 81, 100, 110, 111, 125, 129,
      160, 162, 168, 246, 277
<223> OTHER INFORMATION: n = A,T,C or G

<400> SEQUENCE: 20
tttttttttt tttttttttt ttttttctna acaaaccctg ttnttgggng ggngngggta      60
taatactaag ttganatgat ntcatttacg ggggaaggcn ctttgtgaan naggccttat    120
ttctnttgnc ctttcgtaca gggaggaatt tgaagtaaan anaaaccnac ctggattact    180
ccggtctgaa ctcaaatcac gtaggacttt aatcgttgaa caaacaaacc tttaatagcg    240
gctgcnccat tgggatgtcc tgatccaaca tcgaggncgt aaaccctatt gttgatatgg    300
actctaaaaa taggattgcg ctgttatccc tagggtaact tgttcccgtg gtcaaagtta    360
ttggatcaat tgagtataag tagttcgctt tgactg                               396

<210> SEQ ID NO 21
```

<211> LENGTH: 396
<212> TYPE: DNA
<213> ORGANISM: Homo sapiens
<220> FEATURE:
<221> NAME/KEY: misc_feature
<222> LOCATION: 6, 9, 18, 23, 37, 43, 48, 55, 65, 73, 75, 103, 110, 117,
      123, 125, 134, 153, 182, 195, 202, 205, 213, 216, 223, 239,
      249, 276, 293, 294, 302, 307, 344, 356, 359, 369, 374, 381, 392
<223> OTHER INFORMATION: n = A,T,C or G

<400> SEQUENCE: 21
acatanatnt tatactanca ttnaccatct cacttgnagg aanactanta tatcnctcac    60
acctnatatc ctncntacta tgcctagaag gaataatact atngctgttn attatancta   120
ctntnataac cctnaacacc cactccctct tanccaatat tgtgcctatt gccatactag   180
tntttgccgc ctgcnaagca gnggngggcc tanccntact agnctcaatc tccaacacnt   240
atggcctana ctacgtacat aacctaaacc tactcnaatg ctaaaactaa tcnncccaac   300
anttatntta ctaccactga catgactttc caaaaaacac atantttgaa tcaacncanc   360
cacccacanc ctanttatta ncatcatccc cntact                             396

<210> SEQ ID NO 22
<211> LENGTH: 396
<212> TYPE: DNA
<213> ORGANISM: Homo sapiens
<220> FEATURE:
<221> NAME/KEY: misc_feature
<222> LOCATION: 17, 244
<223> OTHER INFORMATION: n = A,T,C or G

<400> SEQUENCE: 22
tttttttttt ttttganaaa agccggcata aagcacttt attgcaataa taaaacttga     60
gactcataaa tggtgctggg ggaagggtgc agcaacgatt tctcaccaaa tcactacaca   120
ggacagcaaa gggtgagaa ggggctgagg gaggaaaagc caggaaactg agatcagcag    180
agggagccaa gcatcaaaaa acaggagatg ctgaagctgc gatgaccagc atcattttct   240
taanagaaca ttcaaggatt tgtcatgatg gctgggcttt cactgggtgt taagtctaca   300
aacagcacct tcaattgaaa ctgtcaatta agttcttaa gatttaggaa gtggtggagc    360
ttggaaagtt atgagattac aaaattcctg aaagtc                             396

<210> SEQ ID NO 23
<211> LENGTH: 396
<212> TYPE: DNA
<213> ORGANISM: Homo sapiens

<400> SEQUENCE: 23
acaaaggcgg ttccaagcta aggaattcca tcagtgcttt tttcgcagcc accaaattta    60
gcaggcctgt gaggttttca tatcctgaag agatgtattt taaagctttt ttttttttaat  120 gaaaaatgt cagacacaca caaaagtaga atagtaccat ggagtcccca cgtacccagc    180
ctgcagcttc aacagttacc acatttgcca accggagaga ctgccaaggc aggaaaaagc   240
cctggaaagc ccacggcccc ttttcccctt gggtcagagg ccttagagct ggctgccaaa   300
gcagccaacc aaaggggcag ctcagctcct tcgtggcacc agcagtgttc ctgatgcagt   360
tgaagagttg atgtctttga caacatacgg acactg                             396

<210> SEQ ID NO 24
<211> LENGTH: 396
<212> TYPE: DNA
<213> ORGANISM: Homo sapiens

```
<220> FEATURE:
<221> NAME/KEY: misc_feature
<222> LOCATION: 313, 337, 340, 350, 351, 352, 353, 354, 355, 356, 366,
      376, 377, 378, 382, 384, 385, 387, 389, 390, 392, 393, 396
<223> OTHER INFORMATION: n = A,T,C or G

<400> SEQUENCE: 24
cgactatcct ctcagattct tatctggcac taatttataa ctattatatt atcagagact      60
atgtagcaat atatcagtgc acaggcgcat cccaggcctg tacagatgta tgtctacacg     120
taagtataaa tgaatttgca taccaggttt tacacttgca tctctaatag agattaaaaa     180
caacaaattg gcctcttcct aagtatatta atatcattta tccttacatt ttatgcctcc     240
ccctaaatta atgactgagt tggtggaaag cggctaggtt ttattcatac tgttttttgt     300
tctcaacttc aanagtaatc tacctctgaa aaatttntan tttaatattn nnnnnagga     360 atttgngcca ctttannnct tncnntntnn tnnccn                               396

<210> SEQ ID NO 25
<211> LENGTH: 396
<212> TYPE: DNA
<213> ORGANISM: Homo sapiens
<220> FEATURE:
<221> NAME/KEY: misc_feature
<222> LOCATION: 90, 125, 136, 278, 299, 301, 305, 344, 347, 353, 355,
      356, 357, 359, 360, 361, 365, 369, 378, 380, 381, 382, 383, 384,
      385, 386, 391, 392, 393, 395, 396
<223> OTHER INFORMATION: n = A,T,C or G

<400> SEQUENCE: 25
tttttttttt tttttttttt gtcttttaaa aaatataaaa gtgttattat tttaaaacat      60
caagcattac agactgtaaa atcaattaan aactttctgt atatgaggac aaaaatacat     120
ttaanacata tacaanaaga tgcttttttcc tgagtagaat gcaaactttt atattaagct    180
tctttgaatt ttcaaaatgt aaaataccaa ggcttttttca catcagacaa aaatcaggaa    240
tgttcacctt cacatccaaa aagaaaaaaa aaaaaaancc aatttttcaag ttgaagttna    300 ncaanaatga tgtaaaatct gaaaaagtg gccaaaattt taanttncaa canannngnn     360
ncagntttna tggatctntn nnnnnncttc nnntnn                              396

<210> SEQ ID NO 26
<211> LENGTH: 396
<212> TYPE: DNA
<213> ORGANISM: Homo sapiens
<220> FEATURE:
<221> NAME/KEY: misc_feature
<222> LOCATION: 313, 314, 316, 318, 321, 343, 344, 352, 353, 356, 363,
      366, 370, 372, 373, 374, 375, 377, 378, 379, 383, 384, 385, 386,
      387, 391, 393, 394, 395, 396
<223> OTHER INFORMATION: n = A,T,C or G

<400> SEQUENCE: 26
gacgctcccc cctccccccg agcgccgctc cggctgcacc gcgctcgctc cgagtttcag      60
gctcgtgcta agctagcgcc gtcgtcgtct cccttcagtc gccatcatga ttatctaccg    120
ggacctcatc agccacgatg agatgttctc cgacatctac aagatccggg agatcgcgga    180
cgggttgtgc ctggaggtgg aggggaagat ggtcagtagg acagaaggta acattgatga    240
ctcgctcatt ggtggaaatg cctccgctga aggcccgag ggcgaaggta cccgaaagca    300
cagtaatcac tgnngncnat nttgtcatga accatcacct gcnngaaaca annttnacaa     360
aanaancctn cnnnnannnc ctnnnnnatt ncnnnn                              396
```

<210> SEQ ID NO 27
<211> LENGTH: 396
<212> TYPE: DNA
<213> ORGANISM: Homo sapiens
<220> FEATURE:
<221> NAME/KEY: misc_feature
<222> LOCATION: 49, 61, 66, 73, 75, 99, 102, 103, 105, 107, 120, 124,
      126, 129, 138, 139, 141, 147, 155, 157, 162, 165, 175, 187, 191,
      193, 198, 207, 217, 218, 220, 221, 223, 226, 231, 232, 245,
      257, 259, 260, 263, 266, 271, 287, 305, 306, 307, 308
<223> OTHER INFORMATION: n = A,T,C or G
<220> FEATURE:
<221> NAME/KEY: misc_feature
<222> LOCATION: 321, 330, 332, 335, 342, 343, 344, 345, 349, 350, 351,
      352, 354, 355, 356, 357, 365, 366, 367, 370, 371, 372, 373, 374,
      375, 376, 377, 378, 379, 380, 381, 382, 383, 386, 387, 388,
      389, 391, 392, 393, 394, 395, 396
<223> OTHER INFORMATION: n = A,T,C or G

<400> SEQUENCE: 27
tttttttttt tttttttttt tttttttttt tttttttttt tggctaaant ttatgtatac      60
nggttnttca aangngggggg aggggggggg gcatccatnt anncncncca ggtttatggn     120 gggntntttnt actattanna ntttctncctt caaancnaag gnttntcaaa tcatnaaaat    180
tattaanatt ncngctgnta aaaaaangaa tgaaccnncn nanganagga nntttcatgg     240
ggggnatgca tcggggnann ccnaanaacc ncggggccat tcccganagg cccaaaaaat     300
gtttnnnnaa aagggtaaa nttacccccn tnaantttat annnnaaann nnannnnagc      360
ccaannnttn nnnnnnnnnn nnnccnnnna nnnnnn                               396

<210> SEQ ID NO 28
<211> LENGTH: 396
<212> TYPE: DNA
<213> ORGANISM: Homo sapiens
<220> FEATURE:
<221> NAME/KEY: misc_feature
<222> LOCATION: 278, 283, 298, 309, 326, 331, 338, 351, 355, 356, 357,
      358, 360, 371, 377, 378, 383, 386, 387, 391, 393, 394, 395
<223> OTHER INFORMATION: n = A,T,C or G

<400> SEQUENCE: 28
cgaccttttt tttttttttt atagatgaaa gagggtttat ttattaatat atgatagcct      60
tggctcaaaa aagacaaatg agggctcaaa aaggaattac agtaacttta aaaaatatat    120
taaacatatc caagatccta aatatattat tctccccaaa agctagctgc ttccaaactt    180
gatttgatat tttgcatgtt ttccctacgt tgcttggtaa atatatttgc ttctcctttc    240
tgcaatcgac gtctgacagc tgattttgc tgttttgnca acntgacgtt tcaccttntg     300
tttcaccant tctggaggaa ttgttnaaca ncttacanca ctgccttgaa naaannnnan    360
gcctcaaaag ntcttgnnct atnctnnttc ntnnnt                              396

<210> SEQ ID NO 29
<211> LENGTH: 396
<212> TYPE: DNA
<213> ORGANISM: Homo sapiens
<220> FEATURE:
<221> NAME/KEY: misc_feature
<222> LOCATION: 329, 334, 361, 386, 390
<223> OTHER INFORMATION: n = A,T,C or G

<400> SEQUENCE: 29
gacttgctca tttagagttt gcaggaggct ccatactagg ttcagtctga aagaaatctc      60
ctaatggtgc tatagagagg gaggtaacag aaagactctt ttagggcatt tttctgactc    120
atgaaaagag cacagaaaag gatgtttggc aatttgtctt ttaagtctta accttgctaa    180

```
tgtgaatact gggaaagtga ttttttcctc actcgttttt gttgctccat tgtaaagggc    240
ggaggtcagt cttagtggcc ttgagagttg cttttggcat ttaaatattc taagagaatt    300
aactgtattt cctgtcacct attcactant gcangaaata tacttgctcc aaataagtca    360
ntatgagaag tcactgtcaa tgaaanttgn tttgtt                              396
```

<210> SEQ ID NO 30
<211> LENGTH: 396
<212> TYPE: DNA
<213> ORGANISM: Homo sapiens
<220> FEATURE:
<221> NAME/KEY: misc_feature
<222> LOCATION: 28, 83, 126, 138, 254, 275, 298, 310, 311, 353, 363,
      374, 379, 393
<223> OTHER INFORMATION: n = A,T,C or G

<400> SEQUENCE: 30

```
ttttttttt ttttttttg aaatttanaa acaaatttta tttaagatct gaaatacaat    60
tcctaaaata tcaacttttc canaaaaccg tggctacaca ataatgcatt gcctctatca   120
tgttanaacg tgcattanac tcaaatacaa aaaccatgaa acaaatcacc atccttcaac   180
aatttgagca aagatagaat gcctaagaac aacatagatg gacttgcaga ggatgggctg   240
ttttacttca agcnccataa aaaaaaaaaa gagcncaaat gcattgggtt ttcaggtnta   300
tacattaagn ngaacctttg gcactaggaa tcagggcgtt ttgtcacata gcnttaacac   360
atnttaaaaa attntgtant gtcaaaggga tangaa                            396
```

<210> SEQ ID NO 31
<211> LENGTH: 396
<212> TYPE: DNA
<213> ORGANISM: Homo sapiens
<220> FEATURE:
<221> NAME/KEY: misc_feature
<222> LOCATION: 285, 287, 350, 362, 365, 377, 378, 382, 388, 390, 393
<223> OTHER INFORMATION: n = A,T,C or G

<400> SEQUENCE: 31

```
gacgggccag ggccatctgg aaagggaact cggcttttcc agaacgtggt ggatcatctg    60
tcgggtgtgt ggtgaacacg ttcagttcat cagggcctac gctccgggaa ggggccccca   120
gctgtggctc tgccatgccg ggctgtgttt gcagctgtcc gagtctccat ccgcctttag   180
aaaaccagcc acttcttttc ataagcactg acagggccca gcccacagcc acaggtgcga   240
tcagtgcctc acgcaggcaa atgcactgaa acccaggggc acacncncgc agagtgaaca   300
gtgagttccc ccgacagccc acgacagcca ggactgccct ccccaccccn ccccgacccc   360
angancacgg cacacanntc ancctctnan ctngct                            396
```

<210> SEQ ID NO 32
<211> LENGTH: 396
<212> TYPE: DNA
<213> ORGANISM: Homo sapiens
<220> FEATURE:
<221> NAME/KEY: misc_feature
<222> LOCATION: 341
<223> OTHER INFORMATION: n = A,T,C or G

<400> SEQUENCE: 32

```
cgactggcct cataccttgt ctacacagtc cctgcacagg gttcctaacc tgtggttagt    60
aaagaatgtc actttctaac aggtctggaa gctccgagtt tatcttggga actcaagagg   120
agaggatcac ccagttcaca ggtatttgag gatacaaacc cattgctggg ctcggcttta   180
```

```
aaagtcttat ctgaaattcc ttgtgaaaca gagtttcatc aaagccaatc caaaaggcct    240
atgtaaaaat aaccattctt gctgcacttt atgcaaataa tcaggccaaa tataagacta    300
cagtttattt acaatttgtt tttaccaaaa atgaggacta nagagaaaaa tggtgctcca    360
aagcttatca tacatttgtc attaagtcct agtctc                              396
```

```
<210> SEQ ID NO 33
<211> LENGTH: 396
<212> TYPE: DNA
<213> ORGANISM: Homo sapiens
<220> FEATURE:
<221> NAME/KEY: misc_feature
<222> LOCATION: 121, 122, 124, 125, 126, 128, 130, 131, 132, 133, 134,
      136, 137, 153, 154, 155, 156, 157, 158, 159, 168, 169, 170, 171,
      172, 173, 174, 175, 176, 177, 178, 179, 184, 185, 192, 197,
      199, 200, 202, 204, 205, 208, 209, 210, 211, 214, 215
<223> OTHER INFORMATION: n = A,T,C or G
<220> FEATURE:
<221> NAME/KEY: misc_feature
<222> LOCATION: 216, 217, 218, 222, 227, 228, 229, 233, 234, 241, 242,
      244, 245, 246, 247, 248, 249, 252, 260, 261, 262, 263, 264, 265,
      270, 272, 273, 274, 275, 279, 282, 284, 288, 290, 291, 292,
      293, 294, 299, 300, 301, 302, 303, 306, 313, 314, 319
<223> OTHER INFORMATION: n = A,T,C or G
<220> FEATURE:
<221> NAME/KEY: misc_feature
<222> LOCATION: 327, 328, 330, 331, 332, 333, 334, 335, 343, 349, 350,
      351, 352, 355, 360, 369, 370, 371, 375, 379, 387, 388, 390, 391,
      392, 393, 394, 395, 396
<223> OTHER INFORMATION: n = A,T,C or G

<400> SEQUENCE: 33
cctttttttt tttttttttt tttttttttt tttttttttt tttttttttt tttttttttt    60
tttttttttt tttttttttt tttttttttt tttttttttt tttttttttt tttttttttt    120
nngnnntntn nnnnannaaa aaaaaaaaaa aannnnnnna aaaaaaaann nnnnnnnnnt    180
tttnnggggg gnttttnann gnannttnnn nttnnnnnaa anccccnnng ggnnggggg     240 nntnnnnnng gnaaaaaaan nnnnngggn cnnnngggnc cncnccncan nnnnaaaann    300
nnnggntttt ttnnttttna aaaaaanngn nnnnnaacaa aantttttnn nnaantttttn  360 gggggaaann ncccntttnt tttttttnnan nnnnnn                            396
```

```
<210> SEQ ID NO 34
<211> LENGTH: 396
<212> TYPE: DNA
<213> ORGANISM: Homo sapiens
<220> FEATURE:
<221> NAME/KEY: misc_feature
<222> LOCATION: 8, 60, 72, 123, 128, 155, 172, 198, 207, 246, 305, 325,
      348, 349, 369, 371, 380, 393, 394
<223> OTHER INFORMATION: n = A,T,C or G

<400> SEQUENCE: 34
acggaccnag ctggaggagc tgggtgtggg gtgcgttggg ctggtgggga ggcctagttn    60
gggtgcaagt angtctgatt gagcttgtgt tgtgctgaag ggacagccct gggtctaggg    120
ganagagncc ctgagtgtga gacccacctt ccccngtccc agccctccc anttccccca    180 gggacggcca cttcctgntc cccgacncaa ccatggctga agaacaaccg caggtcgaat    240
tgttcntgaa ggctggcagt gatggggcca agattgggaa ctgcccattc tcccacagac    300
tgttnatggt actgtggctc aaggnagtca ccttcaatgt taccaccnnt gacaccaaaa    360
ggcggaccna nacagtgcan aagctgtgcc canngg                              396
```

<210> SEQ ID NO 35
<211> LENGTH: 396
<212> TYPE: DNA
<213> ORGANISM: Homo sapiens

<400> SEQUENCE: 35

| | | | | | |
|---|---|---|---|---|---|
| tcgaccaaaa | tcaaatctgg | cactcacaag | ccctggccga | cccccaatgg | gttttaccac | 60 |
| tcccccctcta | gaccctgtct | tgcaaaatcc | tctccctagc | cagctagtat | tttctgggct | 120 |
| aaagactgta | caaccagttc | ctccatttta | tagaagttta | ctcactccag | gggaaatggt | 180 |
| gagtcctcca | acctcccttt | caaccagtcc | catcattcca | accagtggta | ccatagagca | 240 |
| gcaccccccg | ccaccctctg | agccagtagt | gccagcagtg | atgatggcca | cccatgagcc | 300 |
| cagtgctgac | ctggcaccca | agaaaaagcc | caggaagtca | agcatgcctg | tgaagattga | 360 |
| gaaggaaatt | attgataccg | ccgatgagtt | tgatga | | | 396 |

<210> SEQ ID NO 36
<211> LENGTH: 396
<212> TYPE: DNA
<213> ORGANISM: Homo sapiens

<400> SEQUENCE: 36

| | | | | | |
|---|---|---|---|---|---|
| tcgacgggaa | gagcctgcta | cggtggactg | tgagactcag | tgcactgtcc | tcctcccagc | 60 |
| gaccccacgc | tggaccccct | gccggaccct | ccacccttcg | gccccaagc | ttcccagggg | 120 |
| cttcctttgg | actggactgt | ccctgctcat | ccattctcct | gccaccccca | gacctcctca | 180 |
| gctccaggtt | gccactcct | ctcgccagag | tgatgaggtc | ccggcttctg | ctctccgtgg | 240 |
| cccatctgcc | cacaattcgg | gagaccacgg | aggagatgct | gcttgggggt | cctggacagg | 300 |
| agcccccacc | ctctcctagc | ctggatgact | acgtgaggtc | tatatctcga | ctggcacagc | 360 |
| ccacctctgt | gctggacaag | gccacggccc | agggcc | | | 396 |

<210> SEQ ID NO 37
<211> LENGTH: 396
<212> TYPE: DNA
<213> ORGANISM: Homo sapiens
<220> FEATURE:
<221> NAME/KEY: misc_feature
<222> LOCATION: 376
<223> OTHER INFORMATION: n = A,T,C or G

<400> SEQUENCE: 37

| | | | | | |
|---|---|---|---|---|---|
| cgacggtgtc | agcaactggc | catgccacag | cacataaaga | ttacagtgac | aagaaaaaca | 60 |
| ttgtttgagg | attcctttca | acagataatg | agcttcagtc | cccaagatct | gcgaagacgt | 120 |
| ttgtgggtga | tttttccagg | agaagaaggt | ttagattatg | gaggtgtagc | aagagaatgg | 180 |
| ttctttcttt | tgtcacatga | agtgttgaac | ccaatgtatt | gcctgtttga | atatgcaggg | 240 |
| aaggataact | actgcttgca | gataaacccc | gcttcttaca | tcaatccaga | tcacctgaaa | 300 |
| tattttcgtt | ttattggcag | atttattgcc | atggctctgt | tccatgggaa | aattcataga | 360 |
| cacgggtttt | tctttnccat | tctataagcg | tatctt | | | 396 |

<210> SEQ ID NO 38
<211> LENGTH: 396
<212> TYPE: DNA
<213> ORGANISM: Homo sapiens

<400> SEQUENCE: 38

| | | | | | |
|---|---|---|---|---|---|
| cgaccaaaat | gataaatagc | tttaagaatg | tgctaatgat | aaatgattac | atgtcaattt | 60 |

```
aatgtactta atgtttaata ccttatttga ataattacct gaagaatata ttttttagta    120
ctgcatttca ttgattctaa gttgcactt tt accccccat actgttaaca tatctgaaat    180
cagaatgtgt cttacaatca gtgatcgttt aacattgtga caaagtttaa tggacagttt    240
tttcccatat gtatatataa aataatgtgt tttacaatca gtggcttaga ttcagtgaaa    300
tacagtaatt cattcaatta tgatagtatc tttacagaca ttttaaaaat aagttatttt    360
tatatgctaa tattctatgt tcaagtggaa tttgga                              396
```

<210> SEQ ID NO 39
<211> LENGTH: 396
<212> TYPE: DNA
<213> ORGANISM: Homo sapiens

<400> SEQUENCE: 39

```
tcgaccaaga atagatgctg actgtactcc tcccaggcgc ccttccccc tccaatccca     60 ccaaccctca gagccacccc taaagagata ctttgatatt ttcaacgcag ccctgctttg    120
ggctgccctg gtgctgccac acttcaggct cttctccttt cacaaccttc tgtggctcac    180 agaaccttg gagccaatgg agactgtctc aagagggcac tggtggcccg acagcctggc    240
acagggcaag tgggacaggg catggccagg tggccactcc agaccctgg cttttcactg     300 ctggctgcct tagaaccttt cttacattag cagtttgctt tgtatgcact ttgttttttt    360
ctttgggtct tgtttttttt ttccacttag aaattg                              396
```

<210> SEQ ID NO 40
<211> LENGTH: 396
<212> TYPE: DNA
<213> ORGANISM: Homo sapiens
<220> FEATURE:
<221> NAME/KEY: misc_feature
<222> LOCATION: 200, 375
<223> OTHER INFORMATION: n = A,T,C or G

<400> SEQUENCE: 40

```
tttttttttt ttttgttatt tagtttttat ttcataatca taaacttaac tctgcaatcc     60
agctaggcat gggagggaac aaggaaaaca tggaacccaa agggaactgc agcgagagca    120
caaagattct aggatactgc gagcaaatgg ggtggagggg tgctctcctg agctacagaa    180
ggaatgatct ggtggttaan ataaaacaca agtcaaactt attcgagttg tccacagtca    240
gcaatggtga tcttcttgct ggtcttgcca ttcctggacc caaagcgctc catggcctcc    300
acaatattca tgccttcttt cactttgcca aacaccacat gcttgccatc caaccactca    360
gtcttggcag tgcanatgaa aaactgggaa ccattt                              396
```

<210> SEQ ID NO 41
<211> LENGTH: 396
<212> TYPE: DNA
<213> ORGANISM: Homo sapiens
<220> FEATURE:
<221> NAME/KEY: misc_feature
<222> LOCATION: 288
<223> OTHER INFORMATION: n = A,T,C or G

<400> SEQUENCE: 41

```
tcgacctctt gtgtagtcac ttctgattct gacaatcaat caatcaatgg cctagagcac     60
tgactgttaa cacaaacgtc actagcaaag tagcaacagc tttaagtcta aatacaaagc    120
tgttctgtgt gagaattttt taaaaggcta cttgtataat aaccttgtc attttttaatg    180 tacaaaacgc tattaagtgg cttagaattt gaacatttgt ggtctttatt tactttgctt    240
```
cgtgtgtggg caaagcaaca tcttccctaa atatatatta cccaaagnaa aagcaagaag    300
ccagattagg ttttgacaa aacaaacagg ccaaaagggg gctgacctgg agcagagcat    360
ggtgagaggc aaggcatgag agggcaagtt tgttgt                              396

<210> SEQ ID NO 42
<211> LENGTH: 396
<212> TYPE: DNA
<213> ORGANISM: Homo sapiens
<220> FEATURE:
<221> NAME/KEY: misc_feature
<222> LOCATION: 65, 68, 69, 71, 72, 75, 77, 79, 82, 85, 86, 87, 89, 90,
      97, 98, 105, 107, 109, 112, 117, 121, 122, 124, 126, 149, 152,
      153, 155, 157, 161, 163, 167, 168, 169, 174, 177, 178, 179,
      180, 186, 188, 192, 201, 202, 207, 208, 215, 217, 220
<223> OTHER INFORMATION: n = A,T,C or G
<220> FEATURE:
<221> NAME/KEY: misc_feature
<222> LOCATION: 225, 230, 242, 243, 247, 250, 259, 263, 271, 272, 279,
      284, 295, 298, 299, 308, 309, 312, 323, 342, 348, 351, 363, 366,
      370, 386, 390, 392
<223> OTHER INFORMATION: n = A,T,C or G

<400> SEQUENCE: 42 ctttttttt tttttttttt tttttttttt tttttttttt tttttttttt tttttttttt    60
aaaanccnna nnaananang gnaannnann aaaaaannca aaccncntnt anaaaangcc    120
nntntnaggg gggggggttca aaaccaaang gnngntngga ngnaaannna aaanttnnnn    180 ggggggnanaa anaaaaaggg nngaaanntg acccnanaan gaccngaaan cccgggaaac    240
cnngggntan aaaaaaagnt gancccctaaa nnccccccgna aaangggga agggnaannc    300 caaatccnnt gngggttggg ggngggggaaa aaaaaaaccc cnaaaaantg naaaaaaccg    360
ggnttnaaan atttgggttc ggggggntttn tnttaa                            396

<210> SEQ ID NO 43
<211> LENGTH: 396
<212> TYPE: DNA
<213> ORGANISM: Homo sapiens
<220> FEATURE:
<221> NAME/KEY: misc_feature
<222> LOCATION: 108, 195, 213, 279, 287, 349
<223> OTHER INFORMATION: n = A,T,C or G

<400> SEQUENCE: 43
tttttttttt ttttgcttca ctgctttatt tttgaaatca caagcaattc aaagtgatca    60
tcattgaggc ttctgttaaa agttcttcca agttgccca gttttaanat taaacaatat    120
tgcactttaa gatgaactaa cttttgggat tctcttcaaa gaaggaaagt attgctccat    180
ctgtgctttt cttanactaa aagcatactg canaaaactc tattttaaaa atcaacactg    240
cagggtacag taacatagta aagtacctgc ctatttttana atcctanaga acatttcatt    300
gtaagaaact agcccattat ttaagtgtcc acagtatttt tcatttcant ggtccaagat    360
gccaaggttt ccaaacacaa tcttgttctc taatac                             396

<210> SEQ ID NO 44
<211> LENGTH: 396
<212> TYPE: DNA
<213> ORGANISM: Homo sapiens

<400> SEQUENCE: 44
gacctagttt tacctcttaa atatctctgt tccttctaa gttgtttgct gtgttttctt    60
cagagcaaga aggttatatt ttttaaaatt tacttagtaa tgcacattca aaacacacat    120

```
caagtcttca ggataaagtt caaaaccgct gtcatggccc catgtgatct ctccctcccc      180 taccccctcta tcatttagtt tcttctgcgc aagccactct ggcttccttt cagttttgtg     240
gttcccgttt ttagctagtt cagtggtttt caatgggcat ttcttgcctt tttttttcta     300
aacgacaaat agaaatacat cttctttatt atcctccaaa tccaattcag aggtaatatg     360
ctccacctac acacaatttt agaaataaat taaaaa                                396
```

<210> SEQ ID NO 45
<211> LENGTH: 396
<212> TYPE: DNA
<213> ORGANISM: Homo sapiens
<220> FEATURE:
<221> NAME/KEY: misc_feature
<222> LOCATION: 18, 19, 22, 39, 40, 43, 62, 84, 90, 99, 103, 104, 105,
    117, 120, 123, 128, 134, 139, 141, 142, 143, 144, 145, 182, 187,
    207, 218, 219, 242, 247, 257, 260, 263, 272, 276, 277, 279,
    284, 288, 294, 296, 297, 305, 310, 314, 319, 320, 322
<223> OTHER INFORMATION: n = A,T,C or G
<220> FEATURE:
<221> NAME/KEY: misc_feature
<222> LOCATION: 364, 366, 376, 378, 381, 387, 388, 396
<223> OTHER INFORMATION: n = A,T,C or G

<400> SEQUENCE: 45

```
tttttttttt ttttaaannt tntaaatttt taatgaaann ganttagaac aatgtattat      60
tnacatgtaa ataaaaaaag agancataan ccccatatnc tcnnnaaagg aaggganacn     120
gcnggccntt tatnagaana nnnnncatat aagaccccat taagaagaat ctggatctaa     180
anacttncaa acaggagttc acagtangtg aacagcannc cctaatccca ctgatgtgat     240
gnttcanata aaatcancan cgntgatcgg gnatcnnanc aatntgancg gaanannact    300
gctcnatatn tttnaggann cngatgtggt cattttttac aaagataatg gccacaccct    360
tccngnccga atcgancnga nctcccnntt ctgtgn                                396
```

<210> SEQ ID NO 46
<211> LENGTH: 396
<212> TYPE: DNA
<213> ORGANISM: Homo sapiens
<220> FEATURE:
<221> NAME/KEY: misc_feature
<222> LOCATION: 24, 105, 144, 188, 190, 214, 317, 369, 371, 378
<223> OTHER INFORMATION: n = A,T,C or G

<400> SEQUENCE: 46

```
tttttttttt ttttttttttc tganacagag tctcattctg ttgcctaggc tggattgcag      60
tggtgccatc tcggctcact gcaacctccg cctcctgggt tccanaaatt ctcctgcctc     120
agcctcccgg gtagctggga ctanaggcac acgccaccac gccaggctaa tttttatatt    180
tttagtanan atggcgtttc accatgttga ccanactgat ctcgaactcc cgacctcgtg    240 atccaccac ctcggcctcc caaagtgctg ggattacagg cgtgaaacca ccaggcccgg    300
cctgaaatat ctatttnttt tcagattatt tttaaaattc catttgatga atcttttaaa    360
gtgagctana naaagtgngt gtgtacatgc acacac                                396
```

<210> SEQ ID NO 47
<211> LENGTH: 396
<212> TYPE: DNA
<213> ORGANISM: Homo sapiens
<220> FEATURE:
<221> NAME/KEY: misc_feature
<222> LOCATION: 290
<223> OTHER INFORMATION: n = A,T,C or G

<400> SEQUENCE: 47

```
tttttttttt ttttttttgct gttgccaact gtttattcag ggccctgaac gggtggtgcg      60
tggacatgca acacactcgg gcccacagca gcgtgaccgg ccgctcccaa gccccgggcg     120
cacaaccaca gccaggagca gccctgcca ccactgggcc accgtccagg gccccacagg     180
accagccgaa ggtgccccgg gccgaggcca gctgggtcag gtgtacccct agcctggggt     240
tgagtgagga gcggcacccc cagtatcctg tgtaccccaa gttgcccagn aggccgaggg     300
ggccttgggc tccatctgca ctggccaccc cgtgccaagc atcacagctg cgtgagcagg     360
tttgtgtgtg agcgtgtggc ggggcctggt tgtccc                               396
```

<210> SEQ ID NO 48
<211> LENGTH: 396
<212> TYPE: DNA
<213> ORGANISM: Homo sapiens
<220> FEATURE:
<221> NAME/KEY: misc_feature
<222> LOCATION: 393, 396
<223> OTHER INFORMATION: n = A,T,C or G

<400> SEQUENCE: 48

```
ctgggcctgt gccgaagggt ctgggcagat cttccaaaga tgtacaaaat gtagaaattg      60
ccctcaagca aatgcaaaga tgctcaacac ccttagtcat caagaaaatg caaatggaat     120
ccacagagag atactgcaca ctgacaaaga tggtcgtatt actaaaggtg aataaccagc     180
gcgggggca cgtggagtca ctggaacatt tgtgcaatgc tggtgggaat gtcaacccgt     240
gcggccctct ggaataagcc tggcagctcc tccaagagtt accgtgtga cccagcaatt      300
ccactcctag ctccacccac aggaattgaa agcaaagacg caaacagatg cctgtgcacc     360
aaagttcacg gcagcatcct tcgccatagt ggnaan                               396
```

<210> SEQ ID NO 49
<211> LENGTH: 396
<212> TYPE: DNA
<213> ORGANISM: Homo sapiens
<220> FEATURE:
<221> NAME/KEY: misc_feature
<222> LOCATION: 32, 40, 44, 64, 70, 83, 87, 92, 104, 115, 118, 125, 127,
      130, 137, 155, 168, 171, 173, 175, 192, 201, 206, 208, 218,
      219, 235, 247, 249, 256, 259, 260, 269, 297, 306, 310, 320,
      321, 328, 331, 345, 356, 381, 389, 395
<223> OTHER INFORMATION: n = A,T,C or G

<400> SEQUENCE: 49

```
accccaaaat gggaaaggaa aagactcata tnaacattgn cgtnattgga cacgtacatt      60
cggncaagtn caccactact ggncatntga tntataaatg cggnggcatc gacanaanaa     120
ccatngnaan atttganaag gaggctgctg atatnggaaa gggctccntc nantntgcct     180
gggtcttgga tnaactgaaa nctgancntg aacgtggnnt caccattgat atctncttgt     240
ggaaatntna gaccancann tactatgtna ctatcattga tgccccagga cacaganact     300
ttatcnaaan catgattacn nggacatnta nagctgactg tgctngcctg attgtngctg     360
ctggtgttgg tgaatttgaa nctggtatnt ccaana                               396
```

<210> SEQ ID NO 50
<211> LENGTH: 396
<212> TYPE: DNA
<213> ORGANISM: Homo sapiens

<400> SEQUENCE: 50

```
cgacttcttg ctggtgggtg gggcagtttg gtttagtgtt atactttggt ctaagtattt      60
gagttaaact gctttttgc taatgagtgg gctggttgtt agcaggtttg tttttcctgc       120
tgttgattgt tactagtggc attaactttt agaattgggg ctggtgagat taattttttt     180
taatatccca gctagagata tggcctttaa ctgacctaaa gaggtgtgtt gtgatttaat      240
tttttcccgt tccttttttct tcagtaaacc caacaatagt ctaaccttaa aaattgagtt    300
gatgtcctta taggtcacta cccctaaata aacctgaagc aggtgttttc tcttggacat     360
actaaaaaat acctaaaagg aagcttagat gggctg                               396

<210> SEQ ID NO 51
<211> LENGTH: 396
<212> TYPE: DNA
<213> ORGANISM: Homo sapiens
<220> FEATURE:
<221> NAME/KEY: misc_feature
<222> LOCATION: 18, 52, 59, 148, 267, 321, 332
<223> OTHER INFORMATION: n = A,T,C or G

<400> SEQUENCE: 51
tttttttttt ttcagcgngg atttatttta tttcattttt tactctcaag anaagaana      60 gttactattg caggaacaga cattttttta aaaagcgaaa ctcctgacac ccttaaaaca     120
gaaaacattg ttattcacat aataatgngg ggctctgtct ctgccgacag gggctgggtt    180
cgggcattag ctgtgccgtc gacaatagcc ccattcaccc cattcataaa tgctgctgct    240
acaggaaggg aacagcggct ctcccanaga gggatccacc ctggaacacg agtcacctcc   300
aaagagctgc gactgtttga naatctgcca anaggaaaac cactcaatgg gacctggata   360
acccaggccc gggagtcata gcaggatgtg gtactt                              396

<210> SEQ ID NO 52
<211> LENGTH: 396
<212> TYPE: DNA
<213> ORGANISM: Homo sapiens
<220> FEATURE:
<221> NAME/KEY: misc_feature
<222> LOCATION: 81, 189
<223> OTHER INFORMATION: n = A,T,C or G

<400> SEQUENCE: 52
acctcgctaa gtgttcgcta cgcggggcta ccggatcggt cggaaatggc agaggtggag      60
gagacactga agcgactgca nagccagaag ggagtgcagg gaatcatcgt cgtgaacaca    120
gaaggcattc ccatcaagag caccatggac aaccccacca ccacccagta tgccagcctc    180
atgcacagnt tcatcctgaa ggcacggagc ccgtgcgtg acatcgaccc ccagaacgat    240
ctcaccttcc ttcgaattcg ctccaagaaa aatgaaatta tggttgcacc agataaagac  300
tatttcctga ttgtgattca gaatccaacc gaataagcca ctctcttggc tccctgtgtc   360
attccttaat ttaatgcccc ccaagaatgt taatgt                              396

<210> SEQ ID NO 53
<211> LENGTH: 396
<212> TYPE: DNA
<213> ORGANISM: Homo sapiens
<220> FEATURE:
<221> NAME/KEY: misc_feature
<222> LOCATION: 224, 225, 228, 235, 240, 246, 257, 266, 274, 279, 281,
      282, 283, 285, 287, 288, 290, 291, 292, 293, 294, 295, 296, 297,
      300, 301, 303, 307, 311, 313, 314, 317, 318, 319, 320, 321,
      323, 324, 328, 329, 330, 336, 337, 338, 339, 340, 341
<223> OTHER INFORMATION: n = A,T,C or G
```

<220> FEATURE:
<221> NAME/KEY: misc_feature
<222> LOCATION: 342, 343, 344, 345, 346, 347, 348, 349, 350, 351, 352,
      356, 357, 358, 359, 362, 363, 364, 365, 366, 367, 373, 380, 381,
      382, 385, 387, 388, 389, 390, 392
<223> OTHER INFORMATION: n = A,T,C or G

<400> SEQUENCE: 53
tttttttttt tttttttttt tttttttttt tttttttttt tttttttttt tttttttttt      60
tttttttttt tttttttttt tttttttttt tttttttttt tttttttttt tttttttttt     120
tttttttttt tttttttttt tttttttttt tttttttttt tttttttttt tttttttttt     180
tttttttttt tttttttttt tttttttttt tttttttttt ttannttntt ttttnttttn     240
cctttntttt aattcanaaa aagaanaaga aaanataana nnnancnnan nnnnnnnatn     300
ntncttnata ntnnttnnnn nannggnnnn gcgagnnnnn nnnnnnnnnn nntctnnnnt     360
tnnnnnnctt gcncccttn nnttngnnnn angcaa                               396

<210> SEQ ID NO 54
<211> LENGTH: 396
<212> TYPE: DNA
<213> ORGANISM: Homo sapiens
<220> FEATURE:
<221> NAME/KEY: misc_feature
<222> LOCATION: 367
<223> OTHER INFORMATION: n = A,T,C or G

<400> SEQUENCE: 54
ctcttggggc tgctgggact cgcgtcggtt ggcgactccc ggacgtaggt agtttgttgg      60
gccgggttct gaggccttgc ttctctttac ttttccactc taggccacga tgccgcagta     120
ccagacctgg gaggagttca gccgcgctgc cgagaagctt tacctcgctg accctatgaa     180
ggcacgtgtg gttctcaaat ataggcattc tgatgggaac ttgtgtgtta aagtaacaga     240
tgatttagtt tgtttggtgt ataaaacaga ccaagctcaa gatgtaaaga agattgagaa     300
attccacagt caactaatgc gacttatggt agccaaggaa gcccgcaatg ttaccatgga     360
aactgantga atggtttgaa atgaagactt tgtcgt                              396

<210> SEQ ID NO 55
<211> LENGTH: 396
<212> TYPE: DNA
<213> ORGANISM: Homo sapiens

<400> SEQUENCE: 55
cgacggtttg ccgccagaac acaggtgtcg tgaaaactac ccctaaaagc caaaatggga      60
aaggaaaaga ctcatatcaa cattgtcgtc attggacacg tagattcggg caagtccacc     120
actactggcc atctgatcta taaatgcggt ggcatcgaca aaagaaccat tgaaaaattt     180
gagaaggagg ctgctgagat gggaaagggc tccttcaagt atgcctgggt cttggataaa     240
ctgaaagctg agcgtgaacg tggtatcacc attgatatct ccttgtggaa atttgagacc     300
agcaagtact atgtgactat cattgatgcc ccaggacaca gagactttat caaaaacatg     360
attacaggga catctcaggc tgactgtgct gtcctg                              396

<210> SEQ ID NO 56
<211> LENGTH: 396
<212> TYPE: DNA
<213> ORGANISM: Homo sapiens
<220> FEATURE:
<221> NAME/KEY: misc_feature
<222> LOCATION: 134, 145, 255, 279, 337, 344, 369

<223> OTHER INFORMATION: n = A,T,C or G

<400> SEQUENCE: 56

```
tttttttttt ttttttctca tttaacttttt ttaatgggtc tcaaaattct gtgacaaatt      60
tttggtcaag ttgtttccat taaaaagtac tgattttaaa aactaataac ttaaaactgc     120
cacacgcaaa aaanaaaacc aaagnggtcc acaaaacatt ctcctttcct tctgaaggtt     180
ttacgatgca ttgttatcat taaccagtct tttactacta aacttaaatg gccaattgaa     240
acaaacagtt ctganaccgt tcttccacca ctgattaana gtggggtggc aggtattagg     300
gataatattc atttagcctt ctgagctttc tgggcanact tggngacctt gccagctcca     360
gcagccttnt tgtccactgc tttgatgaca cccacc                               396
```

<210> SEQ ID NO 57
<211> LENGTH: 396
<212> TYPE: DNA
<213> ORGANISM: Homo sapiens
<220> FEATURE:
<221> NAME/KEY: misc_feature
<222> LOCATION: 52, 57, 58, 61, 72, 75, 77, 84, 87, 88, 93, 100, 101,
      111, 117, 119, 121, 131, 132, 133, 134, 142, 143, 154, 156, 159,
      167, 168, 170, 175, 176, 182, 183, 185, 186, 190, 192, 194,
      198, 199, 200, 209, 212, 217, 218, 220, 232, 235, 253
<223> OTHER INFORMATION: n = A,T,C or G
<220> FEATURE:
<221> NAME/KEY: misc_feature
<222> LOCATION: 255, 257, 258, 260, 262, 263, 270, 271, 273, 277, 280,
      281, 284, 285, 289, 296, 297, 298, 303, 305, 307, 309, 310, 317,
      322, 324, 337, 338, 342, 344, 346, 347, 349, 351, 356, 358,
      366, 368, 371, 377, 380, 388, 389, 393, 396
<223> OTHER INFORMATION: n = A,T,C or G

<400> SEQUENCE: 57

```
cctttttttt tttttttttt tttttttttt tttttttttt tttttttttt tnaaaanntt      60
nttttttgcaa anccnancaa aaanggnngg aangaaaaan nggaaaaatt nttttttncnt   120
ntttgggaac nnnnagcect tnntttgaaa aaangnggnc ttaaaanngn tgaannaaag    180
gnnanncccn gntncttnnn tttaaaaana anggggnngn ttttttttaa anaanatttt    240
ttttttccct aanancnncn anntgaaacn ngncccnacn nctnncttna aagggnnnaa    300
atnanangnn aaaaaancec tnancccccc ccctttannt tncnannana naaagncntt    360
ttgggncntg naaaaanaan cctttttnnt gcnttn                              396
```

<210> SEQ ID NO 58
<211> LENGTH: 396
<212> TYPE: DNA
<213> ORGANISM: Homo sapiens

<400> SEQUENCE: 58

```
cgacctcaaa tatgccttat tttgcacaaa agactgccaa ggacatgacc agcagctggc      60
tacagcctcg atttatattt ctgtttgtgg tgaactgatt ttttttaaac caaagtttag    120
aaagaggttt tgaaatgcc tatggttct tgaatggta aacttgagca tcttttcact       180
ttccagtagt cagcaaagag cagtttgaat tttcttgtcg cttcctatca aaatattcag    240
agactcgagc acagcaccca gacttcatgc gcccgtggaa tgctcaccac atgttggtcg    300
aagcggccga ccactgactt tgtgacttag gcggctgtgt tgcctatgta gagaacacgc    360
ttcaccccca ctccccgtac agtgcgcaca ggcttt                              396
```

<210> SEQ ID NO 59
<211> LENGTH: 396

```
<212> TYPE: DNA
<213> ORGANISM: Homo sapiens
<220> FEATURE:
<221> NAME/KEY: misc_feature
<222> LOCATION: 25, 45, 116, 178, 198, 211, 225, 235, 253, 266, 281,
      324, 367, 377, 389
<223> OTHER INFORMATION: n = A,T,C or G

<400> SEQUENCE: 59 ctttttttt tttttttttt tcagnggaaa ataactttta ttganacccc accaactgca      60
aaatctgttc ctggcattaa gctccttctt cctttgcaat tcggtctttc ttcagnggtc    120
ccatgaatgc tttcttctcc tccatggtct ggaagcggcc atggccaaac ttggaggngg    180
tgtcaatgaa cttaaggnca atcttctcca nagcccgccg cttcntctgc accancaagg    240
acttgcggag ggngagcacc cgcttnttgg ttcccaccac ncagcctttc agcatgacaa    300
agtcattggt cacttcacca tagnggacaa agccacccaa agggttgatg ctccttggca    360
aataggncat agtcacngga ggcattgtnc ttgatc                              396

<210> SEQ ID NO 60
<211> LENGTH: 396
<212> TYPE: DNA
<213> ORGANISM: Homo sapiens

<400> SEQUENCE: 60
acctcagctc tcggcgcacg gcccagcttc cttcaaaatg tctactgttc acgaaatcct     60
gtgcaagctc agcttggagg gtgatcactc tacaccccca agtgcatatg ggtctgtcaa    120
agcctatact aactttgatg ctgagcggga tgctttgaac attgaaacag ccatcaagac    180
caaaggtgtg gatgaggtca ccattgtcaa cattttgacc aaccgcagca atgcacagag    240
acaggatatt gccttcgcct accagagaag gaccaaaaag gaacttgcat cagcactgaa    300
gtcagcctta tctggccacc tggagacggt gattttgggc ctattgaaga cacctgctca    360
gtatgacgct tctgagctaa aagcttccat gaaggg                              396

<210> SEQ ID NO 61
<211> LENGTH: 396
<212> TYPE: DNA
<213> ORGANISM: Homo sapiens

<400> SEQUENCE: 61
tagcttgtcg gggacggtaa ccgggacccg gtgtctgctc ctgtcgcctt cgcctcctaa     60
tccctagcca ctatgcgtga gtgcatctcc atccacgttg gccaggctgg tgtccagatt    120
ggcaatgcct gctgggagct ctactgcctg gaacacggca tccagcccga tggccagatg    180
ccaagtgaca agaccattgg gggaggagat gactccttca acaccttctt cagtgagacg    240
ggcgctggca agcacgtgcc ccgggctgtg tttgtagact tggaacccac agtcattgat    300
gaagttcgca ctggcaccta ccgccagctc ttccaccctg agcagctcat cacaggcaag    360
gaagatgctg ccaataacta tgcccgaggg cactac                              396

<210> SEQ ID NO 62
<211> LENGTH: 396
<212> TYPE: DNA
<213> ORGANISM: Homo sapiens
<220> FEATURE:
<221> NAME/KEY: misc_feature
<222> LOCATION: 261, 269, 313, 333, 346, 354, 359, 390, 394, 395, 396
<223> OTHER INFORMATION: n = A,T,C or G

<400> SEQUENCE: 62
```

```
tcgacgtttc ctaaagaaaa ccactctttg atcatggctc tctctgccag aattgtgtgc      60
actctgtaac atctttgtgg tagtcctgtt ttcctaataa ctttgttact gtgctgtgaa     120
agattacaga tttgaacatg tagtgtacgt gctgttgagt tgtgaactgg tgggccgtat     180
gtaacagctg accaacgtga agatactggt acttgatagc ctcttaagga aaatttgctt     240
ccaaatttta agctggaaag ncactggant aactttaaaa aagaattaca atacatggct     300
ttttagaatt tcnttacgta tgttaagatt tgngtacaaa ttgaantgtc tgtnctganc     360
ctcaaccaat aaaatctcag tttatgaaan aaannn                              396

<210> SEQ ID NO 63
<211> LENGTH: 396
<212> TYPE: DNA
<213> ORGANISM: Homo sapiens
<220> FEATURE:
<221> NAME/KEY: misc_feature
<222> LOCATION: 3, 11, 16, 18, 23, 26, 30, 34, 37, 50, 51, 60, 61, 62,
      63, 64, 75, 82, 83, 84, 85, 87, 89, 93, 94, 97, 98, 99, 118,
      119, 120, 122, 134, 136, 138, 139, 141, 144, 145, 147, 152,
      156, 187, 188, 193, 195, 204, 211, 214, 216, 222, 226
<223> OTHER INFORMATION: n = A,T,C or G
<220> FEATURE:
<221> NAME/KEY: misc_feature
<222> LOCATION: 228, 235, 242, 258, 264, 265, 269, 275, 294, 298, 301,
      307, 316, 326, 334, 335, 339, 340, 343, 350, 351, 355, 373, 378,
      390
<223> OTHER INFORMATION: n = A,T,C or G

<400> SEQUENCE: 63
ttnttttttt nttttntntt ttntcnttgn ttgnacngaa cccggcgctn nttccccacn      60
nnnnacggcc gcccntattc annnntncnt canntannna ccgcaccctc ggactgcnnn     120
tngggccccg ccgncnannc nccnncnccc anttcnccgc cgccgccgcc gcctttttt     180 attggcnncc atnanaaccg gggncacctc ncangngcgc cnaaantngg ggcangactc     240 anaggggggcc atcaaccncc aagnncaanc tggaanctcta caaacggcct acgntttntg     300
nccatgnggg tagggnttta cccgcnatga tgannatgnn aanaactttn ncaanccctt     360
tattaaccaa tgnggtgngg agacggaacn tggtta                               396

<210> SEQ ID NO 64
<211> LENGTH: 396
<212> TYPE: DNA
<213> ORGANISM: Homo sapiens
<220> FEATURE:
<221> NAME/KEY: misc_feature
<222> LOCATION: 175, 177, 340, 393
<223> OTHER INFORMATION: n = A,T,C or G

<400> SEQUENCE: 64
tcgacgtcgg ggtttcctgc ttcaacagtg cttggacgga acccggcgct cgttccccac      60
cccggccggc cgcccatagc cagccctccg tcacctcttc accgcaccct cggactgccc     120
caaggccccc gccgccgctc cagcgccgcg cagccaccgc cgccgccgcc gctntnctt     180 agtcgccgcc atgacgaccg cgtccacctc gcaggtgcgc cagaactacc accaggactc     240
agaggccgcc atcaaccgcc agatcaacct ggagctctac gcctcctacg tttacctgtc     300
catgtcttac tactttgacc gcgatgatgt ggctttgaan aactttgcca aatactttct     360
tcccaatctc atgaggagaa ggaacatgct ganaaa                               396

<210> SEQ ID NO 65
<211> LENGTH: 396
```

```
<212> TYPE: DNA
<213> ORGANISM: Homo sapiens
<220> FEATURE:
<221> NAME/KEY: misc_feature
<222> LOCATION: 26, 56, 103, 122, 145, 151, 154, 187, 189, 203, 224,
      256, 273, 305, 344
<223> OTHER INFORMATION: n = A,T,C or G

<400> SEQUENCE: 65
tttttttttt ttttttttt tttttnacca ataatgcttt tattttccac atcaanatta    60
atttatatgt tagttttagt acaagtacta aaatgtatac ttnttgccct aatagctaag   120
gnatacataa gcttcaccat acatnttgca nccncctgtc tgtcctatgt cattgttata   180
aatgtanana ttttaggaaa ctnttttatt caacctggga catntatact gtaggagtta   240
gcactgacct gatgtnttat ttaaaagtaa tgnatattac ctttacatat attccttata   300
tattnaaacg tatttccatg ttatccagct taaaatcaca tggnggttaa aagcatgagt   360
tctgagtcaa atctggactg aaatcctgat gctccc                            396

<210> SEQ ID NO 66
<211> LENGTH: 396
<212> TYPE: DNA
<213> ORGANISM: Homo sapiens

<400> SEQUENCE: 66 tcgactttt tttttccagg acattgtcat aattttttat tatgtatcaa attgtcttca    60
atataagtta caacttgatt aaagttgata gacatttgta tctatttaaa gacaaaaaaa   120
ttcttttatg tacaatatct tgtctagagt ctagcaaata tagtacctttt cattgcagga   180 tttctgctta ataacaag caaaaacaaa caactgaaaa aatataaacc aaagcaaacc   240
aaaccccccg ctcaactaca aatgtcaata ttgaatgaag cattaaaaga caaacataaa   300
gtaacttcag cttttatcta gcaatgcaga atgaatacta aaattagtgg caaaaaaaca   360
aacaacaaac aacaaacaaa acaaaacaaa caaaca                            396

<210> SEQ ID NO 67
<211> LENGTH: 396
<212> TYPE: DNA
<213> ORGANISM: Homo sapiens

<400> SEQUENCE: 67
acgcttttgt ccttcatttt aactgttatg tcatactgtt atgttgacat atttctttat    60
aagagaatag aggcaaaagt atagaactga ggatcatttg tattttttgag ttggaaatta   120 tgaaacttca ccatattatg atcatacata ttttgaagaa cagactgacc aaagctcacc   180
tgttttttgt gttaggtgct ttggctgaac ttgattccag ccccctttc cctttggtgt    240 tgtgtatgtc tcttcatttc ctctcaaatc ttcaactctt gccccatgtc tccttggcag   300
caggatgctg gcatctgtgt agtcctcata ctgtttacta taacccaca aattcatttt    360 catggcagac ctaagctcag accctgcctt gtcctg                             396

<210> SEQ ID NO 68
<211> LENGTH: 396
<212> TYPE: DNA
<213> ORGANISM: Homo sapiens

<400> SEQUENCE: 68
acctgagtcc tgtcctttct ctctccccgg acagcatgag cttcaccact cgctccacct    60
tctccaccaa ctaccggtcc ctgggctctg tccaggcgcc cagctacggc gcccggccgg   120
```

-continued

```
tcagcagcgc ggccagcgtc tatgcaggcg ctgggggctc tggttcccgg atctccgtgt      180
cccgctccac cagcttcagg ggcggcatgg ggtccggggg cctggccacc gggatagccg      240
ggggtctggc aggaatggga ggcatccaga acgagaagga gaccatgcaa agcctgaacg      300
accgcctggc ctcttacctg gacagagtga ggagcctgga gaccgagaac cggaggctgg      360
agagcaaaat ccgggagcac ttggagaaga agggac                                396
```

<210> SEQ ID NO 69
<211> LENGTH: 396
<212> TYPE: DNA
<213> ORGANISM: Homo sapiens
<220> FEATURE:
<221> NAME/KEY: misc_feature
<222> LOCATION: 1, 4, 6, 8, 9, 11, 18, 19, 36, 53, 60, 64, 79, 84, 92,
    94, 97, 105, 114, 120, 123, 127, 129, 134, 137, 138, 139, 142,
    143, 147, 149, 151, 152, 156, 158, 167, 170, 172, 180, 182,
    184, 187, 188, 189, 194, 197, 201, 209, 212, 218, 219
<223> OTHER INFORMATION: n = A,T,C or G
<220> FEATURE:
<221> NAME/KEY: misc_feature
<222> LOCATION: 220, 222, 223, 225, 228, 229, 230, 232, 233, 236, 242,
    244, 247, 250, 251, 253, 256, 257, 259, 261, 270, 271, 274, 277,
    278, 279, 282, 284, 288, 289, 296, 298, 300, 310, 315, 316,
    320, 321, 324, 328, 330, 331, 334, 336, 340, 347, 350
<223> OTHER INFORMATION: n = A,T,C or G
<220> FEATURE:
<221> NAME/KEY: misc_feature
<222> LOCATION: 352, 353, 355, 359, 361, 362, 364, 367, 370, 372, 374,
    376, 382, 388, 390, 394, 396
<223> OTHER INFORMATION: n = A,T,C or G

<400> SEQUENCE: 69

```
ntcncngnng ntgtggtnnt tttttttaatt tttatntttt ctttttttttt ctngctagcn      60 cttncttttt ttggaattnc ggtnccttt tntntcnatt ttttngacaa aaanaacctn      120
ttntttnana ccanagnnng gnncacncnt nnaatntncc ccttttncgn tngggagctn      180
cncnttnnnc gccnacntca ntcgagacng tncttttnnn tnnancannn tnngtncgtt      240
gncngcnttn ntncannnant nttccctatn nacntgnnnt cncncatnnt tggacnancn      300
cctagccttn ccatnntttn nttntttntn natnancctn gaaaacntcn gnntnttcnc      360
nncnttnccn cncncnccett cntatgtncn atgncn                               396
```

<210> SEQ ID NO 70
<211> LENGTH: 396
<212> TYPE: DNA
<213> ORGANISM: Homo sapiens
<220> FEATURE:
<221> NAME/KEY: misc_feature
<222> LOCATION: 15, 38, 57, 59, 63, 64, 65, 66, 68, 78, 79, 84, 87, 90,
    97, 114, 115, 127, 128, 141, 143, 145, 151, 159, 168, 169, 172,
    173, 176, 178, 197, 198, 207, 209, 211, 215, 220, 221, 223,
    225, 228, 240, 248, 249, 260, 262, 263, 273, 283, 287
<223> OTHER INFORMATION: n = A,T,C or G
<220> FEATURE:
<221> NAME/KEY: misc_feature
<222> LOCATION: 294, 304, 314, 334, 339, 340, 348, 362, 367, 376, 382,
    384, 386, 395
<223> OTHER INFORMATION: n = A,T,C or G

<400> SEQUENCE: 70

```
tttttttttt ttttntttt ttttttttt tttttttntt tttttttttt ttttttntnc      60
aannnntnaa cttttaanng gccnccngcn ccccaanggg gaccctgctt tgnnggcta      120 aatgccnnaa aactttgggg nantnggtat naaacccnc tttgcccnnc annttncngg      180
gggggggggg ttttgnngg ggaacangna naacntttn ncnanggnat caccaaaaan      240
```

```
aaagcccnnc cctttttccn annggggggg ggnggggga aantcancec ccanattgac    300 cttnatttca aaangggct tataatcctg ggcntggann cttccctnta cccggggtt     360 gnccacnttt tattanaggg gnangnggat ccccnt                            396
```

```
<210> SEQ ID NO 71
<211> LENGTH: 396
<212> TYPE: DNA
<213> ORGANISM: Homo sapiens
<220> FEATURE:
<221> NAME/KEY: misc_feature
<222> LOCATION: 15, 21, 30, 33, 35, 36, 42, 43, 44, 45, 46, 51, 56, 58,
      59, 63, 70, 77, 81, 88, 94, 95, 96, 97, 101, 102, 109, 114,
      118, 119, 120, 124, 131, 132, 133, 134, 135, 141, 142, 143,
      144, 145, 146, 148, 149, 154, 158, 162, 164, 166, 172
<223> OTHER INFORMATION: n = A,T,C or G
<220> FEATURE:
<221> NAME/KEY: misc_feature
<222> LOCATION: 177, 179, 181, 184, 185, 213, 216, 218, 219, 222, 223,
      224, 230, 231, 240, 241, 242, 245, 247, 251, 252, 255, 258, 259,
      261, 264, 268, 269, 272, 276, 285, 288, 289, 291, 292, 293,
      297, 299, 300, 307, 312, 315, 316, 317, 325, 329, 334
<223> OTHER INFORMATION: n = A,T,C or G
<220> FEATURE:
<221> NAME/KEY: misc_feature
<222> LOCATION: 340, 341, 347, 350, 354, 355, 357, 360, 361, 367, 368,
      370, 371, 376, 377, 378, 387, 393, 394
<223> OTHER INFORMATION: n = A,T,C or G

<400> SEQUENCE: 71
gcatctagag ggccngttta ntctagaggn ccngnntaaa cnnnnncatc nacctncnnt    60 gncctgctn gttgccncc ntctgtgnct tgcnnnncc nngagcgtnc cttnaccnnn     120
gaangtgcct nnnnnactga nnnnnncnna taanatgngg anantncgtc gncattntnt   180 natnngggt gatgctattc tgggggtgg ggnggngnna tnnnatactn ngggacgtn     240 nnatnangag nnatntcnng nttntctnnt gntttntggg gggcnatnng nnntctntnn   300
ggactcntcg cncannnatc aatancttna ttcngtgtan ngtccgnccn tagnncngcn   360
ngtactnnan ngttgnnntc attactnttc gtnngg                            396
```

```
<210> SEQ ID NO 72
<211> LENGTH: 396
<212> TYPE: DNA
<213> ORGANISM: Homo sapiens
<220> FEATURE:
<221> NAME/KEY: misc_feature
<222> LOCATION: 2, 23, 27, 34, 35, 36, 37, 39, 41, 45, 55, 56, 59, 61,
      88, 92, 96, 97, 98, 101, 103, 104, 106, 108, 111, 114, 115,
      121, 128, 129, 131, 159, 170, 191, 202, 227, 233, 235, 240,
      262, 268, 271, 272, 280, 281, 303, 304, 305, 311, 316, 317
<223> OTHER INFORMATION: n = A,T,C or G
<220> FEATURE:
<221> NAME/KEY: misc_feature
<222> LOCATION: 321, 324, 336, 344, 345, 353, 360, 362, 363, 364, 365,
      366, 370, 373, 389, 391, 392, 394, 395
<223> OTHER INFORMATION: n = A,T,C or G

<400> SEQUENCE: 72 tnttttttt ttctaaaac atnactnttt attnnnnang ntttntgaac ctctnngcnt     60
natggtgaga gtttgtctga ttaataanaa tnggannntt nannanangc ntgnncgcaa   120
ngatggcnnc nctgtatatc ccaccatccc attacactnt gaacctttn tttgattaat   180 aaaaggaagg natgcgggga angggaaag agaatgcttg aacattncca tgngnccttn   240
gacaaacttt ccaatggagg cnggaacnaa nnaccaccan ncaactcccc tttttgtaat  300
ttnnnaactt ncaacnncta nctntttatt ttggcntccc tggnngaaac agnctgtatn  360
```
annnnnaagn ccntgagaac atccctggnt nncnna                              396

<210> SEQ ID NO 73
<211> LENGTH: 396
<212> TYPE: DNA
<213> ORGANISM: Homo sapiens
<220> FEATURE:
<221> NAME/KEY: misc_feature
<222> LOCATION: 1, 7, 9, 14, 23, 35, 38, 44, 48, 50, 61, 74, 76, 79, 80,
      85, 86, 91, 95, 101, 109, 112, 113, 117, 118, 121, 122, 127, 129,
      132, 137, 141, 146, 214, 234, 243, 251, 266, 296, 305, 306, 336
<223> OTHER INFORMATION: n = A,T,C or G

<400> SEQUENCE: 73
ntcaacntng actnctgtga ggnatggtgc tgggngcnta tgcngtgngn ttttggatac    60
naccttatgg acantngcnn tcccnnggaa ngatnataat ncttactgna gnnactnnaa   120
nnttccntnt cnaaaangtt naaaancatt ggatgtgcca caatgatgac agtttatttg   180
ctactcttga gtgctataat gatgaagatc ttanccacca ttatcttaac tgangcaccc   240
aanatggtga nttggggaac atatanagta cacctaagtt cacatgaagt tgtttnttcc   300
caggnnctaa agagcaagcc taactcaagc cattgncaca caggtgagac acctctattt   360
tgtacttctc acttttaagg gattagaaaa tagcca                             396

<210> SEQ ID NO 74
<211> LENGTH: 396
<212> TYPE: DNA
<213> ORGANISM: Homo sapiens
<220> FEATURE:
<221> NAME/KEY: misc_feature
<222> LOCATION: 22, 118
<223> OTHER INFORMATION: n = A,T,C or G

<400> SEQUENCE: 74 ccttttttt tttttttact gngaatatat acttttatt tagtcatttt tgtttacaat     60
tgaaactctg ggaattcaaa attaacatcc ttgcccgtga gcttcttata gacaccanaa   120
aaagtttcaa cctgtgttc cacattgttc tgctgtgctt tgtccaaatg aacctttatg    180
agccggctgc catctagttt gacgcggatt ctcttgccca caatttcgct tgggaagacc   240
aagtcctcaa ggatggcatc gtgcacagct gtcagagtac ggctcctggg acgcttttgc   300
ttattttttg tacggctttt tcgagttggc ttaggcagaa ttctcctctg agcgataaag   360
acgacatgct tcccactgaa cttttttctcc aattcg                            396

<210> SEQ ID NO 75
<211> LENGTH: 396
<212> TYPE: DNA
<213> ORGANISM: Homo sapiens
<220> FEATURE:
<221> NAME/KEY: misc_feature
<222> LOCATION: 14, 38, 41, 43, 47, 53, 73, 75, 78, 83, 96, 112, 113,
      117, 124, 127, 146, 160, 167, 169, 176, 177, 178, 179, 194, 197,
      198, 209, 210, 220, 222, 226, 227, 231, 238, 241, 244, 258,
      259, 260, 270, 271, 274, 288, 301, 302, 305, 307, 316
<223> OTHER INFORMATION: n = A,T,C or G
<220> FEATURE:
<221> NAME/KEY: misc_feature
<222> LOCATION: 319, 328, 339, 344, 347, 354, 359, 364, 367, 369, 370,
      371, 373, 374, 381, 384, 387, 388
<223> OTHER INFORMATION: n = A,T,C or G

<400> SEQUENCE: 75 ttttttttt tttnttttt ttttttttt tttttttnaa ntntaanggg ganggccct       60

-continued

```
tttttttaaa ctngnccntt ttnctttcct tttttnaaaa ggaaaaaaaa anntttnttt      120
ttcnttnaaa aacccttttt cccacnaaca aaaaaaaccn ttccccntnc cttttnnnna      180
aaaaaaaggg gctnggnntt tccccttann caaaaaaccn tntccnnggg naaaaaantt      240
ntcnccgggg gggaaacnnn tgggggtgtn nccnaaattt ggggcctc ggaaggggg         300 nnccncncct aaagangtnt ttcaaaanaa aaacccccnt cctnttntaa aaanaaaana      360
aaanaangnn ngnnttttt ntcnttnncc ccccaa                                396
```

<210> SEQ ID NO 76
<211> LENGTH: 396
<212> TYPE: DNA
<213> ORGANISM: Homo sapiens
<220> FEATURE:
<221> NAME/KEY: misc_feature
<222> LOCATION: 87, 94, 102, 108, 138, 139, 143, 144, 145, 146, 151,
      152, 158, 168, 170, 171, 187, 204, 206, 224, 261, 262, 267, 268,
      270, 287, 305, 306, 313, 315, 319, 320, 330, 331, 333, 342,
      344, 348, 349, 356, 358, 360, 362, 368, 374, 376, 381
<223> OTHER INFORMATION: n = A,T,C or G
<220> FEATURE:
<221> NAME/KEY: misc_feature
<222> LOCATION: 390
<223> OTHER INFORMATION: n = A,T,C or G

<400> SEQUENCE: 76

```
acattcttca gaaatacagt gatgaaaatt cattttgaaa ctcaaatatt ttcattttgg      60
atattctcct gttttatta aaccagngat tacnnctggc cntccctnta aatgttctag      120
gaaggcatgt ctgttgtnnt ttnnnnaaaa nnaaattntt ttttttttngn naaacccaa     180 atcccanttt atcaggaagt tagncnaatg aaatggaaat tggntaatgg acaaaagcta    240
gcttgtaaaa aggaccaccc nnccacnngn ctttacccc ttggttngtt gggggaaaaa      300
ccatnnttaa ccntntggnn aaaattgggn ncntaaagtt tncntggnna acagtncntn    360
cngtattnaa ttgncnttat nggaaaatcn gggatt                              396
```

<210> SEQ ID NO 77
<211> LENGTH: 396
<212> TYPE: DNA
<213> ORGANISM: Homo sapiens
<220> FEATURE:
<221> NAME/KEY: misc_feature
<222> LOCATION: 63, 66, 81, 83, 89, 107, 115, 118, 147, 151, 190, 232,
      275, 288, 294, 304, 323, 332, 369, 392
<223> OTHER INFORMATION: n = A,T,C or G

<400> SEQUENCE: 77

```
tttttttttt tttttttttt tttttttttt tatcaacatt tatatgcttt attgaaagtt     60
ganaanggca acagttaaat ncnggacnc cttacaattg tgtaaanaac atgcncanaa      120
acatatgcat ataactacta tacaggngat ntgcaaaaac ccctactggg aaatccattt    180
cattagttan aactgagcat ttttcaaagt attcaaccag ctcaattgaa anacttcagt    240
gaacaaggat ttacttcagc gtattcagca gctanatttc aaattacnca aagngagtaa    300
ctgngccaaa ttcttaaaat ttntttaggg gnggttttg gcatgtacca gttttatgt      360 aaatctatnt ataaaagtcc acacctcctc anacag                              396
```

<210> SEQ ID NO 78
<211> LENGTH: 396
<212> TYPE: DNA
<213> ORGANISM: Homo sapiens
<220> FEATURE:
<221> NAME/KEY: misc_feature

```
<222> LOCATION: 8, 14, 16, 20, 26, 28, 36, 38, 39, 40, 51, 52, 55, 57,
      58, 67, 71, 114, 120, 132, 138, 142, 159, 165, 169, 172, 174,
      175, 183, 187, 195, 197, 198, 200, 202, 206, 209, 243, 259,
      260, 267, 283, 292, 305, 311, 315, 317, 319, 323, 324
<223> OTHER INFORMATION: n = A,T,C or G
<220> FEATURE:
<221> NAME/KEY: misc_feature
<222> LOCATION: 331, 333, 334, 338, 343, 348, 353, 355, 357, 366, 376,
      388
<223> OTHER INFORMATION: n = A,T,C or G

<400> SEQUENCE: 78
agctggcnaa aggngnatgn gctgcnangc gattangnnn ggtaacgtca nnggntnncc      60
agtgcangac nttgtaaaac gacggccaca tgaattgtaa tacgactcac tatngggcgn    120
attgggccgt gnaggatngt gntcacactc gaatgtatnc tggcngatnc ananngcttt    180
atngctnttg acggngnntn anccanctng ggctttaggg ggtatcccct cgcccctgct    240
tcnttgattt gcacgggcnn ctccganttc cttcataata ccngacgctt cnatccccta    300
gctcngacct ntcantntnt tcnntgggtt ntnnccgntc acngcttncc cgnangntat    360
aatctnggct cctttnggga tccattantc tttact                              396

<210> SEQ ID NO 79
<211> LENGTH: 396
<212> TYPE: DNA
<213> ORGANISM: Homo sapiens
<220> FEATURE:
<221> NAME/KEY: misc_feature
<222> LOCATION: 116, 153, 189, 194, 210, 218, 241, 270, 272, 288, 291,
      304, 324, 325, 329, 333, 334, 338, 340, 342, 366, 372, 377, 384,
      396
<223> OTHER INFORMATION: n = A,T,C or G

<400> SEQUENCE: 79
caccaaccaa aacctggcgc cgttggcatc gtagagtgaa cacaacccaa aaacgatacg      60
ccatctgttc tgcccctggct gcctcagccc taccagcact ggtcatgtct aaaggncatc    120
gtattgagga agttcctgaa cttcctttgg tangttgaag ataaagctga aggctacaag    180
aagaccaang aagntgtttt gctccttaan aaacttanac gcctggaatg atatcaaaaa    240
ngctatgcct ctcagcgaat gagactggan angcaaaatg agaaaccntc nccgcatcca    300 gcgnagggggc cgtgcatctc tatnntgang atnntggnan cnttcaaggc cttcagaacc    360
tccctngaaa tnctctnctt taangaacca aactgn                              396

<210> SEQ ID NO 80
<211> LENGTH: 396
<212> TYPE: DNA
<213> ORGANISM: Homo sapiens
<220> FEATURE:
<221> NAME/KEY: misc_feature
<222> LOCATION: 312, 319, 353, 383
<223> OTHER INFORMATION: n = A,T,C or G

<400> SEQUENCE: 80
tgtacatagg catcttattc actgcaccct gtcacaccca gcaccccccg ccccgcacat      60
tatttgaaag actgggaatt taatggttag ggacagtaaa tctacttctt tttccaggga    120
cgactgtccc ctctaaagtt aaagtcaata caagaaaact gtctattttt agcctaaagt    180
aaaggctgtg aagaaaattc attttacatt gggtagacag taaaaaacaa gtaaataac    240 ttgacatgag cacctttaga tccttcccct catgggcctt tgggcccaga atgacctttg    300
aggcctgtaa anggattgna atttcctata agctgtatag tggagggatt ggngggtcat    360
```
ttgagtaagc cctccaagat acnttcaata cctggg      396

```
<210> SEQ ID NO 81
<211> LENGTH: 396
<212> TYPE: DNA
<213> ORGANISM: Homo sapiens
<220> FEATURE:
<221> NAME/KEY: misc_feature
<222> LOCATION: 240, 286, 361, 364, 374, 375, 379, 380, 381, 387
<223> OTHER INFORMATION: n = A,T,C or G
```

<400> SEQUENCE: 81
gcagctgaag ttcagcaggt gctgaatcga ttctcctcgg cccctctcat tccacttcca      60 accccctccca ttattccagt actacctcag caatttgtgc ccctacaaa tgttagagac     120 tgtatacgcc ttcgaggtct tccctatgca gccacaattg aggacatcct gcatttcctg    180
ggggagttcg ccacagatat tcgtactcat ggggttcaca tggttttgaa tcaccagggn    240
ccgccatcag gagatgcctt tatccagatg aagtctgcgg acagancatt tatggctgca    300
cagaagtggc ataaaaaaaa catgaaggac agatatgttg aagttttcag tgtcagctga    360
nganagaaca ttgnngtann nggggnact ttaaat                                396

```
<210> SEQ ID NO 82
<211> LENGTH: 396
<212> TYPE: DNA
<213> ORGANISM: Homo sapiens
<220> FEATURE:
<221> NAME/KEY: misc_feature
<222> LOCATION: 220, 251, 297, 301, 309, 349, 395
<223> OTHER INFORMATION: n = A,T,C or G
```

<400> SEQUENCE: 82
gactcagaaa tgtcagtctc atgaagttca aaagatcgag aatgtttgct atcttggtgg      60
agcagccgca gccaagcaag taacttgtaa aatgaggaat gccatcaccc ctcgagtgtc    120
catcccacat aacttggggt tagagcacaa gcgttcccag gaactactca ccttaccatc    180
ttggccgttt catttgcttc caccagttct ggaaagagan ggcctagaag ttcaaaaaaa    240
aagtaggaaa ngtgcttttg gagaaaatca cctgctcctc agaactgggc ttacaanctg    300
ngaagtacnc tatgtgccac ctaatcctca tatatgacct caagagacnc caataagcat    360
atttccacca cggaatgacc agtgctttgg gtaana                               396

```
<210> SEQ ID NO 83
<211> LENGTH: 396
<212> TYPE: DNA
<213> ORGANISM: Homo sapiens
<220> FEATURE:
<221> NAME/KEY: misc_feature
<222> LOCATION: 13, 372, 379, 393
<223> OTHER INFORMATION: n = A,T,C or G
```

<400> SEQUENCE: 83
tttgatttaa ganatttatt attttttttaa aaaaagcaac ttccagggtt gtcattgtac      60
aggttttgcc cagtctccta tagcatggta tagtgataac tgatttttta taacaatgac    120
tcagaggcat tgaagatcca taactatctt ctgaattatc acagaaagaa gaaagttaga    180
agagtttaat gttaagtgta ttaaaaatca tattctaatt cttttaattt ggttatctga    240
gtatgataat ataggagagc tcagataaca aggaaaaggc attggggtaa gaacactcct    300
tcccacagga tggcattaac agacttttc tgcatatgct ttatatagtt gccaactaat     360
tcacctttta cncagcttna ttttttttta ctnggg                               396

<210> SEQ ID NO 84
<211> LENGTH: 396
<212> TYPE: DNA
<213> ORGANISM: Homo sapiens
<220> FEATURE:
<221> NAME/KEY: misc_feature
<222> LOCATION: 61, 232, 254, 270, 271, 286, 354, 356, 368, 374, 389,
      394
<223> OTHER INFORMATION: n = A,T,C or G

<400> SEQUENCE: 84
tttttacagc aatttttttt tattgatgtt taacctgtat acaaccatac ccattttaag      60
ngtacagaca aatgaatttt gacaaattca ttcactcatc taatcatcac tataaccatg    120
atacagattt ttatcactcc aaaagtccat cctgtgctct tttcaagtcc atcctcctca    180
tctgataccc caagccacca ttgttttgct ttctggaact acagttttgg gnttttagaa    240
tttcatatat ggtngaatca taccatttgn natttggggc tgacgncttt cctccaataa    300
tggatttgag aattatctac attttgcatg gatcctgggt tatttatacc aacnagggt    360 tattatgnaa aatnggacca caatttggng gcanta                              396

<210> SEQ ID NO 85
<211> LENGTH: 396
<212> TYPE: DNA
<213> ORGANISM: Homo sapiens
<220> FEATURE:
<221> NAME/KEY: misc_feature
<222> LOCATION: 293, 305, 306, 317, 347, 357, 372, 377, 386, 391
<223> OTHER INFORMATION: n = A,T,C or G

<400> SEQUENCE: 85
cagtgaccgt gctcctaccc agctctgctc cacagcgccc acctgtctcc gcccctcggc     60
ccctcgcccg gctttgccta accgccacga tgatgttctc gggcttcaac gcagactacg    120
aggcgtcatc ctcccgctgc agcagcgcgt ccccggccgg ggatagcctc tcttactacc    180
actcacccgc agactccttc tccagcatgg gctcgcctgc aacgcgcagg acttctgcac    240
ggacctggcc gctccagtgc caacttcatt ccacggcact gcatctcgac canccggact    300
tgcannggtt ggggaanccg ccccttgtttc tccgtggccc atctaanacc aaacccntca    360 cctttttcgga gncccncccc ctccgntggg nttact                              396

<210> SEQ ID NO 86
<211> LENGTH: 396
<212> TYPE: DNA
<213> ORGANISM: Homo sapiens
<220> FEATURE:
<221> NAME/KEY: misc_feature
<222> LOCATION: 5, 6, 28, 50, 58, 90, 108, 110, 118, 145, 154, 194, 244,
      285, 292, 300, 312, 315, 342, 344, 346, 359, 374, 378, 380, 396
<223> OTHER INFORMATION: n = A,T,C or G

<400> SEQUENCE: 86
ttttnnactg aatgtttaat acatttgnag gaacagaaga aatgcagtan ggattaanat     60
tttataatta gacattaatg taacagatgn ttcattttc aaagaagntn ccccttntc    120 cctatctttt tttaatcttc cttanagcaa taantagtaa ttactatatt tgtggacaag   180
ctgctccact gtgntggaca gtaattatta aatctttatg tttcacatca ttattacctt    240
ccanaattct accttcattt ccctgcacag gttcactgga ctggntcaca ancaaattgn    300
actccactca antanaagag cccaaagaaa ttagagtaac gncnantcct atgaattana    360
gacccaaaga tttnaggngn tgattagaaa cataan                                    396

<210> SEQ ID NO 87
<211> LENGTH: 396
<212> TYPE: DNA
<213> ORGANISM: Homo sapiens
<220> FEATURE:
<221> NAME/KEY: misc_feature
<222> LOCATION: 231, 277, 285, 296, 341, 351, 372, 377, 380
<223> OTHER INFORMATION: n = A,T,C or G

<400> SEQUENCE: 87
atggaggcgc tggggaagct gaagcagttc gatgcctacc ccaagacttt ggaggacttc      60
cgggtcaaga cctgcggggg cgccaccgtg accattgtca gtggccttct catgctgcta     120
ctgttcctgt ccgagctgca gtattacctc accacggagg tgcatcctga gctctacgtg     180
gacaagtcgc ggggagataa actgaagatc aacatcgatg tacttttttcc ncacatgcct    240 tgtgcctatc tgagtattga tgccatggat gtggccngag aacancagct ggatgnggaa     300
cacaacctgt ttaagccacc actagataaa gatgcatccc ngtgagctca nagctgagcg     360
gcatgagctt gngaaaantcn aggtgaccgg gtttga                              396

<210> SEQ ID NO 88
<211> LENGTH: 396
<212> TYPE: DNA
<213> ORGANISM: Homo sapiens
<220> FEATURE:
<221> NAME/KEY: misc_feature
<222> LOCATION: 246, 266, 301, 328, 347, 349, 368, 370, 371, 374, 379,
      387, 391
<223> OTHER INFORMATION: n = A,T,C or G

<400> SEQUENCE: 88
tccagagcag agtcagccag catgaccgag cgccgcgtcc ccttctcgct cctgcggggc      60
cccagctggg acccccttccg cgactggtac ccgcatagcc gctcttcgac caggccttcg    120
ggctgccccg gctgccggag gagtggtcgc agtggttagg cggcagcagc tggccaggct    180
acgtgcgccc cctgcccccc gccgcatcga gagccccgca gtggccgcgc ccgctacagc    240
cgcgcngctc agccggcaac tcacancggg gctcggagat ccgggacact gcggaccgct    300
ngcgcgtgcc ctgatgtca ccactttngc ccggacaact gacggtnana caaggatggg     360
gggtgganan nccngtaanc caagaanggg naggac                              396

<210> SEQ ID NO 89
<211> LENGTH: 396
<212> TYPE: DNA
<213> ORGANISM: Homo sapiens
<220> FEATURE:
<221> NAME/KEY: misc_feature
<222> LOCATION: 37, 76, 230, 295, 306, 333, 346, 370, 376, 377, 395
<223> OTHER INFORMATION: n = A,T,C or G

<400> SEQUENCE: 89
gagagaacag taaacatcca gccttagcat ctctcangag tactgcagat cttcattagc     60
tatattcaca tggagnaatg ctattcaacc tatttctctt atcaaaacta attttgtatt    120
ctttgaccaa tgttcctaaa ttcactctgc ttctctatct caatcttttt cccctttctc    180
atctttcctc cttttttcag tttctaactt tcactggttc tttggaatgn ttttttctttc   240 atctcttttc tttacattt tggggtgtcc cctctctttt cttaccctct ttctncatcc     300
ttcttnttct tttgaattgg ctgcccttta tcntctcatc tgctgncatc ttcatttctc    360

```
ctccctcctn tttccnntca ttctactctc tcccnt                              396
```

<210> SEQ ID NO 90
<211> LENGTH: 396
<212> TYPE: DNA
<213> ORGANISM: Homo sapiens
<220> FEATURE:
<221> NAME/KEY: misc_feature
<222> LOCATION: 82, 110, 115, 120, 121, 125, 126, 129, 131, 140, 141,
      144, 145, 146, 148, 149, 150, 153, 154, 157, 158, 160, 161, 163,
      164, 166, 170, 172, 173, 174, 175, 179, 182, 184, 189, 193,
      194, 195, 200, 206, 213, 215, 217, 218, 219, 220, 227
<223> OTHER INFORMATION: n = A,T,C or G
<220> FEATURE:
<221> NAME/KEY: misc_feature
<222> LOCATION: 228, 231, 233, 236, 241, 247, 248, 249, 250, 254, 259,
      262, 269, 273, 274, 275, 280, 281, 282, 286, 287, 289, 293, 294,
      301, 302, 304, 309, 311, 318, 319, 324, 325, 330, 331, 333,
      334, 336, 337, 341, 342, 343, 344, 349, 352, 353, 358
<223> OTHER INFORMATION: n = A,T,C or G
<220> FEATURE:
<221> NAME/KEY: misc_feature
<222> LOCATION: 361, 365, 367, 373, 377, 381, 385, 386, 387, 392
<223> OTHER INFORMATION: n = A,T,C or G

<400> SEQUENCE: 90

```
gggcgccggc gcgcccccc  accccgccc  cacgtctcgt cgcgcgcgcg tccgctgggg    60
gcggggagcg gtcgggccgg cngcggtcgg ccggcggcag ggtggtgcgn tttcnttttn   120
nattnnccnc nttcttcttn nttnnncnnn ctnntannnn ntnncnttcn cnnnnttttnc  180 tntntcttna ccnnnttttn taatcntctt ctncntnnnn tctcttnnat ntnttnctta   240
nttcctnnnn tttnttctnt cntttctcnc ctnnntctcn nnctcnncnc tcnncatttt   300
nntnttttnt nccttctnnt cttnnttctn ntnntnnttt nnnnttctnt tnntcatntt   360 nccntntntta ctntcanctt ntatnnncct cntttt                           396
```

<210> SEQ ID NO 91
<211> LENGTH: 396
<212> TYPE: DNA
<213> ORGANISM: Homo sapiens
<220> FEATURE:
<221> NAME/KEY: misc_feature
<222> LOCATION: 1, 3, 8, 9, 16, 17, 18, 21, 22, 32, 33, 45, 50, 63, 64,
      68, 75, 82, 92, 95, 98, 102, 106, 108, 110, 111, 116, 121, 135,
      151, 154, 158, 162, 167, 170, 176, 181, 185, 187, 209, 212,
      215, 225, 231, 245, 257, 278, 283, 288, 290, 292, 293
<223> OTHER INFORMATION: n = A,T,C or G
<220> FEATURE:
<221> NAME/KEY: misc_feature
<222> LOCATION: 312, 324, 326, 330, 331, 333, 334, 344, 345, 349, 351,
      352, 357, 358, 382, 384, 390, 392
<223> OTHER INFORMATION: n = A,T,C or G

<400> SEQUENCE: 91

```
ntntcctnna tttttnnntc nncttttttt tnnaattttt ctttntttn  tttataaaaa    60 tcnncacnta aaacngcgga anagggggatt tnttnttngg gngtancncn nggccncaaa   120
naaccccaaa aatancccaa aatgcacagg nccngggnaa angaccnacn tgggtnttt    180 ntttntnaac aagggggtt  ttaaagggna tnggnatcaa agggnataaa ntttaaacct   240
ttganaaatt ttttaanagg cttgcccccc actttggncc ccncccncn  gnngggatcc   300 aatttttttt cnttggggct cccngncccn nannttccgg gttnntggnc nntcctnntt   360 ttttttttt  tgccttcacc cntnccattn cnttttt                           396
```

<210> SEQ ID NO 92
<211> LENGTH: 396

```
<212> TYPE: DNA
<213> ORGANISM: Homo sapiens
<220> FEATURE:
<221> NAME/KEY: misc_feature
<222> LOCATION: 3, 7, 8, 9, 11, 31, 149, 152, 221, 233, 259, 263, 264,
      265, 266, 274, 278, 279, 283, 286, 294, 302, 307, 309, 310, 311,
      314, 316, 320, 343, 351, 363, 372, 377, 386, 393
<223> OTHER INFORMATION: n = A,T,C or G

<400> SEQUENCE: 92
ctntttnnnt nttttttttcc ccatcatcca naaatgggtt ttattctcag ccgagggaca    60
gcaggactgg taaaaactgt caggccacac ggttgcctgc acagcacccc catgcttggt   120 aggggtggg agggatggcg ggggctggnt gnccacaggc cggcatgac aaggaggctc    180 actggaggtg gcacactttg gagtgggatg tcggggaca ncttctttgg tanttgggcc    240
acaagattcc caaggatanc acnnnnactg attnccannc tanagncaag cggntggcca   300
tntgtangnn nttntntatn tgactattta tagattttta tanaacaggg naagggcata   360
ccncaaaagg gnccaanttt ttaccnccgg gcnccc                             396

<210> SEQ ID NO 93
<211> LENGTH: 396
<212> TYPE: DNA
<213> ORGANISM: Homo sapiens
<220> FEATURE:
<221> NAME/KEY: misc_feature
<222> LOCATION: 290, 304, 313, 320, 325, 333, 337, 348, 351
<223> OTHER INFORMATION: n = A,T,C or G

<400> SEQUENCE: 93
gctgccacag atctgttcct ttgtccgttt ttgggatcca caggccctat gtatttgaag    60
ggaaatgtgt atggctcaga tccttttttga aacatatcat acaggttgca gtcctgaccc   120
aagaacagtt ttaatggacc actatgagcc cagttacata agaaaaagg agtgctaccc    180 atgttctcat ccttcagaag aatcctgcga acggagcttc agtaatatat cgtggcttca   240
catgtgagga agctacttaa cactagttac tctcacaatg aaggacctgn aatgaaaaat    300
ctgnttctaa ccnagtcctn tttanatttt agngcanatc cagaccancg ncggtgctcg    360
agtaattctt tcatgggacc tttggaaaac tttcag                              396

<210> SEQ ID NO 94
<211> LENGTH: 396
<212> TYPE: DNA
<213> ORGANISM: Homo sapiens
<220> FEATURE:
<221> NAME/KEY: misc_feature
<222> LOCATION: 115, 204, 205, 243, 266, 276, 316, 319, 355, 357, 364
<223> OTHER INFORMATION: n = A,T,C or G

<400> SEQUENCE: 94
tgccttaacc agtctctcaa gtgatgagac agtgaagtaa aattgagtgc actaaacgaa    60
taagattctg aggaagtctt atcttctgca gtgagtatgg cccaatgctt tctgnggcta   120
aacagatgta atgggaagaa ataaaagcct acgtgttggt aaatccaaca gcaagggaga   180 ttttttgaatc ataataactc atanngtgct atctgtcagt gatgccctca gagctcttgc   240
tgntagctgg cagctgacgc ttctangata gttagnttgg aaatggtctt cataataact    300
acacaaggaa agtcanccnc cgggcttatg aggaattgga cttaataaat ttagngngct    360
tccnacctaa aatatatctt ttggaagtaa aattta                              396

<210> SEQ ID NO 95
```

```
<211> LENGTH: 396
<212> TYPE: DNA
<213> ORGANISM: Homo sapiens
<220> FEATURE:
<221> NAME/KEY: misc_feature
<222> LOCATION: 11, 16, 31, 36, 42, 49, 53, 56, 57, 60, 67, 70, 84, 89,
      91, 92, 99, 105, 106, 112, 120, 121, 125, 127, 128, 133, 137,
      141, 151, 152, 153, 154, 155, 162, 166, 167, 168, 174, 177,
      179, 186, 188, 194, 195, 199, 203, 205, 213, 217, 221
<223> OTHER INFORMATION: n = A,T,C or G
<220> FEATURE:
<221> NAME/KEY: misc_feature
<222> LOCATION: 227, 232, 235, 236, 240, 242, 260, 261, 265, 266, 291,
      297, 318, 325, 330, 339, 348, 351, 352, 354, 356, 362, 364, 372,
      380, 392, 395, 396
<223> OTHER INFORMATION: n = A,T,C or G

<400> SEQUENCE: 95
cctcccaccc ncttanttca tgagattcga naatgncact tntgtgctnt ttnctnnttn    60
tattctnacn atttctttct tgggncggna nnaatcccnt ttttnnggcc gnctctcccn   120
ncttntnntt tcntggngct ntcccttttc nnnnnaaact tntacnnngt ttanaantnt   180
ttctgnangg gggnntccna aananttttt ccnccctncct nattccnctc tnaanncctn   240
cnaattgttt ccccccccn ntagnntatt ttttctaaaa aattaactcc nacggnaaaa   300
attttcccta aaatttcncc tccanatttn gaaaaaacnc gcccgganct nntntncgaa   360
tntnaatttt tnaaaaaaan ttattttcat cnggnn                             396

<210> SEQ ID NO 96
<211> LENGTH: 396
<212> TYPE: DNA
<213> ORGANISM: Homo sapiens
<220> FEATURE:
<221> NAME/KEY: misc_feature
<222> LOCATION: 161, 193, 253, 259, 281, 288, 299, 309, 318, 319, 335,
      340, 344, 352, 355, 356, 387, 396
<223> OTHER INFORMATION: n = A,T,C or G

<400> SEQUENCE: 96
cctgggtacc aaatttcttt atttgaagga atggtacaaa tcaaagaact taagtggatg    60
ttttggacaa cttatagaaa aggtaaagga aaccccaaca tgcatgcact gccttggcga   120
ccagggaagt caccccacgg ctatggggaa attagcccga ngcttaactt tcattatcac   180
tgcttccaag gggntgcttg gcaaaaaaat attccgccaa ccaaatcggg cgctccatct   240
tgcccagttg gtnccgggnc cccaattctt ggatgctttc ncctcttntt ccggaatgng   300
ctcatgaant cccccaanng gggcattttg ccagnggcc tttngccatt cnagnnggcc   360
tgatccattt tttccaatgt aatgccnctt cattgn                             396

<210> SEQ ID NO 97
<211> LENGTH: 396
<212> TYPE: DNA
<213> ORGANISM: Homo sapiens
<220> FEATURE:
<221> NAME/KEY: misc_feature
<222> LOCATION: 13, 15, 16, 19, 23, 31, 38, 39, 41, 45, 68, 94, 95, 100,
      119, 131, 133, 141, 144, 164, 171, 182, 186, 190, 191, 195,
      196, 198, 213, 229, 231, 235, 239, 247, 257, 265, 269, 272,
      278, 279, 286, 289, 291, 306, 309, 310, 312, 317, 320
<223> OTHER INFORMATION: n = A,T,C or G
<220> FEATURE:
<221> NAME/KEY: misc_feature
<222> LOCATION: 321, 327, 328, 337, 340, 343, 351, 360, 361, 368, 375,
      381, 385, 386, 387, 388
<223> OTHER INFORMATION: n = A,T,C or G

<400> SEQUENCE: 97
```

```
ctcaccctcc tcntnnttnt canaatattg ngaacttnnt nctgntcgaa tcactggcat    60
taaagganca ctagctaatg gcactaaatt tacnnactan ggaaacttttt ttataatant   120 gcaaaaacat ntnaaaaaga ntgnagttcg cccatttctg cttnggaaga nctcttcact   180
tntaancccn natgnngncc tttgggtcaa aanctccgcg attattacng ngttncccnc   240
tatttgncct tccttntcc ccaangccnc anatttcnna actttnccnt naaatgcctt    300
tatttnatnn cntttcnacn ncttaanntt ccctttnaan aangatccct ncttcaaatn   360
ntttcccngt tcctngcatt nccncnnnnat ttctct                            396
```

\<210> SEQ ID NO 98
\<211> LENGTH: 396
\<212> TYPE: DNA
\<213> ORGANISM: Homo sapiens
\<220> FEATURE:
\<221> NAME/KEY: misc_feature
\<222> LOCATION: 130, 202, 285, 296, 299, 308, 314, 321, 322, 336, 373
\<223> OTHER INFORMATION: n = A,T,C or G

\<400> SEQUENCE: 98

```
acagggacaa tgaagccttt gaagtgccag tctatgaaga ggccgtggtg ggactagaat    60
cccagtgccg cccccaagag ttggaccaac caccccctac agcactgttg tgataccccc   120
agcacctgan gaggaacaac ctaccatcca gagggccag gaaaagccaa actggaacag    180
aggcgaatgg ctcagagggg tncatggcca agaaggaagc cctggaagaa cttcaatcac   240
cttcggtttc gggaccaccg gcttgtgtcc ctgttctgac tgcanaactt ggcgcngtnc   300
cccattanaa cctntgactc nnccttgct ataagnctgt tttggcccct gatgatgata    360 gggttttttat gangacactt gggcacccc ttaatg                             396
```

\<210> SEQ ID NO 99
\<211> LENGTH: 396
\<212> TYPE: DNA
\<213> ORGANISM: Homo sapiens
\<220> FEATURE:
\<221> NAME/KEY: misc_feature
\<222> LOCATION: 1, 4, 13, 15, 26, 31, 43, 46, 48, 52, 54, 55, 60, 62,
    68, 72, 93, 112, 118, 119, 122, 131, 132, 133, 134, 145, 147,
    152, 157, 163, 164, 186, 190, 225, 231, 239, 246, 247, 250,
    255, 262, 285, 314, 316, 319, 325, 332, 339, 343, 345
\<223> OTHER INFORMATION: n = A,T,C or G
\<220> FEATURE:
\<221> NAME/KEY: misc_feature
\<222> LOCATION: 348, 351, 352, 355, 357, 361, 370, 387
\<223> OTHER INFORMATION: n = A,T,C or G

\<400> SEQUENCE: 99

```
nttnttttc cgncnaaagg gcaagngttt ncatctttcc tgnccncnca ananngggtn    60
tntgtgcntt tnttttttcc caaaaccggg gtngggaca ccttttgagg anccactnnt   120
cntccggggc nnnnttttag aaggngncta anaagcntct tgnnggggga aaaacatctt   180 tttgcnccn acataccccc aaggggggg ggtgtctggg agganactaa ngacttttnt   240
tttttnnccn caaanaactg anggccccca ttgctcccccc ccantctttt aaaaaacccc   300
ttcaatttcc ttgncnggna aaaanggttg gnaaaaaang agngngcntc nnttncnttt   360
natggaaggn aaaaggtttt tggttgnaaa accccg                             396
```

\<210> SEQ ID NO 100
\<211> LENGTH: 396
\<212> TYPE: DNA
\<213> ORGANISM: Homo sapiens

```
<220> FEATURE:
<221> NAME/KEY: misc_feature
<222> LOCATION: 229, 286, 303, 312, 334, 335, 348, 350, 357, 364, 371,
      395
<223> OTHER INFORMATION: n = A,T,C or G

<400> SEQUENCE: 100
ctaacacggt gaaaccctgt ctctactaaa aatacaaaaa aattagccag gcgtggtggc      60
gggcacctgt agtcccagct gctcaggaag ctgaggcagg agaatggcgt gaacccagaa     120
ggcggagctt gcagtgagct gagatcgtgt cagtgcactc cagcctgggc gacagagcga     180
gactcccgct caaaaaaaaa aaaaaaaga gaaaagaaaa agctgcagng agctgggaat     240
gggccctatc ccctccttgg ggatcaatga gaccccttt caaaanaaaa aaaaaaataa      300
tgngattttg gnaacatatg gcactggtgc ttcnnggaat tctgttttntn ggcatgnccc    360 cctntgactg nggaaaaatc cagcaggagg cccana                              396

<210> SEQ ID NO 101
<211> LENGTH: 396
<212> TYPE: DNA
<213> ORGANISM: Homo sapiens
<220> FEATURE:
<221> NAME/KEY: misc_feature
<222> LOCATION: 93, 99, 100, 111, 168, 172, 174, 199, 209, 216, 218,
      219, 227, 242, 243, 269, 272, 297, 300, 301, 308, 315, 317, 323,
      331, 341, 344, 348, 357, 359, 363, 364, 366, 376, 379, 386, 389,
      392
<223> OTHER INFORMATION: n = A,T,C or G

<400> SEQUENCE: 101
agttataact caacagttca tttatatgct gttcatttaa cagttcattt aaacagttca     60
ttataactgt ttaaaatat atatgcttat agncaaaann tgttgtggcg nagttgttgc     120
cgcttatagc tgagcattat ttcttaaatt cttgaatgtt cttttggngg gntnctaaaa    180
ccgtatatga tccattttna tgggaaacng aattcntnnc attatcncac cttggaaata    240
cnnaacgtgg gggaaaaaaa tcattcccnc cntccaaaac tatacttctt ttatctngan    300
nttcttgntc ctgcncnggt ttngaatata nctgggcaaa nggntttncc aaatccntnt    360
acnntncttt gggaantanc ggcaantcnt cncttt                              396

<210> SEQ ID NO 102
<211> LENGTH: 396
<212> TYPE: DNA
<213> ORGANISM: Homo sapiens
<220> FEATURE:
<221> NAME/KEY: misc_feature
<222> LOCATION: 17, 93, 136, 183, 317
<223> OTHER INFORMATION: n = A,T,C or G

<400> SEQUENCE: 102
actatacata agaacangct cacatgggag gctggaggtg ggtacccagc tgctgtggaa     60
cgggtatgga caggtcataa acctagagtc agngtcctgt tggcctagcc catttcagca    120
ccctgccact tggagnggac ccctctactc ttcttagcgc ctaccctcat acctatctcc    180
ctnctcccat ctcctacgga ctggcgccaa atggctttcc tgccaatttt gggatcttct    240
ctggctctcc agcctgctta ctcctctatt tttaaagggc caaacaaatc ccttctcttt    300
ctcaaacaca gtaatgnggc actgacccta ccacacctca tgaagggggc ttgttgcttt    360
tatttgggcc cgatctgggg ggggcaaaat attttg                              396

<210> SEQ ID NO 103
```

```
<211> LENGTH: 396
<212> TYPE: DNA
<213> ORGANISM: Homo sapiens
<220> FEATURE:
<221> NAME/KEY: misc_feature
<222> LOCATION: 91, 174, 176, 188, 201, 214, 254, 277, 299, 325, 349,
      355, 365, 372, 390
<223> OTHER INFORMATION: n = A,T,C or G

<400> SEQUENCE: 103
ttgtgttggg actgctgata ggaagatgtc ttcaggaaat gctaaaattg ggcaccctgc      60
cccaacttca aagccacagc tggtatgcca natggtcagg ttaaagatat caacctgctg    120
actacaaagg aaaatatggt ggggtcttct tttaccctct tgacttccct ttgngngccc    180
cccgaganca ttgctttccg ngatagggca aaanaaatta aaaaacttaa ctggccagtg    240
aatgggcttt ctgnggatct ccttctggca ttacatnggc aatccctaaa aaacaagang    300
actgggaccc ataacattct tttgnatcaa ccgaagcccc cattgttang atatngggct    360
taaangctga tnaagcatct cgtccgggcn ttttat                              396

<210> SEQ ID NO 104
<211> LENGTH: 396
<212> TYPE: DNA
<213> ORGANISM: Homo sapiens
<220> FEATURE:
<221> NAME/KEY: misc_feature
<222> LOCATION: 32, 53, 86, 141, 154, 156, 181, 182, 197, 204, 219, 224,
      226, 229, 232, 245, 253, 260, 262, 271, 273, 276, 292, 301,
      303, 305, 321, 325, 332, 343, 352, 382, 392
<223> OTHER INFORMATION: n = A,T,C or G

<400> SEQUENCE: 104
aagggagggc gcgccaagac cttcccactc gngcacactg ggggcgccga cangacgcaa      60
cccagtccaa cttggatacc cttggnttta gttctcggac acttctttta tctctccgtc    120
gcaacttgtc aagttctcaa nactgtctct ctgngntatc ttttttcttc gctgctcttc    180
nnccccgac gtatttntca aaangtctgc aattgttgna tacntngaac tncaccactg    240
ttacnaggtc atnaatttcn cntcaactct ntnccncttg ttccctgata tntcggccgg    300
ngncnccaat tctgtatttt nctcntcaac gntctcactt ttncctcctc cnggccactt    360
tctccccttc cttattccgg cnttgtttgc cnccat                              396

<210> SEQ ID NO 105
<211> LENGTH: 396
<212> TYPE: DNA
<213> ORGANISM: Homo sapiens
<220> FEATURE:
<221> NAME/KEY: misc_feature
<222> LOCATION: 57, 306, 356, 388, 391
<223> OTHER INFORMATION: n = A,T,C or G

<400> SEQUENCE: 105
tcaatagcca gccagtgttc atttttatcc ttgagctttt agtaaaaact tcctggnttt      60
atttttagtc attgggtcat acagcactaa agtctgctat ttatgaaaac taacttttt    120
gttttaatc caggccaaca tgtatgtaaa ttaaattttt agataattga ttatctcttt    180
gtactacttg agatttgatt atgagatgtg catattgctt tgggaagagc tcgaggaagg    240
aaataattct ctcctttggt ttgaacctca actagataaa ccctaggaat tgttaactgc    300
acaagnattt tcattccaca aaacctgagg cagctctttt gccagagcgt tcctgnaccc    360
ccccacccca cttgccttgg gtctttanaa ngagcc                              396
```

<210> SEQ ID NO 106
<211> LENGTH: 396
<212> TYPE: DNA
<213> ORGANISM: Homo sapiens

<400> SEQUENCE: 106

```
gctgtgtagc acactgagtg acgcaatcaa tgtttactcg aacagaatgc atttcttcac    60
tccgaagcca aatgacaaat aaagtccaaa ggcattttct cctgtgctga ccaaccaaat   120
aatatgtata gacacacaca catatgcaca cacacacaca cacacccaca gagagagagc   180
tgcaagagca tggaattcat gtgtttaaag ataatccttt ccatgtgaag tttaaaatta   240
ctatatattt gctgatggct agattgagag aataaaagac agtaaccttt ctcttcaaag   300
ataaaatgaa aagcaattgc tcttttcttc ctaaaaaatg caaaagattt acattgctgc   360
caaatcattt caactgaaaa gaacagtatt gctttg                             396
```

<210> SEQ ID NO 107
<211> LENGTH: 396
<212> TYPE: DNA
<213> ORGANISM: Homo sapiens
<220> FEATURE:
<221> NAME/KEY: misc_feature
<222> LOCATION: 12, 210, 257, 261, 271, 302, 311, 314, 318, 368, 374,
      385, 389, 396
<223> OTHER INFORMATION: n = A,T,C or G

<400> SEQUENCE: 107

```
ttcacagaac anggtggttt attatttcaa tagcaaagag ctgaaaaatg tcgggtccca    60
taaaggagca gaacctgacc cagagcctgc agtacatttc caccccacag gggtgcaggc   120
tgggccaggc agggccaaag gcagcagaaa tgggagtaag agactgtgcc cactgagaag   180
ctctgctggg tgtgggcagg tgggcatgan atgatgatga tgtagtgtaa ggaccaggta   240
ggcaaaacct gtcaggnttg ntgaatgtca nagtggatcc aaaaggctga ggggtcgtc    300
anaaggccgg nggncccncc cttgcccgta tgggccttca aaaagtatgc ttgctcatcc   360
gttgtttncc ccanggagct gccanggana aggctn                             396
```

<210> SEQ ID NO 108
<211> LENGTH: 396
<212> TYPE: DNA
<213> ORGANISM: Homo sapiens
<220> FEATURE:
<221> NAME/KEY: misc_feature
<222> LOCATION: 280, 281, 286, 305, 311, 313, 323, 326, 327, 340, 352,
      356, 363, 369, 378, 388, 392
<223> OTHER INFORMATION: n = A,T,C or G

<400> SEQUENCE: 108

```
gcctgctttt gatgatgtct acagaaaatg ctggctgagc tgaacacatt tgcccaattc    60
caggtgtgca cagaaaaccg agaatattca aaattccaaa ttttttttctt aggagcaaga   120
agaaaatgtg gccctaaagg gggttagttg aggggtaggg ggtagtgagg atcttgattt   180
ggatctcttt ttatttaaat gtgaatttca acttttgaca atcaaagaaa agactttgt    240
tgaaatagct ttactgcttc tcacgtgttt tggagaaaan natcanccct gcaatcactt   300
tttgnaactg ncnttgattt tcngcnncca agctatatcn aatatcgtct gngtanaaaa   360
tgncctggnc ttttgaanga atacatgngt gntgct                             396
```

<210> SEQ ID NO 109
<211> LENGTH: 396

```
<212> TYPE: DNA
<213> ORGANISM: Homo sapiens
<220> FEATURE:
<221> NAME/KEY: misc_feature
<222> LOCATION: 237, 279, 284, 291, 305, 307, 308, 313, 326, 343, 351,
      366, 376, 392, 394, 395
<223> OTHER INFORMATION: n = A,T,C or G

<400> SEQUENCE: 109
ggccgtaggc agccatggcg cccagcccgg aatggcatgg tcttgaagcc ccacttccac      60
aaggactggc agcggcgcgt ggccacgtgg ttcaaccagc cggcccggaa gatccgcaga     120
cgtaaggccc ggcaagccaa ggcgcgccgc atcgctccgc gccccgcgtc gggtcccatc     180
cggcccatcg tgcgctgccc acggttcggt accacacgaa gggcgcgccg gcgcggnttc     240
agcctggagg agctcaggt ggccggattt acaagaagng gccngacatc ngtattcttg     300
ggatncnnga agnggaacaa gtcacngagt ccttgcagcc acntcagcgg ntgatgacac     360
cgttcnaact catctnttcc caagaaacct cngnnc                              396

<210> SEQ ID NO 110
<211> LENGTH: 396
<212> TYPE: DNA
<213> ORGANISM: Homo sapiens
<220> FEATURE:
<221> NAME/KEY: misc_feature
<222> LOCATION: 1, 2, 12, 13, 16, 18, 29, 39, 60, 66, 70, 86, 90, 104,
      121, 122, 127, 128, 146, 165, 171, 172, 173, 176, 188, 189, 193,
      195, 205, 210, 211, 224, 226, 227, 231, 233, 240, 243, 244,
      248, 249, 255, 257, 258, 260, 266, 268, 272, 273, 275
<223> OTHER INFORMATION: n = A,T,C or G
<220> FEATURE:
<221> NAME/KEY: misc_feature
<222> LOCATION: 278, 280, 287, 292, 294, 303, 308, 312, 315, 320, 322,
      332, 333, 334, 335, 345, 347, 351, 363, 364, 369, 371, 372, 379,
      381, 382, 386, 391, 393
<223> OTHER INFORMATION: n = A,T,C or G

<400> SEQUENCE: 110
nntgggctcc tnncantnat aataaaccng actcatacnc cacaaggaga tgaacaggan      60
tatgtncatn ctgacgcgga aacagngcan ggagctgagg aggngccaag atgagaccta    120
nnggccnngg tgggcgcatt cccggnggag ggggccacta aggantacga nnntcnagcg    180
gctcttgnng gcngncctcc tcacncctgn ntattcgatt gtcncnnatg ncntcctatn    240
atnntcanna ttctntnntn atctcntnta cnncntcncn ttcatgntta cngntccctc    300
tcnttctnac cnttntctgn anctcctttc tnnnncttc atctntnttc ngctttcttt    360
ctnnaatcnt nntttaacnt nntctncttt ntnatt                              396

<210> SEQ ID NO 111
<211> LENGTH: 396
<212> TYPE: DNA
<213> ORGANISM: Homo sapiens
<220> FEATURE:
<221> NAME/KEY: misc_feature
<222> LOCATION: 4, 7, 11, 16, 19, 25, 26, 30, 33, 39, 54, 60, 69, 75,
      81, 99, 102, 130, 132, 143, 154, 156, 166, 180, 182, 188, 190,
      192, 194, 198, 201, 226, 242, 253, 261, 264, 295, 305, 313,
      315, 320, 323, 325, 330, 334, 337, 340, 344, 348, 349
<223> OTHER INFORMATION: n = A,T,C or G
<220> FEATURE:
<221> NAME/KEY: misc_feature
<222> LOCATION: 351, 352, 357, 358, 359, 361, 362, 381, 387, 388, 389,
      394
<223> OTHER INFORMATION: n = A,T,C or G

<400> SEQUENCE: 111
```

```
taangancat nctggnttnt gcctnnccgn ctnattgant gttaaaggca attntgtggn      60
tgtcccagng aatgncggct nattttcttt ccacattgng cncattcact cctcccactc    120
ttggcatgtn gngacataag canggtacat aatngnaaaa atctgnattt ctgatgccan    180
angggtanan cntnttgnat ntcattccat tgatatacag ccactntttt attttgatc     240 ancggccttc ggntcactgc ncanggtact tgacctcagt gtcactatta tgggntttgg    300
tttcnctctt ttncnggccn ttntntttcn cacnttncan cttncttnnt nnaaaannna    360
nncactctct cttgctctct ngatacnnng tctnaa                              396
```

<210> SEQ ID NO 112
<211> LENGTH: 396
<212> TYPE: DNA
<213> ORGANISM: Homo sapiens
<220> FEATURE:
<221> NAME/KEY: misc_feature
<222> LOCATION: 172, 186, 378, 380, 382, 388
<223> OTHER INFORMATION: n = A,T,C or G

<400> SEQUENCE: 112

```
tcaacgtcac caattactgc catttagccc acgagctgcg tctcagctgc atggagagga    60
aaaaggtcca gattcgaagc atggatccct ccgccttggc aagcgaccga tttaacctca   120
tactggcaga taccaacagt gaccggctct tcacagtgaa cgatgttaaa gntgaggct    180 ccaagnatgg tatcatcaac ctgcaaagtc tgaagacccc tacgctcaag gtgttcatgc   240
acgaaaacct ctacttcacc aaccggaagg tgaattcggg gggctgggcc tcgctgaatc   300
acttggattc cacattctgc tatgcctcat gggactcgca gaacttcagg ctggccaccc   360
tgctcccacc atcactgntn gncaatantc acccag                              396
```

<210> SEQ ID NO 113
<211> LENGTH: 396
<212> TYPE: DNA
<213> ORGANISM: Homo sapiens
<220> FEATURE:
<221> NAME/KEY: misc_feature
<222> LOCATION: 1, 2, 3, 4, 7, 8, 9, 10, 11, 65, 273, 279, 280, 289,
      321, 338, 380
<223> OTHER INFORMATION: n = A,T,C or G

<400> SEQUENCE: 113

```
nnnnttnnnn nggagcctta atttcagagt tttattgtat tgcactaaag gaacagcagg    60
atggntatac aatttctctc cattcagttt tgaaaatctg tagtacctgc aaattcttaa   120
gaataccttt accaccagat tagaacagta agcataataa ccaatttctt ataagtaat    180 gtcttacaaa taaaaacaca tttaaaatag ctttaaatgc attcttcaca agtaattcag   240
catatatttt atatcatggt tacttatgct tangaattnn agcaggatnt ttattcttt    300 gatgaaata tggaaaaact ntattcatgc atatacangg ataatattca gcgaagggaa   360
aatcccgttt ttattttggn aatgattcat atataa                              396
```

<210> SEQ ID NO 114
<211> LENGTH: 396
<212> TYPE: DNA
<213> ORGANISM: Homo sapiens
<220> FEATURE:
<221> NAME/KEY: misc_feature
<222> LOCATION: 40, 82, 114, 116, 146, 164, 166, 174, 185, 212, 215,
      219, 224, 236, 242, 254, 258, 263, 270, 286, 299, 308, 327, 328,
      329, 345, 363, 378, 382, 385
<223> OTHER INFORMATION: n = A,T,C or G

<400> SEQUENCE: 114

```
aaatgggaca acgtgattct tttgttttaa ataaatactn agaacacgga cttggctcct      60
acaagcattt ggactctaag gnttagaact ggagagtctt acccatgggc ccncncagg      120
gacgccacgg ttccctccca ccccgngatc aagacacgga atcngntggc gatngttgga    180
tcgcnatgtg cccttatct atagccttcc cnggncatnt acangcagga tgcggntggg      240
anaactacaa ctgnaatntc tcnaacggtn atggtcccca ccgataaga ttctacctng      300
tcttttcntc ccctggagtg tgagtgnnng aggaagaagc ccttnccta catcacctttt    360
tgnacttctg aacaaganca anacnatggc ccccc                                396
```

<210> SEQ ID NO 115
<211> LENGTH: 396
<212> TYPE: DNA
<213> ORGANISM: Homo sapiens
<220> FEATURE:
<221> NAME/KEY: misc_feature
<222> LOCATION: 277, 297, 321, 341, 381, 391
<223> OTHER INFORMATION: n = A,T,C or G

<400> SEQUENCE: 115

```
ccgcctggtt cggcccgcct gcctccactc ctgcctctac catgtccatc agggtgaccc      60
agaagtccta caaggtgtcc acctctggcc ccgggccttt cagcagccgc tcctacacga    120
gtgggcccgg ttcccgcatc agctcctcga gcttctcccg agtgggcagc agcaactttc    180
gcggtggcct ggcggcggct atggtggggc cagcggcatg ggaggcatca cccgcagtta    240
cggcaaccag agcctgctga gccccttgcc tggaggngga ccccaacatc aagccgngcg    300
cacccaggaa aaggagcaga ncaagaccct caacaacaag nttgcttctt catagacaag    360
ggaccggtcc ttgaacagca naacaagatg ntggag                               396
```

<210> SEQ ID NO 116
<211> LENGTH: 396
<212> TYPE: DNA
<213> ORGANISM: Homo sapiens
<220> FEATURE:
<221> NAME/KEY: misc_feature
<222> LOCATION: 267, 290, 343, 351, 376
<223> OTHER INFORMATION: n = A,T,C or G

<400> SEQUENCE: 116

```
atctcagttt actagctaag tgactttggg caagggattt aacctctcgt ccctcagttt      60
cctcctatgt aaaatgacaa ggataatagt accaacccaa tgtagattaa atgagtttac    120
gaagtgttag aatagtgctt ggcacattag tgctttacaa ctgctatttt gattgttgtt    180
gtgggctctc tcaaatgcat tgtctctaga tgccagtgac ccaggtcaaa atttacctt      240
aaccaagctg catgtttccc agactgntgc acagtcctct accctgagan aaagcttcca    300
cccaaggata cttttacttt ctgctggaaa actgatgagc aanggcaaca ngggacactt    360
atcgccaact ggaaangaga aattcttcct tttgct                               396
```

<210> SEQ ID NO 117
<211> LENGTH: 396
<212> TYPE: DNA
<213> ORGANISM: Homo sapiens
<220> FEATURE:
<221> NAME/KEY: misc_feature
<222> LOCATION: 228, 267, 318, 331, 357, 368, 376
<223> OTHER INFORMATION: n = A,T,C or G

<400> SEQUENCE: 117

```
aaacattttt taataaaatt cctatagaaa gctcagtcat agggcaaata ctcagttctc    60
tttcccatat caccgaggat tgagagctcc caatattctt tggagaataa gcagtagttt   120
tgctggatgt tgccaggact cagagagatc acccatttac acattcaaac cagtagttcc   180
tattgcacat attaacatta cttgcccta gcaccctaaa tatatggnac ctcaacaaat    240
aacttaaaga tttccgtggg gcgcganacc atttcaattt gaactaatat ccttgaaaaa   300
aatcacatta ttacaagntt taataaatac nggaagaaga gctggcattt ttctaanatc   360
tgaattcnga cttggnttta ttccataaat acggtt                            396
```

<210> SEQ ID NO 118
<211> LENGTH: 396
<212> TYPE: DNA
<213> ORGANISM: Homo sapiens
<220> FEATURE:
<221> NAME/KEY: misc_feature
<222> LOCATION: 4, 5, 12, 14, 15, 16, 24, 59, 80, 87, 225, 280, 286, 287, 295, 297, 298, 337, 349, 362, 375, 387, 394
<223> OTHER INFORMATION: n = A,T,C or G

<400> SEQUENCE: 118

```
accnncacct gntnnntttt aacnattaca acttctttat atggcagttt ttactgggng    60
cctaacactc tctttactgn ctcaagngga agtccaaaca aatttcattt ttgtagtaaa   120
aaatctttat ttccaaaatg atttgttagc caaagaact ataaaccacc taacaagact    180
ttggaagaaa gagacttgat gcttcttata aattccccat tgcanacaaa aaataacaat   240
ccaacaagag catggtaccc attcttacca ttaacctggn tttaanctc caaancnnga    300 tttaaaaatg accccactgg gcccaatcca acatganacc tagggggnt tgccttgatt    360 angaatcccc cttanggact ttatctnggc tganaa                            396
```

<210> SEQ ID NO 119
<211> LENGTH: 396
<212> TYPE: DNA
<213> ORGANISM: Homo sapiens
<220> FEATURE:
<221> NAME/KEY: misc_feature
<222> LOCATION: 251, 281, 298, 301, 308, 326, 332, 337, 351, 358, 362, 388, 394
<223> OTHER INFORMATION: n = A,T,C or G

<400> SEQUENCE: 119

```
atggccagct cactttaaat accacctcaa gactcatcga aatgaccgct ccttcatctg    60
tcctgcagaa ggttgtggga aaagcttcta tgtgctgcag aggctgaagg tgcacatgag   120
gacccacaat ggagagaagc cctttatgtg ccatgagtct ggctgtggta agcagtttac   180
tacagctgga aacctgaaga accaccggcg catccacaca ggagagaaac ctttcctttg   240
tgaagcccaa ngatgtggcc gtcctttgct gagtattcta ncttcgaaaa catctggngg   300
ntactcanga gagaaagcct cattantgcc antctgnggg aaaaccttct ntcagagngg   360
angcaggaat gtgcatatta aaaagctncc ttgnac                            396
```

<210> SEQ ID NO 120
<211> LENGTH: 396
<212> TYPE: DNA
<213> ORGANISM: Homo sapiens
<220> FEATURE:
<221> NAME/KEY: misc_feature
<222> LOCATION: 261, 263, 265, 272, 273, 288, 308, 310, 330, 379
<223> OTHER INFORMATION: n = A,T,C or G

```
<400> SEQUENCE: 120
catgggtcag tcggtcctga gagttcgaag agggcacatt cccaaagaca ttcccagtca      60
tgaaatgtag aagactggaa aattaagaca ttatgtaaag gtagatatgg ctttagagt      120 tacattatgc ttggcatgaa taaggtgcca ggaaaacagt ttaaaattat acatcagcat      180
acagactgct gttagaaggt atgggatcat attaagataa tctgcagctc tactacgcat      240
ttattgttaa ttgagttaca nangncattc annactgagt ttatagancc atattgctct      300
atctctgngn agaacatttg attccattgn gaagaatgca gtttaaaata tctgaatgcc      360
atctagatgt attgtaccna aaggggaaaa ataaca                                396

<210> SEQ ID NO 121
<211> LENGTH: 396
<212> TYPE: DNA
<213> ORGANISM: Homo sapiens
<220> FEATURE:
<221> NAME/KEY: misc_feature
<222> LOCATION: 77, 125, 130, 142, 155, 162, 166, 176, 204, 227, 242,
      243, 245, 246, 249, 251, 252, 265, 279, 306, 310, 314, 336, 341,
      354, 367, 382, 385, 390, 395
<223> OTHER INFORMATION: n = A,T,C or G

<400> SEQUENCE: 121 ttttttttt ttttttttaa aatcaagtta tgtttaataa acattaataa atgtttactt      60
aaaagggtta ataaacnttt actacatggc aaattatttt agctagaatg cttttggctt     120
caagncatan aaaccagatt cnaatgccct taaanaattt tnaaanatcc attgangggg     180
ataactgtaa tccccaaggg gaanagggtt gggtatgaca ggtacanggg gccagcccag     240
tnntnncana nncagactct taccntcttt ctgctgtgnc accctcaggc attggctcca     300
ttctcnggng tgcncatggg aagatggctt tggacntaac nacacccttt tgtncacgta     360
aaggccngat gcagggtcaa anagnttccn ccatnt                               396

<210> SEQ ID NO 122
<211> LENGTH: 396
<212> TYPE: DNA
<213> ORGANISM: Homo sapiens

<400> SEQUENCE: 122
gtcgacatgg ctgccctctg ggctcccaga acccacaaca tgaaagaaat ggtgctaccc      60
agctcaagcc tgggcctttg aatccggaca caaaaccctc tagcttggaa atgaatatgc     120
tgcactttac aaccactgca ctacctgact caggaatcgg ctctggaagg tgaagctaga     180
ggaaccagac ctcatcagcc caacatcaaa gacaccatcg aacagcagc gcccgcagca     240 cccacccgc accggcgact ccatcttcat ggccacccc tgcggtggac ggttgaccac      300
cagccaccac atcatcccag agctgagctc ctccagcggg atgacgccgt cccaccacc     360 tccctcttct tcttttcat ccttctgtct ctttgt                                396

<210> SEQ ID NO 123
<211> LENGTH: 396
<212> TYPE: DNA
<213> ORGANISM: Homo sapiens
<220> FEATURE:
<221> NAME/KEY: misc_feature
<222> LOCATION: 74, 94, 142, 149, 194, 219, 233, 279, 316, 335, 368
<223> OTHER INFORMATION: n = A,T,C or G

<400> SEQUENCE: 123 gcccttttt ttttttttt tttcctagtg ccaggtttat tccctcacat gggtggttca      60
```

```
catacacagc acanaggcac gggcaccatg gganagggca gcactcctgc cttctgaggg      120
gatcttggcc tcacggtgta anaagggana ggatggtttc tcttctgccc tcactagggc      180
ctagggaacc cagnagcaaa tcccaccacg ccttccatnt ctcagccaag ganaagccac      240
cttggtgacg tttagttcca accattatag taagtggana agggattggc ctggtcccaa      300
ccattacagg gtgaanatat aaacagtaaa ggaanataca gtttggatga ggccacagga      360
aggagcanat gacaccatca aaagcatatg caggga                                396

<210> SEQ ID NO 124
<211> LENGTH: 396
<212> TYPE: DNA
<213> ORGANISM: Homo sapiens

<400> SEQUENCE: 124
gaccattgcc ccagacctgg aagatataac attcagttcc caccatctga ttaaaacaac       60 ttcctcccctt acagagcata aacagaggg ggcacccggg gaggagagca catactgtgt      120
tccaatttca cgcttttaat tctcatttgt tctcacacca acagtgtgaa gtgcgtggta      180
taatctccat ttcaaaacca aggaagcagc ctcagagtgg tcgagtgaca cacctcacgc      240
aggctgagtc cagagcttgt gctcctcttg attcctggtt tgactcagtt ccaggcctga      300
tcttgcctgt ctggctcagg gtcaaagaca gaatggtgga gtgtagcctc cacctgatat      360
tcaggctact cattcagtcc caaatatgta ttttcc                                396

<210> SEQ ID NO 125
<211> LENGTH: 396
<212> TYPE: DNA
<213> ORGANISM: Homo sapiens
<220> FEATURE:
<221> NAME/KEY: misc_feature
<222> LOCATION: 43, 88, 91, 94, 139, 141, 150, 163, 193, 202, 212, 215,
      222, 238, 253, 256, 286, 297, 331, 343, 350, 360, 376, 385, 396
<223> OTHER INFORMATION: n = A,T,C or G

<400> SEQUENCE: 125 ccctttttttt tttttttttt tttttttttt tttttttactt tgnaacaaaa atttattagg     60
attaagtcaa attaaaaaac ttcatgcncc nccncttgtc atatttacct gaaatgacaa      120
agttatactt agcttgagng naaaacttgn gccccaaaaa ttntgtttgg aaagcaaaaa      180
aataattgat gcncatagca ngggcctga tnccnccaca gngaatgttg tttaaggnct       240
aacaaacagg ggcancaaa gcatacatta cttttaagct ttgggnccaa ggaaaangtc      300
attccctacc tccttcaaaa gcaaactcat natagcctgg gcncctaggn ctggagcctn      360 tttttcgag tctaanatga acatntggat ttcaan                                 396

<210> SEQ ID NO 126
<211> LENGTH: 396
<212> TYPE: DNA
<213> ORGANISM: Homo sapiens

<400> SEQUENCE: 126
cgcgtcgact cgcaagtgga atgtgacgtc cctggagacc ctgaaggctt tgcttgaagt       60
caacaaaggg cacgaaatga gtcctcaggt ggccaccctg atcgaccgct ttgtgaaggg      120
aaggggccag ctagacaaag acaccctaga caccctgacc gccttctacc ctgggtacct      180
gtgctccctc agccccgagg agctgagctc cgtgccccccc agcagcatct gggcggtcag      240
gccccacgac ctggacacgc tggggctacg gctacagggc ggcatcccca acggctacct      300
```

```
ggtcctagac ctcagcatgc aagaggccct ctcggggacg ccctgcctcc taggacctgg    360
acctgttctc accgtcctgg cactgctcct agcctc                              396
```

<210> SEQ ID NO 127
<211> LENGTH: 396
<212> TYPE: DNA
<213> ORGANISM: Homo sapiens
<220> FEATURE:
<221> NAME/KEY: misc_feature
<222> LOCATION: 15
<223> OTHER INFORMATION: n = A,T,C or G

<400> SEQUENCE: 127

```
tttttttttt ttggnggtaa aatgcaaatg ttttaaaata tgtttatttt gtatgtttta     60
caatgaatac ttcagcaaag aaaataatta taatttcaaa atgcaatccc tggatttgat    120
aaatatcctt tataatcgat tacactaatc aatatctaga aatatacata gacaaagtta   180
gctaatgaat aaaataagta aatgactac ataaactcaa tttcagggat gagggatcat    240
gcatgatcag ttaagtcact ctgccacttt ttaaaataat acgattcaca tttgcttcaa   300
tcacataaac attcattgca ggagttacac ggctaatcat tgaaaattat gatctttgtt   360
agcttaaaag aaaattcagt ttaatacaaa gacatt                              396
```

<210> SEQ ID NO 128
<211> LENGTH: 396
<212> TYPE: DNA
<213> ORGANISM: Homo sapiens
<220> FEATURE:
<221> NAME/KEY: misc_feature
<222> LOCATION: 220, 244, 351, 384
<223> OTHER INFORMATION: n = A,T,C or G

<400> SEQUENCE: 128

```
gcccttttt tttttttta aaggcaaata aataagttt attgggatgt aaccccatca       60
taaattgagg agcatccata caggcaagct ataaatctg gaaaatttaa atcaaattaa    120
attctgcttt taaaaggtg ccttaagtta accaagcatt tgataacac attcaaattt     180 aatatataaa aatagatgta tcctggaaga tataatgaan aacatgccat gtgtataaat   240
tcanaatacg cttttacac aaagaactac aaaaagttac aaagacagcc ttcaggaacc    300
acacttagga aaagtgagcc gagcagcctt cacgcaaagc ctccttcaaa naagtctcac   360
aaagactcca gaaccagccg agtntgtgaa aaagga                              396
```

<210> SEQ ID NO 129
<211> LENGTH: 396
<212> TYPE: DNA
<213> ORGANISM: Homo sapiens
<220> FEATURE:
<221> NAME/KEY: misc_feature
<222> LOCATION: 104, 164, 177, 204, 217, 234, 273, 312, 350, 353, 370
<223> OTHER INFORMATION: n = A,T,C or G

<400> SEQUENCE: 129

```
gcccttttt tttttttttt ttttactcag acaggcaata tttgctcaca tttattctct     60
tgcatcgtaa atagtagcca actcacaaaa ataaagtata caanaatgta atatttttta   120
aaataagatt aacagtgtaa gaaggaaaat ctcaaaaaaa gcanatagac aatgtanaaa   180
attgaaatga aatcccacag taanaaaaaa aaaacanaaa agtgcctatt taanaattat   240
gctacatgtg gaacttaact agaccatttt aanaaagacc aatttctaat gcaaatttttc  300
```

```
tgaggttttc anattttatt tttaaaatat gttatagcta catgttgtcn acncggccgc    360
tcgagtctan agggcccgtt taaacccgct gatcag                              396
```

<210> SEQ ID NO 130
<211> LENGTH: 396
<212> TYPE: DNA
<213> ORGANISM: Homo sapiens
<220> FEATURE:
<221> NAME/KEY: misc_feature
<222> LOCATION: 23, 24, 26, 32, 56, 191, 286, 355
<223> OTHER INFORMATION: n = A,T,C or G

<400> SEQUENCE: 130

```
cgccctttt ttttttttt tanngnacgt gnctttattt ctggatgata taaaanaaaa      60
aacttaaaaa acaccccaaa ccaaacacca atggatcccc aaagcgatgt gactccctct    120
tcccacccgg ataaatagag acttctgtat gtcagtctac cctcccgccc ccataacccc    180
ctctgctata nacatactct gggtatatat tactctactc ggcaatagac atctcccgaa    240
aatagaattc ctgccctgac acctgactct tccctggccg catcanacca cccgccactg    300
tagcacactg gtgtccttgc cccctgtggt cagggccatg ctgtcatccc acaanaaggc    360
cacatttgtc acatggctgc tgtgtccacc gtactt                              396
```

<210> SEQ ID NO 131
<211> LENGTH: 396
<212> TYPE: DNA
<213> ORGANISM: Homo sapiens
<220> FEATURE:
<221> NAME/KEY: misc_feature
<222> LOCATION: 49, 68, 69, 83, 88, 93, 136, 140, 154, 158, 166, 167,
      168, 170, 172, 173, 187, 226, 239, 241, 247, 257, 259, 271, 293,
      301, 318, 334, 336, 342, 344, 357, 377, 384
<223> OTHER INFORMATION: n = A,T,C or G

<400> SEQUENCE: 131

```
gcccttttt tttttttt ttttttttt ttcagtttac acaaaaacnc tttaattgac         60
agtatacnnt tttccaaaat atnttttngt aanaaaatgc aataattatt aactatagtt    120
tttacaaaca agtttntcan taaattccag tgtncttnaa acccnnncn annaaaacat     180 atatgancc ccagttcctg ggcaaactgt tgaacattca ctgcanacaa aaagaccanc     240
nccaaanagt catctgngnc ctccatgctg ngtttgcacc aaacctgagg gancagctag    300
ngaccgtgac aaaagctntg ctacagtttt actntngccc tntntgcctc ccccatnatg    360
tttccttggt ccctcantcc tgtnggagta agttcc                              396
```

<210> SEQ ID NO 132
<211> LENGTH: 396
<212> TYPE: DNA
<213> ORGANISM: Homo sapiens
<220> FEATURE:
<221> NAME/KEY: misc_feature
<222> LOCATION: 69
<223> OTHER INFORMATION: n = A,T,C or G

<400> SEQUENCE: 132

```
cgcgtcgacc gcggccgtag cagccgggct ggtcctgctg cgagccggcg gcccggagtg    60
gggcggcgnt atgtaccttc cacattgagt attcagaaag aagtgatctg aactctgacc    120
attctttatg gatacattaa gtcaaatata agagtctgac tacttgacac actggctcgg    180
tgagttctgc ttttcttttt taatataaat ttattatgtt ggtaaattta gcttttggct    240
tttcactttg ctctcatgat ataagaaaat gtaggttttc tctttcagtt tgaattttcc    300
```
tattcagtaa acaacatgc tagaaaacaa acttttggaa aggcattgta actatttttt    360
caaatagaac cataataaca agtcttgtct taccct    396

<210> SEQ ID NO 133
<211> LENGTH: 396
<212> TYPE: DNA
<213> ORGANISM: Homo sapiens
<220> FEATURE:
<221> NAME/KEY: misc_feature
<222> LOCATION: 1, 17, 18, 20, 21, 25, 26, 30, 31, 40, 44, 45, 46, 51,
      52, 66, 67, 68, 74, 89, 109, 122, 166, 193, 214, 218, 266, 269,
      291, 307, 315, 348, 375, 378, 379, 386, 393
<223> OTHER INFORMATION: n = A,T,C or G

<400> SEQUENCE: 133 ntattaccccc tcctggnnan ntggnnatan nctgcaaggn gatnnncccg nngaacttca    60
ctgatnnncc aatnaaaact gctttaaanc tgactgcaca tatgaattnt aatacttact    120
tngcgggagg ggtggggcag ggacagcaag ggggaggatt gggaanacaa tagacaggca    180
tgctggggat gcngcgggct ctatggcttc tgangcgnaa agaaccagct gggggctctag    240 ggggtatccc cacgcgccct gtagcngcnc attaaacgcg gcgggtgtgg nggttacttc    300
gcaaagngac cgatncactt gccagcgccc tagctgcccg ctcctttngc tttcttccct    360
tcctttctcg ccacnttnnc cggctntccc cgncaa    396

<210> SEQ ID NO 134
<211> LENGTH: 396
<212> TYPE: DNA
<213> ORGANISM: Homo sapiens
<220> FEATURE:
<221> NAME/KEY: misc_feature
<222> LOCATION: 133, 144, 221, 229, 302, 358
<223> OTHER INFORMATION: n = A,T,C or G

<400> SEQUENCE: 134 ttttttttttt ttctgctttt tatatgttta aaaatctctc attctattgc tgctttattt    60
aaagaaagat tactttcttc cctacaagat ctttattaat tgtaaaggga aaatgaataa    120
ctttacaatg ganacacctg gcanacacca tcttaaccaa agcttgaagt taacataacc    180
agtaatagaa ctgatcaata tcttgtgcct cctgatatgg ngtactaana aaaacacaac    240
atcatgccat gatagtcttg ccaaaagtgc ataacctaaa tctaatcata aggaaacatt    300
anacaaactc aaattgaagg acattctaca aagtgccctg tattaaggaa ttattcanag    360
taaaggagac ttaaaagaca tggcaacaat gcagta    396

<210> SEQ ID NO 135
<211> LENGTH: 396
<212> TYPE: DNA
<213> ORGANISM: Homo sapiens

<400> SEQUENCE: 135
gcgtcgacgc tggcagagcc acaccccaag tgcctgtgcc cagagggctt cagtcagctg    60
ctcactcctc cagggcactt ttaggaaagg gttttttagct agtgttttttc ctcgcttttta    120 atgacctcag ccccgcctgc agtggctaga agccagcagg tgcccatgtg ctactgacaa    180
gtgcctcagc ttccccccgg ccccgggtcag gccgtgggag ccgctattat ctgcgttctc    240
tgccaaagac tcgtggggc catcacacct gccctgtgca gcggagccgg accaggctct    300
tgtgtcctca ctcaggtttg cttcccctgt gccactgct gtatgatctg ggggccacca    360 cctgtgccg gtggcctctg ggctgcctcc cgtggt 396

<210> SEQ ID NO 136
<211> LENGTH: 396
<212> TYPE: DNA
<213> ORGANISM: Homo sapiens
<220> FEATURE:
<221> NAME/KEY: misc_feature
<222> LOCATION: 18, 185, 188, 191, 193, 396
<223> OTHER INFORMATION: n = A,T,C or G

<400> SEQUENCE: 136
ttatgcttcc ggctcgtntg ttgtgtggaa ttgtgagcgg ataacaattt cacacaggaa    60
acagctatga ccatgattac gccaagctat ttaggtgaca ctatagaata ctcaagctat   120
gcatcaagct tggtaccgag ctcggatcca ctagtaacgg ccgccagtgt gctgaattc    180 gcggncgntc nantctagag ggcccgttta aacccgctga tcagcctcga ctgtgccttc   240
tagttgccag ccatctgttg tttgcccctc cccgtgcct tccttgaccc tggaaggtgc    300
cactcccact gtcctttcct aataaaatga ggaaattgca tcgcattgtc tgagtaggtg   360
tcattctatt ctgggggtg gggtggggca ggacan                              396

<210> SEQ ID NO 137
<211> LENGTH: 396
<212> TYPE: DNA
<213> ORGANISM: Homo sapiens
<220> FEATURE:
<221> NAME/KEY: misc_feature
<222> LOCATION: 156, 216
<223> OTHER INFORMATION: n = A,T,C or G

<400> SEQUENCE: 137
tttttttttt ttctgctttg tacttgagtt tatttcacaa aaccacggag aaagatactg    60
aaatggagct ctttccagcc tccaagcaag gaggccccag cagccagtct ccagccctt   120 gagccctttt tgttaggccc acacccaaaa gagganaacc agtgtgtgcg cgaaggtaca   180
tggcaaggca cttttgaaaa catcccagtt taccgnggtg aaattgaact tactctgaaa   240
cagatgaaaa gggacatgca aaattgctga gcacatggag gtgtttgtta gtaggtgaaa   300
atcatgtcct gggtataacc cagcttctcc aggttagggt gagccgccgt ctggatcagt   360
ggtggcgggc cacacaccag gatgagcgtg gacttc                             396

<210> SEQ ID NO 138
<211> LENGTH: 396
<212> TYPE: DNA
<213> ORGANISM: Homo sapiens
<220> FEATURE:
<221> NAME/KEY: misc_feature
<222> LOCATION: 69, 136, 265, 272
<223> OTHER INFORMATION: n = A,T,C or G

<400> SEQUENCE: 138
cccttttttt ttttttttac aaatgagaaa atgttatt aagaaaacaa tttagcagct     60
ctcctttana attttacaga ctaaagcaca acccgaaggc aattacagtt tcaatcatta   120
acacactact taaggngctt gcttactcta caactggaaa gttgctgaag tttgtgacat   180
gccactgtaa atgtaagtat tattaaaaat tacaaattgt ttggtgatta ttttgatgac   240
ctcttgagca gcagctcccc ccaanaatgc ancaatggta tgtggctcac cagctccata   300
tcggcaaaat tcgtggacat aatcatcttt caccattaca gataaaccat attcctgaag   360
gaagccagtg agacaagact tcaactttcc tatatc                             396

<210> SEQ ID NO 139
<211> LENGTH: 396
<212> TYPE: DNA
<213> ORGANISM: Homo sapiens
<220> FEATURE:
<221> NAME/KEY: misc_feature
<222> LOCATION: 51, 105, 126, 147, 210, 212, 236, 241, 258, 263, 348
<223> OTHER INFORMATION: n = A,T,C or G

<400> SEQUENCE: 139

```
ccgccctttt tttttttttt ttcacaaaag cactttttat ttgaggcaaa nagaagtctt      60
gctgaaagga ttccagttcc aagcagtcaa aactcaaccg ttagnggcac tattttgacc     120
tggtanattt tgcttctctt tggtcanaaa agggtattca ggttgtactt tccccagcag     180
ggtaaaaaga agggcaaagc aaactggaan anacttctac tctactgaca gggctnttga    240
natccaacat caagctanac acnccctcgc tggccactct acaggttgct gtcccactgc    300
tgagtgacac aggccatact acatttgcaa ggaaaaaaat gaggcaanaa acacaggtat    360
aggtcacttg gggacgagca ggcaaccaca gcttca                              396
```

<210> SEQ ID NO 140
<211> LENGTH: 396
<212> TYPE: DNA
<213> ORGANISM: Homo sapiens
<220> FEATURE:
<221> NAME/KEY: misc_feature
<222> LOCATION: 50, 60, 63, 100, 133, 135, 172, 183, 190, 196, 220, 240,
      262, 266, 273, 278, 293, 327, 332, 341, 348, 355, 380, 391
<223> OTHER INFORMATION: n = A,T,C or G

<400> SEQUENCE: 140

```
tttttttttt tttttttttt ttttttctc atttaacttt tttaatgggn ctcaaaattn      60
tgngacaaat ttttggtcaa gttgttcca ttaaaaagtn ctgattttaa aaactaataa     120
cttaaaactg ccncncccaa aaaaaaaaac caaaggggtc cacaaaacat tntcctttcc    180
ttntgaaggn tttacnatgc attgttatca ttaaccagtn ttttactact aaacttaaan    240
ggccaattga aacaaacagt tntganaccg ttnttccncc actgattaaa agnggggggg    300
caggtattag ggataatatt catttancct tntgagcttt ntgggcanac ttggngacct    360
tgccagctcc agcagccttn ttgtccactg ntttga                              396
```

<210> SEQ ID NO 141
<211> LENGTH: 396
<212> TYPE: DNA
<213> ORGANISM: Homo sapiens

<400> SEQUENCE: 141

```
acgccgagcc acatcgctca gacaccatgg ggaaggtgaa ggtcggagtc aacggatttg     60
gtcgtattgg cgcctggtc accagggctg cttttaactc tggtaaagtg gatattgttg    120
ccatcaatga ccccttcatt gacctcaact acatggttta catgttccaa tatgattcca    180
cccatggcaa attccatggc accgtcaagg ctgagaacgg gaagcttgtc atcaatggaa    240
atcccatcac catcttccag gagcgagatc cctccaaaat caagtggggc gatgctggcg    300
ctgagtacgt cgtggagtcc actggcgtct tcaccaccat ggagaaggct ggggctcatt    360
tgcagggggg agccaaaagg gtcatcatct ctgccc                              396
```

<210> SEQ ID NO 142
<211> LENGTH: 396

<212> TYPE: DNA
<213> ORGANISM: Homo sapiens

<400> SEQUENCE: 142
acgcaggaga ggaagcccag cctgttctac cagagaactt gcccaggtca gaggtctgcg    60
tagaagccct tttctgagca tcctctcctc tcctcacacc tgccactgtc ctctgcgttg   120
ctgtcgaatt aaatcttgca tcaccatggt gcacttctgt ggcctactca ccctccaccg   180
ggagccagtg ccgctgaaga gtatctctgt gagcgtgaac atttacgagt tgtggctgg    240 tgtgtctgca actttgaact acgagaatga ggagaaagtt cctttggagg ccttctttgt   300
gttccccatg gatgaagact ctgctgttta cagctttgag gccttggtgg atgggaagaa   360
aattgtagca gaattacaag acaagatgaa ggcccg                             396

<210> SEQ ID NO 143
<211> LENGTH: 396
<212> TYPE: DNA
<213> ORGANISM: Homo sapiens
<220> FEATURE:
<221> NAME/KEY: misc_feature
<222> LOCATION: 19, 48, 69, 122, 183, 227, 332, 390
<223> OTHER INFORMATION: n = A,T,C or G

<400> SEQUENCE: 143
tttttttttt tttccatana aataggatt tattttcaca tttaaggnga acacaaatcc    60
atgttccana aatgttttat gcataacaca tcatgagtag attgaatttc tttaacacac   120 anaaaatca aagcctacca ggaaatgctt ccctccggag cacaggagct tacaggccac    180
ttntgttagc aacacaggaa ttcacattgt ctaggcacag ctcaagngag gtttgttccc   240
aggttcaact gctcctaccc ccatgggccc tcctcaaaaa cgacagcagc aaaccaacag   300
gcttcacagt aaccaggagg aaagatctca gnggggggaac cttcacaaaa gccctgagtt   360
gtgtttcaaa agccaagctc tggggtctgn ggcctg                             396

<210> SEQ ID NO 144
<211> LENGTH: 396
<212> TYPE: DNA
<213> ORGANISM: Homo sapiens
<220> FEATURE:
<221> NAME/KEY: misc_feature
<222> LOCATION: 221, 331
<223> OTHER INFORMATION: n = A,T,C or G

<400> SEQUENCE: 144
tttttttttt tttcgctctt tggtctgaca agaaaagagt tttaggtgtg tgaagtaggg    60
tgggaaaaaa ggtcagtttc aaattcagta acatatggta acactaagtt aggctgctgc   120
attcttttct ttgggtactt aagccagctg gcacttccac tttgtaacca attatattat   180
gatcaacaac taatcagtta gttcctcagc ttcaactgaa nagttcctga ttacctgatg   240
aaggacatac ttgctctggc ttcaattagc atgctgtcaa gcatccctct ccatgcttaa   300
catggcaaca caaacccaa gagtccttct nttttttca ttagccatga ataaacactc   360
acaaagggga agagtagaca ctgcttttag taaacg                             396

<210> SEQ ID NO 145
<211> LENGTH: 396
<212> TYPE: DNA
<213> ORGANISM: Homo sapiens
<220> FEATURE:
<221> NAME/KEY: misc_feature
<222> LOCATION: 45, 56, 61, 63, 120, 122, 147, 151, 158, 259, 262, 274, 339, 345, 353
<223> OTHER INFORMATION: n = A,T,C or G

<400> SEQUENCE: 145
tttttttttt ttttttcaa tggatccgtt agctttacta ctaanatctt gctganatca 60
nanaagggct tctgggcagg ctgagcactg ggggtgtgca acatggtaac tctgaataan 120
anaaaccctg agttttactg ggcaaanaaa naacaagngg taggtatgat ttctgaacct 180
ggaaatagcg aaaatgaagg aaattccaaa agcgcgtatt tccaaataat gacaggccag 240
caagaggaca ccaaacctnt anaaagaggt attntttctt ccagctactg atggctttgg 300
catcccacag gcacattcct ttggccttca ggatcttana tgcanatgtg ganagtcaag 360
aggtaggctg actctgagtc ttcagctaaa ttcttt 396

<210> SEQ ID NO 146
<211> LENGTH: 396
<212> TYPE: DNA
<213> ORGANISM: Homo sapiens
<220> FEATURE:
<221> NAME/KEY: misc_feature
<222> LOCATION: 120, 130, 176, 180, 185, 208, 238, 254, 259, 261, 275,
      285, 296, 347
<223> OTHER INFORMATION: n = A,T,C or G

<400> SEQUENCE: 146
tttttttttt ttttcattag caaggaagga tttattttt cttttgaggg gagggcggaa 60
cagccgggat ttttggaaca ctaccttttgt ctttcacttt gttgtttgtg tgttaacacn 120
aataaatcan aagcgacttt aaatctccct tcgcaggact gtcttcacgt atcagngcan 180
acaanaaaac agtggcttta caaaaaaanat gttcaagtag ctgcactttt gcctctgngg 240
gtgaggcaca ctgngggana nacaaggtcc cctgnaacca gaggngggaa ggacanagct 300
ggctgactcc ctgctctccc gcattctctc ctccatgtgt tttgaanagg gaagcaacat 360
gttgaggtct gatcatttct acccagggaa cctgtt 396

<210> SEQ ID NO 147
<211> LENGTH: 396
<212> TYPE: DNA
<213> ORGANISM: Homo sapiens

<400> SEQUENCE: 147
acggggaagc caagtgaccg tagtctcatc agacatgagg gaatgggtgg ctccagagaa 60
agcagacatc attgtcagtg agcttctggg ctcatttgct gacaatgaat tgtcgcctga 120
gtgcctggat ggagcccagc acttcctaaa agatgatggt gtgagcatcc ccggggagta 180
cacttccttt ctggctccca tctcttcctc caagctgtac aatgaggtcc gagcctgtag 240
ggagaaggac cgtgaccctg aggcccagtt tgagatgcct tatgtggtac ggctgcacaa 300
cttccaccag ctctctgcac cccagccctg tttcaccttc agccatccca acagagatcc 360
tatgattgac aacaaccgct attgcacctt ggaatt 396

<210> SEQ ID NO 148
<211> LENGTH: 396
<212> TYPE: DNA
<213> ORGANISM: Homo sapiens

<400> SEQUENCE: 148 acgtccatg attgttccag accatgactc ttcctggttg tgggtttgtt acagagcagg 60
agaagcagag gttatgacag ttatgcagac tttcccctc cttttctct tttctcttcc 120

```
ccttgctttt ccactgtttc ttcctgctgc caccctgggcc ttgaattcct gggctgtgaa      180
gacatgtagc agctgcaggg tttaccacac gtgggagggc agcccagtac tgtccctctg      240
ccttccccac tttgagaata tggcagcccc tttcattcct ggcttggggt aggggagacc      300
attgaagtag aagcctcaaa gcagactttt ccctttactg tgtgtactcc aggacgaaga      360
aggaagatca tgcttgatac ttagattggt tttccc                                396
```

```
<210> SEQ ID NO 149
<211> LENGTH: 396
<212> TYPE: DNA
<213> ORGANISM: Homo sapiens
<220> FEATURE:
<221> NAME/KEY: misc_feature
<222> LOCATION: 214, 295
<223> OTHER INFORMATION: n = A,T,C or G

<400> SEQUENCE: 149
tttttttttt ttaaagagt cacattttat tcaatgccta tttgtacatg ttactagcaa        60
taaactcttt tatctttaat tttgagaagt tttacaaata cagcaaagca gaatgactaa     120
tagagccggt aaccaggaca cagatttgga aaaataggtc taattggttg ttacactgtg     180
tttatgtcat acatttcgct tatttttatc aaanaaaaat cagaatttat aaaatgttaa     240
ttaaaaggaa aacattctga gtaaatttag tcccgtgttt cttcctccaa atctntttgt     300
tctacactaa caggtcagga taagtatgga tggggaggct ggaaaaaggg catccttccc     360
catgcggtcc ccagagccac cctctccaag caggac                                396
```

```
<210> SEQ ID NO 150
<211> LENGTH: 396
<212> TYPE: DNA
<213> ORGANISM: Homo sapiens

<400> SEQUENCE: 150
acgcctctct tcagttggca cccaaacatc tggattggca aatcagtggc aagaagttcc       60
agcatctgga cttttcagaa ttgatcttaa gtctactgtc atttccagat gcattatttt     120
acaactgtat ccttggaaat atatttctag ggagaatatt attgaagaaa atgttaatag     180
cctgagtcaa atttcagcag acttaccagc atttgtatca gtggtagcaa atgaagccaa     240
actgtatctt gaaaaacctg ttgttccttt aaatatgatg ttgccacaag ctgcattgga     300
gactcattgc agtaatattt ccaatgtgcc acctacaaga gagatacttc aagtcttttct    360 tactgatgta cacatgaagg aagtaattca gcagtt                                396
```

```
<210> SEQ ID NO 151
<211> LENGTH: 396
<212> TYPE: DNA
<213> ORGANISM: Homo sapiens
<220> FEATURE:
<221> NAME/KEY: misc_feature
<222> LOCATION: 146, 299, 332
<223> OTHER INFORMATION: n = A,T,C or G

<400> SEQUENCE: 151
acaaaatgcc cagcctacag agtctgagaa ggaaatttat aatcaggtga atgtagtatt       60
aaaagatgca gaaggcatct tggaggactt gcagtcatac agaggagctg ccacgaaat      120 acgagaggca atccagcatc cagcanatga gaagttgcaa gagaaggcat ggggtgcagt     180
tgttccacta gtaggcaaat taagaaaatt ttacgaattt tctcagaggt tagaagcagc     240
```

-continued attaagaggt cttctgggag ccttaacaag tacccatat tctcccaccc agcatctana    300
gcgagagcag gctcttgcta aacagtttgc anaaattctt catttcacac tccggtttga    360
tgaactcaag atgacaaatc ctgccataca gaatga    396

<210> SEQ ID NO 152
<211> LENGTH: 396
<212> TYPE: DNA
<213> ORGANISM: Homo sapiens
<220> FEATURE:
<221> NAME/KEY: misc_feature
<222> LOCATION: 249
<223> OTHER INFORMATION: n = A,T,C or G

<400> SEQUENCE: 152
acgcagcgct cggcttcctg gtaattcttc acctcttttc tcagctccct gcagcatggg    60
tgctgggccc tccttgctgc tcgccgccct cctgctgctt ctctccggcg acggcgccgt    120
gcgctgcgac acacctgcca actgcaccta tcttgacctg ctgggcacct gggtcttcca    180
ggtgggctcc agcggttccc agcgcgatgt caactgctcg gttatgggac acaagaaaa    240 aaaagtagng gtgtaccttc agaagctgga tacagcatat gatgaccttg gcaattctgg    300
ccatttcacc atcatttaca accaaggctt tgagattgtg ttgaatgact acaagtggtt    360
tgcctttttt aagtataaag aagagggcag caaggt    396

<210> SEQ ID NO 153
<211> LENGTH: 396
<212> TYPE: DNA
<213> ORGANISM: Homo sapiens

<400> SEQUENCE: 153
ccagagacaa cttcgcggtg tggtgaactc tctgaggaaa aacacgtgcg tggcaacaag    60
tgactgagac ctagaaatcc aagcgttgga ggtcctgagg ccagcctaag tcgcttcaaa    120
atggaacgaa ggcgtttgcg gggttccatt cagagccgat acatcagcat gagtgtgtgg    180
acaagcccac ggagacttgt ggagctggca gggcagagcc tgctgaagga tgaggccctg    240
gccattgccg ccctggagtt gctgcccagg gagctcttcc cgccactctt catggcagcc    300
tttgacggga gacacagcca gaccctgaag gcaatggtgc aggcctggcc cttcacctgc    360
ctccctctgg gagtgctgat gaagggacaa catctt    396

<210> SEQ ID NO 154
<211> LENGTH: 396
<212> TYPE: DNA
<213> ORGANISM: Homo sapiens
<220> FEATURE:
<221> NAME/KEY: misc_feature
<222> LOCATION: 42, 45, 59, 82
<223> OTHER INFORMATION: n = A,T,C or G

<400> SEQUENCE: 154
acagcaaacc tcctcacagc ccactggtcc tcaagagggg cnacntcttc acacatcanc    60
acaactacgc attgcctccc tncactcgga aggactatcc tgctgccaag agggtcaagt    120
tggacagtgt cagagtcctg agacagatca gcaacaaccg aaaatgcacc agccccaggt    180
cctcggacac cgaggagaat gtcaagaggc gaacacacaa cgtcttggag cgccagagga    240
ggaacgagct aaaacggagc ttttttgccc tgcgtgacca gatcccggag ttggaaaaca    300
atgaaaaggc cccaaggta gttatcctta aaaaagccac agcatacatc ctgtccgtcc    360
aagcagagga gcaaaagctc atttctgaag aggact    396

<210> SEQ ID NO 155
<211> LENGTH: 396
<212> TYPE: DNA
<213> ORGANISM: Homo sapiens
<220> FEATURE:
<221> NAME/KEY: misc_feature
<222> LOCATION: 15, 17, 202, 280, 339
<223> OTHER INFORMATION: n = A,T,C or G

<400> SEQUENCE: 155
tttttttttt tgaananaca ggtctttaat gtacggagtc tcacaaggca caaacaccct      60
caccaggacc aaataaataa ctccacggtt gcaggaaggc gcggtctggg gaggatgcgg     120
catctgagct ctcccagggc tggtgggcga gccggggtc tgcagtctgt gaggggcctc      180
ctgggtgtgt ccgggcctct anagcggtc cagtctccag gatgggatc gctcactcac       240 tctccgagtc ggagtagtcc gccacgaggg aggagccgan actgcagggg tgccgcgtgt    300 cggggtgtc agctgcctcc tgggaggagc ctgctggcna caggggcttg tcctgacggc     360
tcccttcctg cccctcggg ctgctgcact tgggggg                               396

<210> SEQ ID NO 156
<211> LENGTH: 396
<212> TYPE: DNA
<213> ORGANISM: Homo sapiens
<220> FEATURE:
<221> NAME/KEY: misc_feature
<222> LOCATION: 11, 30, 32, 37, 309, 332
<223> OTHER INFORMATION: n = A,T,C or G

<400> SEQUENCE: 156 gaagggggc ngggcagggg cggaatgtan anattantgc catgattgaa gatttaagaa       60
acgtgagatt caggattttc accacatccc catttagtta gcttgctcgt ttggctggtg    120
caaatgccag atggattatg aacaatgaca gtaaattaat gcaacataat caggtaatga    180
tgccaagcgt atctggtgtt ccaggtattg tacctttacc ggaacaaatc agtaaatcca    240
caatccctgg cacctgttag gcagctatta acctagtaaa tgctccccca tcccatctca    300
atcagcaang acaatcaaaa acatttgctt tnagtggcag gaacactggt acattttac     360 ttgctccaag ggctgtgcca acgctccctc tctctg                               396

<210> SEQ ID NO 157
<211> LENGTH: 396
<212> TYPE: DNA
<213> ORGANISM: Homo sapiens
<220> FEATURE:
<221> NAME/KEY: misc_feature
<222> LOCATION: 121, 202, 204, 255, 314, 332, 368
<223> OTHER INFORMATION: n = A,T,C or G

<400> SEQUENCE: 157
tttttttttt tttttgggga atgtaaatct tttattaaaa cagttgtctt tccacagtag      60
taaagctttg gcacatacag tataaaaaat aatcacccac cataattata ccaaattcct    120
nttatcaact gcatactaag tgttttcaat acaattttt ccgtataaaa atactgggaa     180
aaattgataa ataacaggta ananaaagat atttctaggc aattactagg atcatttgga    240
aaaagtgagt actgnggata tttaaaatat cacagtaaca agatcatgct tgttcctaca    300
gtattgcggg ccanacactt aagtgaaagc anaagtgttt gggtgacttt cctacttaaa    360
attttggnca tatcatttca aaacatttgc atcttg                               396

```
<210> SEQ ID NO 158
<211> LENGTH: 396
<212> TYPE: DNA
<213> ORGANISM: Homo sapiens

<400> SEQUENCE: 158
tttccgaaga cgggcagctt cagagaagag gattattcgg gagattgctg gtgtggccca      60
tagactcttt ggcatagact ctttcgcagg cagccactct gagtgtggcc agttctataa     120
ccatccccaa actagctgga gcctgatgga taggaacggg tagtctgtcc tcttccccat     180
aaaaatgttc caaaaagtta tctccagaga gagtccctta tgaagacagt tgccaagctg     240
tattctcatt ctttaaacca atacccaggt cagggctagt tcacactagc actgttaggg     300
acatggtgtg gctagaaatg aattgagtgt gacttctccc tacaaccccca ggcccaggga    360 taggaggagg cagaggggtg cctggagttt ctgcac                              396

<210> SEQ ID NO 159
<211> LENGTH: 396
<212> TYPE: DNA
<213> ORGANISM: Homo sapiens

<400> SEQUENCE: 159
tccgcgcgtt gggaggtgta gcgcggctct gaacgcgctg agggccgttg agtgtcgcag      60
gcggcgaggg cgcgagtgag gagcagaccc aggcatcgcg cgccgagaag gccgggcgtc     120
cccacactga aggtccggaa aggcgacttc cggggggcttt ggcacctggc ggaccctccc    180
ggagcgtcgg cacctgaacg cgaggcgctc cattgcgcgt gcgcgttgag gggcttcccg    240
cacctgatcg cgagacccca acggctggtg gcgtcgcctg cgcgtctcgg ctgagctggc    300
catggcgcag ctgtgcgggc tgaggcggag ccgggcgttt ctcgccctgc tgggatcgct    360
gctcctctct ggggtcctgg cggccgaccg agaacg                              396

<210> SEQ ID NO 160
<211> LENGTH: 396
<212> TYPE: DNA
<213> ORGANISM: Homo sapiens
<220> FEATURE:
<221> NAME/KEY: misc_feature
<222> LOCATION: 96, 102, 122, 124, 129, 146, 148, 184, 189, 196, 205,
      208, 229, 246, 259, 261, 269, 272, 281, 297, 305, 308, 327, 331,
      337, 338, 339, 343, 346, 354, 366, 367, 369, 378, 379, 380,
      381, 391, 395
<223> OTHER INFORMATION: n = A,T,C or G

<400> SEQUENCE: 160
ggaaaccttc tcaactaaga gaacatcatt tctggcaaac tatttttgtt agctcacaat      60
atatgtcgta cactctacaa tgtaaatagc actganccac ancttacaga aggtaaaaag     120
angnataana acttccttta caaaanantt cctgttgttc ttaatactcc ccattgctta     180
tganaattnt ctatangtct ctcangantg ttcgcaccca tttcttttnt aacttctact    240
aaaaanccat ttacattgna nagtgtacna cntatatttg ngagctaaca aaaaatngtt    300
ttccnganat gatgttcttt tagtttnaga nggttcnnnc aanttnctac tccngcccgc    360
cactgnncnc cacatttnnn naattacacc ncacng                              396

<210> SEQ ID NO 161
<211> LENGTH: 396
<212> TYPE: DNA
<213> ORGANISM: Homo sapiens
<220> FEATURE:
```

```
<221> NAME/KEY: misc_feature
<222> LOCATION: 271, 273, 325, 364
<223> OTHER INFORMATION: n = A,T,C or G

<400> SEQUENCE: 161
tttttgtttg attattttta ttataatgaa attaaactta tgactattac agtatgctca      60
gcttaaaaca tttatgagta ctgcaaggac taacagaaac aggaaaaatc ctactaaaaa     120
tatttgttga tgggaaatca ttgtgaaagc aaacctccaa atattcattt gtaagccata     180
agaggataag cacaaccata tgggaggaga taaccagtct ctcccttcat atatattctt     240
ttttatttct tggtatacct tcccaaaaca nanacattca acagtagtta gaatggccat     300
ctcccaacat tttaaaaaaa ctgcncccccc caatgggtga acaaagtaaa gagtagtaac    360
ctanagttca gctgagtaag ccactgtgga gcctta                               396

<210> SEQ ID NO 162
<211> LENGTH: 396
<212> TYPE: DNA
<213> ORGANISM: Homo sapiens
<220> FEATURE:
<221> NAME/KEY: misc_feature
<222> LOCATION: 33, 38, 51, 62, 71, 72, 88, 97, 98, 100, 106, 142, 155,
      160, 161, 163, 168, 170, 174, 183, 190, 194, 203, 214, 216, 231,
      232, 241, 242, 252, 258, 260, 264, 265, 267, 276, 278, 282,
      287, 289, 292, 295, 297, 301, 311, 319, 322, 325
<223> OTHER INFORMATION: n = A,T,C or G
<220> FEATURE:
<221> NAME/KEY: misc_feature
<222> LOCATION: 330, 337, 341, 342, 347, 348, 354, 356, 361, 367, 368,
      375, 379, 385, 391, 394, 395
<223> OTHER INFORMATION: n = A,T,C or G

<400> SEQUENCE: 162
tttttttttt tttttttttt tttttttttt ttngggncc aaattttttt ntttgaagga       60
angggacaaa nnaaaaaact taaggggntg ttttggnncn acttanaaaa aagggaaagg     120 aaacccaac atgcatgccc tnccttgggg accanggaan ncnccccncn ggtntgggga      180
aantaacccn aggnttaact ttnattatca ctgncccca gggggggctt nnaaaaaaaa      240 nnttcccca anccaaantn gggnncncc attttncnca anttggncnc cnggncnccc       300
nattttttga ngggtttcnc cngcncattn agggaanggg nntcaannaa accncncaaa    360
ngggggnnat ttttntcang ggccnatttg ngcnnt                               396

<210> SEQ ID NO 163
<211> LENGTH: 396
<212> TYPE: DNA
<213> ORGANISM: Homo sapiens

<400> SEQUENCE: 163
cactgtccgg ctctaacaca gctattaagt gctacctgcc tctcaggcac tctcctcgcc     60
cagtttctga ggtcagacga gtgtctgcga tgtcttcccg cactctattc ccccagcctc    120
tttctgcttt catgctcagc acatcatctt cctaggcagt ctcttcccca aagtctcacc    180
ttttcttcca atagaaaatt ccgcttgacc tttggtgcac tgcccacttc ccagctccac    240
tggcccaagt ctgagccgga ggccttgtt ttggggggcgg ggggagagtt ggatgtgatt    300
gcccttgaag aacaaggctg acctgagagg ttcctggcgc cctgaggtgg ctcagcacct    360
gcccagggta ggcctggcat gagggggttag gtcagc                              396

<210> SEQ ID NO 164
<211> LENGTH: 396
```

```
<212> TYPE: DNA
<213> ORGANISM: Homo sapiens

<400> SEQUENCE: 164
gacacgcggc ggtgtcctgt gttggccatg gccgactacc tgattagtgg gggcacgtcc      60
tacgtgccag acgacggact cacagcacag cagctcttca actgcggaga cggcctcacc     120
tacaatgact ttctcattct ccctgggtac atcgacttca ctgcagacca ggtgacctg     180 acttctgctc tgaccaagaa aatcactctt aagacccccac tggtttcctc tcccatggac    240
acagtcacag aggctgggat ggccatagca atggcgctta caggcggtat tggcttcatc    300
caccacaact gtacacctga attccaggcc aatgaagttc ggaaagtgaa gaaatatgaa    360
cagggattca tcacagaccc tgtggtcctc agcccc                                396

<210> SEQ ID NO 165
<211> LENGTH: 396
<212> TYPE: DNA
<213> ORGANISM: Homo sapiens
<220> FEATURE:
<221> NAME/KEY: misc_feature
<222> LOCATION: 29, 33, 55, 57, 65, 77, 82, 87, 98, 101, 103, 114, 118,
      124, 169, 171, 173, 183, 186, 188, 216, 219, 227, 230, 242, 243,
      245, 252, 265, 273, 290, 296, 321, 324, 332, 338, 340, 342,
      345, 359, 372, 380
<223> OTHER INFORMATION: n = A,T,C or G

<400> SEQUENCE: 165
tttttttttt ttttttttt tttttcang ggncactgag gcttttattt ttgancncaa        60
aaccnccggg gatctancct gnggccnccc cggaaatnac ncnaggctca catnactnta    120
aacncttggg ggaaagggag gcaaaaaaaa caatgacttg ggccaattnc ncnactgcaa    180
agntananct gccaacaggg ctccagggag cttggnttnt gtaaaanttn taaggaagcg    240
gnncnaactc cncgggggggg gggcnctaac tancagggac ccctgcaagn gttggncggg    300
ggcctcaacc tgcctgagct nacncaaggg gngggggtntn tntanccaac aggggaccna    360
agggcttgcc tncccacagn ttacttggcc aagggg                               396

<210> SEQ ID NO 166
<211> LENGTH: 396
<212> TYPE: DNA
<213> ORGANISM: Homo sapiens
<220> FEATURE:
<221> NAME/KEY: misc_feature
<222> LOCATION: 151, 255
<223> OTHER INFORMATION: n = A,T,C or G

<400> SEQUENCE: 166 tttttttcaaa ttcagagcat ttttattaaa agaacaaaat attaaggcac aaaatacatc      60
aatttttcaa atgaaaaccc ttcaaacggt tatgtcctac attcaacgaa acttcttcca    120 aattacgaa taatttaact ttttaaaata naaaaataca agttcttaaa tgcctaaaat    180
ttctccccaa ataaatgttt tcttagtttt aatgaagtct cttcatgcag tactgagctc    240
caatattata atgtncactt ccttaaaaat ctagttttgc cacttatata cattcaatat    300
gtttaaccag tatattaacc agtatattaa ccaatatgtt aaacttcttt taagtataag    360
gcttggtatt ttgtattgct tattgcatgc tttgat                               396

<210> SEQ ID NO 167
<211> LENGTH: 396
<212> TYPE: DNA
<213> ORGANISM: Homo sapiens
```

<400> SEQUENCE: 167

```
tggcggcagc ggcggtggcg gtggctgagc agaggacccg gcgggcggcc tcgcgggtca      60
ggacacaatg tttgcacgag gactgaagag gaaatgtgtt ggccacgagg aagacgtgga     120
gggagccctg gccggcttga agacagtgtc ctcatacagc ctgcagcggc agtcgctcct     180
ggacatgtct ctggtgaagt tgcagctttg ccacatgctt gtggagccca atctgtgccg     240
ctcagtcctc attgccaaca cggtccggca gatccaagag gagatgacgc aggatgggac     300
gtggcgcaca gtggcacccc aggctgcaga gcgggcgccg ctcgaccgct tggtctccac     360
ggagatcctg tgccgtgcag cgtgggggca agaggg                               396
```

<210> SEQ ID NO 168
<211> LENGTH: 396
<212> TYPE: DNA
<213> ORGANISM: Homo sapiens

<400> SEQUENCE: 168

```
taggatggta agagtattat aaggattggt acaaggcatg atgagtcctt ttgcttttag      60
gcttttgact tctggttta gactttcttt agcttctgtt gttagacaac attgtgcaag     120
cttggttttt ataagtttgc atggattaaa ctgaacttaa tgaaattgtc cctccccca     180
aattctcagc acaatttta ggcccacaag gagtcaagca cctcaaggag atcttcagtt     240
tgaacttggt gtagacacag ggatactgat gaatcaatat tcaaattagc tgttacctac     300
ttaagaaaga gaggagacct tggggatttc gaggaagggt tcataaggga gatttagct     360
gagaaatacc atttgcacag tcaatcactt ctgacc                               396
```

<210> SEQ ID NO 169
<211> LENGTH: 396
<212> TYPE: DNA
<213> ORGANISM: Homo sapiens
<220> FEATURE:
<221> NAME/KEY: misc_feature
<222> LOCATION: 16, 58, 76, 84, 99, 111, 114, 124, 136, 140, 161, 167,
      184, 189, 204, 206, 210, 228, 230, 232, 243, 275, 277, 289, 301,
      303, 312, 319, 321, 323, 325, 333, 345, 349, 355, 359, 364,
      365, 372, 375, 377, 379, 383, 387, 389, 394, 396
<223> OTHER INFORMATION: n = A,T,C or G

<400> SEQUENCE: 169

```
tttttttttt tttcanaatt aaattcttta atacaaaatg cttttttttt tttaaaanat      60
atctgtattt ctttgncgtt gttnaaaaat aaatatgtnc tacggaatat ntcnaaaaac     120
tgcnctaaaa acaaanacgn gatgttaata tcttttcccc ncaattntta cggataaaca     180
gtancccna taaataaatg atancnaatn ttaaaattaa aaaagganan anatttagta     240
tgnaaaattc tctattttt cttggtttgg ttttncntat aaaaaacana atagcaatgt     300
ntnttttatc anaatcccnt ntntncctaa acnttttttt ttttntttnc cccnaatnc     360
aagnngccaa anatntntnt agnatgnana tgtntn                               396
```

<210> SEQ ID NO 170
<211> LENGTH: 396
<212> TYPE: DNA
<213> ORGANISM: Homo sapiens

<400> SEQUENCE: 170

```
tgagaagtac catgccgctt ctgcagagga acaggcaacc atcgaacgca acccctacac      60
catcttccat caagcactga aaaactgtga gcctatgatt gggctggtac ccatcctcaa     120
```

```
gggaggccgt tctaccagg tccctgtacc cctacccgac cggcgtcgcc gcttcctagc      180
catgaagtgg atgatcactg agtgccggga taaaaagcac cagcggacac tgatgccgga      240
gaagctgtca cacaagctgc tggaggcttt ccataaccag gccccgtga tcaagaggaa       300 gcatgacttg cacaagatgg cagaggccaa ccgtgccctg ccccactacc gctggtggta     360
gagtctccag gaggagccca gggccctctg cgcaag                                396
```

<210> SEQ ID NO 171
<211> LENGTH: 396
<212> TYPE: DNA
<213> ORGANISM: Homo sapiens
<220> FEATURE:
<221> NAME/KEY: misc_feature
<222> LOCATION: 133, 224, 260, 264, 268, 279, 283, 317, 322, 338, 360,
      370, 371, 378
<223> OTHER INFORMATION: n = A,T,C or G

<400> SEQUENCE: 171

```
ggtcctcgtc gtggtgagcg cagccactca ggctggtcct gggggtgggg ctgtagggga       60
aagtgctaaa gccgctgagt gaagtaagaa ctctgctaga gaggaaaatg ggcttgcttt      120
catcatcatc ctnctcagct ggtggggtca agtgggaagt tctgtcactg ggatctggtt      180
cagtgtctca agaccttgcc ccaccacgga aagcctttt cacntacccc aaaggacttg      240
gagagatgtt agaagatggn tctnaaanat tcctctgcna atntgttttt agctatcaag      300
tggcttcccc ccttaancag gnaaaacatg atcagcangt tgctcggatg gaaaaactan      360
cttggtttgn naaaaaanct ggaggcttga caatgg                                396
```

<210> SEQ ID NO 172
<211> LENGTH: 396
<212> TYPE: DNA
<213> ORGANISM: Homo sapiens
<220> FEATURE:
<221> NAME/KEY: misc_feature
<222> LOCATION: 239, 242, 244, 246, 249, 257, 260, 314, 329, 355, 372,
      378, 385, 387, 388, 395
<223> OTHER INFORMATION: n = A,T,C or G

<400> SEQUENCE: 172

```
agccttgggc caccctcttg gagcatctgg ctgtcgaatt cttgtgaccc tgttacacac       60
actggagaga atgggcagaa gtcgtggtgt tgcagccctg tgcattgggg gtgggatggg      120
aatagcaatg tgtgttcaga gagaatgaat tgcttaaact ttgaacaacc tcaatttctt      180
tttaaactaa taaagtacta ggttgcaata tgtgaaaaaa aaaaaaaaag ggcggccgnt      240
cnantntana gggcccnttn aaacccgttg atcaacctcg actgtgcctt ctagttgcca      300
gccatctgtt gttngcccct ccccgtgnc tttcttgacc ttgaaagggg cccncccct        360 gtctttccta anaaaaanga agaantnncc ttccnt                               396
```

<210> SEQ ID NO 173
<211> LENGTH: 396
<212> TYPE: DNA
<213> ORGANISM: Homo sapiens
<220> FEATURE:
<221> NAME/KEY: misc_feature
<222> LOCATION: 209, 210, 232, 244, 270, 275, 284, 341, 343, 349, 359,
      364, 368, 376, 380, 382, 388, 389, 390, 392
<223> OTHER INFORMATION: n = A,T,C or G

<400> SEQUENCE: 173

```
aagcatgtgg atatgtttag ctacgtttac tcacagccag cgaactgaca ttaaaataac       60
```

```
taacaaacag attcttttat gtgatgctgg aactcttgac agctataatt attattcaga    120
aatgactttt tgaaagtaaa agcagcataa agaatttgtc acaggaaggc tgtctcagat    180
aaattatggt aaaattttgc aggggacann cttttttaaga cttgcacaat tnccggatcc   240
tgcnctgact ttggaaaagg catatatgtn ctagnggcat gganaatgcc ccatactcat    300
gcatgcaaat taaacaacca agtttgaatc tttttgggg ngngctatnc tttaacccng    360
tacnggcntt attatntaan gnccctgnnn cntgtg                              396

<210> SEQ ID NO 174
<211> LENGTH: 924
<212> TYPE: DNA
<213> ORGANISM: Homo sapiens

<400> SEQUENCE: 174
cctgacgacc cggcgacggc gacgtctctt ttgactaaaa gacagtgtcc agtgctccag     60
cctaggagtc tacggggacc gcctcccgcg ccgccaccat gcccaacttc tctggcaact   120
ggaaaatcat ccgatcggaa aacttcgagg aattgctcaa agtgctgggg gtgaatgtga   180
tgctgaggaa gattgctgtg gctgcagcgt ccaagccagc agtggagatc aaacaggagg   240
gagacacttt ctacatcaaa acctccacca ccgtgcgcac cacagagatt aacttcaagg   300
ttggggagga gtttgaggag cagactgtgg atgggaggcc ctgtaagagc ctggtgaaat   360
gggagagtga gaataaaatg gtctgtgagc agaagctcct gaagggagag ggccccaaga   420
cctcgtggac cagagaactg accaacgatg gggaactgat cctgaccatg acggcggatg   480
acgttgtgtg caccagggtc tacgtccgag agtgagtggc cacaggtaga accgcggccg   540
aagcccacca ctggccatgc tcaccgccct gcttcactgc cccctccgtc ccaccccctc   600
cttctaggat agcgctcccc ttaccccagt cacttctggg ggtcactggg atgcctcttg   660
cagggtcttg ctttctttga cctcttctct cctcccctac accaacaaag aggaatggct   720
gcaagagccc agatcaccca ttccgggttc actccccgcc tccccaagtc agcagtccta   780
gccccaaacc agcccagagc agggtctctc taaagggggac ttgagggcct gagcaggaaa   840
gactggccct ctagcttcta ccctttgtcc ctgtagccta tacagtttag aatatttatt   900
tgttaatttt attaaaatgc ttta                                           924

<210> SEQ ID NO 175
<211> LENGTH: 3321
<212> TYPE: DNA
<213> ORGANISM: Homo sapiens

<400> SEQUENCE: 175
atgaagattt tgatacttgg tattttttctg tttttatgta gtaccccagc ctgggcgaaa    60
gaaaagcatt attcattgg aattattgaa acgacttggg attatgcctc tgaccatggg   120
gaaaagaaac ttatttctgt tgacacggaa cattccaata tctatcttca aaatggccca   180
gatagaattg ggagactata taagaaggcc ctttatcttc agtacacaga tgaaacccttt   240 aggacaacta tagaaaaacc ggtctggctt gggttttttag gccctattat caaagctgaa   300
actggagata agtttatgt acacttaaaa aaccttgcct ctaggcccta cacctttcat   360
tcacatggaa taacttacta taaggaacat gagggggcca tctaccctga taacaccaca   420
gattttcaaa gagcagatga caaagtatat ccaggagagc agtatacata catgttgctt   480
gccactgaag aacaaagtcc tgggaagga gatggcaatt gtgtgactag gatttaccat   540
```

```
tcccacattg atgctccaaa agatattgcc tcaggactca tcggacctttt aataatctgt    600
aaaaaagatt ctctagataa agaaaaagaa aaacatattg accgagaatt tgtggtgatg    660
ttttctgtgg tggatgaaaa tttcagctgg tacctagaag acaacattaa aacctactgc    720
tcagaaccag agaaagttga caaagacaac gaagacttcc aggagagtaa cagaatgtat    780
tctgtgaatg gatacacttt tggaagtctc ccaggactct ccatgtgtgc tgaagacaga    840
gtaaaatggt acctttttgg tatgggtaat gaagttgatg tgcacgcagc tttctttcac    900
gggcaagcac tgactaacaa gaactaccgt attgacacaa tcaacctctt tcctgctacc    960
ctgtttgatg cttatatggt ggcccagaac cctggagaat ggatgctcag ctgtcagaat   1020
ctaaaccatc tgaaagccgg tttgcaagcc ttttttccagg tccaggagtg taacaagtct   1080
tcatcaaagg ataatatccg tgggaagcat gttagacact actacattgc cgctgaggaa   1140
atcatctgga actatgctcc ctctggtata gacatcttca ctaaagaaaa cttaacagca   1200
cctgaagtg actcagcggt gtttttttgaa caaggtacca caagaattgg aggctcttat   1260
aaaaagctgg tttatcgtga gtacacagat gcctccttca caaatcgaaa ggagagaggc   1320
cctgaagaag agcatcttgg catcctgggt cctgtcattt gggcagaggt gggagacacc   1380
atcagagtaa ccttccataa caaaggagca tatcccctca gtattgagcc gattggggtg   1440
agattcaata gaacaacgga gggcacatac tattccccaa attacaaccc ccagagcaga   1500
agtgtgcctc cttcagcctc ccatgtggca cccacagaaa cattcaccta tgaatggact   1560
gtccccaaag aagtaggacc cactaatgca gatcctgtgt gtctagctaa gatgtattat   1620
tctgctgtgg atcccactaa agatatattc actgggctta ttgggccaat gaaaatatgc   1680
aagaaaggaa gtttacatgc aaatgggaga cagaaagatg tagacaagga attctatttg   1740
tttcctacag tatttgatga gaatgagagt ttactcctgg aagataatat tagaatgttt   1800
acaactgcac ctgatcaggt ggataaggaa gatgaagact ttcaggaatc taataaaatg   1860
cactccatga atggattcat gtatgggaat cagccgggtc tcactatgtg caaaggagat   1920
tcggtcgtgt ggtacttatt cagcgccgga aatgaggccg atgtacatgg aatatacttt   1980
tcaggaaaca catatctgtg gagaggagaa cggagagaca cagcaaacct cttccctcaa   2040
acaagtctta cgctccacat gtggcctgac acagagggga cttttaatgt tgaatgcctt   2100
acaactgatc attacacagg cggcatgaag caaaaatata ctgtgaacca atgcaggcgg   2160
cagtctgagg attccacctt ctacctggga gagaggacat actatatcgc agcagtggag   2220
gtggaatggg attattcccc acaaagggag tgggaaaagg agctgcatca tttacaagag   2280
cagaatgttt caaatgcatt tttagataag ggagagtttt acataggctc aaagtacaag   2340
aaagttgtgt atcggcagta tactgatagc acattccgtg ttccagtgga gagaaaagct   2400
gaagaagaac atctgggaat tctaggtcca caacttcatg cagatgttgg agacaaagtc   2460
aaaattatct ttaaaaacat ggccacaagg ccctactcaa tacatgccca tggggtacaa   2520
acagagagtt ctacagttac tccaacatta ccaggtgaaa ctctcactta cgtatggaaa   2580
atcccagaaa gatctggagc tggaacagag gattctgctt gtattccatg gcttattat    2640
tcaactgtgg atcaagttaa ggacctctac agtggattaa ttggcccccct gattgtttgt   2700
cgaagacctt acttgaaagt attcaatccc agaaggaagc tggaatttgc ccttctgttt   2760
ctagtttttg atgagaatga atcttggtac ttagatgaca acatcaaaac atactctgat   2820
cacccccgaga aagtaaacaa agatgatgag gaattcatag aaagcaataa aatgcatgct   2880
attaatggaa gaatgtttgg aaacctacaa ggcctcacaa tgcacgtggg agatgaagtc   2940
```

```
aactggtatc tgatgggaat gggcaatgaa atagacttac acactgtaca ttttcacggc    3000
catagcttcc aatacaagca caggggagtt tatagttctg atgtctttga catttccct    3060 ggaacatacc aaaccctaga aatgtttcca agaacacctg gaatttggtt actccactgc    3120
catgtgaccg accacattca tgctggaatg gaaaccactt acaccgttct acaaaatgaa    3180
gacaccaaat ctggctgaat gaaataaatt ggtgataagt ggaaaaaaga gaaaaaccaa    3240
tgattcataa caatgtatgt gaaagtgtaa aatagaatgt tactttggaa tgactataaa    3300
cattaaaaga gactggagca t                                              3321

<210> SEQ ID NO 176
<211> LENGTH: 487
<212> TYPE: DNA
<213> ORGANISM: Homo sapiens

<400> SEQUENCE: 176
gaaatacttt ctgtcttatt aaaattaata aattattggt ctttacaaga cttggataca     60
ttacagcaga catggaaata taattttaaa aaatttctct ccaacctcct tcaaattcag    120
tcaccactgt tatattacct tctccaggaa ccctccagtg ggaaggctg cgatattaga    180 tttccttgta tgcaaagttt ttgttgaaag ctgtgctcag aggaggtgag aggagaggaa    240
ggagaaaact gcatcataac tttacagaat tgaatctaga gtcttccccg aaaagcccag    300
aaacttctct gcagtatctg gcttgtccat ctggtctaag gtggctgctt cttccccagc    360
catgagtcag tttgtgccca tgaataatac acgacctgtt atttccatga ctgctttact    420
gtatttttaa ggtcaatata ctgtacattt gataataaaa taatattctc ccaaaaaaaa    480
aaaaaaa                                                              487

<210> SEQ ID NO 177
<211> LENGTH: 3999
<212> TYPE: DNA
<213> ORGANISM: Homo sapiens

<400> SEQUENCE: 177
caagattcca catttgatgg ggtgactgac aaacccatct tagactgctg tgcctgcgga     60
actgccaagt acagactcac attttatggg aattggtccg agaagacaca cccaaaggat    120
taccctcgtc gggccaacca ctggtctgcg atcatcggag gatcccactc caagaattat    180
gtactgtggg aatatggagg atatgccagc gaaggcgtca acaagttgc agaattgggc    240 tcacccgtga aaatggagga agaaattcga caacagagtg atgaggtcct caccgtcatc    300
aaagccaaag cccaatggcc agcctggcag cctctcaacg tgagagcagc accttcagct    360
gaattttccg tggacagaac gcgccattta atgtccttcc tgaccatgat gggccctagt    420
cccgactgga acgtaggctt atctgcagaa gatctgtgca ccaaggaatg tggctgggtc    480
cagaaggtgg tgcaagacct gattccctgg gacgctggca ccgacagcgg ggtgacctat    540
gagtcaccca caaacccac cattcccag gagaaaatcc ggcccctgac cagcctggac    600
catcctcaga gtccttteta tgacccagag ggtgggtcca tcactcaagt agccagagtt    660
gtcatcgaga gaatcgcacg gaagggtgaa caatgcaata ttgtacctga caatgtcgat    720
gatattgtag ctgacctggc tccagaagag aaagatgaag atgacacccc tgaaacctgc    780
atctactcca actggtcccc atggtccgcc tgcagctcct ccacctgtga caaaggcaag    840
aggatgcgac agcgcatgct gaaagcacag ctggaccteg gcgtcccctg ccctgacacc    900
```

-continued

```
caggacttcc agccctgcat gggccctggc tgcagtgacg aagacggctc cacctgcacc      960
atgtccgagt ggatcacctg gtcgccctgc agcatctcct gcggcatggg catgaggtcc     1020
cgggagaggt atgtgaagca gttcccggag gacggctccg tgtgcacgct gcccactgag     1080
gaaacggaga agtgcacggt caacgaggag tgctctccca gcagctgcct gatgaccgag     1140
tggggcgagt gggacgagtg cagcgccacc tgcggcatgg gcatgaagaa gcggcaccgc     1200
atgatcaaga tgaaccccgc agatggctcc atgtgcaaag ccgagacatc acaggcagag     1260
aagtgcatga tgccagagtg ccacaccatc ccatgcttgc tgtccccatg gtccgagtgg     1320
agtgactgca gcgtgacctg cgggaagggc atgcgaaccc gacagcggat gctcaagtct     1380
ctggcagaac ttggagactg caatgaggat ctggagcagg tggagaagtg catgctccct     1440
gaatgcccca ttgactgtga gctcaccgag tggtcccagt ggtcggaatg taacaagtca     1500
tgtgggaaag gccacgtgat tcgaacccgg atgatccaaa tggagcctca gtttggaggt     1560
gcaccctgcc cagagactgt gcagcgaaaa aagtgccgca tccgaaaatg ccttcgaaat     1620
ccatccatcc aaaagctacg ctggagggag gcccgagaga gcggcggag tgagcagctg     1680
aaggaagagt ctgaaggga gcagttccca ggttgtagga tgcgcccatg gacggcctgg     1740
tcagaatgca ccaaactgtg cggaggtgga attcaggaac gttacatgac tgtaaagaag     1800
agattcaaaa gctcccagtt taccagctgc aaagacaaga aggagatcag agcatgcaat     1860
gttcatcctt gttagcaagg gtacgagttc cccagggctg cactctagat tccagagtca     1920
ccaatggctg gattatttgc ttgtttaaga caatttaaat tgtgtacgct agttttcatt     1980
tttgcagtgt ggttcgccca gtagtcttgt ggatgccaga gacatccttt ctgaatactt     2040
cttgatgggg acaggctgag tggggcgccc tcacctccag ccagcctctt cctgcagagg     2100
agtagtgtca gccaccttgt actaagctga acatgtccc tctggagctt ccacctggcc     2160
agggaggacg gagactttga cctactccac atggagaggc aaccatgtct ggaagtgact     2220
atgcctgagt cccagggtgc ggcaggtagg aaacattcac agatgaagac agcagattcc     2280
ccacattctc atctttggcc tgttcaatga aaccattgtt tgcccatctc ttcttagtgg     2340
aactttaggt ctctttttcaa gtctcctcag tcatcaatag ttcctgggga aaaacagagc     2400
tggtagactt gaagaggagc attgatgttg ggtggctttt gttctttcac tgagaaattc     2460
ggaatacatt tgtctcaccc ctgatattgg ttcctgatgc cccccaaca aaaataaata     2520
aataaattat ggctgcttta tttaaatata aggtagctag ttttacaccc tgagataaat     2580
aataagctta gagtgtattt ttccccttgct tttgggggtt cagaggagta tgtacaattc     2640
ttctgggaag ccagccttct gaacttttg gtactaaatc cttattggaa ccaagacaaa     2700
ggaagcaaaa ttggtctctt tagagaccaa tttgcctaaa ttttaaaatc ttcctacaca     2760
catctagacg ttcaagtttg caaatcagtt tttagcaaga aaacattttt gctatacaaa     2820
cattttgcta agtctgccca agccccccc aatgcattcc ttcaacaaaa tacaatctct     2880
gtactttaaa gttattttag tcatgaaatt ttatatgcag agagaaaaag ttaccgagac     2940
agaaaacaaa tctaagggaa aggaatatta tgggattaag ctgagcaagc aattctggtg     3000
gaaagtcaaa cctgtcagtg ctccacacca gggctgtggt cctcccagac atgcatagga     3060
atggccacag gtttacactg ccttcccagc aattataagc acaccagatt cagggagact     3120
gaccaccaag ggatagtgta aaaggacatt ttctcagttg ggtccatcag cagttttct     3180
tcctgcattt attgttgaaa actattgttt catttcttct tttataggcc ttattactgc     3240
ttaatccaaa tgtgtaccat tggtgagaca catacaatgc tctgaataca ctacgaattt     3300
```

| | | |
|---|---|---|
| gtattaaaca catcagaata tttccaaata caacatagta tagtcctgaa tatgtacttt | 3360 |
| taacacaaga gagactattc aataaaaact cactgggtct ttcatgtctt taagctaagt | 3420 |
| aagtgttcag aaggttcttt tttatattgt cctccacctc catcattttc aataaaagat | 3480 |
| agggcttttg ctcccttgtt cttggaggga ccattattac atctctgaac tacctttgta | 3540 |
| tccaacatgt tttaaatcct taaatgaatt gctttctccc aaaaaaagca aatataaag | 3600 |
| aaacacaaga tttaattatt tttctacttg ggggaaaaa agtcctcatg tagaagcacc | 3660 |
| cacttttgca atgttgttct aagctatcta tctaactctc agcccatgat aaagttcctt | 3720 |
| aagctggtga ttcctaatca aggacaagcc accctagtgt ctcatgtttg tatttggtcc | 3780 |
| cagttgggta catttaaaa tcctgatttt ggagacttaa aaccaggtta atggctaaga | 3840 |
| atgggtaaca tgactcttgt tggattgtta tttttttgttt gcaatgggga atttataaga | 3900 |
| agcatcaagt ctctttctta ccaaagtctt gttaggtggt ttatagttct tttggctaac | 3960 |
| aaatcatttt ggaaataaag attttttact acaaaatg | 3999 |

```
<210> SEQ ID NO 178
<211> LENGTH: 1069
<212> TYPE: DNA
<213> ORGANISM: Homo sapiens

<400> SEQUENCE: 178
```

| | | |
|---|---|---|
| aaaaaagatg aataaatgaa taagagagat gaataaacaa atttacatta catgtgatag | 60 |
| ttatcatggt atggccttca tgacaagatg gatgagaata tcactgatag gatattagcc | 120 |
| ttctttcata tctttatatt gaaatatggg ctttacttca atttgaaggt ctttcatgaa | 180 |
| caataaaaga gagtagaagg actgtctgag aaggcaggag acatataaaa cagatgactg | 240 |
| aaagactgac tagctcctgg aaagggaaac atttggaaca tccagagtaa gggcaaatgg | 300 |
| gcttctacca gcacaacaaa gagcctccag gtggcaacat ggaagcaggt tatcagagaa | 360 |
| aataaatgtg caaattcctt atttacaatg actcacttaa ccccacaaac atgtttcact | 420 |
| gctgccttcc ccagttgtcg cttatgtact gttgttacct ttcagttaca tgcctttgat | 480 |
| cctaaaattc tctactttg gtgccttatc agttctttgc aatctgcctg tggttatcag | 540 |
| cacttaaagc acaattttga agggaaaaa atgataatc accttagtcc caaagaaata | 600 |
| atttgtcaaa ctgccttatt agtattaaaa acagacacac tgaatgaagt agcatgatac | 660 |
| gcatatatcc tactcagtat cattggcctt ttatcaaatg gggaaactat acttttgtat | 720 |
| tacatagttt tagaaatcga agttagaga ctctttataa gtaatgtcaa ggaacagtaa | 780 |
| tttaaaaaca aagttctaac aaatatattg tttgcttaat cacaatgccc tcaacttgta | 840 |
| tttgaataac taaataggac atgtcttcct tggagctgtg ggcattagtt cagaagcact | 900 |
| acctgcatct taattttcaa aacttaagtt ttattagcaa atcctcttct ctgtaagact | 960 |
| tagctatgaa gtggtatatt ttttccaaat atttttctga aaacatttgt tgttgtaact | 1020 |
| gcacaataaa agtccagttg caattaaaaa aaaaaaaaaa aaaaaaaa | 1069 |

```
<210> SEQ ID NO 179
<211> LENGTH: 1817
<212> TYPE: DNA
<213> ORGANISM: Homo sapiens

<400> SEQUENCE: 179
```

| | | |
|---|---|---|
| tgctattctg ccaaaagaca atttctagag tagttttgaa tgggttgatt tcccccactc | 60 |

-continued

| | |
|---|---|
| ccacaaactc tgaagccagt gtctagctta ctaaaaaaag agttgtatat aatatttaag | 120 |
| atgctgagta tttcatagga aagctgaatg ctgctgtaaa gtgctcttta agtcttttt | 180 |
| ttttttaatc cccttctaat gaatgaaact aggggaattt caggggacag agatgggatt | 240 |
| tgttgtatga taaactgtat gtagttttta gtctttctgt tttgagaagc agtggttggg | 300 |
| gcattttaa gatggctggc tactcttgtt ttccctcatg ataataaatt tgtcataact | 360 |
| cagtaacatg aacttgcccc tagaggtagt tgttaataat tttgaaatat taaggtcttg | 420 |
| ccaagcttct gatgattcac acctgtacta ctgattatta agcaggacag actgagcttt | 480 |
| ctgttgcaaa taccttggag gagaaagtaa tttctaaata tacagagagg taacttgact | 540 |
| atatatgttg catcctgtgc ctcccttcat attaatattt gataaagatt ttaatttatg | 600 |
| taaaacttct aaagcagaat caaagctcct cttggggaaa tggcaagtct ttaggatagg | 660 |
| caagaccctg tatgaatagt accaaagcat taccgcatgg tagagaacac actcgattaa | 720 |
| aaatgttaag ctatctgaaa aataaaatgt gcaagtcttc aggatggcac aaaacaaagg | 780 |
| ttaatgcttc ttggggcaca tttcttagag ggcttgctga gtgtgtaaat ataatcgact | 840 |
| tttgtttgtg ttacatgact tctgtgactt cattgaaaat ctgcacaatt cagtttcagc | 900 |
| tctggattac ttcagttgac ctttgtgaag gttttatct gtgtagaatg ggtgtttgac | 960 |
| ttgtttagc ctattaaatt tttatttct ttcactctgt attaaaagta aaacttacta | 1020 |
| aaagaaaaga ggtttgtgtt cacattaaat ggttttggtt tggcttctt tagtcaggct | 1080 |
| ttctgaacat tgagatatcc tgaacttaga gctcttcaat cctaagattt tcatgaaaag | 1140 |
| cctctcactt gaacccaaac cagagtactc ttactgcctc ttttctaaat gttcaggaaa | 1200 |
| agcattgcca gttcagtctt ttcaaaatga gggagaaaca tttgcctgcc ttgtaataac | 1260 |
| aagactcagt gcttattttt taaactgcat tttaaaaatt ggatagtata ataacaataa | 1320 |
| ggagtaagcc acctttata ggcaccctgt agtttatag ttcttaatct aaacatttta | 1380 |
| tatttccttc ttttggaaaa aacctacatg ctacaagcca ccatatgcac agactataca | 1440 |
| gtgagttgag ttggctctcc cacagtcttt gaggtgaatt acaaaagtcc agccattatc | 1500 |
| atcctcctga gttatttgaa atgatttttt ttgtacattt tggctgcagt attggtggta | 1560 |
| gaatatacta taatatggat catctctact tctgtattta tttatttatt actagacctc | 1620 |
| aaccacagtc ttcttttcc ccttccacct ctctttgcct gtaggatgta ctgtatgtag | 1680 |
| tcatgcactt tgtattaata tattagaaat ctacagatct gttttgtact ttttatactg | 1740 |
| ttggatactt ataatcaaaa cttttactag ggtattgaat aaatctagtc ttactagaaa | 1800 |
| aaaaaaaaaa aaaaaaa | 1817 |

<210> SEQ ID NO 180
<211> LENGTH: 2382
<212> TYPE: DNA
<213> ORGANISM: Homo sapiens

<400> SEQUENCE: 180

| | |
|---|---|
| acttttattg gaagcagcag ccacatccct gcatgatttg cattgcaata caaccataac | 60 |
| cgggcagcca ctcctgagtg ataaccagta taacataaac gtagcagcct caattttgc | 120 |
| ctttatgacg acagcttgtt atggttgcag tttgggtctg gctttacgaa gatggcgacc | 180 |
| gtaacactcc ttagaaactg gcagtcgtat gttagtttca cttgtctact ttatatgtct | 240 |
| gatcaatttg gataccattt tgtccagatg caaaaacatt ccaaaagtaa tgtgtttagt | 300 |
| agagagagac tctaagctca agttctggtt tatttcatgg atggaatgtt aatttatta | 360 |

```
tgatattaaa gaaatggcct tttattttac atctctcccc ttttttcccctt tccccctttaa      420 ttttcctcct tttctttctg aaagtttcct tttatgtcca taaaatacaa atatattgtt      480
cataaaaaat tagtatccct tttgtttggt tgctgagtca cctgaacctt aattttaatt      540
ggtaattaca gccctaaaa aaaacacatt tcaaataggc ttcccactaa actctatatt      600
ttagtgtaaa ccaggaattg gcacactttt tttagaatgg gccagatggt aaatatttat      660
gcttcacggt ccatacagtc tctgtcacaa ctattcagtt ctgctagtat agcgtgaaag      720
cagctataca caatacagaa atgaatgagt gtggttatgt tctaataaaa cttatttata      780
aaaacaaggg gaggctgggt ttagcctgtg ggccatagtt tgtcaaccac tggtgtaaaa      840
ccttagttat atatgatctg cattttcttg aactgatcat tgaaaactta taaacctaac      900
agaaaagcca cataatattt agtgtcatta tgcaataatc acattgcctt tgtgttaata      960
gtcaaatact tacctttgga gaatacttac ctttggagga atgtataaaa tttctcaggc     1020
agagtcctgg ataggaaa aagtaattta tgaagtaaac ttcagttgct taatcaaact     1080
aatgatagtc taacaactga gcaagatcct catctgagag tgcttaaaat gggatcccca     1140
gagaccatta accaatactg gaactggtat ctagctactg atgtcttact ttgagtttat     1200
ttatgcttca gaatacagtt gtttgccctg tgcatgaata tacccatatt tgtgtgtgga     1260
tatgtgaagc ttttccaaat agagctctca gaagaattaa gttttact tctaattattt     1320 tgcattactt tgagttaaat ttgaatagag tattaaatat aaagttgtag attcttatgt     1380 gttttttgtat tagcccagac atctgtaatg tttttgcact ggtgacagac aaaatctgtt     1440
ttaaaatcat atccagcaca aaaactattt ctggctgaat agcacagaaa agtattttaa     1500
cctacctgta gagatcctcg tcatggaaag gtgccaaact gttttgaatg gaaggacaag     1560
taagagtgag gccacagttc ccaccacacg agggcttttg tattgttcta cttttcagc     1620 cctttacttt ctggctgaag catccccttg gagtgccatg tataagttgg gctattagag     1680
ttcatggaac atagaacaac catgaatgag tggcatgatc cgtgcttaat gatcaagtgt     1740
tacttatcta ataatcctct agaaagaacc ctgttagatc ttggtttgtg ataaaaatat     1800
aaagacagaa gacatgagga aaaacaaaag gtttgaggaa atcaggcata tgactttata     1860
cttaacatca gatcttttct ataatatcct actactttgg ttttcctagc tccataccac     1920
acacctaaac ctgtattatg aattacatat tacaaagtca taaatgtgcc atatggatat     1980
acagtacatt ctagttggaa tcgtttactc tgctagaatt taggtgtgag attttttgtt     2040
tcccaggtat agcaggctta tgtttggtgg cattaaattg gtttctttaa aatgctttgg     2100
tggcactttt gtaaacagat tgcttctaga ttgttacaaa ccaagcctaa gacacatctg     2160
tgaatactta gatttgtagc ttaatcacat tctagacttg tgagttgaat gacaaagcag     2220
ttgaacaaaa attatggcat ttaagaattt aacatgtctt agctgtaaaa atgagaaagt     2280
gttggttggt tttaaaatct ggtaactcca tgatgaaaag aaatttattt tatacgtgtt     2340
atgtctctaa taaagtattc atttgataaa aaaaaaaaa aa                         2382

<210> SEQ ID NO 181
<211> LENGTH: 2377
<212> TYPE: DNA
<213> ORGANISM: Homo sapiens

<400> SEQUENCE: 181
atctttatgc aagacaagag tcagccatca gacactgaaa tatattatga tagattatga       60
```

```
agaattttct ctgtagaatt atattcttcc tggaacctgg tagagtagat tagactcaaa    120
ggcttttttct tccttttctt actcctgttt tttccactca ctcttcccaa gagatttcct    180
aaagcttcaa gcttaataag cctaatagtg aaaaataact gaatttaatg gtataatgaa    240
gttcttcatt tccagacatc tttaattgat cttaaagctc atttgagtct ttgcccctga    300
acaaagacag acccattaaa atctaagaat tctaaatttt cacaactgtt tgagcttctt    360
ttcattttga aggatttgga atatatatgt tttcataaaa gtatcaagtg aaatatagtt    420
acatgggagc tcaatcatgt gcagattgca ttctgttatg ttgactcaat atttaattta    480
caactatcct tatttatatt gacctcaaga actccatttt atgcaatgca gaccactgag    540
atatagctaa cattctttca ataattttc cttttctttt ataattcctc tatagcaaat     600
ttttatgtat aactgattat acatatccat atttatattt cattgattcc aagacatcac    660
tttttcaatt taacatctct gaaattgtga catttcttgc aactgttggc acttcagatg    720
cagtgtttaa aattatgctt gaataaatat tacactaatc caactttacc taaatgttta    780
tgcatctagg caaattttgt tttcttataa agatttgaga gcccatttat gacaaaatat    840
gaaggcgaaa tttaaggaca actgagtcac gcacaactca acatggagcc taactgatta    900
tcagctcaga tcccgcatat cttgagttta caaaagctct ttcaggtccc catttatact    960
ttacgtgagt gcgaatgatt tcagcaaacc ctaacttaac taacaagaat gggtaggtat   1020
gtctacgttt cattaacaaa ttttttattat tttttattcta ttatatgaga tccttttata   1080
ttatcatctc acttttaaac aaaattaact ggaaaaatat tacatggaac tgtcatagtt   1140
aggttttgca gcatcttaca tgtcttgtat caatggcagg agaaaaatat gataaaaaca   1200
atcagtgctg tgaaaaacaa cttttcttcta gagtcctctt acttttattt cttctttatc   1260
atttgtgggt ttttccccct tggctctcac tttaacttca agcttatgta acgactgtta   1320
taaaactgca tatttaaatt atttgaatta tatgaaataa ttgttcagct atctgggcag   1380
ctgttaatgt aaacctgaga gtaataacac tactctttta tctacctgga atactttttct   1440
gcataaaatt tatctttgta agctaactct attaatcagg tttcttctag cctctgcaac   1500
ctacttcagt tagaattgtc taatactgct ctattaatca ggtttctacc ctctacaacc   1560
tacttcagtt aaaattgtct aatacagcaa tatttaaaaa aaaaacactg caattgtcaa   1620
ggatggaaaa tgtgtgattt gtgtaaacaa ttttttaccaa ctttacattt tcctacagat   1680
aaatgtgaaa ttttgataag aagtctacgc aatgacaagt acggtacata aattttatta   1740
agaatattga gtataaagta ctttaattct aaattataag aaaatataca tttgcacata   1800
ttaatataga aattcatttt gtgtatattt aacatagctt ttaaactatt ttacattagc   1860
tacttcatta tggtttcttg aacttctgaa aaaaattaga aatgtattaa acttatcagt   1920
aacataaaaa cttatttttgt ttcacctaac gaatactgcg tttgtaaaaa taaatttaat   1980
atagaatata ttttttaaatt aaatatttga atataaaata gctctaagaa agaagcaaat   2040
tatcactgaa catatttctt attatttctg gctttgaatt atacgtaact taaattgtct   2100
taaatgatac agaatattgg agaatatgat actttcacat aatatactat gaacctgttc   2160
atataactct gattgactac taacttctgt tttatgtatt tattaaagag ctgacactgt   2220
agtttgtggt gagatgttta tttttctaac agagcttata acagttagga caaggcattt   2280
aattaatgca tcattctgtt tagtagtagg tgttaatcaa tatgaaattc tctgttttaa   2340
aataaaaatg taaaaatcta aaaaaaaaaa aaaaaaa                             2377
```

<210> SEQ ID NO 182
<211> LENGTH: 1370
<212> TYPE: DNA
<213> ORGANISM: Homo sapiens

<400> SEQUENCE: 182

```
tgtgagcatg gtattttgtc tcggaagaaa aaaatatggg tcaggcgcaa agtaagccca      60
ccccactggg aactatgtta aaaaaaaatt tcaagattta agggagatta cggtgttact     120
atgacaccag aaaaacttag aactttgtgt gaaatagact ggctaacatt agaggtgggt     180
tggctatcag aagaaagcct ggagaggtcc cttgtttcaa aggtatggca caaggtaacc     240
tgtaagccaa agcacccgga ccagtttcta tacatagaca gttacagctg gtttagaccc     300
cttccccctc tccccacagt agttaagaga acagcagcat aagcagctgg cagaggcaag     360
gaaagaccag cagagagaaa aaaaggccat ctataccaat tttaagttaa tttagactga     420
acaagggctt attaatagca aaggataatt gaaatcacaa acttataagg gtttcaacaa     480
aagtgaagtt tgctaaaagt taacagtgta acatgtatta tggtaacttc taatcttgtg     540
gccttagaca gtctagtcaa aacacataaa gaaagtttgc tttaaaaaaa caatggttat     600
cttcaaaaat aaaggggaga ggcagaattt atataaaaag agttatatga taaattcttg     660
tcctgaaata aattaactgg ttgtttaaag aaaagaatgt ttgtaataag tcaaaaagtt     720
aaaacatgtt taaaaaattg tctgcaaaag tcataaaaga aaaaatttta ttaaaaaaat     780
tttaagcaaa aaatgttgta taatttaaaa gtaataaggc ctcctgtgta ctattaagac     840
agatgcaaat tcctggttga aatggatcaa atattccatc tgcacattaa acaaaagcaa     900
ttgttatgct tgtgcacatg gcaggccaga ggccctgatt gtccccttc cactaaggtg     960
gtcctctagt cgaccaggcg tggactgcat ggtagctctt ttccaggatt ctacagcctg    1020
gagtaataag tcatgccaag ctctctctgc tatatcccaa agtctctgcg ggtcagcccc    1080
caagggccat gcagcttctg tctcccaaca ctaagttcac ttcgtgtctc tcacggcaga    1140
gaggaaactt agtattcctt ggagacctga agggatgcag tgagcttaag aattttcaag    1200
agcttatcaa tcagtcagcc cttgttcatc cccgagtgga tgtgtggtgg tattgtggtg    1260
gacctttact gggcactctg ccaaataact agtgtggcac ttgtgcttta gtccatttgg    1320
ctatcccttt caccctggca tttcatcaac caaaaaaaaa aaaaaaaaaa                1370
```

<210> SEQ ID NO 183
<211> LENGTH: 2060
<212> TYPE: DNA
<213> ORGANISM: Homo sapiens
<220> FEATURE:
<221> NAME/KEY: misc_feature
<222> LOCATION: 2003
<223> OTHER INFORMATION: n = A,T,C or G

<400> SEQUENCE: 183

```
gtttcagggg aggagacaag gtttcttgtt tgccgtatat gctcctgcag agaagaggaa      60
gtgaccgtgg aggccatctg gccctgtgtt ttgatatggc aaaattaatg aatgcaatca     120
gaagaccttt gagcaagaaa gtaccctgga acaacccaat ttggactgca agtattagtt     180
gggtcttcca ggtgcctctc acagcagcag tcatggcagc agtgactcta gccatgtcca     240
tgaccaactg ctgcataaca aatagccccg agactcagca gcttacaaca gggtccccag     300
cccacagact ggcactggtc catggcttgt taggaacctg actgcgcagc agaaggtgag     360
tgagcattac tgcctgagct ctgcctcctg tcagatcatc aggggcatta gattctcata     420
```

-continued

```
ggagcgtgaa ccctattgca aaccgcgcat gcgaaggatg tacgttgcgt gctccttatg      480
agaatctaac taatgcctga tgatttgagg tggggcagtt tcatcccccaa accatctctc     540 tcccttcatg tccatggaaa aattgtcttc tacaaaacca gtccgtggtg ccaaaaaggt      600
tggagactgc tggtttacaa ccgcaatgaa cattcatcat cccacacagt gtcagagggt      660
cgggaacacg ggtgccctgc ctgtgtgctt ccggttccag atttctcagt gggttgtgat      720
caaggtatca gcggaggccg tattcatctg caagcttgac caggaataga agagccactt      780
catgggtggc tcactcagat gccagcaggt cagtgctggt ggctggcagg cagcctcagc      840
tcctcacctc atggatctct cctgagcaca gttttcctgt ccttacaacc tggtagctgg      900
cttctccaga gcaggtgact caggagagga caaggtgaga gcccagcacc ttatggtcta      960
gtctcagaag tcacacgcca tcatttctgc aatgtcattt tggggttcca ggtcagctgt     1020
atcactgtgg gaggtgagta tatagatgtc ctagaccatt caggctgcta tgacagaaca     1080
ccatgaactg agtggctcat gaacaacaga aatttcccac agttctgtag ctgggaaat      1140 ccaagatcaa ggtggcagca ggttcagcgt ctgctaagct cctgcttttc atggattgca     1200
tcttctcact gtgtcctcac gtgatggaca gagcaaatga gctctcaggc actagtccca     1260
gccatgagga ctctgctttc atgactcatc actccgcaaa ggcccacctc catcagaaga     1320
cagctgctaa ctgcagctgc catcctccaa gacgggagac acagaattgg gggacatata     1380
cattgagatc tgaaaggcct ggacagcaac aggtgtggga tcgtgggggca tcttggaggg    1440 tggctgccgc agtaacattt ctgacccatg ctttctgctt gcactcatct cctgcctttg     1500
atcttcatta tctcargcag tccccacaac gactgtatct aggagttcat tttaccctca     1560
ttttacagat gaaacgtctc agagggtaat gtgcttgccc agtgtctcac aaatgcaaag     1620
tcactgaggt aggatttcaa cctaggtcca atcatctctg cagcattagg ggttcaccat     1680
tgccatagac ttaactgtgt cccccaaaat ttgtatgttg aagccctacc agcctccccc    1740
ccccaatgtg ctgatgtttg gagaaagggc ctttgggagg taattaggtt tagatgagat     1800
catgagggtg ggactctcat aatggcatta atgccatcag gtgaagagat accagagacc     1860
ttgtgtcctc tctctctgca atgtgaggac acagtgagaa ggcagctgtc tgcaagctgg     1920
gaagagagta ctgaccagga acttaatcag agggcatctt gatcttggac ttcccagcct     1980
ccagaactct gaaaagttaa tgnctattat ttaagccacg cagtctatgg aattttgtta     2040
gagccaaccc caagcttact                                                 2060
```

<210> SEQ ID NO 184
<211> LENGTH: 3079
<212> TYPE: DNA
<213> ORGANISM: Homo sapiens

<400> SEQUENCE: 184

```
ggcacaaagt tggggccgc gaagatgagg ctgtccccgg cgcccctgaa gctgagccgg        60
actccggcac tgctggccct ggcgctgccc ctggccgcgg cgctggcctt ctccgacgag      120
accctggaca aagtgcccaa gtcagagggc tactgtagcc gtatcctgcg cgcccagggc      180
acgcggcgcg agggctacac cgagttcagc ctccgcgtgg agggcgaccc cgacttctac     240
aagccgggaa ccagctaccg cgtaacactt cagctgctc ctccctccta cttcaggaga      300
ttcacattaa ttgccctcag agagaacaga gagggtgata aggaagaaga ccatgctggg     360
accttccaga tcatagacga agaagaaact cagtttatga gcaattgccc tgttgcagtc     420
actgaaagca ctccacggag gaggacccgg atccaggtgt tttggatagc accaccagcg     480
```

```
ggaacaggct gcgtgattct gaaggccagc atcgtacaaa aacgcattat ttattttcaa    540
gatgagggct ctctgaccaa gaaactttgt gaacaagatt ccacatttga tggggtgact    600
gacaaaccca tcttagactg ctgtgcctgc ggaactgcca agtacagact cacatttat     660
gggaattggt ccgagaagac acacccaaag gattaccctc gtcgggccaa ccactggtct    720
gcgatcatcg gaggatccca ctccaagaat tatgtactgt gggaatatgg aggatatgcc    780
agcgaaggcg tcaaacaagt tgcagaattg ggctcacccg tgaaaatgga ggaagaaatt    840
cgacaacaga gtgatgaggt cctcaccgtc atcaaagcca agcccaatg gccagcctgg     900
cagcctctca acgtgagagc agcaccttca gctgaatttt ccgtggacag aacgcgccat    960
ttaatgtcct tcctgaccat gatgggccct agtcccgact ggaacgtagg cttatctgca   1020
gaagatctgt gcaccaagga atgtggctgg gtccagaagg tggtgcaaga cctgattccc   1080
tgggacgctg gcaccgacag cggggtgacc tatgagtcac ccaacaaacc caccattccc   1140
caggagaaaa tccggcccct gaccagcctg gaccatcctc agagtccttt ctatgaccca   1200
gagggtgggt ccatcactca gtagccaga gttgtcatcg agagaatcgc acggaagggt    1260
gaacaatgca atattgtacc tgacaatgtc gatgatattg tagctgacct ggctccagaa   1320
gagaaagatg aagatgacac ccctgaaacc tgcatctact ccaactggtc cccatggtcc   1380
gcctgcagct cctccacctg tgacaaaggc aagaggatgc gacagcgcat gctgaaagca   1440
cagctggacc tcagcgtccc ctgccctgac acccaggact ccagccctg catgggccct    1500
ggctgcagtg acgaagacgg ctccacctgc accatgtccg agtggatcac ctggtcgccc   1560
tgcagcatct cctgcggcat gggcatgagg tcccgggaga ggtatgtgaa gcagttcccg   1620
gaggacggct ccgtgtgcac gctgcccact gaggaaatgg agaagtgcac ggtcaacaga   1680
gagtgctctc ccagcagctg cctgatgacc gagtggggcg agtgggacga gtgcagcgcc   1740
acctgcggca tgggcatgaa gaagcggcac cgcatgatca gatgaaaccc cgcagatggc   1800
tccatgtgca aagccgagac atcacaggca gagaagtgca tgatgccaga gtgccacacc   1860
atcccatgct tgctgtcccc atggtccgag tggagtgact gcagcgtgac ctgcgggaag   1920
gcatgcgaa cccgacagcg gatgctcaag tctctggcag aacttggaga ctgcaatgag    1980
gatctggagc aggtggagaa gtgcatgctc cctgaatgcc ccattgactg tgagctcacc   2040
gagtggtccc agtggtcgga atgtaacaag tcatgtggga aggccacgt gattcgaacc    2100
cggatgatca aaatggagcc tcagtttgga ggtgcaccct gcccagagac tgtgcagcga   2160
aaaaagtgcc gcatccgaaa atgccttcga aatccatcca tccaaaagcc acgctggagg   2220
gaggcccgag agagccggcg gagtgagcag ctgaaggaag agtctgaagg ggagcagttc   2280
ccaggttgta ggatgcgccc atggacggcc tggtcagaat gcaccaaact gtgcggaggt   2340
ggaattcagg aacgttacat gactgtaaag aagagattca aaagctccca gtttaccagc   2400
tgcaaagaca agaaggagat cagagcatgc aatgttcatc cttgttagca agggtacgag   2460
ttcccccaggg ctgcactcta gattccgag tcaccaatgg ctggattatt tgcttgttta   2520
agacaattta aattgtgtac gctagttttc attttgcag tgtggttcgc ccagtagtct    2580
tgtggatgcc agagacatcc tttctgaata cttcttgatg ggtacaggct gagtgggcg    2640
ccctcacctc cagccagcct cttcctgcag aggagtagtg tcagccacct tgtactaagc   2700
tgaaacatgt ccctctggag cttccacctg gccaggagg acggagactt tgacctactc    2760
cacatggaga ggcaaccatg tctggaagtg actatgcctg agtcccaggg tgcggcaggt   2820
```

| | |
|---|---:|
| aggaaacatt cacagatgaa gacagcagat tccccacatt ctcatctttg gcctgttcaa | 2880 |
| tgaaaccatt gtttgcccat ctcttcttag tggaacttta ggtctctttt caagtctcct | 2940 |
| cagtcatcaa tagttcctgg ggaaaaacag agctggtaga cttgaagagg agcattgatg | 3000 |
| ttgggtggct tttgttcttt cactgagaaa ttcggaatac atttgtctca ccctgatat | 3060 |
| tggttcctga tgccccagc | 3079 |

<210> SEQ ID NO 185
<211> LENGTH: 3000
<212> TYPE: DNA
<213> ORGANISM: Homo sapiens

<400> SEQUENCE: 185

| | |
|---|---:|
| gtttcagggg aggagacaag gtttcttgtt tgccgtatat gctcctgcag agaagaggaa | 60 |
| gtgaccgtgg aggccatctg gccctgtgtt ttgatatggc aaaattaatg aatgcaatca | 120 |
| gaagaccttt gagcaagaaa gtaccctgga acaacccaat ttggactgca agtattagtt | 180 |
| gggtcttcca ggtgcctctc acagcagcag tcatggcagc agtgactcta gccatgtcca | 240 |
| tgaccaactg ctgcataaca aatagccccg agactcagca gcttacaaca gggtccccag | 300 |
| cccacagact ggcactggtc catggcttgt taggaacctg actgcgcagc agaaggtgag | 360 |
| tgagcattac tgcctgagct ctgcctcctg tcagatcatc aggggcatta gattctcata | 420 |
| ggagcgtgaa ccctattgca aaccgcgcat gcgaaggatg tacgttgcgt gctccttatg | 480 |
| agaatctaac taatgcctga tgatttgagg tggggcagtt tcatccccaa accatctctc | 540 |
| tcccttcatg tccatggaaa aattgtcttc tacaaaacca gtccgtggtg ccaaaaaggt | 600 |
| tggagactgc tggtttacaa ccgcaatgaa cattcatcat cccacacagt gtcagagggt | 660 |
| cgggaacacg ggtgccctgc ctgtgtgctt ccggttccag atttctcagt gggttgtgat | 720 |
| caaggtatca gcggaggccg tattcatctg caagcttgac caggaataga agagccactt | 780 |
| catgggtggc tcactcagat gccagcaggt cagtgctggt ggctggcagg cagcctcagc | 840 |
| tcctcacctc atggatctct cctgagcaca gttttcctgt ccttacaacc tggtagctgg | 900 |
| cttctccaga gcaggtgact caggagagga caaggtgaga gccacagcac cttatggtct | 960 |
| agtctcagaa gtcacacgcc atcatttctg caatgtcatt ttgggggttcc aggtcagctg | 1020 |
| tatcactgtg ggaggtgagt atatagatgt cctagaccat tcaggctgct atgacagaac | 1080 |
| accatgaact gagtggctca tgaacaacag aaatttccca cagttctgta ggctgggaaa | 1140 |
| tccaagatca aggtggcagc aggttcagcg tctgctaagc tcctgctttt catggattgc | 1200 |
| atcttctcac tgtgtcctca cgtgatggac agagcaaatg agctctcagg cactagtccc | 1260 |
| agccatgagg actctgcttt catgactcat cactccgcaa aggcccacct ccatcagaag | 1320 |
| acagctgcta actgcagctg ccatcctcca agacgggaga cacagaattg ggggacatat | 1380 |
| acattgagat ctgaaaggcc tggacagcaa caggtgggga tcgtggggc atcttggagg | 1440 |
| gtggctgccg cagtaacatt tctgacccat gctttctgct tgcactcatc tcctgccttt | 1500 |
| gatcttcatt atctcaggca gtccccacaa cgactgtatc taggagttca ttttaccctc | 1560 |
| attttacaga tgaaacgtct cagagggtaa tgtgcttgcc cagtgtctca caaatgcaaa | 1620 |
| gtcactgagg taggatttca acctaggtcc aatcatctct gcagcattag gggttcacca | 1680 |
| ttgccataga cttaactgtg tccccaaaaa tttgtatgtt gaagccctac cagcctcccc | 1740 |
| cccccaatgt gctgatgttt ggagaaaggg cctttgggag gtaattaggt ttagatgaga | 1800 |
| tcatgagggt gggactctca taatggcatt aatgccatca ggtgaagaga taccagagac | 1860 |

```
cttgtgtcct ctctctctgc aatgtgagga cacagtgaga aggcagctgt ctgcaagctg      1920
ggaagagagt actgaccagg aacttaatca gagggcatct tgatcttgga cttcccagcc      1980
tccagaactc tgaaaagtta atgtctatta tttaagccac gcagtctatg gaattttgtt      2040
agagccaacc caagcttact aagataatca gtatgctgca ctttctataa atgtaatttt      2100
tacatttata aaacaaaac aagagatttg ctgctctata acaactgtac ctacattgta       2160
gatggaataa caaatctaca tacagattta gtaatctcta tgtagatata aacatagtg       2220 tatctaatag agacatagtg tctgtggtct gatgttaatt ttaggaatta gccgtcactg      2280
attgggcctt gtccaggtat tcttctccct tgtcctggct ctgtaaccta gttatccttg      2340
tctttgctaa cccataacca actattgtat caggactatt atgccactac agatgatgca      2400
gtttgggttt actgtttctc accatttaga caatacttca tcaaatatat ttctgtatga      2460
ctttagtgat atcagttttt gattcattcc tgcatagatc tgggcaaatt gtagacctta     2520
ggaggtgtat tcaccatcca gttctctgga actgcttatg acatttttct ctgagctttc      2580
ttgtcccaaa aggagccttc ctaaaatagt ctttaagtgc ctttaaaaag agaaagagaa      2640
attaagagaa aaaaacccc aaactcattc ctttactctg atgtgacagt cctcccagga       2700
cactgcagtg gcctgagttt tgctgttaat ttcattcact tatgtttggg ctatgtaaat      2760
tctgcctaga gctggaatgt cattatgtaa agaaatattt tttgtttata ttctttaata     2820
gtaccagtaa tgtatatctt attcagcttc gagaatataa ttgggttgtt tataaaaacc     2880
acacatcatc aaactcacat tgtaacgatt atttcacttt tcaaaaaaaa tggcattaga     2940
aaaacttgaa tgatgttagt tatcttaaag aagtgtgtac tatgtttaaa aaaaaaaaa      3000
```

<210> SEQ ID NO 186
<211> LENGTH: 807
<212> TYPE: PRT
<213> ORGANISM: Homo sapiens

<400> SEQUENCE: 186

```
Met Arg Leu Ser Pro Ala Pro Leu Lys Leu Ser Arg Thr Pro Ala Leu
  1               5                  10                  15

Leu Ala Leu Ala Leu Pro Leu Ala Ala Ala Leu Ala Phe Ser Asp Glu
                 20                  25                  30

Thr Leu Asp Lys Val Pro Lys Ser Glu Gly Tyr Cys Ser Arg Ile Leu
             35                  40                  45

Arg Ala Gln Gly Thr Arg Arg Glu Gly Tyr Thr Glu Phe Ser Leu Arg
         50                  55                  60

Val Glu Gly Asp Pro Asp Phe Tyr Lys Pro Gly Thr Ser Tyr Arg Val
 65                  70                  75                  80

Thr Leu Ser Ala Ala Pro Pro Ser Tyr Phe Arg Gly Phe Thr Leu Ile
                 85                  90                  95

Ala Leu Arg Glu Asn Arg Glu Gly Asp Lys Glu Asp His Ala Gly
                100                 105                 110

Thr Phe Gln Ile Ile Asp Glu Glu Thr Gln Phe Met Ser Asn Cys
            115                 120                 125

Pro Val Ala Val Thr Glu Ser Thr Pro Arg Arg Thr Arg Ile Gln
        130                 135                 140

Val Phe Trp Ile Ala Pro Pro Ala Gly Thr Gly Cys Val Ile Leu Lys
145                 150                 155                 160

Ala Ser Ile Val Gln Lys Arg Ile Ile Tyr Phe Gln Asp Glu Gly Ser
                165                 170                 175
```

-continued

```
Leu Thr Lys Lys Leu Cys Glu Gln Asp Ser Thr Phe Asp Gly Val Thr
            180                 185                 190
Asp Lys Pro Ile Leu Asp Cys Cys Ala Cys Gly Thr Ala Lys Tyr Arg
        195                 200                 205
Leu Thr Phe Tyr Gly Asn Trp Ser Glu Lys Thr His Pro Lys Asp Tyr
    210                 215                 220
Pro Arg Arg Ala Asn His Trp Ser Ala Ile Ile Gly Gly Ser His Ser
225                 230                 235                 240
Lys Asn Tyr Val Leu Trp Glu Tyr Gly Gly Tyr Ala Ser Glu Gly Val
                245                 250                 255
Lys Gln Val Ala Glu Leu Gly Ser Pro Val Lys Met Glu Glu Glu Ile
            260                 265                 270
Arg Gln Gln Ser Asp Glu Val Leu Thr Val Ile Lys Ala Lys Ala Gln
        275                 280                 285
Trp Pro Ala Trp Gln Pro Leu Asn Val Arg Ala Ala Pro Ser Ala Glu
    290                 295                 300
Phe Ser Val Asp Arg Thr Arg His Leu Met Ser Phe Leu Thr Met Met
305                 310                 315                 320
Gly Pro Ser Pro Asp Trp Asn Val Gly Leu Ser Ala Glu Asp Leu Cys
                325                 330                 335
Thr Lys Glu Cys Gly Trp Val Gln Lys Val Val Gln Asp Leu Ile Pro
            340                 345                 350
Trp Asp Ala Gly Thr Asp Ser Gly Val Thr Tyr Glu Ser Pro Asn Lys
        355                 360                 365
Pro Thr Ile Pro Gln Glu Lys Ile Arg Pro Leu Thr Ser Leu Asp His
    370                 375                 380
Pro Gln Ser Pro Phe Tyr Asp Pro Glu Gly Gly Ser Ile Thr Gln Val
385                 390                 395                 400
Ala Arg Val Val Ile Glu Arg Ile Ala Arg Lys Gly Glu Gln Cys Asn
                405                 410                 415
Ile Val Pro Asp Asn Val Asp Asp Ile Val Ala Asp Leu Ala Pro Glu
            420                 425                 430
Glu Lys Asp Glu Asp Thr Pro Glu Thr Cys Ile Tyr Ser Asn Trp
        435                 440                 445
Ser Pro Trp Ser Ala Cys Ser Ser Thr Cys Asp Lys Gly Lys Arg
    450                 455                 460
Met Arg Gln Arg Met Leu Lys Ala Gln Leu Asp Leu Ser Val Pro Cys
465                 470                 475                 480
Pro Asp Thr Gln Asp Phe Gln Pro Cys Met Gly Pro Gly Cys Ser Asp
                485                 490                 495
Glu Asp Gly Ser Thr Cys Thr Met Ser Glu Trp Ile Thr Trp Ser Pro
            500                 505                 510
Cys Ser Ile Ser Cys Gly Met Gly Met Arg Ser Arg Glu Arg Tyr Val
        515                 520                 525
Lys Gln Phe Pro Glu Asp Gly Ser Val Cys Thr Leu Pro Thr Glu Glu
    530                 535                 540
Met Glu Lys Cys Thr Val Asn Glu Glu Cys Ser Pro Ser Ser Cys Leu
545                 550                 555                 560
Met Thr Glu Trp Gly Glu Trp Asp Glu Cys Ser Ala Thr Cys Gly Met
                565                 570                 575
Gly Met Lys Lys Arg His Arg Met Ile Lys Met Asn Pro Ala Asp Gly
            580                 585                 590
```

-continued

Ser Met Cys Lys Ala Glu Thr Ser Gln Ala Glu Lys Cys Met Met Pro
        595                 600                 605

Glu Cys His Thr Ile Pro Cys Leu Leu Ser Pro Trp Ser Glu Trp Ser
        610                 615                 620

Asp Cys Ser Val Thr Cys Gly Lys Gly Met Arg Thr Arg Gln Arg Met
625                 630                 635                 640

Leu Lys Ser Leu Ala Glu Leu Gly Asp Cys Asn Glu Asp Leu Glu Gln
                645                 650                 655

Val Glu Lys Cys Met Leu Pro Glu Cys Pro Ile Asp Cys Glu Leu Thr
            660                 665                 670

Glu Trp Ser Gln Trp Ser Glu Cys Asn Lys Ser Cys Gly Lys Gly His
        675                 680                 685

Val Ile Arg Thr Arg Met Ile Gln Met Glu Pro Gln Phe Gly Gly Ala
        690                 695                 700

Pro Cys Pro Glu Thr Val Gln Arg Lys Lys Cys Arg Ile Arg Lys Cys
705                 710                 715                 720

Leu Arg Asn Pro Ser Ile Gln Lys Pro Arg Trp Arg Glu Ala Arg Glu
                725                 730                 735

Ser Arg Arg Ser Glu Gln Leu Lys Glu Ser Glu Gly Glu Gln Phe
            740                 745                 750

Pro Gly Cys Arg Met Arg Pro Trp Thr Ala Trp Ser Glu Cys Thr Lys
        755                 760                 765

Leu Cys Gly Gly Gly Ile Gln Glu Arg Tyr Met Thr Val Lys Lys Arg
        770                 775                 780

Phe Lys Ser Ser Gln Phe Thr Ser Cys Lys Asp Lys Lys Glu Ile Arg
785                 790                 795                 800

Ala Cys Asn Val His Pro Cys
                805

<210> SEQ ID NO 187
<211> LENGTH: 892
<212> TYPE: DNA
<213> ORGANISM: Homo sapiens

<400> SEQUENCE: 187
tttattgatg tttcaacagg cacttattca aataagttat atatttgaaa acagccatgg      60
taagcatcct tggcttctca cccattcctc atgtggcatg ctttctagac tttaaaatga     120
ggtaccctga atagcactaa gtgctctgta agctcaagga atctgtgcag tgctacaaag     180
cccacaggca gagaaagaac tcctcaagtg cttgtggtca gagactaggt tccatatgag     240
gcacacctat gatgaaggtc ttcacctcca gaaggtgaca ctgttcgag atcctcattt     300
cctggagagt gggagaaaat ccctcctttg ggaaatccct tttcccagca gcagagccca     360
cctcattgct tagtgatcat ttggaaggca ctgagagcct tcaggggctg acagcagaga     420
aatgaaaatg agtacagttc agatggtgga agaagcatgg cagtgacatc ttccatgctc     480
tttttctcag tgtctgcaac tccaaagatc aaggccataa cccaggagac catcaacgga     540
agattagttc tttgtcaagt gaatgaaatc caaaagcacg catgagacca atgaaagttt     600
ccgcctgttg taaaatctat tttccccaa ggaaagtcct tgcacagaca ccagtgagtg     660
agttctaaaa gataccttg gaattatcag actcagaaac ttttattttt ttttctgta     720
acagtctcac cagacttctc ataatgctct taatatattg cacttttcta atcaaagtgc     780
gagtttatga gggtaaagct ctactttcct actgcagcct tcagattctc atcatttgc     840
atctattttg tagccaataa aactccgcac tagcaaaaaa aaaaaaaaaa aa           892

<210> SEQ ID NO 188
<211> LENGTH: 1448
<212> TYPE: DNA
<213> ORGANISM: Homo sapiens
<220> FEATURE:
<221> NAME/KEY: misc_feature
<222> LOCATION: 1124
<223> OTHER INFORMATION: n = A,T,C or G

<400> SEQUENCE: 188

| | | | | | |
|---|---|---|---|---|---|
| tgtgactcac | atttcttta | ctgtgacaca | ataatgtgat | cctaaaactg | gcttatcctt | 60 |
| gagtgtttac | aactcaaaca | acttttgaa | tgcagtagtt | tttttttt | aaaaacaaac | 120 |
| ttttatgtca | aattttttt | cttagaagta | gtcttcatta | ttataaattt | gtacaccaaa | 180 |
| aggccatggg | gaactttgtg | caagtacctc | atcgctgagc | aaatggagct | tgctatgttt | 240 |
| taatttcaga | aaatttcctc | atatacgtag | tgtgtagaat | caagtctttt | aataattcat | 300 |
| tttttcttca | taatatttac | tcaaagttaa | gcttaaaaat | aagttttatc | ttaaaatcat | 360 |
| atttgaagac | agtaagacag | taaactattt | taggaagtca | acccccattg | cactctgtgg | 420 |
| cagttattct | ggtaaaaata | ggcaaaagtg | acctgaatct | acaatggtgt | cccaaagtaa | 480 |
| ccaagtaaga | gagattgtaa | atgataaacc | gagctttaaa | ggataaagtg | ttaataaaga | 540 |
| aaggaagctg | ggcacatgtc | aaaagggag | atcgaaatgt | taggtaatca | tttagaaagg | 600 |
| acagaaaata | tttaaagtgg | ctcataggta | atgaatattt | ctgacttaga | tgtaaatcca | 660 |
| tctggaatct | ttacatcctt | tgccagctga | acaagaaag | tgaagggaca | atgatatttc | 720 |
| atggtcagtt | tatttttgtaa | gagacagaag | aaattatatc | tatacattac | cttgtagcag | 780 |
| cagtacctgg | aagccccagc | ccgtcacaga | agtgtggagg | ggggctcctg | actagacaat | 840 |
| ttccctagcc | cttgtgattt | gaagcatgaa | agttctggca | ggttatgagc | agcactaggg | 900 |
| ataaagtatg | gttttatttt | ggtgtaattt | aggttttca | acaaagccct | tgtctaaaat | 960 |
| aaaaggcatt | attggaaata | tttgaaaact | agaaaatgat | ggataaaagg | gctgataaga | 1020 |
| aaatttctga | ctgtcagtag | aagtgagata | agatcctcag | aggaaacagt | aagaagggat | 1080 |
| aatcattaag | atagtaaaac | aggcaaagca | gaatcacatg | tgcncacaca | catacacatg | 1140 |
| taaacattgg | aatgcataag | ttttaatatt | ttagcgctat | cagtttctaa | atgcattaat | 1200 |
| tactaactgc | cctctcccaa | gattcattta | gttcaaacag | tatccgtaaa | ctaggaataa | 1260 |
| tgccacatgc | attcaatggg | atctttaag | tactcttcag | tttgttccaa | gaaatgtgcc | 1320 |
| tactgaaatc | aaattaattt | gtattcaatg | tgtacttcaa | gactgctaat | tgtttcatct | 1380 |
| gaaagcctac | aatgaatcat | tgttcamcct | tgaaaaataa | aattttgtaa | atcaaaaaaa | 1440 |
| aaaaaaaa | | | | | | 1448 |

<210> SEQ ID NO 189
<211> LENGTH: 460
<212> TYPE: DNA
<213> ORGANISM: Homo sapiens

<400> SEQUENCE: 189

| | | | | | |
|---|---|---|---|---|---|
| ttttgggagc | acggactgtc | agttctctgg | gaagtggtca | gcgcatcctg | cagggcttct | 60 |
| cctcctctgt | cttttggaga | accagggctc | ttctcagggg | ctctagggac | tgccaggctg | 120 |
| tttcagccag | gaaggccaaa | atcaagagtg | agatgtagaa | agttgtaaaa | tagaaaaagt | 180 |
| ggagttggtg | aatcggttgt | tctttcctca | catttggatg | attgtcataa | ggttttagc | 240 |

```
atgttcctcc ttttcttcac cctccccttt tttcttctat taatcaagag aaacttcaaa    300
gttaatggga tggtcggatc tcacaggctg agaactcgtt cacctccaag catttcatga    360
aaaagctgct tcttattaat catacaaact ctcaccatga tgtgaagagt ttcacaaatc    420
cttcaaaata aaagtaatg acttaaaaaa aaaaaaaaa                            460
```

```
<210> SEQ ID NO 190
<211> LENGTH: 481
<212> TYPE: DNA
<213> ORGANISM: Homo sapiens

<400> SEQUENCE: 190
aggtggtgga agaaactgtg gcacgaggtg actgaggtat ctgtgggagc taatcctgtc     60
caggtggaag taggagaatt tgatgatggt gcagaggaaa ccgaagagga ggtggtggcg    120
gaaaatccct gccagaacca ccactgcaaa cacggcaagg tgtgcgagct ggatgagaac    180
aacaccccca tgtgcgtgtg ccaggacccc accagctgcc cagcccccat ggcgagttt     240 gagaaggtgt gcagcaatga caacaagacc tcgactctt cctgccactt ctttgccaca    300
aagtgcaccc tggagggcac caagaagggc cacaagctcc acctggacta catcgggcct    360
tgcaaataca tccccccttg cctggactct gagctgaccg aattccccct gcgcatgcgg    420
gactggctca gaacgtcct ggtcaccctg tatgagaggg atgaggacaa caaccttctg    480
a                                                                    481
```

```
<210> SEQ ID NO 191
<211> LENGTH: 489
<212> TYPE: DNA
<213> ORGANISM: Homo sapiens
<220> FEATURE:
<221> NAME/KEY: misc_feature
<222> LOCATION: 312, 455
<223> OTHER INFORMATION: n = A,T,C or G

<400> SEQUENCE: 191
atataaatta gactaagtgt tttcaaataa atctaaatct tcagcatgat gtgttgtgta     60
taattggagt agatattaat taagtcccct gtataatgtt ttgtaatttt gcaaaacata    120
tcttgagttg tttaaacagt caaaatgttt gatattttat accagcttat gagctcaaag    180
tactacagca aagcctagcc tgcatatcat tcacccaaaa caaagtaata gcgcctcttt    240
tattattttg actgaatgtt ttatggaatt gaaagaaaca tacgttcttt tcaagacttc    300
ctcatgaatc tntcaattat aggaaaagtt attgtgataa aataggaaca gctgaaagat    360
tgattaatga actattgtta attcttccta ttttaatgaa tgacattgaa ctgaattttt    420
tgtctgttaa atgaacttga tagctaataa aaagncaact agccatcaaa aaaaaaaaa    480 aaaaaaaaa                                                            489
```

```
<210> SEQ ID NO 192
<211> LENGTH: 516
<212> TYPE: DNA
<213> ORGANISM: Homo sapiens

<400> SEQUENCE: 192
acttcaaagc cagctgaagg aaagaggaag tgctagagag agccccttc agtgtgcttc      60 tgacttttac ggacttggct tgttagaagg ctgaaagatg atggcaggaa tgaaaatcca    120
gcttgtatgc atgctactcc tggctttcag ctcctggagt ctgtgctcag attcagaaga    180
ggaaatgaaa gcattagaag cagatttctt gaccaatatg catacatcaa agattagtaa    240
```

```
agcacatgtt ccctcttgga agatgactct gctaaatgtt tgcagtcttg taaataattt    300
gaacagccca gctgaggaaa caggagaagt tcatgaagag gagcttgttg caagaaggaa    360
cttcttactg ctttagatgg ctttagcttg gaagcaatgt tgacaatata ccagctccac    420
aaaatctgtc acagcagggc ttttcaacac tgggagttaa tccaggaaga tattcttgat    480
actggaaatg acaaaaatgg aaaggaagaa gtcata                              516
```

<210> SEQ ID NO 193
<211> LENGTH: 1409
<212> TYPE: DNA
<213> ORGANISM: Homo sapiens

<400> SEQUENCE: 193

```
tgattctttt ccaaaacttt tagccatagg gtcttttata gacagggata gtaaaatgaa     60
aattgagaaa tataagatga aaaggaatgg taaaaatatc ttttagggggg cttttaattg    120 gtgatctgaa atcttgggag aagctgttct tttcaggcct gaggtgctct tgactgtcgc    180
ctgcgcactg tgtaccccga gcaacattct aagggtgtgc tttcgccttg ctaactcct    240 ttgacctcat tcttcatata gtagtctagg aaaagttgc aggtaattta aactgtctag    300
tggtacatag taactgaatt tctattccta tgagaaatga gaattattta tttgccatca    360
acacatttta tactttgcat ctccaaattt attgcggcga gacttgtcca ttgtgaaagt    420
tagagaacat tatgtttgta tcatttcttt cataaaacct caagagcatt tttaagccct    480
tttcatcaga cccagtgaaa actaaggata gatgttttt aactggaggt ctcctgataa    540
ggagaacaca atccaccatt gtcatttaag taataagaca ggaaattgac cttgacgctt    600
tcttgttaaa tagatttaac aggaacatct gcacatcttt tttccttgtg cactatttgt    660
ttaattgcag tggattaata cagcaagagt gccacattat aactaggcaa ttatccattc    720
ttcaagactt agttattgtc acactaattg atcgtttaag gcataagatg gtctagcatt    780
aggaacatgt gaagctaatc tgctcaaaaa gatcaacaaa ttaatattgt tgctgatatt    840
tgcataattg gctgcaatta tttaatgttt aattgggttg atcaaatgag attcagcaat    900
tcacaagtgc attaatataa acagaactgg ggcacttaaa atgataatga ttaacttata    960
ttgcatgttc tcttcctttc acttttttca gtgtctacat ttcagaccga gtttgtcagc   1020
ttttttgaaa acacatcagt agaaaccaag atttaaaat gaagtgtcaa gacgaaggca   1080
aaacctgagc agttcctaaa aagatttgct gttagaaatt ttctttgtgg cagtcattta   1140
ttaaggattc aactcgtgat acaccaaaag aagagttgac ttcagagatg tgttccatgc   1200
tctctagcac aggaatgaat aaatttataa caccctgcttt agcctttgtt ttcaaaagca   1260
caaaggaaaa gtgaaaggga aagagaaaca agtgactgag aagtcttgtt aaggaatcag   1320 gtttttcta cctggtaaac attctctatt cttttctcaa aagattgttg taagaaaaaa   1380
tgtaagmcaa aaaaaaaaaa aaaaaaaa                                      1409
```

<210> SEQ ID NO 194
<211> LENGTH: 441
<212> TYPE: DNA
<213> ORGANISM: Homo sapiens

<400> SEQUENCE: 194

```
cagatttcgg tagccatctc cctccaaata tgtctcttc tgcttcttta gtgcccatta     60
tttccccttc tcctttcttc tgtcactgcc atctccttct tggtcttccc attgttcttt    120
```

```
aactggccgt aatgtggaat tgatatttac attttgatac ggttttttc ttggcctgtg      180 tacgggattg cctcatttcc tgctctgaat tttaaaatta gatattaaag ctgtcatatg      240
gtttcctcac aaaagtcaac aaagtccaaa caaaaatagt ttgccgtttt actttcatcc      300
attgaaaaag gaaattgtgc ctcttgcagc ctaggcaaag gacatttagt actatcgatt      360
ctttccaccc tcacgatgac ttgcggttct ctctgtagaa aagggatggc ctaagaaata      420
caactaaaaa aaaaaaaaaa a                                                441

<210> SEQ ID NO 195
<211> LENGTH: 707
<212> TYPE: DNA
<213> ORGANISM: Homo sapiens

<400> SEQUENCE: 195
cagaaaaata tttggaaaaa atataccact tcatagctaa gtcttacaga gaagaggatt       60
tgctaataaa acttaagttt tgaaaattaa gatgcaggta gagcttctga actaatgccc      120
acagctccaa ggaagacatg tcctatttag ttattcaaat acaagttgag ggcattgtga      180
ttaagcaaac aatatatttg ttagaacttt gttttttaaat tactgttcct tgacattact      240
tataaagagt ctctaacttt cgatttctaa aactatgtaa tacaaaagta tagtttcccc      300
atttgataaa aggccaatga tactgagtag gatatatgcg tatcatgcta cttcattcag      360
tgtgtctgtt tttaatacta ataaggcagt ttgacagaaa ttatttcttt gggactaagg      420
tgattatcat ttttttcccc ttcaaaattg tgctttaagt gctgataacc acaggcagat      480
tgcaaagaac tgataaggca acaaaagtag agaattttag gatcaaaggc atgtaactga      540
aaggtaacaa cagtacataa gcgacaactg gggaaggcag cagtgaaaca tgtttgtggg      600
gttaagtgag tcattgtaaa taaggaattt gcacatttat tttctgtcga cgcggccgcc      660
actgtgctgg atatctgcag aattccacca cactggacta gtggatc                   707

<210> SEQ ID NO 196
<211> LENGTH: 552
<212> TYPE: DNA
<213> ORGANISM: Homo sapiens
<220> FEATURE:
<221> NAME/KEY: misc_feature
<222> LOCATION: 61, 129, 189, 222, 241, 278, 324, 338, 363, 408, 415,
      463, 483
<223> OTHER INFORMATION: n = A,T,C or G

<400> SEQUENCE: 196
tggccagcca gcctgatgtg gatggcttcc ttggggtggt gcttccctca gcccgaatt       60 ngtggacatc atcaatgcca acaatgagc cccatccatt ttccctaccc ttcctgccaa      120
gccagggant aagcagccca gaagcccagt aactgccctt tccctgcata tgcttttgat      180
ggtgtcatnt gctccttcct gtggcctcat ccaaactgta tnttccttta ctgtttatat      240
nttcaccctg taatggttgg gaccaggcca atcccttntc cacttactat aatggttgga      300
actaaacgtc accaaggtgg cttntccttg gctgaganat ggaaggcgtg gtgggatttg      360
ctnctgggtt ccctaggccc tagtgagggc agaagagaaa ccatcctntc ccttnttaca      420
ccgtgaggcc aagatcccct cagaaggcag gagtgctgcc ctntcccatg gtgcccgtgc      480
ctntgtgctg tgtatgtgaa ccacccatgt gagggaataa acctggcact aggaaaaaaa      540
aaaaaaaaaa aa                                                          552

<210> SEQ ID NO 197
```

```
<211> LENGTH: 449
<212> TYPE: DNA
<213> ORGANISM: Homo sapiens
<220> FEATURE:
<221> NAME/KEY: misc_feature
<222> LOCATION: 56, 58, 76
<223> OTHER INFORMATION: n = A,T,C or G

<400> SEQUENCE: 197
ctccagagac aacttcgcgg tgtggtgaac tctctgagga aaaacacgtg cgtggnanca        60
agtgactgag acctanaaat ccaagcgttg gaggtcctga ggccagccta agtcgcttca       120
aaatggaacg aaggcgtttg cggggttcca ttcagagccg atacatcagc atgagtgtgt       180
ggacaagccc acggagactt gtggagctgg cagggcagag cctgctgaag gatgaggccc       240
tggccattgc ccgccctgga gttgctgccc agggagctct tcccgccact cttcatggca       300
gcctttgacg ggagacacag ccagaccctg aaggcaatgg tgcaggcctg cccttcacc       360
tgcctccctc tgggagtgct gatgaaggga caacatcttc acctggagac cttcaaagct       420
gtgcttgatg gacttgatgt gctccttgc                                         449

<210> SEQ ID NO 198
<211> LENGTH: 606
<212> TYPE: DNA
<213> ORGANISM: Homo sapiens

<400> SEQUENCE: 198
tgagtttgcc cccttacccc catcccagtg aatatttgca attcctaaag acgtgttttg        60
attgtcacac ctgggtgggg aacatgctac tggcatctaa tgcatagagg gcagtaatgc       120
tgctaaacat ctttcaacgc acaggacaga gccccacaaa agagaattat ctagccccaa       180
atgtccataa cactgctgtt gagaaaacct accgcaggat cttactgggc ttcataggta       240
agcttgcctt tgttctggct tctgtagata tataaaataa agacactgcc cagtccctcc       300
ctcaacgtcc cgagccaggg ctcaaggcaa ttccaataac agtagaatga acactaaata       360
ttgatttcaa aatctcagca actagaagaa tgaccaacca tcctggttgg cctgggactg       420
tcctagtttt agcattgaaa gtttcaggtt ccaggaaagc cctcaggcct gggctgctgg       480
tcaccctagc agctgaggga ctcttcaata cagaattagt ctttgtgcac tggagatgaa       540
tatactttaa tttgtaacat gtgaaaacat ctataaacat ctactgaagc ctgttcttgt       600
ctgcac                                                                  606

<210> SEQ ID NO 199
<211> LENGTH: 369
<212> TYPE: DNA
<213> ORGANISM: Homo sapiens
<220> FEATURE:
<221> NAME/KEY: misc_feature
<222> LOCATION: 29, 345
<223> OTHER INFORMATION: n = A,T,C or G

<400> SEQUENCE: 199
ggcaactttt tgcggattgt tcttgcttnc aggctttgcg ctgcaaatcc agtgctacca        60
gtgtgaagaa ttccagctga acaacgactg ctcctccccc gagttcattg tgaattgcac       120
ggtgaacgtt caagacatgt gtcagaaaga agtgatggag caaagtgccg ggatcatgta       180
ccgcaagtcc tgtgcatcat cagcggcctg tctcatcgcc tctgccgggt accagtcctt       240
ctgctccccc gggaaactga actcagtttg catcagctgc tgcaacaccc ctctttgtaa       300
cgggccaagg cccaagaaaa ggggaagttc tgcctcggcc ctcangccat ggctccgcac       360
``` caccatcct                                                    369

<210> SEQ ID NO 200
<211> LENGTH: 55
<212> TYPE: PRT
<213> ORGANISM: Homo sapiens

<400> SEQUENCE: 200

Met Tyr Arg Asn Trp Ser Gly Cys Phe Gly Leu Gln Val Thr Leu Cys
1               5                   10                  15

His Thr Phe Glu Thr Arg Asp Leu Ser Arg Leu Ser Ser Asp Ser Gln
            20                  25                  30

Pro Thr Ser Asn Val Ser Gln Ser Ile Ser His Lys Val Leu Ser Phe
        35                  40                  45

Ser Gly Val Ile Val Thr Pro
    50                  55

<210> SEQ ID NO 201
<211> LENGTH: 67
<212> TYPE: PRT
<213> ORGANISM: Homo sapiens

<400> SEQUENCE: 201

Met Gln Leu Leu Ser Pro Asn Thr Lys Phe Thr Ser Cys Leu Ser Arg
1               5                   10                  15

Gln Arg Gly Asn Leu Val Phe Leu Gly Asp Leu Lys Gly Cys Ser Glu
            20                  25                  30

Leu Lys Asn Phe Gln Glu Leu Ile Asn Gln Ser Ala Leu Val His Pro
        35                  40                  45

Arg Val Asp Val Trp Trp Tyr Cys Gly Gly Pro Leu Leu Gly Thr Leu
    50                  55                  60

Pro Asn Asn
65

<210> SEQ ID NO 202
<211> LENGTH: 73
<212> TYPE: PRT
<213> ORGANISM: Homo sapiens

<400> SEQUENCE: 202

Met Thr Pro Glu Lys Leu Arg Thr Leu Cys Glu Ile Asp Trp Leu Thr
1               5                   10                  15

Leu Glu Val Gly Trp Leu Ser Glu Glu Ser Leu Glu Arg Ser Leu Val
            20                  25                  30

Ser Lys Val Trp His Lys Val Thr Cys Lys Pro Lys His Pro Asp Gln
        35                  40                  45

Phe Leu Tyr Ile Asp Ser Tyr Ser Trp Phe Arg Pro Leu Pro Pro Leu
    50                  55                  60

Pro Thr Val Val Lys Arg Thr Ala Ala
65                  70

<210> SEQ ID NO 203
<211> LENGTH: 2008
<212> TYPE: DNA
<213> ORGANISM: Homo sapiens

<400> SEQUENCE: 203
ctccagagac aacttcgcgg tgtggtgaac tctctgagga aaaacacgtg cgtggtaaca     60

```
agtgactgag acctagaaat ccaagcgttg gaggtcctga ggccagccta agtcgcttca    120
aaatggaacg aaggcgtttg cggggttcca ttcagagccg atacatcagc atgagtgtgt    180
ggacaagccc acggagactt gtggagctgg cagggcagag cctgctgaag gatgaggccc    240
tggccattgc ccgccctgga gttgctgccc agggagctct tcccgccact cttcatggca    300
gcctttgacg ggagacacag ccagaccctg aaggcaatgg tgcaggcctg gcccttcacc    360
tgcctccctc tgggagtgct gatgaaggga caacatcttc acctggagac cttcaaagct    420
gtgcttgatg gacttgatgt gctccttgcc caggaggttc gccccaggag gtggaaactt    480
caagtgctgg atttacggaa gaactctcat caggacttct ggactgtatg gtctggaaac    540
agggccagtc tgtactcatt tccagagcca gaagcagctc agcccatgac aaagaagcga    600
aaagtagatg gtttgagcac agaggcagag cagcccttca ttccagtaga ggtgctcgta    660
gacctgttcc tcaaggaagg tgcctgtgat gaattgttct cctacctcat gagaaagtg     720 aagcgaaaga aaaatgtact acgcctgtgc tgtaagaagc tgaagatttt tgcaatgccc    780
atgcaggata tcaagatgat cctgaaaatg gtgcagctgg actctattga agatttggaa    840
gtgacttgta cctggaagct acccaccttg gcgaaatttt ctccttacct gggccagatg    900
attaatctgc gtagactcct cctctcccac atccatgcat cttcctacat ttccccggag    960
aaggaagagc agtatatcgc ccagttcacc tctcagttcc tcagtctgca gtgcctgcag   1020
gctctctatg tggactcttt attttccctt agaggccgcc tggatcagtt gctcaggcac   1080
gtgatgaacc ccttggaaac cctctcaata actaactgcc ggctttcgga aggggatgtg   1140
atgcatctgt cccagagtcc cagcgtcagt cagctaagtg tcctgagtct aagtggggtc   1200
atgctgaccg atgtaagtcc cgagcccctc aagctctgc tggagagagc ctctgccacc    1260
ctccaggacc tggtctttga tgagtgtggg atcacggatg atcagctcct tgccctcctg   1320
ccttccctga gccactgctc ccagcttaca accttaagct tctacgggaa ttccatctcc   1380
atatctgcct tgcagagtct cctgcagcac ctcatcgggc tgagcaatct gacccacgtg   1440
ctgtatcctg tcccctgga gagttatgag acatccatg gtaccctcca cctggagagg    1500
cttgcctatc tgcatgccag gctcagggag ttgctgtgtg agttggggcg gcccagcatg   1560
gtctggctta gtgccaaccc ctgtcctcac tgtggggaca gaaccttcta tgacccggag   1620
cccatcctgt gcccctgttt catgcctaac tagctgggtg cacatatcaa atgcttcatt   1680
ctgcatactt ggacactaaa gccaggatgt gcatgcatct tgaagcaaca aagcagccac   1740
agtttcagac aaatgttcag tgtgagtgag gaaaacatgt tcagtgagga aaaaacattc   1800
agacaaatgt tcagtgagga aaaaagggg aagttgggga taggcagatg ttgacttgag   1860
gagttaatgt gatctttggg gagatacatc ttatagagtt agaaatagaa tctgaatttc   1920
taaagggaga ttctggcttg ggaagtacat gtaggagtta atccctgtgt agactgttgt   1980
aaagaaactg ttgaaaaaaa aaaaaaaa                                      2008
```

<210> SEQ ID NO 204
<211> LENGTH: 923
<212> TYPE: DNA
<213> ORGANISM: Homo sapiens

<400> SEQUENCE: 204

```
tgagtttgcc cccttacccc catcccagtg aatatttgca attcctaaag acgtgttttg     60
attgtcacac ctgggtgggg aacatgctac tggcatctaa tgcatagagg gcagtaatgc    120
tgctaaacat ctttcaacgc acaggacaga gccccacaaa agagaattat ctagccccaa    180
```

| | |
|---|---|
| atgtccataa cactgctgtt gagaaaacct accgcaggat cttactgggc ttcataggta | 240 |
| agcttgcctt tgttctggct tctgtagata tataaaataa agacactgcc cagtccctcc | 300 |
| ctcaacgtcc cgagccaggg ctcaaggcaa ttccataac agtagaatga acactaaata | 360 |
| ttgatttcaa aatctcagca actagaagaa tgaccaacca tcctggttgg cctgggactg | 420 |
| tcctagtttt agcattgaaa gtttcaggtt ccaggaaagc cctcaggcct gggctgctgg | 480 |
| tcaccctagc agctgaggga ctcttcaata cagaattagt cttttgtgcac tggagatgaa | 540 |
| tatactttaa tttgtaacat gtgaaaacat ctataaacat ctactgaagc ctgttctgtc | 600 |
| tgcaccgaca ttttcattga gtacggattc ttcctaccag atacagctgc tctacaactt | 660 |
| tcgagggctg gtataaaact agcttttacc tattttttaaa aattacatga atagtaaaaa | 720 |
| cttggattaa cccagtattc gggtattttc aatttccttg ggagcttaga ggacggacaa | 780 |
| ataaaaagat tatttcaaca tcaaatatat gctattgttt acatatgaag ataaccacat | 840 |
| atatgtataa attcaccgtt acttttagc aatactataa aatccaacag aaaaaaatag | 900 |
| catttactaa aaaaaaaaaa aaa | 923 |

<210> SEQ ID NO 205
<211> LENGTH: 1619
<212> TYPE: DNA
<213> ORGANISM: Homo sapiens

<400> SEQUENCE: 205

| | |
|---|---|
| ggcaactttt tgcggattgt tcttgcttcc aggctttgcg ctgcaaatcc agtgctacca | 60 |
| gtgtgaagaa ttccagctga caacgactg ctcctccccc gagttcattg tgaattgcac | 120 |
| ggtgaacgtt caagacatgt gtcagaaaga agtgatggag caaagtgccg ggatcatgta | 180 |
| ccgcaagtcc tgtgcatcat cagcggcctg tctcatcgcc tctgccgggt accagtcctt | 240 |
| ctgctcccca gggaaactga actcagtttg catcagctgc tgcaacaccc ctctttgtaa | 300 |
| cgggccaagg cccaagaaaa ggggaagttc tgcctcggcc ctcaggccag ggctccgcac | 360 |
| caccatcctg ttcctcaaat tagccctctt ctcggcacac tgctgaagct gaaggagatg | 420 |
| ccaccccctc ctgcattgtt cttccagccc tcgcccccaa ccccccacct ccctgagtga | 480 |
| gtttcttctg ggtgtccttt tattctgggt agggagcggg agtccgtgtt ctcttttgtt | 540 |
| cctgtgcaaa taatgaaaga gctcggtaaa gcattctgaa taaattcagc ctgactgaat | 600 |
| tttcagtatg tacttgaagg aaggaggtgg agtgaaagtt cacccccatg tctgtgtaac | 660 |
| cggagtcaag gccaggctgg cagagtcagt ccttagaagt cactgaggtg gcatctgcc | 720 |
| ttttgtaaag cctccagtgt ccattccatc cctgatgggg gcatagtttg agactgcaga | 780 |
| gtgagagtga cgttttctta gggctggagg gccagttccc actcaaggct ccctcgcttg | 840 |
| acattcaaac ttcatgctcc tgaaaaccat tctctgcagc agaattggct ggtttcgcgc | 900 |
| ctgagttggg ctctagtgac tcgagactca atgactggga cttagactgg ggctcggcct | 960 |
| cgctctgaaa agtgcttaag aaaatcttct cagttctcct tgcagaggac tggcgccggg | 1020 |
| acgcgaagag caacgggcgc tgcacaaagc gggcgctgtc ggtggtggag tgcgcatgta | 1080 |
| cgcgcaggcg cttctcgtgg ttggcgtgct cagcgacag gcggcagcac agcaccttgc | 1140 |
| acgaacaccc gccgaaactg ctgcgaggac accgtgtaca ggagcgggtt gatgaccgag | 1200 |
| ctgaggtaga aaacgtctc cgagaagggg aggaggatca tgtacgcccg gaagtaggac | 1260 |
| ctcgtccagt cgtgcttggg tttggccgca gccatgatcc tccgaatctg gttgggcatc | 1320 |

```
cagcatacgg ccaatgtcac aacaatcagc cctgggcaga cacgagcagg agggagagac    1380
agagaaaaga aaacacagc atgagaacac agtaaatgaa taaaaccata aaatatttag     1440
cccctctgtt ctgtgcttac tggccaggaa atggtaccaa tttttcagtg ttggacttga    1500
cagcttcttt tgccacaagc aagagagaat ttaacactgt ttcaaacccg ggggagttgg    1560
ctgtgttaaa gaaagaccat taaatgcttt agacagtgta aaaaaaaaaa aaaaaaaa     1619
```

<210> SEQ ID NO 206
<211> LENGTH: 2364
<212> TYPE: DNA
<213> ORGANISM: Homo sapiens

<400> SEQUENCE: 206

```
atgcagcatc accaccatca ccacttctcc gacgagaccc tggacaaagt gcccaagtca      60
gagggctact gtagccgtat cctgcgcgcc cagggcacgc ggcgcgaggg ctacaccgag     120
ttcagcctcc gcgtggaggg cgaccccgac ttctacaagc cgggaaccag ctaccgcgta     180
acactttcag ctgctcctcc ctcctacttc agaggattca cattaattgc cctcagagag     240
aacagagagg tgataagga agaagaccat gctgggacct tccagatcat agacgaagaa      300
gaaactcagt ttatgagcaa ttgccctgtt gcagtcactg aaagcactcc acggaggagg     360
acccggatcc aggtgttttg gatagcacca ccagcgggaa caggctgcgt gattctgaag     420
gccagcatcg tacaaaaacg cattatttat tttcaagatg agggctctct gaccaagaaa     480
ctttgtgaac aagattccac atttgatggg gtgactgaca aacccatctt agactgctgt     540
gcctgcggaa ctgccaagta cagactcaca ttttatggga attggtccga aagacacac      600 ccaaaggatt accctcgtcg ggccaaccac tggtctgcga tcatcggagg atcccactcc     660
aagaattatg tactgtggga atatggagga tatgccagcg aaggcgtcaa acaagttgca     720
gaattgggct cacccgtgaa aatggaggaa gaaattcgac aacagagtga tgaggtcctc     780
accgtcatca agccaaagc ccagtggcca gcctggcagc ctctcaacgt gagagcagca     840
ccttcagctg aatttccgt ggacagaacg cgccatttaa tgtccttcct gaccatgatg     900
ggccctagtc ccgactggaa cgtaggctta tctgcagaag atctgtgcac caaggaatgt    960
ggctgggtcc agaaggtggt gcaagacctg attccctggg acgctggcac cgacagcggg    1020
gtgacctatg agtcacccaa caaacccacc attccccagg agaaaatccg gcccctgacc    1080
agcctggacc atcctcagag tcctttctat gacccagagg gtgggtccat cactcaagta    1140
gccagagttg tcatcgagag aatcgcacgg aagggtgaac aatgcaatat tgtacctgac    1200
aatgtcgatg atattgtagc tgacctggct ccagaagaga agatgaaga tgacaccccct    1260 gaaacctgca tctactccaa ctggtcccca tggtccgcct gcagctcctc cacctgtgac    1320
aaaggcaaga ggatgcgaca gcgcatgctg aaagcacagc tggacctcag cgtcccctgc    1380
cctgacaccc aggacttcca gcctgcatg ggccctggct gcagtgacga agacggctcc    1440
acctgcacca tgtccgagtg gatcacctgg tcgccctgca gcatctcctg cggcatgggc    1500
atgaggtccc gggagaggta tgtgaagcag ttccgagg acggctccgt gtgcacgctg    1560
cccactgagg aaacggagaa gtgcacggtc aacgaggagt gctctcccag cagctgcctg    1620
atgaccgagt ggggcgagtg ggacgagtgc agcgccacct cggcatggg catgaagaag    1680 cggcaccgca tgatcaagat gaacccgca gatggctcca tgtgcaaagc cgagacatca    1740
caggcagaga agtgcatgat gccagagtgc acaccatcc catgcttgct gtccccatgg    1800
tccgagtgga gtgactgcag cgtgacctgc gggaagggca tgcgaacccg acagcggatg    1860
```

```
ctcaagtctc tggcagaact tggagactgc aatgaggatc tggagcaggt ggagaagtgc    1920
atgctccctg aatgccccat tgactgtgag ctcaccgagt ggtcccagtg gtcggaatgt    1980
aacaagtcat gtgggaaagg ccacgtgatt cgaacccgga tgatccaaat ggagcctcag    2040
tttggaggtg caccctgccc agagactgtg cagcgaaaaa agtgccgcat ccgaaaatgc    2100
cttcgaaatc catccatcca aaagctacgc tggagggagg cccgagagag ccggcggagt    2160
gagcagctga aggaagagtc tgaaggggag cagttcccag gttgtaggat gcgcccatgg    2220
acggcctggt cagaatgcac caaactgtgc ggaggtggaa ttcaggaacg ttacatgact    2280
gtaaagaaga gattcaaaag ctcccagttt accagctgca aagacaagaa ggagatcaga    2340
gcatgcaatg ttcatccttg ttag                                           2364
```

<210> SEQ ID NO 207
<211> LENGTH: 787
<212> TYPE: PRT
<213> ORGANISM: Homo sapiens

<400> SEQUENCE: 207

```
Met Gln His His His His His His Phe Ser Asp Glu Thr Leu Asp Lys
  1               5                  10                  15

Val Pro Lys Ser Glu Gly Tyr Cys Ser Arg Ile Leu Arg Ala Gln Gly
             20                  25                  30

Thr Arg Arg Glu Gly Tyr Thr Glu Phe Ser Leu Arg Val Glu Gly Asp
         35                  40                  45

Pro Asp Phe Tyr Lys Pro Gly Thr Ser Tyr Arg Val Thr Leu Ser Ala
     50                  55                  60

Ala Pro Pro Ser Tyr Phe Arg Gly Phe Thr Leu Ile Ala Leu Arg Glu
 65                  70                  75                  80

Asn Arg Glu Gly Asp Lys Glu Glu Asp His Ala Gly Thr Phe Gln Ile
                 85                  90                  95

Ile Asp Glu Glu Glu Thr Gln Phe Met Ser Asn Cys Pro Val Ala Val
            100                 105                 110

Thr Glu Ser Thr Pro Arg Arg Arg Thr Arg Ile Gln Val Phe Trp Ile
        115                 120                 125

Ala Pro Pro Ala Gly Thr Gly Cys Val Ile Leu Lys Ala Ser Ile Val
    130                 135                 140

Gln Lys Arg Ile Ile Tyr Phe Gln Asp Glu Gly Ser Leu Thr Lys Lys
145                 150                 155                 160

Leu Cys Glu Gln Asp Ser Thr Phe Asp Gly Val Thr Asp Lys Pro Ile
                165                 170                 175

Leu Asp Cys Cys Ala Cys Gly Thr Ala Lys Tyr Arg Leu Thr Phe Tyr
            180                 185                 190

Gly Asn Trp Ser Glu Lys Thr His Pro Lys Asp Tyr Pro Arg Arg Ala
        195                 200                 205

Asn His Trp Ser Ala Ile Ile Gly Gly Ser His Ser Lys Asn Tyr Val
    210                 215                 220

Leu Trp Glu Tyr Gly Gly Tyr Ala Ser Glu Gly Val Lys Gln Val Ala
225                 230                 235                 240

Glu Leu Gly Ser Pro Val Lys Met Glu Glu Glu Ile Arg Gln Gln Ser
                245                 250                 255

Asp Glu Val Leu Thr Val Ile Lys Ala Lys Ala Gln Trp Pro Ala Trp
            260                 265                 270

Gln Pro Leu Asn Val Arg Ala Ala Pro Ser Ala Glu Phe Ser Val Asp
```

-continued

```
            275                 280                 285
Arg Thr Arg His Leu Met Ser Phe Leu Thr Met Met Gly Pro Ser Pro
    290                 295                 300

Asp Trp Asn Val Gly Leu Ser Ala Glu Asp Leu Cys Thr Lys Glu Cys
305                 310                 315                 320

Gly Trp Val Gln Lys Val Val Gln Asp Leu Ile Pro Trp Asp Ala Gly
                325                 330                 335

Thr Asp Ser Gly Val Thr Tyr Glu Ser Pro Asn Lys Pro Thr Ile Pro
                340                 345                 350

Gln Glu Lys Ile Arg Pro Leu Thr Ser Leu Asp His Pro Gln Ser Pro
            355                 360                 365

Phe Tyr Asp Pro Glu Gly Gly Ser Ile Thr Gln Val Ala Arg Val Val
    370                 375                 380

Ile Glu Arg Ile Ala Arg Lys Gly Glu Gln Cys Asn Ile Val Pro Asp
385                 390                 395                 400

Asn Val Asp Asp Ile Val Ala Asp Leu Ala Pro Glu Glu Lys Asp Glu
                405                 410                 415

Asp Asp Thr Pro Glu Thr Cys Ile Tyr Ser Asn Trp Ser Pro Trp Ser
                420                 425                 430

Ala Cys Ser Ser Ser Thr Cys Asp Lys Gly Lys Arg Met Arg Gln Arg
            435                 440                 445

Met Leu Lys Ala Gln Leu Asp Leu Ser Val Pro Cys Pro Asp Thr Gln
    450                 455                 460

Asp Phe Gln Pro Cys Met Gly Pro Gly Cys Ser Asp Glu Asp Gly Ser
465                 470                 475                 480

Thr Cys Thr Met Ser Glu Trp Ile Thr Trp Ser Pro Cys Ser Ile Ser
                485                 490                 495

Cys Gly Met Gly Met Arg Ser Arg Glu Arg Tyr Val Lys Gln Phe Pro
                500                 505                 510

Glu Asp Gly Ser Val Cys Thr Leu Pro Thr Glu Glu Thr Glu Lys Cys
            515                 520                 525

Thr Val Asn Glu Glu Cys Ser Pro Ser Ser Cys Leu Met Thr Glu Trp
    530                 535                 540

Gly Glu Trp Asp Glu Cys Ser Ala Thr Cys Gly Met Gly Met Lys Lys
545                 550                 555                 560

Arg His Arg Met Ile Lys Met Asn Pro Ala Asp Gly Ser Met Cys Lys
                565                 570                 575

Ala Glu Thr Ser Gln Ala Glu Lys Cys Met Met Pro Glu Cys His Thr
            580                 585                 590

Ile Pro Cys Leu Leu Ser Pro Trp Ser Glu Trp Ser Asp Cys Ser Val
    595                 600                 605

Thr Cys Gly Lys Gly Met Arg Thr Arg Gln Arg Met Leu Lys Ser Leu
610                 615                 620

Ala Glu Leu Gly Asp Cys Asn Glu Asp Leu Glu Gln Val Glu Lys Cys
625                 630                 635                 640

Met Leu Pro Glu Cys Pro Ile Asp Cys Glu Leu Thr Glu Trp Ser Gln
                645                 650                 655

Trp Ser Glu Cys Asn Lys Ser Cys Gly Lys Gly His Val Ile Arg Thr
            660                 665                 670

Arg Met Ile Gln Met Glu Pro Gln Phe Gly Gly Ala Pro Cys Pro Glu
    675                 680                 685

Thr Val Gln Arg Lys Lys Cys Arg Ile Arg Lys Cys Leu Arg Asn Pro
690                 695                 700
```

```
Ser Ile Gln Lys Leu Arg Trp Arg Glu Ala Arg Glu Ser Arg Arg Ser
705                 710                 715                 720

Glu Gln Leu Lys Glu Glu Ser Glu Gly Glu Gln Phe Pro Gly Cys Arg
            725                 730                 735

Met Arg Pro Trp Thr Ala Trp Ser Glu Cys Thr Lys Leu Cys Gly Gly
            740                 745                 750

Gly Ile Gln Glu Arg Tyr Met Thr Val Lys Lys Arg Phe Lys Ser Ser
            755                 760                 765

Gln Phe Thr Ser Cys Lys Asp Lys Lys Glu Ile Arg Ala Cys Asn Val
            770                 775                 780

His Pro Cys
785

<210> SEQ ID NO 208
<211> LENGTH: 1362
<212> TYPE: DNA
<213> ORGANISM: Homo sapiens

<400> SEQUENCE: 208
```

| | | | | |
|---|---|---|---|---|
| atggcttcac | ccagcctccc | gggcagtgac | tgctcccaaa | tcattgatca | cagtcatgtc | 60 |
| cccgagtttg | aggtggccac | ctggatcaaa | atcacccta | ttctggtgta | cctgatcatc | 120 |
| ttcgtgatgg | gccttctggg | gaacagcgcc | accattcggg | tcacccaggt | gctgcagaag | 180 |
| aaaggatact | tgcagaagga | ggtgacagac | cacatggtga | gtttggcttg | ctcggacatc | 240 |
| ttggtgttcc | tcatcggcat | gcccatggag | ttctacagca | tcatctggaa | tccctgacc | 300 |
| acgtccagct | acaccctgtc | ctgcaagctg | cacactttcc | tcttcgaggc | ctgcagctac | 360 |
| gctacgctgc | tgcacgtgct | gacactcagc | tttgagcgct | acatcgccat | ctgtcacccc | 420 |
| ttcaggtaca | aggctgtgtc | gggaccttgc | caggtgaagc | tgctgattgg | cttcgtctgg | 480 |
| gtcacctccg | ccctggtggc | actgcccttg | ctgtttgcca | tgggtactga | gtaccccctg | 540 |
| gtgaacgtgc | ccagccaccg | gggtctcact | tgcaaccgct | ccagcaccg | ccaccacgag | 600 |
| cagccccgaga | cctccaatat | gtccatctgt | accaacctct | ccagccgctg | accgtgttc | 660 |
| cagtccagca | tcttcggcgc | cttcgtggtc | tacctcgtgg | tcctgctctc | cgtagccttc | 720 |
| atgtgctgga | acatgatgca | ggtgctcatg | aaaagccaga | agggctcgct | ggccggggc | 780 |
| acgcggcctc | cgcagctgag | gaagtccgag | agcgaagaga | gcaggaccgc | caggaggcag | 840 |
| accatcatct | tcctgaggct | gattgttgtg | acattggccg | tatgctggat | gcccaaccag | 900 |
| attcggagga | tcatggctgc | ggccaaaccc | aagcacgact | ggacgaggtc | ctacttccgg | 960 |
| gcgtacatga | tcctcctccc | cttctcggag | acgttttct | acctcagctc | ggtcatcaac | 1020 |
| ccgctcctgt | acacggtgtc | ctcgcagcag | tttcggcggg | tgttcgtgca | ggtgctgtgc | 1080 |
| tgccgcctgt | cgctgcagca | cgccaaccac | gagaagcgcc | tgcgcgtaca | tgcgcactcc | 1140 |
| accaccgaca | gcgcccgctt | tgtgcagcgc | ccgttgctct | tcgcgtcccg | cgccagtcc | 1200 |
| tctgcaagga | gaactgagaa | gatttcttcta | agcacttttc | agagcgaggc | cgagccccag | 1260 |
| tctaagtccc | agtcattgag | tctcgagtca | ctagagccca | actcaggcgc | gaaaccagcc | 1320 |
| aattctgctg | cagagaatgg | tttcaggag | catgaagttt | ga | | 1362 |

```
<210> SEQ ID NO 209
<211> LENGTH: 453
<212> TYPE: PRT
<213> ORGANISM: Homo sapiens
```

<400> SEQUENCE: 209

```
Met Ala Ser Pro Ser Leu Pro Gly Ser Asp Cys Ser Gln Ile Ile Asp
  1               5                  10                  15

His Ser His Val Pro Glu Phe Glu Val Ala Thr Trp Ile Lys Ile Thr
             20                  25                  30

Leu Ile Leu Val Tyr Leu Ile Ile Phe Val Met Gly Leu Leu Gly Asn
         35                  40                  45

Ser Ala Thr Ile Arg Val Thr Gln Val Leu Gln Lys Lys Gly Tyr Leu
     50                  55                  60

Gln Lys Glu Val Thr Asp His Met Val Ser Leu Ala Cys Ser Asp Ile
 65                  70                  75                  80

Leu Val Phe Leu Ile Gly Met Pro Met Glu Phe Tyr Ser Ile Ile Trp
                 85                  90                  95

Asn Pro Leu Thr Thr Ser Ser Tyr Thr Leu Ser Cys Lys Leu His Thr
            100                 105                 110

Phe Leu Phe Glu Ala Cys Ser Tyr Ala Thr Leu Leu His Val Leu Thr
        115                 120                 125

Leu Ser Phe Glu Arg Tyr Ile Ala Ile Cys His Pro Phe Arg Tyr Lys
    130                 135                 140

Ala Val Ser Gly Pro Cys Gln Val Lys Leu Leu Ile Gly Phe Val Trp
145                 150                 155                 160

Val Thr Ser Ala Leu Val Ala Leu Pro Leu Leu Phe Ala Met Gly Thr
                165                 170                 175

Glu Tyr Pro Leu Val Asn Val Pro Ser His Arg Gly Leu Thr Cys Asn
            180                 185                 190

Arg Ser Ser Thr Arg His His Glu Gln Pro Glu Thr Ser Asn Met Ser
        195                 200                 205

Ile Cys Thr Asn Leu Ser Ser Arg Trp Thr Val Phe Gln Ser Ser Ile
    210                 215                 220

Phe Gly Ala Phe Val Val Tyr Leu Val Val Leu Ser Val Ala Phe
225                 230                 235                 240

Met Cys Trp Asn Met Met Gln Val Leu Met Lys Ser Gln Lys Gly Ser
                245                 250                 255

Leu Ala Gly Gly Thr Arg Pro Pro Gln Leu Arg Lys Ser Glu Ser Glu
            260                 265                 270

Glu Ser Arg Thr Ala Arg Arg Gln Thr Ile Ile Phe Leu Arg Leu Ile
        275                 280                 285

Val Val Thr Leu Ala Val Cys Trp Met Pro Asn Gln Ile Arg Arg Ile
    290                 295                 300

Met Ala Ala Ala Lys Pro Lys His Asp Trp Thr Arg Ser Tyr Phe Arg
305                 310                 315                 320

Ala Tyr Met Ile Leu Leu Pro Phe Ser Glu Thr Phe Phe Tyr Leu Ser
                325                 330                 335

Ser Val Ile Asn Pro Leu Leu Tyr Thr Val Ser Ser Gln Gln Phe Arg
            340                 345                 350

Arg Val Phe Val Gln Val Leu Cys Cys Arg Leu Ser Leu Gln His Ala
        355                 360                 365

Asn His Glu Lys Arg Leu Arg Val His Ala His Ser Thr Thr Asp Ser
    370                 375                 380

Ala Arg Phe Val Gln Arg Pro Leu Leu Phe Ala Ser Arg Arg Gln Ser
385                 390                 395                 400

Ser Ala Arg Arg Thr Glu Lys Ile Phe Leu Ser Thr Phe Gln Ser Glu
                405                 410                 415
```

```
Ala Glu Pro Gln Ser Lys Ser Gln Ser Leu Ser Leu Glu Ser Leu Glu
        420                 425                 430

Pro Asn Ser Gly Ala Lys Pro Ala Asn Ser Ala Ala Glu Asn Gly Phe
        435                 440                 445

Gln Glu His Glu Val
    450

<210> SEQ ID NO 210
<211> LENGTH: 625
<212> TYPE: DNA
<213> ORGANISM: Homo sapiens
<220> FEATURE:
<221> NAME/KEY: misc_feature
<222> LOCATION: 607
<223> OTHER INFORMATION: n = A,T,C or G

<400> SEQUENCE: 210
agttctcctt gcagaggact ggcgccggga cgcgaagagc aacgggcgct gcacaaagcg      60
ggcgctgtcg gtggtggagt gcgcatgtac gcgcaggcgc ttctcgtggt tggcgtgctg     120
cagcgacagg cggcagcaca gcacctgcac gaacacccgc cgaaactgct gcgaggacac     180
cgtgtacagg agcgggttga tgaccgagct gaggtagaaa acgtctccg agaaggggag      240 gaggatcatg taccgcccgga agtaggacct cgtccagtcg tgcttgggtt tggccgcagc    300
catgatcctc cgaatctggt tgggcatcca gcatacggcc aatgtcacaa caatcagccc     360
tgggcagaca cgagcaggag ggagagacag agaaaagaaa acacagcat gagaacacag      420 taaatgaata aaaccataaa atatttagcc cctctgttct gtgcttactg gccaggaaat     480
ggtaccaatt tttcagtgtt ggacttgaca gcttcttttg ccacaagcaa gagagaattt     540
aacactgttt caaacccggg ggagttggct gtgttaaaga aagaccatta aatgctttag     600
acagtgnaaa aaaaaaaaa aaaaa                                            625

<210> SEQ ID NO 211
<211> LENGTH: 1619
<212> TYPE: DNA
<213> ORGANISM: Homo sapiens

<400> SEQUENCE: 211
ggcaactttt tgcggattgt tcttgcttcc aggctttgcg ctgcaaatcc agtgctacca      60
gtgtgaagaa ttccagctga caacgactg ctcctccccc gagttcattg tgaattgcac      120
ggtgaacgtt caagacatgt gtcagaaaga agtgatggag caaagtgccg ggatcatgta     180
ccgcaagtcc tgtgcatcat cagcggcctg tctcatcgcc tctgccgggt accagtcctt     240
ctgctcccca gggaaactga actcagtttg catcagctgc tgcaacaccc ctctttgtaa     300
cgggccaagg cccaagaaaa ggggaagttc tgcctcggcc ctcaggccag ggctccgcac     360
caccatcctg ttcctcaaat tagccctctt ctcggcacac tgctgaagct gaaggagatg     420
ccaccccctc ctgcattgtt cttccagccc tcgcccccaa ccccccacct cctgagtga      480 gtttcttctg ggtgtccttt tattctgggt agggagcggg agtccgtgtt ctctttttgtt    540 cctgtgcaaa taatgaaaga gctcggtaaa gcattctgaa taaattcagc ctgactgaat     600
tttcagtatg tacttgaagg aaggaggtgg agtgaaagtt cacccccatg tctgtgtaac     660
cggagtcaag gccaggctgg cagagtcagt ccttagaagt cactgaggtg gcatctgcc     720 ttttgtaaag cctccagtgt ccattccatc cctgatgggg gcatagtttg agactgcaga    780
gtgagagtga cgttttctta gggctggagg gccagttccc actcaaggct ccctcgcttg    840
```

| | |
|---|---|
| acattcaaac ttcatgctcc tgaaaaccat tctctgcagc agaattggct ggtttcgcgc | 900 |
| ctgagttggg ctctagtgac tcgagactca atgactggga cttagactgg ggctcggcct | 960 |
| cgctctgaaa agtgcttaag aaaatcttct cagttctcct tgcagaggac tggcgccggg | 1020 |
| acgcgaagag caacgggcgc tgcacaaagc gggcgctgtc ggtggtggag tgcgcatgta | 1080 |
| cgcgcaggcg cttctcgtgg ttggcgtgct gcagcgacag gcggcagcac agcaccttgc | 1140 |
| acgaacaccc gccgaaactg ctgcgaggac accgtgtaca ggagcgggtt gatgaccgag | 1200 |
| ctgaggtaga aaacgtctc cgagaagggg aggaggatca tgtacgcccg gaagtaggac | 1260 |
| ctcgtccagt cgtgcttggg tttggccgca gccatgatcc tccgaatctg gttgggcatc | 1320 |
| cagcatacgg ccaatgtcac aacaatcagc cctgggcaga cacgagcagg agggagagac | 1380 |
| agagaaaaga aaacacagc atgagaacac agtaaatgaa taaaaccata aaatatttag | 1440 |
| cccctctgtt ctgtgcttac tggccaggaa atggtaccaa ttttcagtg ttggacttga | 1500 |
| cagcttcttt tgccacaagc aagagagaat ttaacactgt ttcaaacccg ggggagttgg | 1560 |
| ctgtgttaaa gaaagaccat taaatgcttt agacagtgta aaaaaaaaaa aaaaaaaa | 1619 |

<210> SEQ ID NO 212
<211> LENGTH: 1010
<212> TYPE: DNA
<213> ORGANISM: Homo sapiens

<400> SEQUENCE: 212

| | |
|---|---|
| ccgcagccgg gagcccgagc gcgggcgatg caggctccgc gagcggcacc tgcggctcct | 60 |
| ctaagctacg accgtcgtct ccgctggcag cagctgcggg ccccagcagc ctcggcagcc | 120 |
| acagccgctg cagcctgggg cagcctccgc tgctgtcgcc tcctctgatg cgcttgccct | 180 |
| ctccctggcc ccgggactcc gggagaatgt gggtcctagg catcgcggca actttttgcg | 240 |
| gattgttctt gcttccaagg cttttgcgctg caaatccagt gctaccagtg tgaagaattc | 300 |
| cagctgaaca acgactgctc ctcccccgag ttcattgtga attgcacggt gaacgttcaa | 360 |
| gacatgtgtc agaaagaagt gatggagcaa agtgccggga tcatgtaccg caagtcctgt | 420 |
| gcatcatcag cggcctgtct catcgcctct gccgggtacc agtccttctg ctccccaggg | 480 |
| aaactgaact cagtttgcat cagctgctgc aacacccctc tttgtaaccg gccaaggcc | 540 |
| caagaaaagg ggaagttctg cctcggccct caggccaggg ctccgaacca ccatcctgtc | 600 |
| cctcaaatta agccctactt tcggcacac tgctggaagc ttgaagggag aaggcaccca | 660 |
| ctcctgcata gtccatccag gcctcgcccc acacacccca ctccctgaga gagcacgccc | 720 |
| agggagacca aaaccggga taggcaacgg accccagac accacaaggg acccgaggac | 780 |
| aaagacgcag acaactcgcg aaagccaccc acgaatacaa cggcccgaac acagatataa | 840 |
| cgcacgagcc ccgaccgaca agagaagaag cagaagaaac acccacagac agaaacagac | 900 |
| accagcaaca agcgaaaaca gcaaaacgac actagcgaga caccacctgc acacaacacc | 960 |
| acagcccaac acagaggaca cgacaacaaa gagacagcac caacgacgaa | 1010 |

<210> SEQ ID NO 213
<211> LENGTH: 480
<212> TYPE: DNA
<213> ORGANISM: Homo sapiens

<400> SEQUENCE: 213

| | |
|---|---|
| gccaactccg gaggctctgg tgctcggccc gggagcgcga gcgggaggag cagagacccg | 60 |

| | |
|---|---|
| cagccgggag cccgagcgcg ggcgatgcag gctccgcgag cggcacctgc ggctcctcta | 120 |
| agctacgacc gtcgtctccg cggcagcagc gcgggcccca gcagcctcgg cagccacagc | 180 |
| cgctgcagcc ggggcagcct ccgctgctgt cgcctcctct gatgcgcttg ccctctcccg | 240 |
| gccccgggac tccgggagaa tgtgggtcct aggcatcgcg gcaactttt gcggattgtt | 300 |
| cttgcttcca ggctttgcgc tgcaaatcca gtgctaccag tgtgaagaat tccagctgaa | 360 |
| caacgactgc tcctcccccg agttcattgt gaattgcacg gtgaacgttc aagacatgtg | 420 |
| tgagaaagaa gtgatggagc aaagtgccgg gatcatgtac cgcaagtcct gtgcatgatc | 480 |

<210> SEQ ID NO 214
<211> LENGTH: 1897
<212> TYPE: DNA
<213> ORGANISM: Homo sapiens

<400> SEQUENCE: 214

| | |
|---|---|
| gccaactccg gaggctctgg tgctcggccc gggagcgcga gcgggaggag cagagacccg | 60 |
| cagccgggag cccgagcgcg ggcgatgcag gctccgcgag cggcacctgc ggctcctcta | 120 |
| agctacgacc gtcgtctccg cggcagcagc gcgggcccca gcagcctcgg cagccacagc | 180 |
| cgctgcagcc ggggcagcct ccgctgctgt cgcctcctct gatgcgcttg ccctctcccg | 240 |
| gccccgggac tccgggagaa tgtgggtcct aggcatcgcg gcaactttt gcggattgtt | 300 |
| cttgcttcca ggctttgcgc tgcaaatcca gtgctaccag tgtgaagaat tccagctgaa | 360 |
| caacgactgc tcctcccccg agttcattgt gaattgcacg gtgaacgttc aagacatgtg | 420 |
| tcagaaagaa gtgatggagc aaagtgccgg gatcatgtac cgcaagtcct gtgcatcatc | 480 |
| agcggcctgt ctcatcgcct ctgccgggta ccagtccttc tgctccccag ggaaactgaa | 540 |
| ctcagtttgc atcagctgct gcaacacccc tctttgtaac gggccaaggc caagaaaag | 600 |
| gggaagttct gcctcggccc tcaggccagg gctccgcacc accatcctgt tcctcaaatt | 660 |
| agccctcttc tcggcacact gctgaagctg aaggagatgc caccccctcc tgcattgttc | 720 |
| ttccagcccct cgccccaac ccccacctc cctgagtgag tttcttctgg gtgtcctttt | 780 |
| attctgggta gggagcggga gtccgtgttc tcttttgttc ctgtgcaaat aatgaaagag | 840 |
| ctcggtaaag cattctgaat aaattcagcy tgactgaatt ttcagtatgt acttgaagga | 900 |
| aggaggtgga gtgaaagttc accccatgt ctgtgtaacc ggagtcaagg ccaggctggc | 960 |
| agagtcwgtc cttagaagtc actgaggtgg gcatctgcct tttgtaaagc ctccagtgtc | 1020 |
| cattccatcc ctgatggggg catagtttga gactgcagag tgagagtgac gttttcttag | 1080 |
| ggctggaggg ccagttccca ctcaaggctc cctcgcttga cattcaaact tcatgctcct | 1140 |
| gaaaaccatt ctctgcagca gaattggctg gtttcgcgcc tgagttgggc tctagtgact | 1200 |
| cgagactcaa tgactgggac ttagactggg gctcggcctc gctctgaaaa gtgcttaaga | 1260 |
| aaatcttctc agttctcctt gcagaggact ggcgccggga cgcgaagagc aacgggcgct | 1320 |
| gcacaaagcg ggcgctgtcg gtggtggagt gcgcatgtac gcgcaggcgc ttctcgtggt | 1380 |
| tggcgtgctg cagcgacagg cggcagcaca gcacctgcac gaacacccgc cgaaactgct | 1440 |
| gcgaggacac cgtgtacagg agcgggttga tgaccgagct gaggtagaaa acgtctccg | 1500 |
| agaaggggag gaggatcatg tacgcccgga agtaggacct cgtccagtcg tgcttgggtt | 1560 |
| tggccgcagc catgatcctc cgaatctggt tgggcatcca gcatacggcc aatgtcacaa | 1620 |
| caatcagccc tgggcagaca cgagcaggag ggagagacag agaaaagaaa acacagcat | 1680 |
| gagaacacag taaatgaata aaaccataaa atatttagcc cctctgttct gtgcttactg | 1740 |

-continued

```
gccaggaaat ggtaccaatt tttcagtgtt ggacttgaca gcttcttttg ccacaagcaa      1800
gagagaattt aacactgttt caaacccggg ggagttggct gtgttaaaga aagaccatta      1860
aatgctttag acagtgtaaa aaaaaaaaaa aaaaaaa                               1897
```

<210> SEQ ID NO 215
<211> LENGTH: 141
<212> TYPE: PRT
<213> ORGANISM: Homo sapiens

<400> SEQUENCE: 215

```
Met Trp Val Leu Gly Ile Ala Ala Thr Phe Cys Gly Leu Phe Leu Leu
 1               5                  10                  15

Pro Gly Phe Ala Leu Gln Ile Gln Cys Tyr Gln Cys Glu Glu Phe Gln
            20                  25                  30

Leu Asn Asn Asp Cys Ser Ser Pro Glu Phe Ile Val Asn Cys Thr Val
        35                  40                  45

Asn Val Gln Asp Met Cys Gln Lys Glu Val Met Glu Gln Ser Ala Gly
    50                  55                  60

Ile Met Tyr Arg Lys Ser Cys Ala Ser Ser Ala Ala Cys Leu Ile Ala
65                  70                  75                  80

Ser Ala Gly Tyr Gln Ser Phe Cys Ser Pro Gly Lys Leu Asn Ser Val
                85                  90                  95

Cys Ile Ser Cys Cys Asn Thr Pro Leu Cys Asn Gly Pro Arg Pro Lys
           100                 105                 110

Lys Arg Gly Ser Ser Ala Ser Ala Leu Arg Pro Gly Leu Arg Thr Thr
       115                 120                 125

Ile Leu Phe Leu Lys Leu Ala Leu Phe Ser Ala His Cys
   130                 135                 140
```

<210> SEQ ID NO 216
<211> LENGTH: 443
<212> TYPE: DNA
<213> ORGANISM: Homo sapiens
<220> FEATURE:
<221> NAME/KEY: misc_feature
<222> LOCATION: 185,208,304,339,348,386,421,428
<223> OTHER INFORMATION: n = A,T,C or G

<400> SEQUENCE: 216

```
ccttttttt tttttttctc agttattgac tggctgggtg tgacttagta cataagtact        60
caatattata aaaacctcaa ataattgact tgattttaca caacatcctt ccctttttcta     120 caagttaatt ttttttacaaa tcatttgggt tatctcctaa ataggttata ttttattgct    180
tctanaaaca atgtttcaaa atatatgngc attatcagta ataatttgta taaatatttc     240
ccacaacaat tttcataatt ttcaaagact aatttcttga ctgaagatat tttgctaggg     300
aagngaaact ttaaaatttt gagattttaa aaaaattgng tgaatggngg catgcaaagg     360
atttatatag tggctcccct aactgngtgc cgatcaggac acatattttt agacatctaa     420
ntctgganct taaatggagg gac                                              443
```

<210> SEQ ID NO 217
<211> LENGTH: 527
<212> TYPE: DNA
<213> ORGANISM: Homo sapiens
<220> FEATURE:
<221> NAME/KEY: misc_feature
<222> LOCATION: 521,523
<223> OTHER INFORMATION: n = A,T,C or G

<400> SEQUENCE: 217

```
agacacaaca gtctgactat gagtgaggaa aatatctggg tcttttcgtc agtttggtgc      60
atttgctgct gctgttgcta ctgtttgcct caaacgctgt gtttaaacaa cgttaaactc     120
ttagcctaca aggtggctct tatgtacata gttgttaata catccaatta atgatgtctg     180
acatgctatt tttgtaggga gaaaatatgt gctaatgata ttttgagtta aaatatcttt     240
tggggaggat ttgctgaaaa gttgcacttt tgttacaatg cttatgcttg gtacaagctt     300
atgctgtctt aaattatttt aaaaaaataa atactgtctg tgagaaacca gctggtttag     360
aaaagtttag tatgtgacga taaactagaa attacccttta tattctagta ttttcagcac     420
tccataaatt ctattaccta aatattgcca cactattttg tgatttaaaa attcttacta     480
aggaataaaa actttaatat acaaaaaaaa aaaaaggggg ngnccgc                   527
```

<210> SEQ ID NO 218
<211> LENGTH: 896
<212> TYPE: DNA
<213> ORGANISM: Homo sapiens
<220> FEATURE:
<221> NAME/KEY: misc_feature
<222> LOCATION: 531,587,589,592,619,636,649,662,663,694,
    723,729,735,737,741,752,783,816,817,819,
    820,822,826,828,830,833,834,839,841,842,
    869,892
<223> OTHER INFORMATION: n = A,T,C or G

<400> SEQUENCE: 218

```
gcagaacatt attttacaga cagcaaggat gcttctgagt gacacctagg aaattatttg      60
aagaaattct ttttatatct acacctgttg tgtaagaaac tttaaaacat tggttatttt     120
ctcacctttt tttctaattc actttgattg ctaggggtca tgtatgcttc gaagttacag     180
gactaaaaga gcaaactgac cggcctaaaa ctaaaatgac attttattccc tagctacaaa     240
catcagcgtt attatgttaa ttataccttg ccctctatca ttataaatgg ttgccatggt     300
gtttctaaaa ataagtgttt taccattaat gtgtagaggg caaacaaagc ataaagtact     360
aagggatcat gcttatccta gggtctcaca gaagagagga catatttaat taatcttgtg     420
aattacagaa caggttgtgg tccagacacc aagaatcata gggttttttt tttaaaaaac     480
ctaatagaag tagggggacc tctctctttg gctaagagtc taaaggaagg naggcatctg     540
tttaattagt tggttcaccc tggctttacc tctggttaat gctttgngnt antaggaagg     600
aaaaatcctt tatcttttnt tccaagccct ccctgnctga cttacccana ctgggattac     660
cnngaaaccc caggggggatt tatgggggga gaanggattt tttcacccttt taaacctctt     720
aanccccang gggananaaa ncctcttggg anagcctatg gccctatttt ttaatatcca     780
ggncccttg gaaaactttt ttttttttaa aagccnntnn antttnantn aannaaaana     840
nncaaccttt tggccccaaa aaaaaaggnc ccccctaag gcccccaccc tntttt          896
```

<210> SEQ ID NO 219
<211> LENGTH: 770
<212> TYPE: DNA
<213> ORGANISM: Homo sapiens
<220> FEATURE:
<221> NAME/KEY: misc_feature
<222> LOCATION: 525,527,574,619,628,730,752
<223> OTHER INFORMATION: n = A,T,C or G

<400> SEQUENCE: 219

```
aaagaaggtt cacttccatt acagtatgag tggcaaaaat tgtctgactc acagaaaatg      60
```

| | | |
|---|---|---|
| cccacttcat ggttagcaga aatgacttca tctgttatat ctgtaaaaaa tgcctcttct | 120 |
| gagtactctg ggacatacag ctgtacagtc agaaacagag tgggctctga tcagtgcctg | 180 |
| ttgcgtctaa acgttgtccc tccttcaaat aaagctggac taattgcagg agccattata | 240 |
| ggaactttgc ttgctctagc gctcattggt cttatcatct tttgctgtcg taaaaagcgc | 300 |
| agagaagaaa aatatgaaaa ggaagttcat cacgatatca gggaagatgt gccacctcca | 360 |
| aagagccgta cgtccactgc cagaagctac atcggcagta atcattcatc cctggggtcc | 420 |
| atgtctcctt ccaacatgga aggatattcc aagactcagt ataaccaagt accaagtgaa | 480 |
| gactttgaac gcactcctca gagtccgact ctcccacctg ctaangnagc tgccctaat | 540 |
| ctaagtcgaa tgggtgcgat tcctgtgatg attncagcac agagcaagga tgggtctata | 600 |
| gtatagagcc tccatatgnc tcatctgngc tctccggggt cctttccttt ttttgatata | 660 |
| tgaaaaccta ttctgggcta aattgggtac tagcctcaaa tcatcaaaaa ataagttaat | 720 |
| caggaactgn accgaaaata ttttttaaaa anttttgttt gggtatattc | 770 |

<210> SEQ ID NO 220
<211> LENGTH: 892
<212> TYPE: DNA
<213> ORGANISM: Homo sapiens
<220> FEATURE:
<221> NAME/KEY: misc_feature
<222> LOCATION: 2,3,208,321,337,542,551,560,590,606,
    613,614,620,639,640,645,646,652,659,661,
    663,666,676,679,707,708,709,717,718,719,
    726,728,730,732,738,742,751,764,773,777,
    782,792,821,825,827,828,831,832,833,870,
    880
<223> OTHER INFORMATION: n = A,T,C or G

<400> SEQUENCE: 220

| | |
|---|---|
| tnnacactca ccgccctcgc cgccgcgcca tggacgcccc caggcaggtg gtcaactttg | 60 |
| ggcctggtcc cgccaagctg ccgcactcag tgttgttaga gatacaaaag gaattattag | 120 |
| actacaaagg agttggcatt agtgttcttg aaatgagtca caggtcatca gattttgcca | 180 |
| agattattaa caatacagag aatcttgngc gggaattgct agctgttcca gacaactata | 240 |
| aggtgatttt tctgcaagga ggtgggtgcg gccagttcag tgctgtcccc ttaaacctca | 300 |
| ttggcttgaa agcaggaagg ngtgcggact atgtggngac aggagcttgg tcagctaagg | 360 |
| ccgcagaaga agccaagaag tttgggacta taaatatcgt tcaccctaaa cttgggagtt | 420 |
| atacaaaaat tccagatcca agcacctgga acctcaccca gatgcctcct acgtgtatta | 480 |
| ttgcgcaaat gagacggtgc atggtggtgg agtttgactt tataccgat gtccagggag | 540 |
| cnagtactgg ntttgtgacn tgtcctcaaa cttcctgtc caagccaggn gggatgtttt | 600 |
| cccaantttg ggnnggtgan tttttttgctg ggggcccnn aaaannaaat gnttggggnt | 660 |
| ncntgncttt gggggnccna ccccgggggg gcggaaattg gttccnnnc gggaatnnna | 720 |
| accccntngn cnggggggngg gnttttttggc ncccctttccc cggnaaaagg cgnggcnccc | 780 |
| cnttcggggg gncccttggg ggaaaataaa ccaaaggggt nggcncnngg nnnttttgggg | 840 |
| gaaacacacc gagcgcttcc cttttttgttn acccaacaan gggcccttc ca | 892 |

<210> SEQ ID NO 221
<211> LENGTH: 629
<212> TYPE: DNA
<213> ORGANISM: Homo sapiens
<220> FEATURE:
<221> NAME/KEY: misc_feature
<222> LOCATION: 408,502,507,540,542,545,550,562,572,576,
      623,628
<223> OTHER INFORMATION: n = A,T,C or G

<400> SEQUENCE: 221 ccttttttttt ttttttttggt acaaattatg taaaacattt gtgctaagaa cttttctccc    60
tccccaaacc aaaagaaaa taaaaaataa aaaattaaa aaaattaaaa attgagtatt    120
ctaactacag ctcaacaatt gaatcaaatg tcactgtttt gtaaatactt tatccataac    180
gaaagatata aacatgcaaa aaacctgaat ccatagtcca aataatacat acacatgttc    240
tgaagtttct gcacttctcc atagactatg ccaataaaac attatgtaca catactattt    300
ttacagtgaa gtggaaaaat acagaaataa aaaagtgtac atggattaag accaaaatgt    360
gtctaacatt ctagtttatg aaaaaattca attttgctac aaattggnga tatgaaaact    420
ccctttattt gcaaccagct gagtaagttt taagatttta gtgaaaaaaa aaaaaaacaa    480
actaaagtct aaaactagaa gnaatgngca ttttccaatc tcatgggctc atcccccaan    540
anaanaaaan cgctccatga gnttttttgg tnggtnaatt ttggatttta aaaaagcaa    600 atgcaatgta acaaaagcgg ggntgaanc                                    629

<210> SEQ ID NO 222
<211> LENGTH: 763
<212> TYPE: DNA
<213> ORGANISM: Homo sapiens
<220> FEATURE:
<221> NAME/KEY: misc_feature
<222> LOCATION: 626,628,634,661,748,751
<223> OTHER INFORMATION: n = A,T,C or G

<400> SEQUENCE: 222
ggaagtgctg aatggtgttg gcagggtat taaacgtgca ttttactca actacctcag    60 gtattcagta atacaatgaa aagcaaaatt gttccttttt tttgaaaatt ttatatactt    120
tataatgata gaagtccaac cgttttttaa aaaataaatt taaaatttaa cagcaatcag    180
ctaacaggca aattaagatt tttacttctg gctggtgaca gtaaagctgg aaaattaatt    240
tcagggtttt ttgaggcttt tgacacagtt attagttaaa tcaaatgttc aaaaatacgg    300
agcagtgcct agtatctgga gagcagcact accatttatt ctttcattta tagttgggaa    360 agttttgac ggtactaaca aagtggtcgc aggagatttt ggaacggctg gtttaaatgg    420
cttcaggaga cttcagtttt ttgtttagct acatgattga atgcataata aatgctttgt    480
gcttctgact atcaatacct aaagaaagtg catcagtgaa gagatgcaag actttcaact    540
gactggcaaa aagcaagctt tagcttgtct tataggatgc ttagtttgcc actacacttc    600
agaccaatgg gacagtcata gatggngnga cagngttaaa cgcaacaaaa ggctacattt    660
ncatggggcc agcactggca tgagcctccc taagcttttt tgaagaattt taagccctgg    720
taaattaaaa aaaaaaaaaa aaagggngg nccccctcca aat                    763

<210> SEQ ID NO 223
<211> LENGTH: 885
<212> TYPE: DNA
<213> ORGANISM: Homo sapiens
<220> FEATURE:
<221> NAME/KEY: misc_feature
<222> LOCATION: 21,571,599,653,714,717,746,755,756,761,
      762,781,782,790,814,849,884
<223> OTHER INFORMATION: n = A,T,C or G

<400> SEQUENCE: 223

```
tggagccgct gtggttgctg nccgcggagt ggaagcgcgt gcttttgttt gtgtccctgg    60
ccatggcgct gcagctctcc cgggagcagg gaatcaccct gcgcgggagc gccgaaatcg   120
tggccgagtt cttctcattc ggcatcaaca gcatttttata tcagcgtggc atatatccat   180
ctgaaacctt tactcgagtg cagaaatacg gactcacctt gcttgtaact actgatcttg   240
agctcataaa ataccaaat aatgtggtgg aacaactgaa agattggtta tacaagtgtt    300
cagttcagaa actggttgta gttatctcaa atattgaaag tggtgaggtc ctggaaagat   360
ggcagtttga tattgagtgt gacaagactg caaaagatga cagtgcaccc agagaaaagt   420
ctcagaaagc tatccaggat gaaatccgtt cagtgatcag acagatcaca gctacggtga   480
catttctgcc actgttggaa gtttcttgtc atttgatctg ctgatttata cagacaaaga   540
tttggttgta cctgaaaaat gggaagagtc nggaccacag tttattaccc aattctgang   600
aagtcccgcc ttcgttcatt tactactaca atccacaaag taaatagcat ggngggctac   660
aaaaaattcc tgtcaatgac tgaggatgac atgaaggaaa aaaatggaaa ttgnaanttt   720
tgaaaagggg gtttcctgaa aacagncatc tatanntgga nnttggttta tttcattggg   780
nnaatttttn cctgggggggg aaaaacccca aaanggatac cttttactgga accggggggg   840 gaaattggnc ctttttattt tttttttggg cccccaattt tggnc                    885

<210> SEQ ID NO 224
<211> LENGTH: 541
<212> TYPE: DNA
<213> ORGANISM: Homo sapiens
<220> FEATURE:
<221> NAME/KEY: misc_feature
<222> LOCATION: 300,311,350,422,490,508,526
<223> OTHER INFORMATION: n = A,T,C or G

<400> SEQUENCE: 224 ccttttttt ttttttttaaa acaaacttaa ctttatttcc tcactttcac ttaaaacttg    60
attttataaa acacatgaaa aaacatttt aagagttctg tatcacagaa cattaaacag    120
tacaaatatc cattgcttca taggttcaag ttacataaat taaagtcaaa taattggaaa   180
ctgattcaat agggaaaact atacatgaaa tgaaggtcaa aaggagctat acagcaatat   240
ttcattggtt atagattatg agttactttc aggaccttaa caaagattct gaatattan    300 acttcctttg ntggattta tacttaaata tctccctacc tatactgagn caaactactt   360
gaccaaaaca tctgatttag gaaagcatct agctttatag cacaagtttt tccatctaca   420
gntactatct tcaaggaat atacatcaca atgttgacaa aaaaacctcc tggttccttt    480
tgaacaatgn gcaataaatt catgatgnta accccatggg gaaggncaaa aaggggaccc   540
a                                                                    541

<210> SEQ ID NO 225
<211> LENGTH: 543
<212> TYPE: DNA
<213> ORGANISM: Homo sapiens
<220> FEATURE:
<221> NAME/KEY: misc_feature
<222> LOCATION: 23,226,295,316,327,345,428,445,476,479,
      521,522
<223> OTHER INFORMATION: n = A,T,C or G

<400> SEQUENCE: 225 ccttttttt tttttttgta agnttaaatt tattttttaa aaatgcttgt cttcctcact     60
agacaatcaa ctctatgagg gcagagacta tgtcaccact gtcccaccag cccctggcac   120
```

| | |
|---|---|
| acagtaggta ctcaataaat atatgttgga aggatggatg gaggtaatgg atggaaagat | 180 |
| ggatggaagg atgaatggag ggatggatgt gacccagctg aagtgngagt aggaacattc | 240 |
| tcttattatg ggtggaggaa agagagagga gattgagaaa ataagataaa atacnttgat | 300 |
| gagcatcatt tttggngttc gaaaagnagg attgaattag gactnataaa tctagagaat | 360 |
| tttacctctt tcaatgccca agccacactt ttctatcact ttgaaaccga aaaagaaata | 420 |
| ctttcccnac atttgctttg ctggnaggaa atgctttaat aaaaatgcaa tctctnagnt | 480 |
| gccatggcat cattaaaaga aaggatgtca tgcccaggcc nnaacttgaa ggggggaggc | 540 |
| ccc | 543 |

<210> SEQ ID NO 226
<211> LENGTH: 703
<212> TYPE: DNA
<213> ORGANISM: Homo sapiens
<220> FEATURE:
<221> NAME/KEY: misc_feature
<222> LOCATION: 530,535,560,567,584,600,664,671
<223> OTHER INFORMATION: n = A,T,C or G

<400> SEQUENCE: 226

| | |
|---|---|
| tgttaatgca attatagaaa tacatcggag acacaacatg atgtggccat tacaggtttc | 60 |
| ataaaattac actgacttgg ctgttacttg atcttaggaa acagcacagt ttaagatatt | 120 |
| gtgaattctg acttatactt tattaaatgc tataaatcta aatagatcct gttggatgtg | 180 |
| atgggtctag tccagtttat ttaagttcat gtttcactgt ttgcactttg cattgaacaa | 240 |
| tgggtttatt cgctgatgta aacggttcga gtgaagaatt aatgcagtaa gtatgacaac | 300 |
| acatacacac ttgcctctcc ccatctccag aagaggggag cagagtccga gcttatctaa | 360 |
| atatgaatgt ggccacaaag ctgtggaagg tgacaaagct taaacaccttt gccctggct | 420 |
| ctgcattgtc acctagagag caagaggtct atagaaacat catgtcacat gaaacgattc | 480 |
| tctgcttttt ggtctgaact tgaaggccct aaactgcaaa atctaagagn tgggngggta | 540 |
| ttaaaatgct tttaaaaagn taactgnggc accaattcta atgnaatccc acttgggacn | 600 |
| gggttttttt ggtttggttt ggttttgggg gggggggggg ggggccctg ggaaaagggg | 660 |
| aacnaacatg nttttgaaat acatattggg aaaaaaaatg ggg | 703 |

<210> SEQ ID NO 227
<211> LENGTH: 501
<212> TYPE: DNA
<213> ORGANISM: Homo sapiens
<220> FEATURE:
<221> NAME/KEY: misc_feature
<222> LOCATION: 1,5,154,239,281,292,336,421,459,470
<223> OTHER INFORMATION: n = A,T,C or G

<400> SEQUENCE: 227

| | |
|---|---|
| ngtgnccctg gccatggcgc tgcagctctc ccgggagcag ggaatcaccc tgcgcgggag | 60 |
| cgccgaaatc gtggccgagt tcttctcatt cggcatcaac agcatttat atcagcgtgg | 120 |
| catatatcca tctgaaacct ttactcgagt gcanaaatac ggactcacct tgcttgtaac | 180 |
| tactgatctt gagctcataa aatacctaaa taatgtggtg aacaactga aagattggnt | 240 |
| atacaagtgt tcagttcaga aactggttgt agttatctca natattgaaa gnggtgaggt | 300 |
| cctggaaaga tggcagtttg atattgagtg tgacangact gcaaaagatg acagtgcacc | 360 |
| cagagaaaag tctcagaaag ctatccagga tgaaatccgt tcagtgatca gacagatcac | 420 |
| ngctacgggg acatttctgc cctgttggaa ggttcttgnt catttgatcn gctgatttat | 480 | acagacaaaa gatttggttt g                                              501

<210> SEQ ID NO 228
<211> LENGTH: 539
<212> TYPE: DNA
<213> ORGANISM: Homo sapiens
<220> FEATURE:
<221> NAME/KEY: misc_feature
<222> LOCATION: 3,13,101,405,440,456,465,513,526
<223> OTHER INFORMATION: n = A,T,C or G

<400> SEQUENCE: 228
ggnttatact gcnaaagtta tgcattacac catattcagt tggtaacata aaccgagata     60
taagaattta tatattggct tctggttatt ttcttagcac nggagtgcct tttccaacca    120
ttgagtgcat gatcagatta cacaaataca agcacatatc atgtgttctc ccatgagaca    180
ttattcactt aggattgtct acaataaaaa aagttaaagt acaagcaata ataaattcat    240
aagaattttt tgaatttaaa ataaatgcat gtgtctttga aacatttct tttgaaattc     300 atattttta aaataacaag tttcttaaat cagtcttta gtcgtgtttt catatggtat     360
ttatcagtag gtggaaacac ttcacatcat ttaaccccaa aaggnataat aattaaactg    420
caattaaagg gaggaacagn tgaatcatta caacantaat acggngtaca aatcagagtt    480
ggccacacaa tacacatgtg taatactgga aanaaataca atatcngaat cctggatgg    539

<210> SEQ ID NO 229
<211> LENGTH: 790
<212> TYPE: DNA
<213> ORGANISM: Homo sapiens
<220> FEATURE:
<221> NAME/KEY: misc_feature
<222> LOCATION: 576,622,678,706,738,755,766
<223> OTHER INFORMATION: n = A,T,C or G

<400> SEQUENCE: 229
cagagagcat gatcagtgct gatactgaca agtacttttt taccttaaaa tcaacttcta    60
tggaactaca agatcaatct agctcccgag tgacattttc cattgtctgt aataatgccc   120
tcggatgagt tgtgtctaaa attaagttca tctttattta tatgcgaact taactgccat   180
agtccctaat gtattgcgtt tgtaacctga tcgtattatg tttacagctg aaagatttca   240
tctagacatg tctttcgtcc ttattattca aagtgtaatt gaaagagata tttagtatta   300
agacatgttc cccaattgag aattttccag aatattctac ttaagaagaa gaagagcaat   360
taactgcctt tagtgtaagg gcgagagtgc atagaaatat gcaatgtaaa atgtttgcat   420
gaattatttc acatcatgta agctttccca tattcataag atgaacacta tagaagtctc   480
atttctctgt gatcttctgc cattaggaaa gtaaggagat tggtatctat atctagtctc   540 cttttccatat tgaactgcat ggctctaatc ctcagnggat ttttatccct tctccggtta   600
tttaaaattt gccctattta anctggaagc ctggataaac tgctgagccc cgaatattcc   660
tggggattgg gagtttantt gctgggagaa ccacttggtt gaagancacc atttttttcc   720 ctttttttc ttttccnga attttttccc tcaanccatt ggtttnctct taaatggaaa    780 aaccccccccg                                                          790

<210> SEQ ID NO 230
<211> LENGTH: 744
<212> TYPE: DNA
<213> ORGANISM: Homo sapiens
<220> FEATURE:

<221> NAME/KEY: misc_feature
<222> LOCATION: 603,618,636,723,724
<223> OTHER INFORMATION: n = A,T,C or G

<400> SEQUENCE: 230

```
aaattttatg ggtgggtgcc aaatactgct gtgaatctat tgtatagta tccatgaatg      60
aatttatgga aatagatatt tgtgcagctc aatttatgca gagattaaat gacatcataa    120
tactggatga aaacttgcat agaattctga ttaaatagtg ggtctgtttc acatgtgcag    180
tttgaagtat ttaaataacc actcctttca cagtttattt tcttctcaag cgttttcaag    240
atctagcatg tggattttaa aagatttgcc ctcattaaca agaataacat ttaaaggaga    300
ttgtttcaaa atattttgc aaattgagat aaggacagaa agattgagaa acattgtata    360
ttttgcaaaa acaagatgtt tgtagctgtt tcagagagag tacggtatat ttatggtaat    420
tttatccact agcaaatctt gatttagttt gatagtgtgt ggaattttat tttgaaggat    480
aagaccatgg gaaaattgtg gtaaagactg tttgacccctt catgaaataa ttctgaagtt    540
gccatcagtt ttactaatct tctgtgaaag catagatatg cgcatggtca cttttattgg    600
ggncttataa ttaaatgnaa aattgaaatt catttntgtt caaggggat atcttccaat      660
agccttttta gtagtattca aatatcagtc tatggataat gatttattt ctttcttagg    720
agnntcaatg tggactaatt cagt                                            744
```

<210> SEQ ID NO 231
<211> LENGTH: 797
<212> TYPE: DNA
<213> ORGANISM: Homo sapiens
<220> FEATURE:
<221> NAME/KEY: misc_feature
<222> LOCATION: 429,446,495,523,537,626,628,642,664,707,
       711,713,727,733,786,793
<223> OTHER INFORMATION: n = A,T,C or G

<400> SEQUENCE: 231

```
gtgccgcctc caaagagccg tacgtccgct gccagaagct gcataggcag taatcattca     60
tccctggaat ccatgtctcc ttccaacatg gagggatatt ccaagactca gtataaacaa    120
gtaccgagtg aagactttga acgcactcct cagagtccaa ctctcccacc tgctaaggta    180
gctgccccta atctaggtcg aatgggcgtg attcctgtga tgattcccgc acagagcaag    240
gatgggtcta tagtatagag cctccatacg tctcatctgt gctttccgtg ttcctttcct    300
tttttgatat atgaaaacct attctggtct aaattttgtt actagcctca aaatgtatcc    360
aaaaataagt taatcaggag ctgtaaggaa tatatttttt aaaattttc tttggttata    420
tcgaaatang ttacaggcat taaagntagt aaagacaagt ttaccatctg aaaaagctgg    480
atttctttaa gaggntgatt ataaagggtt ctaaatttat cantacctaa gtaagangta    540
gcacttttga atatgaaatc ataagtgaag acattggtga acttacttgc atacccaagt    600
tgatactttg agtaaccatc tgaaangngg gacttggata antttacca ttattttta     660
ggangggat cttaattatt tatgggcccc cagtctcccc cccaaantaa ntncgaaaa      720
cattccnttg acnaaaatta cccccctgggg ggggttgga cctttggttt tcccaggttt    780
cttggnaaaa ctntggg                                                    797
```

<210> SEQ ID NO 232
<211> LENGTH: 635
<212> TYPE: DNA
<213> ORGANISM: Homo sapiens
<220> FEATURE:

<221> NAME/KEY: misc_feature
<222> LOCATION: 501,531,556,623,633
<223> OTHER INFORMATION: n = A,T,C or G

<400> SEQUENCE: 232

| | | | | | |
|---|---|---|---|---|---|
| tattattagg | atggtaagag | tattataagg | attggtacaa | ggcatgatga | gtccttttgc | 60 |
| ttttaggctt | ttgacttctg | gttttagact | ttctttagct | tctgttgtta | gacaacattg | 120 |
| tgcaagcttg | gtttttataa | gtttgcatgg | attaaactga | acttaatgaa | attgtccctc | 180 |
| cccccaaatt | ctcagcacaa | ttttaggcc | cacaaggagt | caagcacctc | aaggagatct | 240 |
| tcagtttgaa | cttggtgtag | acacagggat | actgatgaat | caatattcaa | attagctgtt | 300 |
| acctacttaa | gaaagagagg | agaccttggg | gatttcgagg | aagggttcat | aagggagatt | 360 |
| ttagctgaga | aataccattt | gcacagtcaa | tcacttctga | ccaagttatc | agaaaaagga | 420 |
| gaaaagaatg | tctccccact | aaatgttcta | gggtggtgag | aaatctaggg | tgggtatcta | 480 |
| aatcacaata | tttggatatt | ncaatatcta | aatattggtg | gaaatactct | nctgaagtgt | 540 |
| cattgactct | aaaaanacac | ttgtgatcat | ggcaggggtt | aaggtcattt | ttattcctat | 600 |
| aatccttata | ttaacaattc | ctntgattaa | ganaa | | | 635 |

<210> SEQ ID NO 233
<211> LENGTH: 663
<212> TYPE: DNA
<213> ORGANISM: Homo sapiens
<220> FEATURE:
<221> NAME/KEY: misc_feature
<222> LOCATION: 429,432,437,475,485,491,493,535,550,555,
      571,612,640,653
<223> OTHER INFORMATION: n = A,T,C or G

<400> SEQUENCE: 233

| | | | | | |
|---|---|---|---|---|---|
| cctctgtata | gaaatctaaa | agaattttac | cattcagtta | attcaatgtg | aacactggca | 60 |
| cactgctctt | aagaaactat | gaagatctga | gattttttg | tgtatgtttt | tgactctttt | 120 |
| gagtggtaat | catatgtgtc | tttatagatg | tacatacctc | cttgcacaaa | tggaggggaa | 180 |
| ttcatttca | tcactgggag | tgtccttagt | gtatgaaaac | catgctggta | tatggcttca | 240 |
| agttgtaaaa | atgaaagtga | ctttaaaaga | aaatagggga | tggtccagga | tctccactga | 300 |
| taagactgtt | tttaagtaac | ttaaggacct | ttgggtctac | aagtatatgt | gaaaaaatg | 360 |
| agacttactg | ggtgaggaaa | tccattgttt | aaagatggtc | cgtgtgtgtg | tgtgtgtgtg | 420 |
| tgtgtgtgnt | gngttgngtt | ttgtttttta | agggagggaa | tttattattt | accgntgctt | 480 |
| gaaantactg | ngnaaatata | tgtctgataa | tgatttgctc | tttgacaact | aaaantagga | 540 |
| ctgtataagn | cctanatgcc | tcctgggggg | ntgatcttac | aagatattgg | tgataccct | 600 |
| ttaaaaattg | gncccccggc | attttccccc | tttgcttctn | caaattaaaa | ggnctttttc | 660 |
| cca | | | | | | 663 |

<210> SEQ ID NO 234
<211> LENGTH: 873
<212> TYPE: DNA
<213> ORGANISM: Homo sapiens
<220> FEATURE:
<221> NAME/KEY: misc_feature
<222> LOCATION: 20,29,58,603,630,652,678,711,715,745,
      752,756,766,774,789,820,823,840,873
<223> OTHER INFORMATION: n = A,T,C or G

<400> SEQUENCE: 234

| | | | | | |
|---|---|---|---|---|---|
| acttggggat | tctcatgttn | atggatacng | tttggcaatc | actacattga | atgtagtntt | 60 |

```
ttaaaaaaat taacttatgc tattagttga cccatcattg ctaatttttgg cccacacagt      120 gtttgcatta caaaaacctg ttctttactt cctagtcttg tttcagtctt aatatcagaa      180
gttcttgagt tcaaaataag cacaacatgt catccaggga tggctagctt gtttgggatt      240
catctaaact gctggcaata tctagacaaa acattccac agtccagcta atatggttgt       300
cacaactctt gaaaagggcc caacatctgg atggcaagtg aaaatgtgat cagggtttaa      360 gaactacccca ctaataaata aacatggagc tatttccatg tcttgggtgt tgtgtttcta    420
agaagagaca gcctttccat cagaaaattt ctgggaggga agaaaaagaa cagttttgat     480
gaattcgctt tgcaaatcat catccaatgt tctttgtaac cagaaaggtt ttcttctgct     540
ttcttgcagc tggtatactt tctgctgagt gccctgggc ctgacggtct gtgtgctggc      600
cgnggccttt gcccgcccac cactattcgn cagctcacac cagtttacct gngagacccc    660
ctccgacttt tggccagngc aaactggccc cttccttcgg gagccggctc nagcnaggac     720 cctttttggtt ttacccgggg atggngaccg gnctgnaccc agccgnccac tggnccctt     780 tcaaacctng ttccttttccc tcatccccag aaggaatttn ttnaaatttt gggccttggn   840
ggcccttggg ggggcctttg ggttgggccc ctn                                  873

<210> SEQ ID NO 235
<211> LENGTH: 51
<212> TYPE: DNA
<213> ORGANISM: Homo sapiens
<220> FEATURE:
<221> NAME/KEY: misc_feature
<222> LOCATION: 26,48
<223> OTHER INFORMATION: n = A,T,C or G

<400> SEQUENCE: 235
tttttttttt tttttttta atttttngttt tttttttttt ttttttttngg g            51

<210> SEQ ID NO 236
<211> LENGTH: 765
<212> TYPE: DNA
<213> ORGANISM: Homo sapiens
<220> FEATURE:
<221> NAME/KEY: misc_feature
<222> LOCATION: 540,555,590,593,670,685,708,711,714,733,
      760
<223> OTHER INFORMATION: n = A,T,C or G

<400> SEQUENCE: 236
ggagacctaa tgtttcatat gcagcgacaa agaaaacttc ctgaagaaca tgccagattt     60
tactctgcag aaatcagtct agcattaaat tatcttcatg agcgagggat aatttataga    120
gatttgaaac tggacaatgt attactgac tctgaaggcc acattaaact cactgactac     180
ggcatgtgta aggaaggatt acggccagga gatacaacca gcactttctg tggtactcct    240
aattacattg ctcctgaaat tttaagagga gaagattatg gtttcagtgt tgactggtgg   300
gctcttggag tgctcatgtt tgagatgatg gcaggaaggt ctccatttga tattgttggg   360
agctccgata accctgacca gaacacagag gattatctct tccaagttat tttggaaaaa    420
caaattcgca taccacgttc tctgtctgta aaagctgcaa gtgttctgaa gagttttctt   480
aataaggacc ctaaggaacg attgggttgt catcctcaaa caggatttgc tgatattcan   540
ggaccccgtc tttcnaaatg ttgattggga tatgatggac aaaaacaggn ggnaccttcc   600
tttaaccaaa tatttctggg gaatttggt ttggacacct tgattctca atttactaat    660 ggaacctggn ccagctcact cccanaatga cgaatgacct ttggggangg naanaattgg   720
```

```
gatcaagtct ggnaattttg gaaagggttt ttggaggtan tattc              765
```

```
<210> SEQ ID NO 237
<211> LENGTH: 739
<212> TYPE: DNA
<213> ORGANISM: Homo sapiens
<220> FEATURE:
<221> NAME/KEY: misc_feature
<222> LOCATION: 460,478,485,509,527,529,554,573,575,578,
      603,607,609,616,621,643,651,674,675,689,
      696,729
<223> OTHER INFORMATION: n = A,T,C or G

<400> SEQUENCE: 237
ctctactgga agtttgaccc tgtgaaggtg aaggctctgg aaggcttccc ccgtctcgtg    60
ggtcctgact tctttggctg tgccgagcct gccaacactt tcctctgacc atggcttgga   120
tgccctcagg ggtgctgacc cctgccaggc cacgaatatc aggctagaga cccatggcca   180
tctttgtggc tgtgggcacc aggcatggga ctgagcccat gtctcctcag ggggatgggg   240
tggggtacaa ccaccatgac aactgccggg agggccacgc aggtcgtggt cacctgccag   300
cgactgtctc agactgggca gggaggcttt ggcatgactt aagaggaagg gcagtcttgg   360
gcccgctatg caggtcctgg caaacctggc tgcctgtctc catccctgtc cctcagggta   420
gcaccatggc aggactgggg gaactggagt gccttgctgn atccctgttg ggagggtnct   480
ttcangggct ggcactgaaa caaggggnt ggggcccat gggcttnanc ctgggtgaac   540
aactgggctt gtanggcaag ggcactttct gangncangg cttgggaagg ggcctgcatc   600
tgnctgncnt tttggntgac naatcctggg aaatctggtt ttnccaaaat nccaggccaa   660
aaaagtttac cagnncaaaa tgggggggang ggggantttt ttttatggca aggaaaaaac   720
ccccagggnc ccttgggaa                                                739
```

```
<210> SEQ ID NO 238
<211> LENGTH: 818
<212> TYPE: DNA
<213> ORGANISM: Homo sapiens
<220> FEATURE:
<221> NAME/KEY: misc_feature
<222> LOCATION: 311,378,441,442,494,505,520,525,540,545,
      551,570,600,602,616,619,639,641,650,656,
      671,684,686,697,701,724,726,732,738,749,
      759,762,792,797
<223> OTHER INFORMATION: n = A,T,C or G

<400> SEQUENCE: 238
cctggtgatc gcttcagtag agatgtctgg tgatatggtg aactgatcag gccctgacat    60
ggatgttccc ctagaggata tcacttctgt cctggagacc tcagtggtag caccactggg   120
cacttcagaa aggacagtgc ttccctctgt ggctgagctg gtcccttcag agccgctgga   180
ctccctcaat ccaggggtca gggaggaagc tagctctgtc tgaatcctcc tagtctcaag   240
gaaggcagga gttgatgtga gaacacttgt atccccatg gtggaggtgg tacacattgg    300
agatgagtca nctaggacag aggactgtga tttatatcca gagctggtgg ttgccacatt   360
ggtccctcct gtgtttgngg aaggatgcac ggcttctgta tgtgcagtgt ctttgtaagt   420
ggtaagtctc tcatgggagg nngggctcaa acttgaagat gaactggttc caggttcttg   480
tgcttgtacc caanatatct gtggntgtcc ccggccagan gganaaagt gaagtcacan    540 ggaagggaa naggggggga tatgtgctan gaatgtggtg gaaaacaagg atgaagtgan   600
gncccggcag gtaaanacna gcgggggaag gaatggaang ncttggtttn ttttcncaaa   660
```

```
agggaagggc ntaggccaat gacncnccct cccgganctt ntgcccattg ggaagggggc    720
attntnttgg gngggggnaa aatccctgna attaactana anaaaggggg tttcccccc     780 aaaaaggggg gnggttncttt ggggttcaaa ataaaggg                           818
```

<210> SEQ ID NO 239
<211> LENGTH: 829
<212> TYPE: DNA
<213> ORGANISM: Homo sapiens
<220> FEATURE:
<221> NAME/KEY: misc_feature
<222> LOCATION: 207,379,714,717,736,762,770
<223> OTHER INFORMATION: n = A,T,C or G

<400> SEQUENCE: 239

```
ctggtcttgg actcctgacc tcaagtgatc cacccccctc agcctcccaa agtgctagga    60
ttacaggcat gagtcactgc gtcaggccaa aattctgtat tttcaattag agtcaaagcc   120
caaggatgtc tctaccatct tgtagcccct gccaatagcc tactcttgtc ttccagggtt   180
cctccaaatc tctctccaaa tatttgntat ctactcattc aatacccttc ttcaaccatc   240
ctcttgcttt ggaattgaca tgaaccaact aggcccgcct tattggtagg aattcatttg   300
ccctgcctgc cagcccccat agagacagaa ccattgccta gtgaaagaag attttaatga   360
cgtgatgaaa atatttttana aagcaccttg aagattagta ttttatgta acttctgttg    420 gagagatgtc ttcaggagac tgaagtagaa gagcgactgt caaaatggaa agtcccagag   480
acatccaatt tatgtaaatc aacatcacct gaattcagaa tctcatccag atttcaacaa   540
agacttctga atgccaacca agaagagga ctgaatttac agactctcac tctaacaata    600
tatgctggtc aatttgaaaa acagaataaa attattttgg caagaaactg gattttaat    660 ggacatatat tggtttaaaa tggtaccaac ttttttattt tacccccattt tggnggnaaa   720 aaacccgggg aataanggga aaagcaaaag ggaaaatata tncaaatatn gggaaggttt   780
ttacctttaa ttttggttca ttaaacctaa cccagaaggc caaacaatt                829
```

<210> SEQ ID NO 240
<211> LENGTH: 177
<212> TYPE: DNA
<213> ORGANISM: Homo sapiens

<400> SEQUENCE: 240

```
ccttttttt tttttttaca tacaaaatgt tttaattgag aaaaaaattc aaaacagtca    60
cacatatcca ttatcatcat ggttctctga atatttttct tatacaaatg aaatatttaa   120
aatggaaaaa ttcattttt caaatctaat taactaatta ttttttgtcct ggtcgac      177
```

<210> SEQ ID NO 241
<211> LENGTH: 591
<212> TYPE: DNA
<213> ORGANISM: Homo sapiens
<220> FEATURE:
<221> NAME/KEY: misc_feature
<222> LOCATION: 96,152,212,246,280,403,436,491,494,501,
      519,568,579
<223> OTHER INFORMATION: n = A,T,C or G

<400> SEQUENCE: 241

```
ccttttttt tttttcatt aaataatcca tcatcacatt agtacaatac aattttatat    60
tttttaaata tactatatat gttaaggata agggngnaag ttttcttcct ttgtaatacc   120
tgttcaagag tttaatggat taggagatta gngttaacct tgaggataaa agtacaaatt   180
```

```
tgtctcatta ggacacttct accaagcatt tnttaaggct atagtttaac atttggtttc    240
aaaaanaaaa aaaaaggttt catttaaaaa ataatttagn gaattacatt ctttcataac    300 ttccaccta attagttaca aagataagtc taaagattct tagttttggg tactaattta    360
```

<br/>

```
tgtctcatta ggacacttct accaagcatt tnttaaggct atagtttaac atttggtttc    240
aaaaanaaaa aaaaaggttt catttaaaaa ataatttagn gaattacatt ctttcataac    300 ttccaccta attagttaca aagataagtc taaagattct tagttttggg tactaattta    360
catttatatt taaagattaa ttttacttgg atcttaaaac aanaatttta tgttggaaaa    420
aagagaacta atacntttg tataaaggct gtaaatgtcc catggcaaat gctctgtctc    480
aatattttct nccncaatta naaacagggc tctgcaaana gagacttggg ttgttcaggt    540
tcacctttcc cgaggaattg ggggctgnca tctgaaganc atagagaaac a            591
```

<210> SEQ ID NO 242
<211> LENGTH: 924
<212> TYPE: DNA
<213> ORGANISM: Homo sapiens
<220> FEATURE:
<221> NAME/KEY: misc_feature
<222> LOCATION: 102,104,591,592,595,596,640,641,650,683,
   706,708,720,734,735,757,759,779,791,804,
   806,825,837,905,912
<223> OTHER INFORMATION: n = A,T,C or G

<400> SEQUENCE: 242

```
aacctttcag gaaatccaa ggaaatacag aagcaaggca gcaccatagt cttcccagcc    60
aaggtggaag tgcctctggt tcctccagca attcccactg gngntatcat aactcaacag    120
tctgttgcaa tcagttgtag aaaggcacag agtgacagct ggaatgcaaa gaaatgtgca    180
caacccagag ctctgtcagc cttgccaaaa ctcaagtgcc cccatgggag ggtcttgcaa    240
catatgttct gttgagcaaa gaggttgcaa accaagcggt tattgcaata aacaccactt    300
gtgacaaaca aagtttgtaa gtttaaattt attttttaaa aatgcttgtc ttcctcacta    360
gacaatcaac tctatgaggg cagagactat gtcaccactg tcccaccagc ccctggcaca    420
cagtaggtac tcaataaata tatgttggga aggatggatg gaggtaatgg atggaaagat    480
ggatggaagg atgaatggag ggaatggatg tgacccagct gaagtgtgag taggaacatt    540
ctcttattat gggtggagga aagagagagg agattgagaa aaataagata nnatnncatt    600
ggatgaagcc atcatttttt gggggttcc gaaaaaagtn ngggatttgn aaatttaagg    660
gaacttaaat aaaaatcctt aanaaaaaaa atttttttaa cccctncntt tttccaaaan    720
gggcccccca aaanncccca acccaacttt tttttttncnt tatttccacc tttttggna    780 aaaaacccc naaaaaaaaa aggntnaaaa attacccctt ttttnccccc aaacccnttt    840 ttggccttt tgccttgggg aaagggaaaa aaggcttttt aaataaaaaa aatggccaat    900
tcttnttaaa anttggccaa tggg                                          924
```

<210> SEQ ID NO 243
<211> LENGTH: 278
<212> TYPE: DNA
<213> ORGANISM: Homo sapiens
<220> FEATURE:
<221> NAME/KEY: misc_feature
<222> LOCATION: 211,276,277
<223> OTHER INFORMATION: n = A,T,C or G

<400> SEQUENCE: 243

```
cctttttttt tttttttaag atttaactct gaatacaaat gtatttttt cttcttctct    60 ccctacatat attctaaacc ttctaaagtt tttttatttt tttaaggatc actttatcat    120
aaaataaaat atccttttca tataataaat tacctaataa aaagtctttt tttttcatat    180
```

| | | |
|---|---|---|
| tagcccaggt tctttgctac atttatatgg naataaacgc ctttattaaa atagaatatt | 240 | |
| aaattataaa gaactgcttt tttttttttt ttttgnna | 278 | |

<210> SEQ ID NO 244
<211> LENGTH: 3072
<212> TYPE: DNA
<213> ORGANISM: Homo sapiens

<400> SEQUENCE: 244

| | |
|---|---|
| gcgcagacgc cccagccccc caccgccccc aaagggggcga gcgacgccaa gctctgcgct | 60 |
| ctctacaaag aggccgagct gcgcctgaag ggcagcagca acaccacgga gtgtgttccc | 120 |
| gtgcccacct ccgagcacgt ggccgagatc gtgggcaggc aaggctgcaa gattaaggcc | 180 |
| ttgagggcca agaccaacac ctacatcaag acaccggtga ggggcgagga accagtgttc | 240 |
| atggtgacag ggcgacggga ggacgtggcc acagcccggc gggaaatcat ctcagcagcg | 300 |
| gagcacttct ccatgatccg tgcctcccgc aacaagtcag gcgccgcctt tggtgtggct | 360 |
| cctgctctgc ccggccaggt gaccatccgt gtgcgggtgc cctaccgcgt ggtggggctg | 420 |
| gtggtgggcc ccaaaggggc aaccatcaag cgcatccagc agcaaaccaa cacatacatt | 480 |
| atcacaccaa gccgtgaccg cgaccccgtg ttcgagatca cgggtgcccc aggcaacgtg | 540 |
| gagcgtgcgc gcgaggagat cgagacgcac atcgcggtgc gcactggcaa gatcctcgag | 600 |
| tacaacaatg aaaacgactt cctggcgggg agccccgacg cagcaatcga tagccgctac | 660 |
| tccgacgcct ggcgggtgca ccagcccggc tgcaagcccc tctccacctt ccggcagaac | 720 |
| agcctgggct gcatcggcga gtgcggagtg gactctggct ttgaggcccc acgcctgggt | 780 |
| gagcagggcg gggactttgg ctacggcggg tacctctttc cgggctatgg cgtgggcaag | 840 |
| caggatgtgt actacggcgt ggccgagact agccccccgc tgtgggcggg ccaggagaac | 900 |
| gccacgccca cctccgtgct cttctcctct gcctcctcct cctcctcctc ttccgccaag | 960 |
| gcccgcgctg ggccccgggg cgcacaccgc tcccctgcca cttccgcggg acccgagctg | 1020 |
| gccggactcc cgaggcgccc cccggggagag ccgctccagg gcttctctaa acttggtggg | 1080 |
| ggcggcctgc ggagccccgg cggcgggcgg gattgcatgg tctgctttga gagcgaagtg | 1140 |
| actgccgccc ttgtgccctg cggacacaac ctgttctgca tggagtgtgc agtacgcatc | 1200 |
| tgcgagagga cggacccaga gtgtcccgtc tgccacatca cagccacgca agccatccga | 1260 |
| atattctcct aagcccgtg ccccatgcct ccggggccca ctccactggg cccaccctgg | 1320 |
| acctgttttc cactaaagcc ttttggaaag cggtgatttg aggggcaagg tgcttagaga | 1380 |
| tactcgctcg ctgggggaagg gggagggag gcagtggtgg ctggagggtg cgccactttc | 1440 |
| agagcctctg gtcaccctgt cctggaaaga ttgggagggg gccagactga aaattttact | 1500 |
| agagttacaa ctctgatacc tcaacacacc cttaaatctg gaagcagcta agagaaactt | 1560 |
| ttgttttgcc agaggtggcc actaaggcat tctgacgccc tctgcccacc tccccgctg | 1620 |
| tgtgtcactc caccccttct tccgaggagg gggtgggtaa aagggagagg gagaattacc | 1680 |
| acctgtatct agaggtgctc tttgcaatcc ctaagccctc tggtcctgac ctccgacctc | 1740 |
| ccagctctgt cttgttcctt gtctttgtct ttcttccctt cccctgccc ctgcccctac | 1800 |
| cagcccagct ttggggacac catccttctg gggagaagta gggggaggaa tatttggatg | 1860 |
| gtccctccat tcctcttcag gcatctggag gccctctccc ccactcctcc aaagaaacat | 1920 |
| ctcaaaattat tgatggaatg tatccccatt tcagtgaaa atgtgaggag gggactaata | 1980 |
| ctggggtaaa gggtcaaacc cccaccttca tcactatggg cattatattt agggagtagt | 2040 |

```
tcttgggctg gattttctgg ttgtggaagt gggggcgcca gagtagtgtg tctgctattt    2100
aaaggagcag gaaagggcgt gaggcaggag gagagactgg tggagggaag agctgctcct    2160
cccatgcagt gcccgactcc ctgcacccct ctcaacctga cctgaacctt tattgaatcc    2220
ttattagctt gaatccttat tagcttgaat cctccatgca aatcatggag tctgtgtccc    2280
acctgatgtg gttgaggaga agccaggtct tcaaagaggg gtcagcctgg ggcaaagcag    2340
gactgggggg aggtgggcag cagggcctat tctgagaatc acatattgtt acaggccttg    2400
cacccccttt gctgcttccc tcctgctcat ttggggctgc caccagctct ccaccctcct    2460
ggttccgctg gccgggccaa gagaggatgg agggatggga gtcccaggag atccttgtaa    2520
atagtggggt gggactgttc tgagtgatca cccgagcact taaagctcca gagtcccatt    2580
cttcctggat ggagcaggtg gaggtgcaga ggggatttcc tcctctcctt cctcctgtcg    2640
agaattaaca cctctccaca gccttcccct ccagaacacc agccaggag gggtggggaa     2700 ggaggtcaca gccaagaaaa ctgccctgtg acgacttccc tccttcccgc ctatgtgagc    2760
catcctgaga tgtctgtaca atagaaacca aaccaaatgg gcaccctcgg ttgccggggg    2820
gcaggtgggg agggggggtgg gaagaaggga tgtctgtctg tcgtcccect cccctctcc    2880 actctttacc cacaaaggca gaagactgtt cactagggg gctcagcaaa ttcaatccca    2940
cccttaccaa ttgagccaaa cctagaaaca aacacaaaac acgaatagtg agagacaaaa    3000
tagaggagag aaagagagca tgagagggag cgagacaggc gaccaacaca gaggagagaa    3060
aacaaaaata gc    3072

<210> SEQ ID NO 245
<211> LENGTH: 2323
<212> TYPE: DNA
<213> ORGANISM: Homo sapiens

<400> SEQUENCE: 245
ggactctggc tttgaggccc cacgcctggg tgagcagggc ggggactttg gctacggcgg    60
gtacctcttt ccgggctatg gcgtgggcaa gcaggatgtg tactacgcgc tggccgagac    120
tagccccccg ctgtgggcgg gccaggagaa cgccacgccc acctccgtgc tcttctcctc    180
ctcctcctcc tcctcctctt ccgccaaggc ccgcgctggg cccccggggcg cacaccgctc    240 ccctgccact tccgcgggac ccgagctggc cggactcccg aggcgccccc cgggagagcc    300
gctccggggc ttctctaaac ttggtggggg cggcctgcgg agcccgcag ccggcgggcg     360 ggattgcatg gtctgctttg agagcgaagt gactgccgcc cttgtgccct gcggacacaa    420
cctgttctgc atggagtgtg cagtacgcat ctgcagagg acggacccag agtgtcccgt     480
ctgccacatc acagccacgc aagccatccg aatattctcc taagcccgt gccccatgcc      540 tccgggccc actccactgg gcccacccctg gacctgtttt ccactaaagc cttttggaaa    600
gcggtgattt gaggggcaag gtgcttagag atactcgctc gctggggaag gggggaggga    660
ggcagtggtg gctggagggt gcgccacttt cagagcctct ggtcaccctg tcctggaaag    720
attgggaggg ggccagactg aaaatttac tagagttaca actctgatac ctcaacacac      780
ccttaaatct ggaagcagct aagagaaact tttgttttgc cagaggtggc cactaaggca    840
ttctgacgcc ctctgcccac ctcccccgct gtgtgtcact ccaccccttc ttccgaggag    900
ggggtgggta aaaggagag ggagaattac cacctgtatc tagaggtgct cttttgcaatc     960 cctaagcccc ctggtcctga cctccgacct cccagctctg tcttgttcct tgtctttgtc    1020
```

```
tttcttccct tccccctgcc cctgccccta ccagcccagc tttggggaca ccatccttct   1080
ggggagaagt aggggagga atatttggat ggtccctcca ttcctcttca ggcatctgga   1140
ggccctctcc cccactcctc caaagaaaca tctcaaatta ttgatggaat gtatccccat   1200
tctcagtgaa aatgtgagga ggggactaat actggggtaa agggtcaaac ccccaccttc   1260
atcactatgg cattatatt tagggagtag ttcttgggct ggattttctg gttgtggaag   1320
tgggggcgcc agagtagtgt gtctgctatt taaaggagca ggaaagggcg tgaggcagga   1380
ggagagactg gtggagggaa gagctgctcc tcccatgcag tgcccgactc cctgcacccc   1440
tctcaacctg acctgaacct ttattgaatc cttattagct tgaatcctta ttagcttgaa   1500
tcctccatgc aaatcatgga gtctgtgtcc cacctgatgt ggttgaggag aagccaggtc   1560
ttcaaagagg ggtcagcctg gggcaaagca ggactggggg gaggtgggca gcagggccta   1620
ttctgagaat cacatattgt tacaggcctt gcaccccctt tgctgcttcc ctcctgctca   1680
tttggggctg ccaccagctc tccaccctcc tggttccgct ggccgggcca agagaggatg   1740
gagggatggg agtcccagga gatccttgta aatagtgggg tgggactgtt ctgagtgatc   1800
acccgagcac ttaaagctcc agagtccat tcttcctgga tggagcaggt ggaggtgcag   1860
aggggatttc ctcctctcct tcctcctgtc gagaattaac acctctccac agccttcccc   1920
tccagaacac cagccaggga ggggtgggga aggaggtcac agccaagaaa actgccctgt   1980
gacgacttcc ctccttcccg cctatgtgag ccatcctgag atgtctgtac aatagaaacc   2040
aaaccaaatg ggcaccctcg gttgccgggg ggcaggtggg gaggggggtg ggaagaaggg   2100
atgtctgtct gtcgtccccc tccccctctc cactctttac ccacaaaggc agaagactgt   2160
tacactaggg ggctcagcaa attcaatccc acccttacca attgagccaa acctagaaac   2220
aaacacaaaa cacgaatagt gagagacaaa atagaggaga gaaagagagc atgagaggga   2280
gcgagacagg cgaccaacac agaggagaga aacaaaaat agc                     2323

<210> SEQ ID NO 246
<211> LENGTH: 5882
<212> TYPE: DNA
<213> ORGANISM: Homo sapiens
<220> FEATURE:
<221> NAME/KEY: misc_feature
<222> LOCATION: 1100,1975,4288,5859,5862,5863,5868
<223> OTHER INFORMATION: n = A,T,C or G

<400> SEQUENCE: 246
gcgcagacgc cccagccccc caccgccccc aaagggcgga gcgacgccaa gctctgcgct     60
ctctacaaag aggccgagct gcgcctgaag ggcagcagca acaccacgga gtgtgttccc    120
gtgcccacct ccgagcacgt ggccgagatc gtgggcaggc aaggctgcaa gattaaggcc    180
ttgagggcca agaccaacac ctacatcaag acaccggtga ggggcgagga accagtgttc    240
atggtgcacag ggcgacggga ggacgtggcc acagcccggc gggaaatcat ctcagcagcg    300
gagcacttct ccatgatccg tgcctcccgc aacaagtcag gcgccgcctt tggtgtggct    360
cctgctctgc ccggccaggt gaccatccgt gtgcgggtgc cctaccgcgt ggtgggctg    420
gtggtgggcc ccaaagggc aaccatcaag cgcatccagc agcaaaccaa cacatacatt    480
atcacaccaa gccgtgaccg cgaccccgtg ttcgagatca cgggtgcccc aggcaacgtg    540
gagcgtgcgc gcgaggagat cgagacgcac atcgcggtgc gcactggcaa gatcctcgag    600
tacaacaatg aaaacgactt cctggcgggg agccccgacg cagcaatcga tagccgctac    660
tccgacgcct ggcgggtgca ccagcccggc tgcaagcccc tctccacctt ccggcagaac    720
```

```
agcctgggct gcatcggcga gtgcggagtg gactctggct ttgaggcccc acgcctgggt    780
gagcagggcg gggactttgg ctacggcggg tacctctttc cgggctatgg cgtgggcaag    840
caggatgtgt actacggcgt ggccgagact agcccccgc tgtgggcggg ccaggagaac     900
gccacgccca cctccgtgct cttctcctct gcctcctcct cctcctcctc ttccgccaag    960
gcccgcgctg gccccgggg cgcacaccgc tcccctgcca cttccgcggg acccgagctg    1020
gccggactcc cgaggcgccc cccgggagag ccgctccagg gcttctctaa acttggtggg    1080
ggcggcctgc ggagccccgs cggcgggcgg gattgcatgg tctgctttga gagcgaagtg    1140
actgccgccc ttgtgccctg cggacacaac ctgttctgca tggagtgtgc agtacgcatc    1200
tgcgagagga cggacccaga gtgtcccgtc tgccacatca cagccacgca agccatccga    1260
atattctcct aagcccgtg ccccatgcct ccggggccca ctccactggg cccaccctgg     1320
acctgttttc cactaaagcc ttttggaaag cggtgatttg aggggcaagg tgcttagaga    1380
tactcgctcg ctggggaagg ggggagggag gcagtggtgg ctggagggtg cgccactttc    1440
agagcctctg gtcaccctgt cctggaaaga ttgggagggg gccagactga aaattttact    1500
agagttacaa ctctgatacc tcaacacacc cttaaatctg gaagcagcta agagaaactt    1560
ttgtttgcc agaggtggcc actaaggcat tctgacgccc tctgcccacc tccccgctg      1620
tgtgtcactc caccccttct tccgaggagg gggtgggtaa aagggagagg gagaattacc    1680
acctgtatct agaggtgctc tttgcaatcc ctaagccctc tggtcctgac ctccgacctc    1740
ctaacatgac cctttaccte ccaccccacc cccatatcct gtttgggaaa ctgtcaccag    1800
tttccagcag tgtaagggag ttggagtcct atcagaagtt gcatagatct tctaggggtt    1860
ggggagagaa gcatgtcaat cgtttctgtg gctgaaaggc tcagaagcca tctgtcccca    1920
caaagctggg ctagaggaat ctggagagga gtcctcctct ctgcccctgt ccccygcagt    1980
gtttcccttc actctctccg cctatcttcc cttcctttgg gatcttccct ttcctcaact    2040
cttttccttc cctccagctc tttgctttgc tttcttttgg tggctgtcac tcccagctct    2100
gtcttgttcc ttgtctttgt cttttcttccc ttccccctgc ccctgcccct accagcccag   2160
ctttggggac accatccttc tggggagaag taggggagg aatatttgga tggtccctcc     2220
attcctcttc aggcatctgg aggccctctc cccactcct ccaaagaaac atctcaaatt     2280
attgatggaa tgtatcccca ttctcagtga aaatgtgagg aggggactaa tactgggta    2340
aagggtcaaa cccccacctt catcactatg ggcattatat ttagggagta gttcttgggc    2400
tggattttct ggttgtggaa gtgggggcgc cagagtagtg tgtctgctat ttaaaggagc    2460
aggaaagggc gtgaggcagg aggagagact ggtggaggga agagctgctc ctcccatgca    2520
gtgcccgact ccctgcaccc ctctcaacct gacctgaacc tttattgaat ccttattagc    2580
ttgaatcctt attagcttga atcctccatg caaatcatgg agtctgtgtc ccacctgatg    2640
tggttgagga gaagccaggt cttcaaagag gggtcagcct ggggcaaagc aggactgggg    2700
ggaggtgggc agcagggcct attctgagaa tcacatattg ttacaggcct tgcaccccct    2760
ttgctgcttc cctcctgctc atttggggct gccaccagct ctccaccctc ctggttccgc    2820
tggccgggcc aagagaggat ggagggatgg gagtcccagg agatccttgt aaatagtggg    2880
gtgggactgt tctgagtgat cacccgagca cttaaagctc cagagtccca ttcttcctgg    2940
atggagcagg tggaggtgca gagggattt cctcctctcc ttcctcctgt cgagaattaa     3000
cacctctcca cagccttccc ctccagaaca ccagccaggg aggggtgggg aaggaggtca    3060
```

```
cagccaagaa aactgccctg tgacgacttc cctccttccc gcctatgtga gccatcctga   3120
gatgtctgta caatagaaac caaaccaaat gggcaccctc ggttgccggg gggcaggtgg   3180
ggaggggggt gggaagaagg gatgtctgtc tgtcgtcccc ctccccctct ccactcttta   3240
cccacaaagg cagaagactg ttacactagg gggctcagca aattcaatcc caccccttacc  3300
aattgagcca aacctagaaa caaacacaaa acacgaatag tgagagacaa aatagaggag   3360
agaaagagag catgagaggg agcgagacag gcgaccaaca cagaggagag aaaacaaaaa   3420
tagcaaaaaa aaaaaaaaaa aagcagttct ttataattta atattctatt ttaataaagg   3480
cgtttattac catataaatg tagcaaagaa cctgggctaa tatgaaaaaa aaagactttt   3540
tattaggtaa tttattatat gaaaaggata ttttatttta tgataaagtg atccttaaaa   3600
aaataaaaaa actttagaag gtttagaata tatgtaggga gagaagaaga aaaaaataca   3660
tttgtattca gagttaaatc ttaaaaaaaa aaagtgtttt taatatatgt ttgggtttac   3720
gttgcttttt tcccccactt ttttttggg gaggaatgtc atttgctttt cttggggggag  3780
catcccgggg gtgaatggtg gagagaggag ctgggggaac ccggtccctc ctgggaccct   3840
tccagtagat tggatttcac tccatggact cctcctcccc tctcccccta cccctcaggg  3900
gagccggcag agccaaacaa agaaagggat taacaagaaa ggaagaagct gtaggactaa   3960
ggactgagga tcctgggtgt tcccccacca ctttcccctg ccctgtcgca ggggcaagtg   4020
aggaggggga atccagaatt aaggcctagc aggcctatag gaaccctcag agatgtgtga   4080
gatttaagag atctagattt ttttttaacc aaaaacaaga gagaaagaga agaaaaagag   4140
aaaccgaggg gtttaaaaga aagaatact acaaaataat aattattaat aataataatt   4200
caaatttatt tcatataatc ctagagagag aaagaaacaa ttactagtta cttagtagac   4260
aatattaaga tagcttaaag tttagtasca ttgagggccc ctgggtccag tagaatgtat   4320
aaaagttgta aggaaaagat aaatagagga gggaagtggc tgagtccacc ctgagttgcc   4380
caatcttcag ataccagggt tggatcaggt tgctagttta agattgggag cttccagtct   4440
gctgggttg attctgagaa tccttggatt tttaaattgt aggacaaaga aatgaggggt    4500
tcatttccca gggtcttgga aaggatgcac actgatcatc tcaataagac aggggctggg   4560
ttggggcag cagaggaggc caagcacatt cacctgcacc cctagtacct gggcagccca    4620
tactccaatg tggtatgtcc cctcctgggg ctcccagctc aaaccctccc atgcctgctt   4680
cccccaggcc taactgagga agtccttctt gaagtgtgac ctcggtccac ttctctacag   4740
attgatttaa gagcctggga agtcattcca caaacagaca cacatgcaca cacgcttctc   4800
accttcagag cttcaagagc actgaggcga tcagtcccct accccctgttc ccatccagct  4860
ttccacttag ctttgacctc catggcagca gtagcagtaa caatctcagt aattgttctt   4920
taaagctgac tcgttcttca cctacttgca aagtgctttc ttgtctcata aaagttagat   4980
tccaagaagg acttcccacg gagtggagtg gaaacactgt ccttgaaggc ctgggagaaa   5040
ggcatcccca tgggcacaga ggctgggaa aggcacaggg actttgggtg accctaaccc    5100
tgaccctctg ctccagttca cctccatcta tatgtgttca ggtaggggtc atctactgta   5160
ccctggcctg gaacacatt gccctcccca cacaaaactg gagggcttgg cttctgcgtg    5220
tgagaaatca acatttttaa agcacttgcc ttctaccaac cccagcttgc aatcactggg   5280
ccttcccctc ctatccaagg ggttggaggg gccccttggc tctccttttg gcaggaggag   5340
cctgcttcat tacaccaatg actctgccat cccctccct ggcccctagac cccaaacaca   5400
tctccctcta cccaatttac tcttctcgcc ccacctaggg acagattccc cctgctcttt   5460
```

-continued

```
ttgtcctaga aacccgcta gtttgggatg gtagcgtctg gggtggggag ggcttcccct    5520
tccccactcg agggtgcggg tggggaaggg ggggtgggtg gagacagccc tggggcaggg    5580
aggatggtct ctccactgta gaaagtagag taggattgtg gtcagactta atttgaggca    5640
tctagtgaag acacgtacaa atccaccaag gaaaagatt tcaaaagcaa aataaaagcg    5700
ggaaataaaa cagacccaag aataatcaag tcaaagtgat gttgcacaaa atgcagagaa    5760
accaagaagg gggagggtta atgtattaaa tgtgctatta agaacttaat tttattaaaa    5820
gtactattac ttaaaaaaaa aaaaaaaaaa aaaaaaawa arwagtcrta tcgaatcgat    5880
gt                                                                 5882
```

<210> SEQ ID NO 247
<211> LENGTH: 343
<212> TYPE: PRT
<213> ORGANISM: Homo sapiens

<400> SEQUENCE: 247

```
Met Val Thr Gly Arg Arg Glu Asp Val Ala Thr Ala Arg Arg Glu Ile
                 5                   10                  15

Ile Ser Ala Ala Glu His Phe Ser Met Ile Arg Ala Ser Arg Asn Lys
             20                  25                  30

Ser Gly Ala Ala Phe Gly Val Ala Pro Ala Leu Pro Gly Gln Val Thr
         35                  40                  45

Ile Arg Val Arg Val Pro Tyr Arg Val Gly Leu Val Val Gly Pro
     50                  55                  60

Lys Gly Ala Thr Ile Lys Arg Ile Gln Gln Gln Thr Asn Thr Tyr Ile
 65                  70                  75                  80

Ile Thr Pro Ser Arg Asp Arg Asp Pro Val Phe Glu Ile Thr Gly Ala
                 85                  90                  95

Pro Gly Asn Val Glu Arg Ala Arg Glu Glu Ile Glu Thr His Ile Ala
            100                 105                 110

Val Arg Thr Gly Lys Ile Leu Glu Tyr Asn Asn Glu Asn Asp Phe Leu
        115                 120                 125

Ala Gly Ser Pro Asp Ala Ala Ile Asp Ser Arg Tyr Ser Asp Ala Trp
    130                 135                 140

Arg Val His Gln Pro Gly Cys Lys Pro Leu Ser Thr Phe Arg Gln Asn
145                 150                 155                 160

Ser Leu Gly Cys Ile Gly Glu Cys Gly Val Asp Ser Gly Phe Glu Ala
                165                 170                 175

Pro Arg Leu Gly Glu Gln Gly Gly Asp Phe Gly Tyr Gly Tyr Leu
            180                 185                 190

Phe Pro Gly Tyr Gly Val Gly Lys Gln Asp Val Tyr Tyr Gly Val Ala
        195                 200                 205

Glu Thr Ser Pro Pro Leu Trp Ala Gly Gln Glu Asn Ala Thr Pro Thr
    210                 215                 220

Ser Val Leu Phe Ser Ser Ala Ser Ser Ser Ser Ser Ser Ala Lys
225                 230                 235                 240

Ala Arg Ala Gly Pro Pro Gly Ala His Arg Ser Pro Ala Thr Ser Ala
                245                 250                 255

Gly Pro Glu Leu Ala Gly Leu Pro Arg Arg Pro Gly Glu Pro Leu
            260                 265                 270

Gln Gly Phe Ser Lys Leu Gly Gly Gly Leu Arg Ser Pro Gly Gly
        275                 280                 285
```

```
Gly Arg Asp Cys Met Val Cys Phe Glu Ser Glu Val Thr Ala Ala Leu
            290                 295                 300

Val Pro Cys Gly His Asn Leu Phe Cys Met Glu Cys Ala Val Arg Ile
305                 310                 315                 320

Cys Glu Arg Thr Asp Pro Glu Cys Pro Val Cys His Ile Thr Ala Thr
                325                 330                 335

Gln Ala Ile Arg Ile Phe Ser
            340

<210> SEQ ID NO 248
<211> LENGTH: 343
<212> TYPE: PRT
<213> ORGANISM: Homo sapiens

<400> SEQUENCE: 248

Met Val Thr Gly Arg Arg Glu Asp Val Ala Thr Ala Arg Arg Glu Ile
1               5                   10                  15

Ile Ser Ala Ala Glu His Phe Ser Met Ile Arg Ala Ser Arg Asn Lys
            20                  25                  30

Ser Gly Ala Ala Phe Gly Val Ala Pro Ala Leu Pro Gly Gln Val Thr
        35                  40                  45

Ile Arg Val Arg Val Pro Tyr Arg Val Gly Leu Val Val Gly Pro
    50                  55                  60

Lys Gly Ala Thr Ile Lys Arg Ile Gln Gln Gln Thr Asn Thr Tyr Ile
65                  70                  75                  80

Ile Thr Pro Ser Arg Asp Arg Asp Pro Val Phe Glu Ile Thr Gly Ala
                85                  90                  95

Pro Gly Asn Val Glu Arg Ala Arg Glu Glu Ile Glu Thr His Ile Ala
            100                 105                 110

Val Arg Thr Gly Lys Ile Leu Glu Tyr Asn Asn Glu Asn Asp Phe Leu
        115                 120                 125

Ala Gly Ser Pro Asp Ala Ala Ile Asp Ser Arg Tyr Ser Asp Ala Trp
    130                 135                 140

Arg Val His Gln Pro Gly Cys Lys Pro Leu Ser Thr Phe Arg Gln Asn
145                 150                 155                 160

Ser Leu Gly Cys Ile Gly Glu Cys Gly Val Asp Ser Gly Phe Glu Ala
                165                 170                 175

Pro Arg Leu Gly Glu Gln Gly Gly Asp Phe Gly Tyr Gly Gly Tyr Leu
            180                 185                 190

Phe Pro Gly Tyr Gly Val Gly Lys Gln Asp Val Tyr Tyr Gly Val Ala
        195                 200                 205

Glu Thr Ser Pro Pro Leu Trp Ala Gly Gln Glu Asn Ala Thr Pro Thr
    210                 215                 220

Ser Val Leu Phe Ser Ser Ala Ser Ser Ser Ser Ser Ser Ala Lys
225                 230                 235                 240

Ala Arg Ala Gly Pro Gly Ala His Arg Ser Pro Ala Thr Ser Ala
                245                 250                 255

Gly Pro Glu Leu Ala Gly Leu Pro Arg Arg Pro Pro Gly Glu Pro Leu
            260                 265                 270

Gln Gly Phe Ser Lys Leu Gly Gly Gly Leu Arg Ser Pro Gly Gly
        275                 280                 285

Gly Arg Asp Cys Met Val Cys Phe Glu Ser Glu Val Thr Ala Ala Leu
    290                 295                 300

Val Pro Cys Gly His Asn Leu Phe Cys Met Glu Cys Ala Val Arg Ile
305                 310                 315                 320
```

```
Cys Glu Arg Thr Asp Pro Glu Cys Pro Val Cys His Ile Thr Ala Thr
                325                 330                 335

Gln Ala Ile Arg Ile Phe Ser
            340
```

<210> SEQ ID NO 249
<211> LENGTH: 343
<212> TYPE: PRT
<213> ORGANISM: Homo sapiens
<220> FEATURE:
<221> NAME/KEY: variant
<222> LOCATION: 287
<223> OTHER INFORMATION: Xaa = Any amino acid

<400> SEQUENCE: 249

```
Met Val Thr Gly Arg Arg Glu Asp Val Ala Thr Ala Arg Arg Glu Ile
                  5                  10                  15

Ile Ser Ala Ala Glu His Phe Ser Met Ile Arg Ala Ser Arg Asn Lys
             20                  25                  30

Ser Gly Ala Ala Phe Gly Val Ala Pro Ala Leu Pro Gly Gln Val Thr
         35                  40                  45

Ile Arg Val Arg Val Pro Tyr Arg Val Val Gly Leu Val Val Gly Pro
     50                  55                  60

Lys Gly Ala Thr Ile Lys Arg Ile Gln Gln Thr Asn Thr Tyr Ile
 65                  70                  75                  80

Ile Thr Pro Ser Arg Asp Arg Asp Pro Val Phe Glu Ile Thr Gly Ala
                 85                  90                  95

Pro Gly Asn Val Glu Arg Ala Arg Glu Glu Ile Glu Thr His Ile Ala
            100                 105                 110

Val Arg Thr Gly Lys Ile Leu Glu Tyr Asn Asn Glu Asn Asp Phe Leu
        115                 120                 125

Ala Gly Ser Pro Asp Ala Ala Ile Asp Ser Arg Tyr Ser Asp Ala Trp
    130                 135                 140

Arg Val His Gln Pro Gly Cys Lys Pro Leu Ser Thr Phe Arg Gln Asn
145                 150                 155                 160

Ser Leu Gly Cys Ile Gly Glu Cys Gly Val Asp Ser Gly Phe Glu Ala
                165                 170                 175

Pro Arg Leu Gly Glu Gln Gly Gly Asp Phe Gly Tyr Gly Gly Tyr Leu
            180                 185                 190

Phe Pro Gly Tyr Gly Val Gly Lys Gln Asp Val Tyr Tyr Gly Val Ala
        195                 200                 205

Glu Thr Ser Pro Pro Leu Trp Ala Gly Gln Glu Asn Ala Thr Pro Thr
    210                 215                 220

Ser Val Leu Phe Ser Ser Ala Ser Ser Ser Ser Ser Ser Ala Lys
225                 230                 235                 240

Ala Arg Ala Gly Pro Pro Gly Ala His Arg Ser Pro Ala Thr Ser Ala
                245                 250                 255

Gly Pro Glu Leu Ala Gly Leu Pro Arg Arg Pro Pro Gly Glu Pro Leu
            260                 265                 270

Gln Gly Phe Ser Lys Leu Gly Gly Gly Leu Arg Ser Pro Xaa Gly
        275                 280                 285

Gly Arg Asp Cys Met Val Cys Phe Glu Ser Glu Val Thr Ala Ala Leu
    290                 295                 300

Val Pro Cys Gly His Asn Leu Phe Cys Met Glu Cys Ala Val Arg Ile
305                 310                 315                 320
```

-continued

Cys Glu Arg Thr Asp Pro Glu Cys Pro Val Cys His Ile Thr Ala Thr
            325                 330                 335

Gln Ala Ile Arg Ile Phe Ser
            340

<210> SEQ ID NO 250
<211> LENGTH: 7993
<212> TYPE: DNA
<213> ORGANISM: Homo sapiens

<400> SEQUENCE: 250

| | | | | | |
|---|---|---|---|---|---|
| aaaaatgttt | tcctttatat | ttctgaggtg | aaattcttcc | ataggcattt | caggaggttt | 60 |
| tttgtcaaac | attttaaaag | caaaattgat | accatgtttc | tataaaatac | gatatgcgaa | 120 |
| atgatgccta | ttgctatttg | ctactgggct | ggaagttagg | aaatagtgac | ggaaaaaccc | 180 |
| caaatgcata | cagagatcat | gagtacagcc | agtgatgcca | gtgatgtatt | acgaagatta | 240 |
| caaaaaggc | cacaaaagtt | caatgctaat | cccttctggg | tcgaacacag | agtgacacat | 300 |
| tcggcagaca | attatatttt | acttatgtaa | cgaataagtc | atattttct | gtactgggca | 360 |
| tttttagagg | aacatataaa | gaatggata | gtgtcttagg | ggtctcattt | tctaatttag | 420 |
| aaatgttttc | actcccatgt | gaaagatttt | gctaatatat | aacagacaat | ctaacttggg | 480 |
| gcatcctatt | aaaataatct | attttccata | acttcaacct | ttttaaaaaa | taagtcagt | 540 |
| gggaatttct | aatttccctg | tgggttttat | ctatatgcat | tttttaggtt | tttttttcc | 600 |
| ttatcatata | ccttccagat | tttatgttta | aataaataaa | tgatatttca | agataaagtt | 660 |
| agtctataaa | gggacactaa | atcagcctac | agatgtcaat | ctctaggttt | aactacagag | 720 |
| atagttccac | ataaatgcca | aaagaagtg | gttttgatgt | caatctttat | gaaaatggtt | 780 |
| ttatttaacc | attgtatcaa | gtctaactat | acttgggcag | atttgagctt | taaaaataaa | 840 |
| gctatgtatt | tcgttttaa | aaatgtgctt | ctctgtttct | tcatttactt | acaactgtgg | 900 |
| aacagaatca | cgagtttgtg | gacgaacaag | tctttgaaga | aagctgcatg | gaagttgcaa | 960 |
| ctgttaatcg | tccttcaagt | cacagtcctt | cactgtcttc | acaacaagga | gtcaccagca | 1020 |
| cctgctgttc | acgacgacac | aaaaaaactt | ttcgcatccc | aaatgccaat | gtatcaggaa | 1080 |
| gccatcaagg | tagtatacaa | gaactcagca | cgattcagat | cagatgtgtg | gagagaacac | 1140 |
| ctctgtctaa | caggtacctg | agattaatct | gtgttgtcta | cacacctgtg | ctggttccca | 1200 |
| gggtgtgtct | tctgcactca | tgttgtcact | tacatggcat | ctaaatccct | agctcctatg | 1260 |
| gttcaggaag | agacaaaaat | ggtagcgtaa | caagtaggaa | aatggttctg | cttgcatatc | 1320 |
| cattaagggt | taaaaatagt | ggttatatca | gtattaaaag | agtcgaaaga | agaagagatg | 1380 |
| attgagtgca | cacaaatgtg | tttttctctc | ttctgttcca | caacctttc | ttatttgggc | 1440 |
| aaggactttt | atactcagga | gtctcttata | tattcaatag | tctgaaatga | tggtggacac | 1500 |
| tactaaaaga | gtcaaatgaa | attgagatca | acatggctaa | aaattattga | acagcatgta | 1560 |
| aaaatataca | aacacactgt | ctgtaacagt | aaaaatgaaa | actttgccta | cataagtcat | 1620 |
| ttctatcaat | atataatttt | gatcagaaag | gtatttttgg | ccatatcaaa | cacaaaatca | 1680 |
| acataataca | aaaataagt | gaagtactaa | aattgtttgc | ctctggttag | tttatgaaca | 1740 |
| aattaagtaa | aacttccata | ttgatatatt | tcctttgctt | ttccttattc | actgttttta | 1800 |
| ccacaaatgt | gtaaaaataa | aaagttgtac | atttaaacaa | tatatgtcat | taaaaatcag | 1860 |
| tttctgccaa | aataattta | ttctgttttc | aaattgaaca | gcatatattg | ttagagtgag | 1920 |
| agtctgtaaa | ttcagtcctc | ttctttgttg | gcattcagaa | gtctttgttg | aaatctggat | 1980 |

-continued

```
gagattctga attcaggtga tgttgattta cataaattgg atgtctctgg gactagaaaa    2040
ttaaaattag gagccataag acttctatct tcaagatatt ttagctttgc agttttatat    2100
cctttataaa gtgaagtcga caatggaaaa ttatctagca agaaaatctt aggacataaa    2160
catcttaatt atgttttcca tgaaaataaa ataatcagtt tcaagcttct gtgtatatcc    2220
ttctctctca tttcccttt atcccccttcc ccacatagag tatacaattc atccaataat    2280
accatttggg agcttgaagt gttagatagt aatagataat tttttatt ctgtaatatg    2340 tgatcatcat taagttcaga ggtttgaggg cattatatat cccaaaaaga catgaaaata    2400
aaaatattct gtggtcaaag gaattaagaa atcaatgtga tatggctctt tcatagtggt    2460
ttctcaaacc tctcagaggt ctgtcttaaa taaaacttct ttgctcagcc caggctgtcc    2520
aaatcttact tgaagctctt tcttcttac atttttttat aatacattta gtttgataaa    2580
tacttgatgg aaccaagtca aactgtcttt tagaaattta tttaatgtta attactatgt    2640
tcatctttaa catagattaa gatttggtgt ttcatatttt taattataat aactttcctt    2700
agacaattaa aatatttta taagcattac aacacatatt cttcagttgt atgaaaaaca    2760
ttttaagtaa acaacttact ttcctaaata tttttttttc tatcagccga tccagtttaa    2820
atgccaaaat ggaagagtgt gttaaactaa actgtgaaca accttatgtg actacagcaa    2880
taataagcat cccaacacct ccagtaacca caccagaagg agacgatagg ccagaatccc    2940
ctgagtactc aggaggaaat attgtcagag tttctgcttt gtaagacaat tggaataagg    3000
tctaagagaa ttcgagccct ggctgtgaaa agaatctcaa catagaagaa agaagaaaca    3060
ataaatattc tgcagattaa tgcagcaaag aaagaaggtt ggtagtgaaa cacaaagctt    3120
ccaatcttaa ggatgtgaat aaaaccacca atggcatttt ctagacagtt tgacctgtta    3180
tacagagtaa tattctgtgg cccttttgact ttgtgaatga gcacaatgaa atgccgccta    3240
ctgatgcttc ttatgatcag aactcttttt taataaaata aataacataa atcgttgaac    3300
ataatgttcc agttgaatgc aaaacaaaaa aaatatggaa aacattttga taaaattttt    3360
tcctgttaaa accatgaaca ttggctatga tgaagattat tacatatgaa aaaaaaactc    3420
acacaacata tttgtattga ctgaaggaaa ccatcataat gcatgctaga attctttgaa    3480
gcagtgatct cagtttcctt atgttgtctt cagaataggc atgataaact ataattgtag    3540
aaaggggtaa tttctgtgca cttacaacaa gctgagtgtt catgttccat ggtgggctgt    3600
gcaaataaac tcctttaga cctgcagtat ttctcatggg gatgctcatt agtaaatcta    3660
aagtgttcag atagttcagt attcattatc gtttaacttt gcacctagat actgttacaa    3720
ctgcaataat ttgttgtaca actgttgtat caggaatcag gatttttttg ttgttgtact    3780
ttccagatcc ttatagatac ggtaagagcc acattcgtag aaaaacttct ggtgtggcca    3840
ggttttaggt aacttttaa tccaaaacta ttgtgccata atgttttc agtaatattt    3900 tttggtccac tgtattcctg tgacacagtg cattatctgt tcttgtattt ctatagcacc    3960
tctctattgg gttatcatc atcaacaaga ctactgttta ctgtagttca agtgactttc    4020
ctacttttgt atttccaaaa aaaattatct tgtaagtagc ttgtcatcaa tcccttgtc    4080 gaaaactaga aaaaaggag ttgacccata taaattatct ctaacgtctt tgttgtttat    4140
ggaaaagccc agatactgga tatatcacta tgtatttat gaacagaatt gactgggact    4200
aatatcacag gatcaatcat ctcagaatct tacttgatgc attatttatt ttgctttaga    4260
tcttgaatac attttgagaa taactaatgt ggattgaaat gtagagatac actggagtgc    4320
```

```
tttatttagc aatatttgat gaaagcatgc tttctacgcc attcaggaag gcagcacaaa    4380
tttatctcag aaaggttcct gtgtattgca aggtacaatt ttctccaata aatcaggaga    4440
acaggagttt gatgatgcaa agttgatctc tgtacattta agtgaaaagt ctttataact    4500
tttcacccct aaaatatttc agcagacatg tctgcacatg acagtgtaaa aaagtttaat    4560
gtcaaatgca aagttttat tcattccaag ccaccactgt aaggaataaa gcttagcttc     4620
tgtacatgga aagagctaat aattatccct ctgtcagaga tgagattttt aaatgcttat    4680
gatatttaat cataaaaagg gattaatcca accattttct agtaaagcca gaaattcttg    4740
cttcccattt ctagaatagt ttctagaaca gtgctatgca catattagat cttaataaac    4800
atttgctgag tgaaagtaag ataaactcaa ctatctcttg ggaagaactg gcttcattcc    4860
tagtacatct tttaaaaagt tactaatttt ccagcagtac aaatattaac aattatatta    4920
acacctgcct catgtcagtt tatgcttcta gagcaatgtc tagtgaaact tatctgatgg    4980
catttattga aaaccttcta aaagtagac taaggaaacc ataatcagaa ttactatgtc     5040
ttttgattcc caatgagaag ttctattttc atgttcttaa tattacatac aagaaaatgc    5100
agttaggtta tttcaattga caattctgcc tcctcttttg atttatcact acccaaaat     5160 tattaattt attaggcttt tggaaaagaa aaaaactttt ttgatgtttt aggtgattta     5220
aaaatatacc gtgttggtgg tgaatgacta ttgatgactg tgttaagtgc atctgtattg    5280
taagtgaaat gtaattattt ctgtgtacca tatggagtaa ctaaggtcat tgttttgac     5340 aattttgttt gaaattcata tatcttattt caaaggatag cataatatct gcattatgct    5400 ggaaaaaat agacctttgg agaatactta aataaaacat gtgcatgctt gaacaggaca     5460
aaatgttgac tgttgcccta ttttcttaga tttcattcct ttcccaaaat taggatatgc    5520
cacactcata atacacatgt tggaggacct tgtgagacat acaactcaaa ggacacagca    5580
attgaaagta atgcttaaat ctcatctgaa tgggtggaga cagtagcttt tgctagtaat    5640
gggaattaag gcagggactt taacagaaaa gatagtatca attaaggaaa gccagtccct    5700 gaacctata tacttcttaa acaccactac ttgcattaag cagagaagct caggggtaat    5760
ggttttggtc agaacttaaa taaattctta atcaaaggct ttattctacc taggaaagcg    5820
gggtgattta tttgcctagc catttgtgtg catgtatgtg tatatgtaga tataaatttg    5880
ttcatacaca tatacataga ttttcattca ttttaatat gcaaccacta atggtttctc     5940
ttaatatctt gaaagggcta aaaagcaaga aaatgttaag agtttataga agaaggaaaa    6000
agacacaaag gaaattattt agtagaaaga ctgattttaa ctggtgatat atatggtcct    6060
cttggtggat agtctctatc ttttcttgtt aattattttc atttatagcc tttgatttat    6120
taggtatcaa tcttgcatta aaaagttcaa tatgcctccc tattccttca acttagtcac    6180
aatgttggct tagaaatagc ctcttgggag ctataatgtg tctgccagta acattgctca    6240
aaagaataaa aaagggttct tgaaagtaaa ttgataactc cttagagttt cataagaaag    6300
gcatcttctc ttccctacag tgtcattaag gtgtttgttt tattaactca ctggtacaag    6360
aatggttatt actctgcact gtgtaaacat ctgaattttc aacacaattg tgtaggcaca    6420 cagtatttt ttaatgaagg tttaaattgt acctacgaag gtttaagtct tatctacttc     6480
agctggttgt attaggatac taaaatattc tttacagagt ttgattttt acttctaagg     6540 aattactagc tttgaacagc aagtttgctt aagataatta taaaatataa ttttacaaaa    6600
tatttttagt tgaaaataat attaaataca tagcatacct ttaatctttc tctttactgc    6660
ctgccctgcc ttttttctcc tttatcttca agcattaatt attattgtag cagatctttg    6720
```

```
cctttcccta attactttt tctctagctt ttctatggaa atcctttagg ttacataact      6780
aatattcatt ctacatataa tccagtttat taaatacaga tgatgggcca gacatggtga      6840
tagagaaata cagattaaga aaccagatca aatcctttt aaggaattat ctagtggaaa       6900
atatctcaac tctcttcttt acactactat tcattatctt acacttcaaa tcttcacctt      6960
tccattttga cagtcgctct tctacttcag tctcctgaag acatctctcc aacgaagtt       7020 acataaaaat actaatcttc aaggtgcttt ctaaaatatt ttcatcacgt cattaaaatc      7080
ttctttcact aggcaatggt tctgtctcta tgggggctgg caggcagggc aaatgaattc      7140
ctacctgccc agagaaagaa caggaaacaa taaaggtaaa acaaaaccca aggaagaag       7200 agcttcatgt ttatgcatta cattaaagtt aaaaggaaat aaactttctc aagtatccac      7260 tctaccttt caactataat ttcagagaat gtgaagaaag ctattaaaat agttttgcag       7320
gaggactgat acacaatgcg tctgtgaatc tgaacaccac acctcaaatt ctattatctg      7380
atgaatccta ttgaaatatc tgagtaattg ggacaacaga aaggtaagtc tgtaatcagg      7440
ggcactcacc aataaggcgg gcctagttgg ttcatgtcaa ttccaaagca agaggatggt      7500
tgaagaaggg tattgaatga gtagataaca aatatttgga gagagatttg gaggaaccct      7560
ggaagacaag agtaggctat tggcaagggc tacaagatgg tagagacatc cttgggcttt      7620
gactctaatt gaaaatacag aattttggcc tgacgcagtg actcatgcct gtaatcctag      7680
cactttggga ggctgagggg ggtggatcac ttgaggtcag gagtccaaga ccagcctcat      7740
caactggtga acccccatct ctactaaaaa agaaaaaaa aaaatagcc aggtgtcctg        7800 gtgcatgcct gtaatctcag ctactcagga gtctgaggca ggagaattgc ttgaactcgg      7860
gaggtggagg ttgcaatgag ctgagattgt gccactgcat tccagcctgg gtgacagggg     7920
gagactccgt cttaaaaaaa gaaaaagaa aaaccagaat tttaaagttc aatttagatc       7980
aaattaattc ctt                                                         7993

<210> SEQ ID NO 251
<211> LENGTH: 3254
<212> TYPE: DNA
<213> ORGANISM: Homo sapiens

<400> SEQUENCE: 251
ggtatggtga catggtgcca aaaccatag cagggaagat ttttggttct atctgttcgc        60
tgagtggggt cttggtcatt gctctacctg ttccggtgat tgtatccaac ttcagtcgca      120
tctaccacca gaatcaacga gcagacaaac gaagggcaca aagaaagct agactggcca      180 ggatccgggc agccaaaagc ggaagcgcaa atgcttacat gcagagcaaa cggaatggtt       240
tactcagtaa tcagctgcag tcctcagagg atgagcaggc ttttgttagc aaatccggct       300
ccagctttga aacccagcac caccacctgc ttcactgcct ggaaaaaaacc acgaatcacg      360 agtttgtgga cgaacaagtc tttgaagaaa gctgcatgga agttgcaact gttaatcgtc      420
cttcaagtca cagtccttca ctgtcttcac aacaaggagt caccagcacc tgctgttcac      480
gacgacacaa aaaaactttt cgcatcccaa atgccaatgt atcaggaagc catcaaggta      540
gtatacaaga actcagcacg attcagatca gatgtgtgga gagaacacct ctgtctaaca      600
gccgatccag tttaaatgcc aaaatggaag agtgtgttaa actaaactgt gaacaacctt      660
atgtgactac agcaataata agcatcccaa cacctccagt aaccacacca gaaggagacg      720
ataggccaga atcccctgag tactcaggag gaaatattgt cagagtttct gctttgtaag      780
```

```
acaattggaa taaggtctaa gagaattcga gccctggctg tgaaaagaat ctcaacatag    840
aagaaagaag aaacaataaa tattctgcag attaatgcag caaagaaaga aggttggtag    900
tgaaacacaa agcttccaat cttaaggatg tgaataaaac caccaaatgg catttctaga    960
cagtttgacc tgttatacag agtaatattc tgtggccctt tgactttgtg aatgagcaca   1020
atgaaatgcc gcctactgat gcttcttatg atcagaactc ttttttaata aaataaataa   1080
cataaatcgt tgaacataat gttccagttg aatgcaaaac aaaaaaaata tggaaaacat   1140
tttgataaaa ttttttcctg ttaaaaccat gaacattggc tatgatgaag attattacat   1200
atgaaaaaaa aactcacaca acatatttgt attgactgaa ggaaaccatc ataatgcatg   1260
ctagaattct ttgaagcagt gatctcagtt tccttatgtt gtcttcagaa taggcatgat   1320
aaactataat tgtagaaagg ggtaatttct gtgcacttac aacaagctga gtgttcatgt   1380
tccatggtgg gctgtgcaaa taaactcctt ttagacctgc agtatttctc atggggatgc   1440
tcattagtaa atctaaagtg ttcagatagt tcagtattca ttatcgttta actttgcacc   1500
tagatactgt tacaactgca ataatttgtt gtacaactgt tgtatcagga atcaggattt   1560
ttttgttgtt gtactttcca gatccttata gatacggtaa gagccacatt cgtagaaaaa   1620
cttctggtgt ggccaggttt taggtaactt tttaatccaa aactattgtg ccataaatgt   1680
ttttcagtaa tattttttgg tccactgtat tcctgtgaca cagtgcatta tctgttcttg   1740
tatttctata gcacctctct attgggttta tcatcatcaa caagactact gtttactgta   1800
gttcaagtga ctttcctact tttgtatttc caaaaaaaat tatcttgtaa gtagcttgtc   1860
atcaatcccc ttgtcgaaaa ctagaaaaaa aggagttgac ccatataaat tatctctaac   1920
gtctttgttg tttatggaaa agcccagata ctggatatat cactatgtat tttatgaaca   1980
gaattgactg ggactaatat cacaggatca atcatctcag aatcttactt gatgcattat   2040
ttattttgct ttagatcttg aatacatttt gagaataact aatgtggatt gaaatgtaga   2100
gatacactgg agtgctttat ttagcaatat ttgatgaaag catgctttct acgccattca   2160
ggaaggcagc acaaatttat ctcagaaagg ttcctgtgta ttgcaaggta caatttctc    2220 caataaatca ggagaacagg agtttgatga tgcaaagttg atctctgtac atttaagtga   2280
aaagtcttta taacttttca cccttaaaat atttcagcag acatgtctgc acatgacagt   2340 gtaaaaagt  ttaatgtcaa atgcaaagtt tttattcatt ccaagccacc actgtaagga   2400
ataaagctta gcttctgtac atggaaagag ctaataatta ccctctgtc agagatgaga    2460 tttttaaatg cttatgatat ttaatcataa aaagggatta atccaaccat tttctagtaa   2520
agccagaaat tcttgcttcc catttctaga atagtttcta gaacagtgct atgcacatat   2580
tagatcttaa taaacatttg ctgagtgaaa gtaagataaa ctcaactatc tcttgggaag   2640
aactggcttc attcctagta catctttta  aaagttacta attttccagc agtacaaata   2700
ttaacaatta tattaacacc tgcctcatgt cagtttatgc ttctagagca atgtctagtg   2760
aaacttatct gatggcattt attgaaaacc ttctaaaaag tagactaagg aaaccataat   2820
cagaattact atgtcttttg attcccaatg agaagttcta ttttcatgtt cttaatatta   2880
catacaagaa aatgcagtta ggttatttca attgacaatt ctgcctcctc ttttgattta   2940
tcacttaccc aaaattatta attttattag gcttttggaa aagaaaaaaa acttttttgat   3000 gttttaggtg atttaaaaat ataccgtgtt ggtggtgaat gactattgat gactgtgtta   3060
agtgcatctg tattgtaagt gaaatgtaat tatttctgtg taccatatgg agtaactaag   3120
gtcattgttt ttgacaattt tgtttgaaat tcatatatct tatttcaaag gatagcataa   3180
```

| | |
|---|---:|
| tatctgcatt atgctggaaa aaaatagacc tttggagaat acttaaataa aacatgtgca | 3240 |
| tgcttgaaca ggac | 3254 |

<210> SEQ ID NO 252
<211> LENGTH: 5333
<212> TYPE: DNA
<213> ORGANISM: Homo sapiens

<400> SEQUENCE: 252

| | |
|---|---:|
| cggctgctcg cgagctgctt tctctcctct tcccttccg ggtgcacggc gaggagaaag | 60 |
| tctctatgca actaagcccc ggcgcgcact tggccaggta tgtaccgcgg gagcggcgcg | 120 |
| ttctgcgcgg aagcagatgc tgctgccgcc acggcggcgg cggctgccag ctcctgagct | 180 |
| ctgtaactgt cacactgcac ctgagctgaa cttgaaaaga gagtgaaggg gcgattgggc | 240 |
| gaacgctttt ggcagacaca gagggtgttt gtagacgtgg gggaggagaa tctctattaa | 300 |
| cgcccccac cgtaaccact gcacatcacc tccatctctg caaatacagc ccgaggagta | 360 |
| gaggcagcag cagctggacc cccaaagaga gacgtgggc agcggctgtg accgcatctc | 420 |
| ctgagctaca acaacaggtc gccttttttga gactcctttg gcgggaaggg ctacttggaa | 480 |
| aggaaggttt gaaagagtga aagggtagg tgtaagggtt ccctaattcg tcgaaagaat | 540 |
| tctattgggt gactctcgtt cgtcttctct atcctacact ccacatactg accctatatt | 600 |
| atccagactg tgccggggag aaatcaaaaa cacctgtttg aagaaacggc tgcacctgtg | 660 |
| tgcttatttg tgccagaggg tggcctagcc cacctgcagg aagagatttg gctgggttct | 720 |
| gttgagggtg attgttagga cgttgtattt tgttgccatt attccaaata cctgtcttgg | 780 |
| agggaaagtt gcccttctga gaactgtgac tttaccagga gccctatctt ggaataagag | 840 |
| ttacacctct ggaccacgtt tctcactagt actttgcttg actggaggaa gtgggtgact | 900 |
| tttggctgct tcggtgaccc attgtagacg cctcgttacc cttcttcctt ccgcttcaag | 960 |
| taatcatggc ggcgggggtg gcagcgtggc tgccttttgc aagggcagcg gctatcgggt | 1020 |
| ggatgcctgt ggcctcgggg cctatgccgg ctccccgag gcaggagagg aaaaggaccc | 1080 |
| aagatgctct cattgtgctg aatgtgagtg gcacccgctt ccagacgtgg caggacaccc | 1140 |
| tggaacgtta cccagacact ctactgggca gttctgagag ggacttttc taccacccag | 1200 |
| aaactcagca gtatttcttt gaccgtgacc cagacatctt ccgccacatc ctgaatttct | 1260 |
| accgcactgg gaagctccac tatcctcgcc acgagtgcat ctctgcttac gatgaagaac | 1320 |
| tggccttctt tggcctcatc ccggaaatca tcggcgactg ctgttatgag gagtacaagg | 1380 |
| atcgcaggcg agagaacgcc gagcgcctgc aggacgacgc ggataccgac accgctgggg | 1440 |
| agagcgcctt gcccaccatg actgcaaggc agagggtctg gagggccttc gagaaccccc | 1500 |
| acaccagcac gatggccctg tgttctact atgtcacggg gttttcatt gccgtctctg | 1560 |
| tcatcgcgaa tgtggtggaa acagtgccgt gcggatcaag cccaggtcac attaaagaac | 1620 |
| tgccctgtgg agagcggtat gctgtggcct tcttctgctt ggacacggcc tgcgtcatga | 1680 |
| tcttcacagt tgagtatttg cttcgcctgg ctgcagcgcc tagtcgttac cgttttgtgc | 1740 |
| gtagtgtcat gagtatcatc gacgtggtgg ccatcctgcc ttattacatt gggctggtga | 1800 |
| tgacagacaa tgaggacgtc agcggagcct tgtcacact ccgagtcttc cgggtcttca | 1860 |
| ggatctttaa gttttcccgc cactctcaag gcctgcgcat cctggggtac acactgaaga | 1920 |
| gttgtgcctc agaattgggc ttcttgcttt tctcgctcac catggctatc atcatcttcg | 1980 |

```
ctacagttat gttctacgca gagaaggggt cttcggctag caagttcacc agcatccctg    2040
cagccttctg gtataccatc gtcaccatga caacactagg gtatggtgac atggtgccaa    2100
aaaccatagc agggaagatt tttggttcta tctgttcgct gagtgggatc ttggtcattg    2160
ctctacctgt tccggtgatt gtatccaact tcagtcgcat ctaccaccag aatcaacgag    2220
cagacaaacg aagggcacaa agaaagcta gactggccag gatccgggca gccaaaagcg     2280
gaagcgcaaa tgcttacatg cagagcaaac ggaatggttt actcagtaat cagctgcagt    2340
cctcagagga tgagcaggct tttgttagca atccggctc cagctttgaa acccagcacc     2400
accacctgct tcactgcctg gaaaaaacca cgaatcacga gtttgtggac gaacaagtct    2460
ttgaagaaag ctgcatggaa gttgcaactg ttaatcgtcc ttcaagtcac agtccttcac    2520
tgtcttcaca acaaggagtc accagcacct gctgttcacg acgacacaaa aaacttttc    2580 gcatcccaaa tgccaatgta tcaggaagcc atcaaggtag tatacaagaa ctcagcacga    2640
ttcagatcag atgtgtggag agaacacctc tgtctaacag ccgatccagt ttaaatgcca    2700
aaatggaaga gtgtgttaaa ctaaactgtg aacaaccttta tgtgactaca gcaataataa    2760
gcatcccaac acctccagta accacaccag aaggagacga taggccagaa tcccctgagt    2820
actcaggagg aaatattgtc agagtttctg ctttgtaaga caattggaat aaggtctaag    2880
agaattcgag ccctggctgt gaaaagaatc tcaacataga agaagaaga aacaataaat    2940 attctgcaga ttaatgcagc aaagaaagaa ggttggtagt gaaacacaaa gcttccaatc    3000
ttaaggatgt gaataaaacc accaaatggc atttctagac agtttgacct gttatacaga    3060
gtaatattct gtggcccttt gactttgtga atgagcacaa tgaaatgccg cctactgatg    3120
cttcttatga tcagaactct tttttaataa aataaataac ataaatcgtt gaacataatg    3180
ttccagttga atgcaaaaca aaaaaaatat ggaaaacatt ttgataaaat tttttcctgt    3240
taaaaccatg aacattggct atgatgaaga ttattacata tgaaaaaaaa actcacacaa    3300
catatttgta ttgactgaag gaaaccatca taatgcatgc tagaattctt tgaagcagtg    3360
atctcagttt ccttatgttg tcttcagaat aggcatgata aactataatt gtagaaaggg    3420
gtaatttctg tgcacttaca acaagctgag tgttcatgtt ccatggtggg ctgtgcaaat    3480
aaactccttt tagacctgca gtatttctca tggggatgct cattagtaaa tctaaagtgt    3540
tcagatagtt cagtattcat tatcgtttaa ctttgcacct agatactgtt acaactgcaa    3600
taatttgttg tacaactgtt gtatcaggaa tcaggatttt tttgttgttg tactttccag    3660
atccttatag atacggtaag agccacattc gtagaaaaac ttctggtgtg gccaggtttt    3720
aggtaacttt ttaatccaaa actattgtgc cataaatgtt tttcagtaat atttttttggt    3780 ccactgtatt cctgtgacac agtgcattat ctgttcttgt atttctatag caccctctcta   3840 ttgggtttat catcatcaac aagactactg tttactgtag ttcaagtgac tttcctactt    3900
ttgtatttcc aaaaaaaatt atcttgtaag tagcttgtca tcaatcccct tgtcgaaaac    3960
tagaaaaaaa ggagttgacc catataaatt atctctaacg tctttgttgt ttatggaaaa    4020
gcccagatac tggatatatc actatgtatt ttatgaacag aattgactgg gactaatatc    4080
acaggatcaa tcatctcaga atcttacttg atgcattatt tattttgctt tagatcttga    4140
atacattttg agaataacta atgtggattg aaatgtagag atacactgga gtgctttatt    4200
tagcaatatt tgatgaaagc atgctttcta cgccattcag gaaggcagca caaatttatc    4260
tcagaaaggt tcctgtgtat tgcaaggtac aattttctcc aataaatcag gagaacagga    4320
gtttgatgat gcaaagttga tctctgtaca tttaagtgaa aagtctttat aacttttcac    4380
```

-continued

```
ccttaaaata tttcagcaga catgtctgca catgacagtg taaaaaagtt taatgtcaaa      4440
tgcaaagttt ttattcattc caagccacca ctgtaaggaa taaagcttag cttctgtaca      4500
tggaaagagc taataattat ccctctgtca gagatgagat ttttaaatgc ttatgatatt      4560
taatcataaa aagggattaa tccaaccatt ttcaagtaaa gccagaaatt cttgcttccc      4620
atttctagaa tagtttctag aacagtgcta tgcacatatt agatcttaat aaacatttgc      4680
tgagtgaaag taagataaac tcaactatct cttgggaaga actggcttca ttcctagtac      4740
atcttttaaa aagttactaa ttttccagca gtacaaatat taacaattat attaacacct      4800
gcctcatgtc agtttatgct tctagagcaa tgtctagtga aacttatctg atggcattta      4860
ttgaaaacct tctaaaaagt agactaagga aaccataatc agaattacta tgtcttttga      4920
ttcccaatga gaagttctat tttcatgttc ttaatattac atacaagaaa atgcagttag      4980
gttatttcaa ttgacaattc tgcctcctct tttgatttat cacttaccca aaattattaa      5040
ttttattagg cttttggaaa agaaaaaaaa cttttttgatg ttttaggtga tttaaaaata     5100
taccgtgttg gtggtgaatg actattgatg actgtgttaa gtgcatctgt attgtaagtg      5160
aaatgtaatt atttctgtgt accatatgga gtaactaagg tcattgtttt tgacaatttt      5220
gtttgaaatt catatatctt atttcaaagg atagcataat atctgcatta tgctggaaaa      5280
aaatagacct ttggagaata cttaaataaa acatgtgcat gcttgaacag gac             5333

<210> SEQ ID NO 253
<211> LENGTH: 2351
<212> TYPE: DNA
<213> ORGANISM: Homo sapiens

<400> SEQUENCE: 253
gaattctatt gggtgactct cgttcgtctt ctctatccta cactccacat actgacccta       60
tattatccag actgtgccgg ggagaaatca aaaacacctg tttgaagaaa cggctgcacc      120
tgtgtgctta tttgtgccag agggtggcct agcccacctg caggaagaga tttggctggg      180
ttctgttgag ggtgattgtt aggacgttgt attttgttgc cattattcca aatacctgtc      240
ttggagggaa agttgcccct ctgagaactg tgactttacc aggagcccta tcttggaata      300
agagttacac ctctgaccaa cgtttctcac tagtactttg cttgactgga ggaagtgggt      360
gacttttggc tgcttcggtg acccattgta gacgcctcgt tacccttctt ccttccgctt      420
caagtaatca tggcggcggg ggtggcagcg tggctgcctt ttgcaagggc agcggctatc      480
gggtggatgc ctgtggcctc ggggcctatg ccggctcccc cgaggcagga gaggaaaagg      540
acccaagatg ctctcattgt gctgaatgtg agtggcaccc gcttccagac gtggcaggac      600
accctggaac gttacccaga cactctactg gcagttctg agagggactt tttctaccac      660
ccagaaactc agcagtattt cttttgaccgt gacccagaca tcttccgcca catcctgaat      720
ttctaccgca ctgggaagct ccactatcct cgccacgagt gcatctctgc ttacgatgaa      780
gaactggcct tctttggcct catcccggaa atcatcggcg actgctgtta tgaggagtac      840
aaggatcgca ggcgagagaa cgccgagcgc ctgcaggacg acgcggatac cgacaccgct      900
ggggagagcg ccttgcccac catgactgca aggcagaggg tctggagggc cttcgagaac      960
ccccacacca gcacgatggc cctggtgttc tactatgtca cggggttttt cattgccgtc     1020
tctgtcatcg cgaatgtggt ggaaacagtg ccgtgcggat caagcccagg tcacattaaa     1080
gaactgccct gtggagagcg gtatgctgtg gccttcttct gcttggacac ggcctgcgtc     1140
```

```
atgatcttca cagttgagta tttgcttcgc ctggctgcag cgcctagtcg ttaccgtttt    1200
gtgcgtagtg tcatgagtat catcgacgtg gtggccatcc tgccttatta cattgggctg    1260
gtgatgacag acaatgagga cgtcagcgga gcctttgtca cactccgagt cttccgggtc    1320
ttcaggatct ttaagttttc ccgccactct caaggcctgc gcatcctggg gtacacactg    1380
aagagttgtg cctcagaatt gggcttcttg cttttctcgc tcaccatggc tatcatcatc    1440
ttcgctacag ttatgttcta cgcagagaag gggtcttcgg ctagcaagtt caccagcatc    1500
cctgcagcct tctggtatac catcgtcacc atgacaacac tagggtatgg tgacatggtg    1560
ccaaaaacca tagcagggaa gattttggt tctatctgtt cgctgagtgg ggtcttggtc     1620
attgctctac ctgttccggt gattgtatcc aacttcagtc gcatctacca ccagaatcaa    1680
cgagcagaca aacgaaggc acaaaagaaa gctagactgg ccaggatccg ggcagccaaa     1740
agcggaagcg caaatgctta catgcagagc aaacggaatg gtttactcag taatcagctg    1800
cagtcctcag aggatgagca ggcttttgtt agcaaatccg gctccagctt tgaaacccag    1860
caccaccacc tgcttcactg cctggaaaaa accacgaatc acgagtttgt ggacgaacaa    1920
gtctttgaag aaagctgcat ggaagttgca actgttaatc gtccttcaag tcacagtcct    1980
tcactgtctt cacaacaagg agtcaccagc acctgctgtt cacgacgaca caaaaaaact    2040
tttcgcatcc caaatgccaa tgtatcagga agccatcaag gtagtataca agaactcagc    2100
acgattcaga tcagatgtgt ggagagaaca cctctgtcta acagccgatc cagtttaaat    2160
gccaaaatgg aagagtgtgt taaactaaac tgtgaacaac cttatgtgac tacagcaata    2220
ataagcatcc caacacctcc agtaaccaca ccagaaggag acgataggcc agaatcccct    2280
gagtactcag aggaaatat tgtcagagtt ctgctttgt aagacaattg gaataaggtc      2340
taagagaatt c                                                          2351
```

<210> SEQ ID NO 254
<211> LENGTH: 5333
<212> TYPE: DNA
<213> ORGANISM: Homo sapiens

<400> SEQUENCE: 254

```
cggctgctcg cgagctgctt tctctcctct tcccttccg ggtgcacggc gaggagaaag       60
tctctatgca actaagcccc ggcgcgcact tggccaggta tgtaccgcgg gagcggcgcg     120
ttctgcgcgg aagcagatgc tgctgccgcc acggcggcgg cggctgccag ctcctgagct    180
ctgtaactgt cacactgcac ctgagctgaa cttgaaaaga gagtgaaggg gcgattgggc    240
gaacgctttt ggcagacaca gagggtgttt gtagacgtgg gggaggagaa tctctattaa    300
cgccccccac cgtaaccact gcacatcacc tccatctctg caaatacagc ccgaggagta    360
gaggcagcag cagctggacc cccaaagaga gacgtggggc agcggctgtg accgcatctc    420
ctgagctaca caacaggtc gccttttga gactcctttg gcgggaaggg ctacttggaa      480
aggaaggttt gaaagagtga gaagggtagg tgtaagggtt ccctaattcg tcgaaagaat    540
tctattgggt gactctcgtt cgtcttctct atcctacact ccacatactg accctatatt    600
atccagactg tgccggggag aaatcaaaaa cacctgtttg aagaaacggc tgcacctgtg    660
tgcttatttg tgccagaggg tggcctagcc cacctgcagg aagagatttg gctgggttct    720
gttgagggtg attgttagga cgttgtattt tgttgccatt attccaaata cctgtcttgg    780
agggaaagtt gcccttctga gaactgtgac tttaccagga gccctatctt ggaataagag    840
ttacacctct ggaccacgtt tctcactagt actttgcttg actggaggaa gtgggtgact    900
```

```
tttggctgct tcggtgaccc attgtagacg cctcgttacc cttcttcctt ccgcttcaag    960
taatcatggc ggcggggtg gcagcgtggc tgccttttgc aagggcagcg gctatcgggt   1020
ggatgcctgt ggcctcgggg cctatgccgg ctcccccgag gcaggagagg aaaaggaccc   1080
aagatgctct cattgtgctg aatgtgagtg gcacccgctt ccagacgtgg caggacaccc   1140
tggaacgtta cccagacact ctactgggca gttctgagag ggacttttc taccacccag   1200
aaactcagca gtatttcttt gaccgtgacc cagacatctt ccgccacatc ctgaatttct   1260
accgcactgg gaagctccac tatcctcgcc acgagtgcat ctctgcttac gatgaagaac   1320
tggccttctt tggcctcatc ccggaaatca tcggcgactg ctgttatgag gagtacaagg   1380
atcgcaggcg agagaacgcc gagcgcctgc aggacgacgc ggataccgac accgctgggg   1440
agagcgcctt gcccaccatg actgcaaggc agagggtctg gagggccttc gagaaccccc   1500
acaccagcac gatggccctg tgttctact atgtcacggg gttttcatt gccgtctctg   1560
tcatcgcgaa tgtggtggaa acagtgccgt gcggatcaag cccaggtcac attaaagaac   1620
tgccctgtgg agagcggtat gctgtggcct tcttctgctt ggacacggcc tgcgtcatga   1680
tcttcacagt tgagtatttg cttcgcctgg ctgcagcgcc tagtcgttac cgttttgtgc   1740
gtagtgtcat gagtatcatc gacgtggtgg ccatcctgcc ttattacatt gggctggtga   1800
tgacagacaa tgaggacgtc agcggagcct tgtcacact ccgagtcttc cgggtcttca   1860
ggatctttaa gttttcccgc cactctcaag gcctgcgcat cctggggtac acactgaaga   1920
gttgtgcctc agaattgggc ttcttgcttt tctcgctcac catggctatc atcatcttcg   1980
ctacagttat gttctacgca gagaagggt cttcggctag caagttcacc agcatccctg   2040
cagccttctg gtataccatc gtcaccatga acaacactagg gtatggtgac atggtgccaa   2100
aaaccatagc agggaagatt tttggttcta tctgttcgct gagtggggtc ttggtcattg   2160
ctctacctgt tccggtgatt gtatccaact tcagtcgcat ctaccaccag aatcaacgag   2220
cagacaaacg aagggcacaa aagaaagcta gactggccag gatccgggca gccaaaagcg   2280
gaagcgcaaa tgcttacatg cagagcaaac ggaatggttt actcagtaat cagctgcagt   2340
cctcagagga tgagcaggct tttgttagca aatccggctc cagctttgaa acccagcacc   2400
accacctgct tcactgcctg gaaaaaacca cgaatcacga gtttgtggac gaacaagtct   2460
ttgaagaaag ctgcatggaa gttgcaactg ttaatcgtcc ttcaagtcac agtccttcac   2520
tgtcttcaca acaaggagtc accagcacct gctgttcacg acgacacaaa aaactttc   2580
gcatcccaaa tgccaatgta tcaggaagcc atcaaggtag tatacaagaa ctcagcacga   2640
ttcagatcag atgtgtggag agaacacctc tgtctaacag ccgatccagt ttaaatgcca   2700
aaatggaaga gtgtgttaaa ctaaactgtg aacaaccta tgtgactaca gcaataataa   2760
gcatcccaac acctccagta accacaccag aaggagacga taggccagaa tcccctgagt   2820
actcaggagg aaatattgtc agagtttctg ctttgtaaga caattggaat aaggtctaag   2880
agaattcgag ccctggctgt gaaaagaatc tcaacataga agaaagaaga aacaataaat   2940
attctgcaga ttaatgcagc aaagaaagaa ggttggtagt gaaacacaaa gcttccaatc   3000
ttaaggatgt gaataaaacc accaaatggc atttctagac agtttgacct gttatacaga   3060
gtaatattct gtggcccttt gactttgtga atgagcacaa tgaaatgccg cctactgatg   3120
cttcttatga tcagaactct tttttaataa aataaataac ataaatcgtt gaacataatg   3180
ttccagttga atgcaaaaca aaaaaaatat ggaaaacatt ttgataaaat ttttccctgt   3240
```

| | |
|---|---|
| taaaaccatg aacattggct atgatgaaga ttattacata tgaaaaaaaa actcacacaa | 3300 |
| catatttgta ttgactgaag gaaaccatca taatgcatgc tagaattctt tgaagcagtg | 3360 |
| atctcagttt ccttatgttg tcttcagaat aggcatgata aactataatt gtagaaaggg | 3420 |
| gtaatttctg tgcacttaca acaagctgag tgttcatgtt ccatggtggg ctgtgcaaat | 3480 |
| aaactccttt tagacctgca gtatttctca tggggatgct cattagtaaa tctaaagtgt | 3540 |
| tcagatagtt cagtattcat tatcgtttaa ctttgcacct agatactgtt acaactgcaa | 3600 |
| taatttgttg tacaactgtt gtatcaggaa tcaggatttt tttgttgttg tactttccag | 3660 |
| atccttatag atacggtaag agccacattc gtagaaaaac ttctggtgtg gccaggtttt | 3720 |
| aggtaacttt ttaatccaaa actattgtgc cataaatgtt tttcagtaat atttttggt | 3780 |
| ccactgtatt cctgtgacac agtgcattat ctgttcttgt atttctatag cacctctcta | 3840 |
| ttgggtttat catcatcaac aagactactg tttactgtag ttcaagtgac tttcctactt | 3900 |
| ttgtatttcc aaaaaaaatt atcttgtaag tagcttgtca tcaatcccct tgtcgaaaac | 3960 |
| tagaaaaaaa ggagttgacc catataaatt atctctaacg tctttgttgt ttatggaaaa | 4020 |
| gcccagatac tggatatatc actatgtatt ttatgaacag aattgactgg gactaatatc | 4080 |
| acaggatcaa tcatctcaga atcttacttg atgcattatt tattttgctt tagatcttga | 4140 |
| atacattttg agaataacta atgtggattg aaatgtagag atacactgga gtgctttatt | 4200 |
| tagcaatatt tgatgaaagc atgctttcta cgccattcag gaaggcagca caaatttatc | 4260 |
| tcagaaaggt tcctgtgtat tgcaaggtac aattttctcc aataaatcag gagaacagga | 4320 |
| gtttgatgat gcaaagttga tctctgtaca tttaagtgaa aagtctttat aacttttcac | 4380 |
| ccttaaaata tttcagcaga catgtctgca catgacagtg taaaaaagtt taatgtcaaa | 4440 |
| tgcaaagttt ttattcattc caagccacca ctgtaaggaa taaagcttag cttctgtaca | 4500 |
| tggaaagagc taataattat ccctctgtca gagatgagat tttaaatgc ttatgatatt | 4560 |
| taatcataaa aagggattaa tccaaccatt ttcaagtaaa gccagaaatt cttgcttccc | 4620 |
| atttctagaa tagtttctag aacagtgcta tgcacatatt agatcttaat aaacatttgc | 4680 |
| tgagtgaaag taagataaac tcaactatct cttgggaaga actggcttca ttcctagtac | 4740 |
| atcttttaaa aagttactaa ttttccagca gtacaaatat taacaattat attaacacct | 4800 |
| gcctcatgtc agtttatgct tctagagcaa tgtctagtga aacttatctg atggcattta | 4860 |
| ttgaaaccct tctaaaaagt agactaagga aaccataatc agaattacta tgtcttttga | 4920 |
| ttcccaatga gaagttctat tttcatgttc ttaatattac atacaagaaa atgcagttag | 4980 |
| gttatttcaa ttgacaattc tgcctcctct tttgatttat cacttaccca aaattattaa | 5040 |
| ttttattagg cttttggaaa agaaaaaaaa ctttttgatg ttttaggtga tttaaaaata | 5100 |
| taccgtgttg gtggtgaatg actattgatg actgtgttaa gtgcatctgt attgtaagtg | 5160 |
| aaatgtaatt atttctgtgt accatatgga gtaactaagg tcattgtttt tgacaatttt | 5220 |
| gtttgaaatt catatatctt atttcaaagg atagcataat atctgcatta tgctggaaaa | 5280 |
| aaatagacct ttgagaaata cttaaataaa acatgtgcat gcttgaacag gac | 5333 |

<210> SEQ ID NO 255
<211> LENGTH: 5404
<212> TYPE: DNA
<213> ORGANISM: Homo sapiens

<400> SEQUENCE: 255

| | |
|---|---|
| ggagatgcag gaccacccac tggcggggaa gcagctagca gccctcccgc gcccccgcgc | 60 |

```
tgccgagcgc cttctgcctc cgcgctcgga cgagagcccg tgccggcccc ggccccggcc    120
ccaccgcgcc aacgccgccc gcccggccgc cccgcagccc cgccgccccg cagcccgca    180 ccgcgctggc caggctcccg cgacagtggc cccgcagtaa gttggcagga gcgagtcccc    240
tccgttctcg cctcccccgc accttttgaa cttgttgctg ctgctctgct cgcctgcgcc    300
tggcttttgg aaggtgaaaa ggaggaggga ggcacggagg gatgggggaa gggaaagaag    360
agctcgcttg agctttattt atgctctctc ggcgcatcgg attcggctgc tcgcgagctg    420
ctttctctcc tcttcccttt ccgggtgcac ggcgaggaga aagtctctat gcaactaagc    480
cccggcgcgc acttggccag gtatgtaccg cgggagcggc gcgttctgcg cggaagcaga    540
tgctgctgcc gccacggcgg cggcggctgc cagctcctga gctctgtaac tgtcacactg    600
cacctgagct gaacttgaaa agagagtgaa ggggcgattg ggcgaacgct tttggcagac    660
acagagggtg tttgtagacg tgggggagga gaatctctat taacgccccc caccgtaacc    720
actgcacatc acctccatct ctgcaaatac agcccgagga gtagaggcag cagcagctgg    780
acccccaaag agagacgtgg ggcagcggct gtgaccgcat ctcctgagct acaacaacag    840
gtcgcctttt tgagactcct ttggcgggaa gggctacttg gaaaggaagg tttgaaagag    900
tgagaagggt aggtgtaagg gttccctaat tcgtcgaaag aattctattg ggtgactctc    960
gttcgtcttc tctatcctac actccacata ctgaccctat attatccaga ctgtgccggg    1020
gagaaatcaa aaacacctgt ttgaagaaac ggctgcacct gtgtgcttat ttgtgccaga    1080
gggtggccta gcccacctgc aggaagagat ttggctgggt tctgttgagg gtgattgtta    1140
ggacgttgta ttttgttgcc attattccaa atacctgtct tggagggaaa gttgcccttc    1200
tgagaactgt gactttacca ggagcccat cttggaataa gagttacacc tctgaccac    1260 gtttctcact agtactttgc ttgactggag gaagtgggtg acttttggct gcttcggtga    1320
cccattgtag acgcctcgtt acccttcttc cttccgcttc aagtaatcat ggcggcgggg    1380
gtggcagcgt ggctgccttt tgcaagggca gcggctatcg ggtggatgcc tgtggcctcg    1440
gggcctatgc cggctccccc gaggcaggag aggaaaagga cccaagatgc tctcattgtg    1500
ctgaatgtga gtggcacccg cttccagacg tggcaggaca ccctggaacg ttacccagac    1560
actctactgg gcagttctga gagggacttt ttctaccacc cagaaactca gcagtatttc    1620
tttgaccgtg acccagacat cttccgccac atcctgaatt tctaccgcac tgggaagctc    1680
cactatcctc gccacgagtg catctctgct tacgatgaag aactggcctt ctttggcctc    1740
atcccggaaa tcatcggcga ctgctgttat gaggagtaca aggatcgcag gcgagagaac    1800 gccgagcgc tgcaggacga cgcggatacc gacaccgctg gggagagcgc cttgcccacc    1860
atgactgcaa ggcagagggt ctggagggcc ttcgagaacc cccacaccag cacgatggcc    1920
ctggtgttct actatgtcac ggggtttttc attgccgtct ctgtcatcgc gaatgtggtg    1980
gaaacagtgc cgtgcggatc aagcccaggt cacattaaag aactgccctg tggagagcgg    2040
tatgctgtgg ccttcttctg cttggacacg gcctgcgtca tgatcttcac agttgagtat    2100
ttgcttcgcc tggctgcagc gcctagtcgt taccgttttg tgcgtagtgt catgagtatc    2160
atcgacgtgg tggccatcct gcctattac attgggctgg tgatgacaga caatgaggac    2220
gtcagcggag cctttgtcac actccgagtc ttccgggtct tcaggatctt taagttttcc    2280
cgccactctc aaggcctgcg catcctgggg tacacactga agagttgtgc ctcagaattg    2340
ggcttcttgc ttttctcgct caccatggct atcatcatct tcgctacagt tatgttctac    2400
```

```
gcagagaagg ggtcttcggc tagcaagttc accagcatcc ctgcagcctt ctggtatacc    2460
atcgtcacca tgacaacact agggtaggtg ccataatggg aaatgggatg gaggttgggt    2520
atgggtgagg cgattgtgga cccatcgagg ttacatggta actccgggga aatcatttgt    2580
tttctttcct gagtttagga aagcattatc taaatggttt ggcaaaactc ttttcatctg    2640
tgaaatgggt ataatacaca cgttgaagta ttaaggcatt gctggcaaat gttgatgcct    2700
gaaagtgata aagatacaaa gaaatttag aattcctgaa tatatgaaag tagtagcaat    2760
atttatatta atatataaaa atgtgacaat gaaaacaaa atctatgccc taataaagac    2820
acaaatatat acaatgtata ttgaaatgtc tataaagtgg ttcaatgcat ttaaatgaaa    2880
agtttccagg tatacttgaa ctattatttt catatgaata gatacttatg gtgtacattt    2940
ttcctctaag aaccataatt cctatttac atcgtaatac atagattgta gatgtaatta    3000
tcaaagtatt ttataatata tatgcacata ttcatatgta tgcactttaa ttatggttga    3060
taggttattc agtcttttag aatatcagag ctgaaactga tcaactctac aatatgcagt    3120
ggaattaaat ttgcaacata tttcaagctc taggttcata gtttcaaaaa agaagcaaa    3180 agactgtcat ccacacattt tttttagaa tctacagatc ccatcaggca atgggtccac    3240
acccattaaa tacacataga agatagagca gtatctggta agattgatgg tcaccaaggc    3300
tggctgtatt ataaaatttg gggtcctaat ttccttttag aattttttg tgaattcttt    3360 tttgggggta taatgaagtt ctgcaaccaa agggacaaat ttctgaattc atgctgttgt    3420
ttttaatata cttttagggc tagaattaag ttttttagg tagtagagaa aaggaaagga    3480
ggcaaatgat taataatgtt aaactgcaga aaagtagcag cattttacat attagagaat    3540
ctaataaaat aaaatggtta gatcttttta cttttatgag ttcttagata agctggggag    3600
tgatgtgagt gccttttctt cagctttgtg ctactattct tgcataggta atcagtttag    3660
tgaggatttg gtaatggcta taagaaaaaa gttattccca aggctactct ttaagctttg    3720
tgttttggga taatttaatt ggcttcttta aatgacattg tggttaaagt caacttaatt    3780
ttattagaca tattgtgttg tacagaattt ctcatgtcat gtggccagct aatggaatag    3840
tttatatatg aagaatttta ggctaggtta aacaagaaat tggggtaaag aaaaatacaa    3900
tgatttatga ttttattta gtctcatttt tttaaagacc tactggtaca tttaaaaaat    3960
gaattagtga aaatccatgt tctacttctt atatttcctt tttatcttgt tggcaaatttt   4020 gtgacagttt ataaggataa ggatgatgca gaatgccttc gcagtgtagg tgctgattct    4080
ttatcaaaga ggtttgtttt tgttgtcttg tcatttgtta gcaggagatc cttattaagg    4140
acaaatgggt agtgcaaatc accatcatga cgtcaaatta gaagtacact tgaataaaaa    4200
agattctgtt ttaataggaa gggagaacta ttaaaatgaa atacacttta aaaattttggt   4260 atatatggct gtgtttcttg aggtatcagt gaatcatttt aatgctatat agtgtctata    4320
tgattgaata taggtataaa aagaatgttg atgagaattc taatttcata tagctaatag    4380
ttctatacta gacttgagaa gttagcatta ttttaaaact tgtttctgga aatgactttc    4440
caatttttat tttatttga agcttatttt tgtttcaagg aaaatatgag acaacattaa    4500
acattagtga caatttttta ttatgtaaat aaaatactta aaagcacca tttttgaaaa    4560 tatttaagaa attgaattat attgcctgag taaaatctat gcagtggatt tagttcacat    4620
gtttcatagg taagtaagtg gattagaagc attgaataca cacgctttct cagaacttgg    4680
aagctaagtg gaagttactt taagacttta gcttcactga atttgaacat ttaattttc     4740 aggaaattaa gctaattaat gatcctgatg gaatagagca gtcatacttt taagatgtgg    4800
```

-continued

```
aaatgtcgat gtaatcaaaa tgagaacata tatggacact tgacaaatca tatgctttat    4860
aatataacag aatttcatag aaaaatgtct ttaatttctc atcaaaatgt attatgtatt    4920
gtaccctgaa gaaacagatt cttataagcc ctgcctttt ggtgccatct ttgtgactca     4980
gttatttaat aatacaaaat attcaataaa agccattgcc taactttatt gtttaggctg    5040
tagttctata cttagaggat gaagtgtaag gtgcaaactt tctgggaaat aatagttgaa    5100
gccaatatcc aactatgtct gaatgattat caagagttat ctgagctctt tttatggggc    5160 tattaattt aatggagcta aatgttcttc aattagtgat aatagaagtg aaaatgtgat     5220
tgtaaacagt ggttattgaa agttccatct cgtatgaacg ttatctacat gagaataaat    5280
aaccaagagc tttgtcattc aggactggca gaatcatttg cagcttctag agtattttag    5340
acaatattca gttggtttta tgatctaaag aactgagtgt gtctatctta gaaccaaggt    5400
gtat                                                                  5404
```

<210> SEQ ID NO 256
<211> LENGTH: 1597
<212> TYPE: DNA
<213> ORGANISM: Homo sapiens

<400> SEQUENCE: 256

```
cggctgctcg cgagctgctt tctctcctct tcccttccg ggtgcacggc gaggagaaag      60
tctctatgca actaagcccc ggcgcgcact tggccaggta tgtaccgcgg gagcggcgcg    120
ttctgcgcgg aagcagatgc tgctgccgcc acggcggcgg cggctgccag ctcctgagct    180
ctgtaactgt cacactgcac ctgagctgaa cttgaaaaga gagtgaaggg gcgattgggc    240
gaacgctttt ggcagacaca gagggtgttt gtagacgtgg gggaggagaa tctctattaa    300
cgccccccac cgtaaccact gcacatcacc tccatctctg caaatacagc ccgaggagta    360
gaggcagcag cagctggacc cccaaagaga gacgtgggc agcggctgtg accgcatctc     420
ctgagctaca caacaggtc gccttttga gactcctttg gcgggaaggg ctacttggaa      480
aggaaggttt gaaagagtga aagggtaggg tgtaagggtt ccctaattcg tcgaaagaat    540
tctattgggt gactctcgtt cgtcttctct atcctacact ccacatactg accctatatt    600
atccagactg tgccggggag aaatcaaaaa cacctgtttg aagaaacggc tgcacctgtg    660
tgcttatttg tgccagaggg tggcctagcc cacctgcagg aagagatttg gctgggttct    720
gttgagggtg attgttagga cgttgtattt tgttgccatt attccaaata cctgtcttgg    780
agggaaagtt gcccttctga gaactgtgac tttaccagga gccctatctt ggaataagag    840
ttacacctct ggaccacgtt tctcactagt actttgcttg actggaggaa gtgggtgact    900
tttggctgct tcggtgaccc attgtagacg cctcgttacc cttcttcctt ccgcttcaag    960
taatcatggc ggcggggtg gcagcgtggc tgccttttgc aagggcagcg gctatcgggt    1020
ggatgcctgt ggcctcgggg cctatgccgg ctcccccgag gcaggagagg aaaaggaccc    1080
aagatgctct cattgtgctg aatgtgagtg gcacccgctt ccagacgtgg caggacaccc    1140
tggaacgtta cccagacact ctactgggca gttctgagag ggacttttc taccacccag     1200 aaactcagca gtatttcttt gaccgtgacc cagacatctt ccgccacatc ctgaatttct    1260
accgcactgg gaagctccac tatcctcgcc acgagtgcat ctctgcttac gatgaagaac    1320
tggccttctt tggcctcatc ccggaaatca tcggcgactg ctgttatgag gagtacaagg    1380
atcgcaggcg agagaacgcc gagcgcctgc aggacgacgc ggataccgac accgctgggg    1440
```

```
agagcgcctt gcccaccatg actgcaaggc agagggtctg gagggccttc gagaacccc     1500 acaccagcac gatggccctg gtgttctact atgtcacggg gttttcatt gccgtctctg    1560 tcatcgcgaa tgtggtggaa acagtgccgt gcggatc                             1597
```

<210> SEQ ID NO 257
<211> LENGTH: 255
<212> TYPE: PRT
<213> ORGANISM: Homo sapiens

<400> SEQUENCE: 257

```
Met Val Pro Lys Thr Ile Ala Gly Lys Ile Phe Gly Ser Ile Cys Ser
                 5                  10                  15

Leu Ser Gly Val Leu Val Ile Ala Leu Pro Val Pro Val Ile Val Ser
            20                  25                  30

Asn Phe Ser Arg Ile Tyr His Gln Asn Gln Arg Ala Asp Lys Arg Arg
        35                  40                  45

Ala Gln Lys Lys Ala Arg Leu Ala Arg Ile Arg Ala Ala Lys Ser Gly
    50                  55                  60

Ser Ala Asn Ala Tyr Met Gln Ser Lys Arg Asn Gly Leu Leu Ser Asn
65                  70                  75                  80

Gln Leu Gln Ser Ser Glu Asp Glu Gln Ala Phe Val Ser Lys Ser Gly
                85                  90                  95

Ser Ser Phe Glu Thr Gln His His His Leu Leu His Cys Leu Glu Lys
            100                 105                 110

Thr Thr Asn His Glu Phe Val Asp Glu Gln Val Phe Glu Glu Ser Cys
        115                 120                 125

Met Glu Val Ala Thr Val Asn Arg Pro Ser Ser His Ser Pro Ser Leu
    130                 135                 140

Ser Ser Gln Gln Gly Val Thr Ser Thr Cys Cys Ser Arg Arg His Lys
145                 150                 155                 160

Lys Thr Phe Arg Ile Pro Asn Ala Asn Val Ser Gly Ser His Gln Gly
                165                 170                 175

Ser Ile Gln Glu Leu Ser Thr Ile Gln Ile Arg Cys Val Glu Arg Thr
            180                 185                 190

Pro Leu Ser Asn Ser Arg Ser Ser Leu Asn Ala Lys Met Glu Glu Cys
        195                 200                 205

Val Lys Leu Asn Cys Glu Gln Pro Tyr Val Thr Thr Ala Ile Ile Ser
    210                 215                 220

Ile Pro Thr Pro Pro Val Thr Pro Glu Gly Asp Asp Arg Pro Glu
225                 230                 235                 240

Ser Pro Glu Tyr Ser Gly Gly Asn Ile Val Arg Val Ser Ala Leu
                245                 250                 255
```

<210> SEQ ID NO 258
<211> LENGTH: 630
<212> TYPE: PRT
<213> ORGANISM: Homo sapiens

<400> SEQUENCE: 258

```
Met Ala Ala Gly Val Ala Ala Trp Leu Pro Phe Ala Arg Ala Ala Ala
                 5                  10                  15

Ile Gly Trp Met Pro Val Ala Ser Gly Pro Met Pro Ala Pro Pro Arg
            20                  25                  30

Gln Glu Arg Lys Arg Thr Gln Asp Ala Leu Ile Val Leu Asn Val Ser
        35                  40                  45
```

```
Gly Thr Arg Phe Gln Thr Trp Gln Asp Thr Leu Glu Arg Tyr Pro Asp
     50                  55                  60

Thr Leu Leu Gly Ser Ser Glu Arg Asp Phe Tyr His Pro Glu Thr
 65              70                  75                  80

Gln Gln Tyr Phe Asp Arg Asp Pro Asp Ile Phe Arg His Ile Leu
                 85                  90                  95

Asn Phe Tyr Arg Thr Gly Lys Leu His Tyr Pro Arg His Glu Cys Ile
                100                 105                 110

Ser Ala Tyr Asp Glu Glu Leu Ala Phe Phe Gly Leu Ile Pro Glu Ile
            115                 120                 125

Ile Gly Asp Cys Cys Tyr Glu Glu Tyr Lys Asp Arg Arg Glu Asn
        130                 135                 140

Ala Glu Arg Leu Gln Asp Asp Ala Asp Thr Asp Thr Ala Gly Glu Ser
145                 150                 155                 160

Ala Leu Pro Thr Met Thr Ala Arg Gln Arg Val Trp Arg Ala Phe Glu
                165                 170                 175

Asn Pro His Thr Ser Thr Met Ala Leu Val Phe Tyr Val Thr Gly
                180                 185                 190

Phe Phe Ile Ala Val Ser Val Ile Ala Asn Val Val Glu Thr Val Pro
            195                 200                 205

Cys Gly Ser Ser Pro Gly His Ile Lys Glu Leu Pro Cys Gly Glu Arg
        210                 215                 220

Tyr Ala Val Ala Phe Phe Cys Leu Asp Thr Ala Cys Val Met Ile Phe
225                 230                 235                 240

Thr Val Glu Tyr Leu Leu Arg Leu Ala Ala Ala Pro Ser Arg Tyr Arg
                245                 250                 255

Phe Val Arg Ser Val Met Ser Ile Ile Asp Val Val Ala Ile Leu Pro
                260                 265                 270

Tyr Tyr Ile Gly Leu Val Met Thr Asp Asn Glu Asp Val Ser Gly Ala
            275                 280                 285

Phe Val Thr Leu Arg Val Phe Arg Val Phe Arg Ile Phe Lys Phe Ser
            290                 295                 300

Arg His Ser Gln Gly Leu Arg Ile Leu Gly Tyr Thr Leu Lys Ser Cys
305                 310                 315                 320

Ala Ser Glu Leu Gly Phe Leu Leu Phe Ser Leu Thr Met Ala Ile Ile
                325                 330                 335

Ile Phe Ala Thr Val Met Phe Tyr Ala Glu Lys Gly Ser Ser Ala Ser
            340                 345                 350

Lys Phe Thr Ser Ile Pro Ala Ala Phe Trp Tyr Thr Ile Val Thr Met
            355                 360                 365

Thr Thr Leu Gly Tyr Gly Asp Met Val Pro Lys Thr Ile Ala Gly Lys
370                 375                 380

Ile Phe Gly Ser Ile Cys Ser Leu Ser Gly Val Leu Val Ile Ala Leu
385                 390                 395                 400

Pro Val Pro Val Ile Val Ser Asn Phe Ser Arg Ile Tyr His Gln Asn
                405                 410                 415

Gln Arg Ala Asp Lys Arg Arg Ala Gln Lys Lys Ala Arg Leu Ala Arg
            420                 425                 430

Ile Arg Ala Ala Lys Ser Gly Ser Ala Asn Ala Tyr Met Gln Ser Lys
            435                 440                 445

Arg Asn Gly Leu Leu Ser Asn Gln Leu Gln Ser Ser Glu Asp Glu Gln
450                 455                 460

Ala Phe Val Ser Lys Ser Gly Ser Ser Phe Glu Thr Gln His His His
```

-continued

```
                465                 470                 475                 480
Leu Leu His Cys Leu Glu Lys Thr Thr Asn His Glu Phe Val Asp Glu
                    485                 490                 495
Gln Val Phe Glu Glu Ser Cys Met Glu Val Ala Thr Val Asn Arg Pro
                500                 505                 510
Ser Ser His Ser Pro Ser Leu Ser Ser Gln Gln Gly Val Thr Ser Thr
                515                 520                 525
Cys Cys Ser Arg Arg His Lys Lys Thr Phe Arg Ile Pro Asn Ala Asn
        530                 535                 540
Val Ser Gly Ser His Gln Gly Ser Ile Gln Glu Leu Ser Thr Ile Gln
545                 550                 555                 560
Ile Arg Cys Val Glu Arg Thr Pro Leu Ser Asn Ser Arg Ser Ser Leu
                565                 570                 575
Asn Ala Lys Met Glu Glu Cys Val Lys Leu Asn Cys Glu Gln Pro Tyr
                580                 585                 590
Val Thr Thr Ala Ile Ile Ser Ile Pro Thr Pro Pro Val Thr Thr Pro
                595                 600                 605
Glu Gly Asp Asp Arg Pro Glu Ser Pro Glu Tyr Ser Gly Gly Asn Ile
            610                 615                 620
Val Arg Val Ser Ala Leu
625                 630

<210> SEQ ID NO 259
<211> LENGTH: 630
<212> TYPE: PRT
<213> ORGANISM: Homo sapiens

<400> SEQUENCE: 259

Met Ala Ala Gly Val Ala Ala Trp Leu Pro Phe Ala Arg Ala Ala Ala
                    5                   10                  15
Ile Gly Trp Met Pro Val Ala Ser Gly Pro Met Pro Ala Pro Pro Arg
                20                  25                  30
Gln Glu Arg Lys Arg Thr Gln Asp Ala Leu Ile Val Leu Asn Val Ser
            35                  40                  45
Gly Thr Arg Phe Gln Thr Trp Gln Asp Thr Leu Glu Arg Tyr Pro Asp
        50                  55                  60
Thr Leu Leu Gly Ser Ser Glu Arg Asp Phe Phe Tyr His Pro Glu Thr
    65                  70                  75                  80
Gln Gln Tyr Phe Phe Asp Arg Asp Pro Asp Ile Phe Arg His Ile Leu
                    85                  90                  95
Asn Phe Tyr Arg Thr Gly Lys Leu His Tyr Pro Arg His Glu Cys Ile
                100                 105                 110
Ser Ala Tyr Asp Glu Glu Leu Ala Phe Phe Gly Leu Ile Pro Glu Ile
            115                 120                 125
Ile Gly Asp Cys Cys Tyr Glu Glu Tyr Lys Asp Arg Arg Arg Glu Asn
        130                 135                 140
Ala Glu Arg Leu Gln Asp Asp Ala Asp Thr Asp Thr Ala Gly Glu Ser
145                 150                 155                 160
Ala Leu Pro Thr Met Thr Ala Arg Gln Arg Val Trp Arg Ala Phe Glu
                165                 170                 175
Asn Pro His Thr Ser Thr Met Ala Leu Val Phe Tyr Tyr Val Thr Gly
                180                 185                 190
Phe Phe Ile Ala Val Ser Val Ile Ala Asn Val Val Glu Thr Val Pro
            195                 200                 205
```

-continued

```
Cys Gly Ser Ser Pro Gly His Ile Lys Glu Leu Pro Cys Gly Glu Arg
    210                 215                 220
Tyr Ala Val Ala Phe Phe Cys Leu Asp Thr Ala Cys Val Met Ile Phe
225                 230                 235                 240
Thr Val Glu Tyr Leu Leu Arg Leu Ala Ala Pro Ser Arg Tyr Arg
            245                 250                 255
Phe Val Arg Ser Val Met Ser Ile Ile Asp Val Ala Ile Leu Pro
        260                 265                 270
Tyr Tyr Ile Gly Leu Val Met Thr Asp Asn Glu Asp Val Ser Gly Ala
            275                 280                 285
Phe Val Thr Leu Arg Val Phe Arg Val Phe Arg Ile Phe Lys Phe Ser
290                 295                 300
Arg His Ser Gln Gly Leu Arg Ile Leu Gly Tyr Thr Leu Lys Ser Cys
305                 310                 315                 320
Ala Ser Glu Leu Gly Phe Leu Leu Phe Ser Leu Thr Met Ala Ile Ile
                325                 330                 335
Ile Phe Ala Thr Val Met Phe Tyr Ala Glu Lys Gly Ser Ser Ala Ser
            340                 345                 350
Lys Phe Thr Ser Ile Pro Ala Ala Phe Trp Tyr Thr Ile Val Thr Met
        355                 360                 365
Thr Thr Leu Gly Tyr Gly Asp Met Val Pro Lys Thr Ile Ala Gly Lys
    370                 375                 380
Ile Phe Gly Ser Ile Cys Ser Leu Ser Gly Val Leu Val Ile Ala Leu
385                 390                 395                 400
Pro Val Pro Val Ile Val Ser Asn Phe Ser Arg Ile Tyr His Gln Asn
                405                 410                 415
Gln Arg Ala Asp Lys Arg Arg Ala Gln Lys Lys Ala Arg Leu Ala Arg
            420                 425                 430
Ile Arg Ala Ala Lys Ser Gly Ser Ala Asn Ala Tyr Met Gln Ser Lys
        435                 440                 445
Arg Asn Gly Leu Leu Ser Asn Gln Leu Gln Ser Ser Glu Asp Glu Gln
    450                 455                 460
Ala Phe Val Ser Lys Ser Gly Ser Ser Phe Glu Thr Gln His His His
465                 470                 475                 480
Leu Leu His Cys Leu Glu Lys Thr Thr Asn His Glu Phe Val Asp Glu
                485                 490                 495
Gln Val Phe Glu Glu Ser Cys Met Glu Val Ala Thr Val Asn Arg Pro
            500                 505                 510
Ser Ser His Ser Pro Ser Leu Ser Ser Gln Gln Gly Val Thr Ser Thr
        515                 520                 525
Cys Cys Ser Arg Arg His Lys Lys Thr Phe Arg Ile Pro Asn Ala Asn
    530                 535                 540
Val Ser Gly Ser His Gln Gly Ser Ile Gln Glu Leu Ser Thr Ile Gln
545                 550                 555                 560
Ile Arg Cys Val Glu Arg Thr Pro Leu Ser Asn Ser Arg Ser Ser Leu
                565                 570                 575
Asn Ala Lys Met Glu Glu Cys Val Lys Leu Asn Cys Glu Gln Pro Tyr
            580                 585                 590
Val Thr Thr Ala Ile Ile Ser Ile Pro Thr Pro Pro Val Thr Thr Pro
        595                 600                 605
Glu Gly Asp Asp Arg Pro Glu Ser Pro Glu Tyr Ser Gly Gly Asn Ile
    610                 615                 620
Val Arg Val Ser Ala Leu
```

```
<210> SEQ ID NO 260
<211> LENGTH: 630
<212> TYPE: PRT
<213> ORGANISM: Homo sapiens

<400> SEQUENCE: 260
```

| | | | | | | | | | | | | | | |
|---|---|---|---|---|---|---|---|---|---|---|---|---|---|---|
| Met | Ala | Ala | Gly | Val | Ala | Ala | Trp | Leu | Pro | Phe | Ala | Arg | Ala | Ala |
| | | | | 5 | | | | | 10 | | | | | 15 |
| Ile | Gly | Trp | Met | Pro | Val | Ala | Ser | Gly | Pro | Met | Pro | Ala | Pro | Pro | Arg |
| | | | 20 | | | | | 25 | | | | | 30 | | |
| Gln | Glu | Arg | Lys | Arg | Thr | Gln | Asp | Ala | Leu | Ile | Val | Leu | Asn | Val | Ser |
| | | | 35 | | | | | 40 | | | | | 45 | | |
| Gly | Thr | Arg | Phe | Gln | Thr | Trp | Gln | Asp | Thr | Leu | Glu | Arg | Tyr | Pro | Asp |
| | | 50 | | | | | 55 | | | | | 60 | | | |
| Thr | Leu | Leu | Gly | Ser | Ser | Glu | Arg | Asp | Phe | Phe | Tyr | His | Pro | Glu | Thr |
| 65 | | | | | 70 | | | | | 75 | | | | | 80 |
| Gln | Gln | Tyr | Phe | Phe | Asp | Arg | Asp | Pro | Asp | Ile | Phe | Arg | His | Ile | Leu |
| | | | | 85 | | | | | 90 | | | | | 95 | |
| Asn | Phe | Tyr | Arg | Thr | Gly | Lys | Leu | His | Tyr | Pro | Arg | His | Glu | Cys | Ile |
| | | | | 100 | | | | | 105 | | | | | 110 | |
| Ser | Ala | Tyr | Asp | Glu | Glu | Leu | Ala | Phe | Phe | Gly | Leu | Ile | Pro | Glu | Ile |
| | | | 115 | | | | | 120 | | | | | 125 | | |
| Ile | Gly | Asp | Cys | Cys | Tyr | Glu | Glu | Tyr | Lys | Asp | Arg | Arg | Arg | Glu | Asn |
| | | 130 | | | | | 135 | | | | | 140 | | | |
| Ala | Glu | Arg | Leu | Gln | Asp | Asp | Ala | Asp | Thr | Asp | Thr | Ala | Gly | Glu | Ser |
| 145 | | | | | 150 | | | | | 155 | | | | | 160 |
| Ala | Leu | Pro | Thr | Met | Thr | Ala | Arg | Gln | Arg | Val | Trp | Arg | Ala | Phe | Glu |
| | | | | 165 | | | | | 170 | | | | | 175 | |
| Asn | Pro | His | Thr | Ser | Thr | Met | Ala | Leu | Val | Phe | Tyr | Tyr | Val | Thr | Gly |
| | | | 180 | | | | | 185 | | | | | 190 | | |
| Phe | Phe | Ile | Ala | Val | Ser | Val | Ile | Ala | Asn | Val | Val | Glu | Thr | Val | Pro |
| | | | 195 | | | | | 200 | | | | | 205 | | |
| Cys | Gly | Ser | Ser | Pro | Gly | His | Ile | Lys | Glu | Leu | Pro | Cys | Gly | Glu | Arg |
| | | 210 | | | | | 215 | | | | | 220 | | | |
| Tyr | Ala | Val | Ala | Phe | Phe | Cys | Leu | Asp | Thr | Ala | Cys | Val | Met | Ile | Phe |
| 225 | | | | | 230 | | | | | 235 | | | | | 240 |
| Thr | Val | Glu | Tyr | Leu | Leu | Arg | Leu | Ala | Ala | Ala | Pro | Ser | Arg | Tyr | Arg |
| | | | | 245 | | | | | 250 | | | | | 255 | |
| Phe | Val | Arg | Ser | Val | Met | Ser | Ile | Ile | Asp | Val | Val | Ala | Ile | Leu | Pro |
| | | | 260 | | | | | 265 | | | | | 270 | | |
| Tyr | Tyr | Ile | Gly | Leu | Val | Met | Thr | Asp | Asn | Glu | Asp | Val | Ser | Gly | Ala |
| | | | 275 | | | | | 280 | | | | | 285 | | |
| Phe | Val | Thr | Leu | Arg | Val | Phe | Arg | Val | Phe | Arg | Ile | Phe | Lys | Phe | Ser |
| | | | 290 | | | | | 295 | | | | | 300 | | |
| Arg | His | Ser | Gln | Gly | Leu | Arg | Ile | Leu | Gly | Tyr | Thr | Leu | Lys | Ser | Cys |
| 305 | | | | | 310 | | | | | 315 | | | | | 320 |
| Ala | Ser | Glu | Leu | Gly | Phe | Leu | Leu | Phe | Ser | Leu | Thr | Met | Ala | Ile | Ile |
| | | | | 325 | | | | | 330 | | | | | 335 | |
| Ile | Phe | Ala | Thr | Val | Met | Phe | Tyr | Ala | Glu | Lys | Gly | Ser | Ser | Ala | Ser |
| | | | 340 | | | | | 345 | | | | | 350 | | |
| Lys | Phe | Thr | Ser | Ile | Pro | Ala | Ala | Phe | Trp | Tyr | Thr | Ile | Val | Thr | Met |
| | | | 355 | | | | | 360 | | | | | 365 | | |

```
Thr Thr Leu Gly Tyr Gly Asp Met Val Pro Lys Thr Ile Ala Gly Lys
    370                 375                 380

Ile Phe Gly Ser Ile Cys Ser Leu Ser Gly Val Leu Val Ile Ala Leu
385                 390                 395                 400

Pro Val Pro Val Ile Val Ser Asn Phe Ser Arg Ile Tyr His Gln Asn
                405                 410                 415

Gln Arg Ala Asp Lys Arg Ala Gln Lys Lys Ala Arg Leu Ala Arg
        420                 425                 430

Ile Arg Ala Ala Lys Ser Gly Ser Ala Asn Ala Tyr Met Gln Ser Lys
        435                 440                 445

Arg Asn Gly Leu Leu Ser Asn Gln Leu Gln Ser Ser Glu Asp Glu Gln
    450                 455                 460

Ala Phe Val Ser Lys Ser Gly Ser Ser Phe Glu Thr Gln His His His
465                 470                 475                 480

Leu Leu His Cys Leu Glu Lys Thr Thr Asn His Glu Phe Val Asp Glu
                485                 490                 495

Gln Val Phe Glu Glu Ser Cys Met Glu Val Ala Thr Val Asn Arg Pro
            500                 505                 510

Ser Ser His Ser Pro Ser Leu Ser Gln Gln Gly Val Thr Ser Thr
        515                 520                 525

Cys Cys Ser Arg Arg His Lys Lys Thr Phe Arg Ile Pro Asn Ala Asn
530                 535                 540

Val Ser Gly Ser His Gln Gly Ser Ile Gln Glu Leu Ser Thr Ile Gln
545                 550                 555                 560

Ile Arg Cys Val Glu Arg Thr Pro Leu Ser Asn Ser Arg Ser Ser Leu
                565                 570                 575

Asn Ala Lys Met Glu Glu Cys Val Lys Leu Asn Cys Glu Gln Pro Tyr
            580                 585                 590

Val Thr Thr Ala Ile Ile Ser Ile Pro Thr Pro Val Thr Thr Pro
        595                 600                 605

Glu Gly Asp Asp Arg Pro Glu Ser Pro Glu Tyr Ser Gly Gly Asn Ile
610                 615                 620

Val Arg Val Ser Ala Leu
625                 630

<210> SEQ ID NO 261
<211> LENGTH: 630
<212> TYPE: PRT
<213> ORGANISM: Homo sapiens

<400> SEQUENCE: 261

Met Ala Ala Gly Val Ala Ala Trp Leu Pro Phe Ala Arg Ala Ala Ala
                5                   10                  15

Ile Gly Trp Met Pro Val Ala Ser Gly Pro Met Pro Ala Pro Pro Arg
            20                  25                  30

Gln Glu Arg Lys Arg Thr Gln Asp Ala Leu Ile Val Leu Asn Val Ser
        35                  40                  45

Gly Thr Arg Phe Gln Thr Trp Gln Asp Thr Leu Glu Arg Tyr Pro Asp
    50                  55                  60

Thr Leu Leu Gly Ser Ser Glu Arg Asp Phe Phe Tyr His Pro Glu Thr
65                  70                  75                  80

Gln Gln Tyr Phe Phe Asp Arg Asp Pro Asp Ile Phe Arg His Ile Leu
                85                  90                  95

Asn Phe Tyr Arg Thr Gly Lys Leu His Tyr Pro Arg His Glu Cys Ile
            100                 105                 110
```

-continued

```
Ser Ala Tyr Asp Glu Glu Leu Ala Phe Phe Gly Leu Ile Pro Glu Ile
        115                 120                 125

Ile Gly Asp Cys Cys Tyr Glu Tyr Lys Asp Arg Arg Glu Asn
    130                 135                 140

Ala Glu Arg Leu Gln Asp Ala Asp Thr Asp Ala Gly Glu Ser
145                 150                 155                 160

Ala Leu Pro Thr Met Thr Ala Arg Gln Arg Val Trp Arg Ala Phe Glu
                165                 170                 175

Asn Pro His Thr Ser Thr Met Ala Leu Val Phe Tyr Val Thr Gly
            180                 185                 190

Phe Phe Ile Ala Val Ser Val Ile Ala Asn Val Val Glu Thr Val Pro
            195                 200                 205

Cys Gly Ser Ser Pro Gly His Ile Lys Glu Leu Pro Cys Gly Glu Arg
    210                 215                 220

Tyr Ala Val Ala Phe Phe Cys Leu Asp Thr Ala Cys Val Met Ile Phe
225                 230                 235                 240

Thr Val Glu Tyr Leu Leu Arg Leu Ala Ala Pro Ser Arg Tyr Arg
                245                 250                 255

Phe Val Arg Ser Val Met Ser Ile Ile Asp Val Val Ala Ile Leu Pro
            260                 265                 270

Tyr Tyr Ile Gly Leu Val Met Thr Asp Asn Glu Asp Val Ser Gly Ala
        275                 280                 285

Phe Val Thr Leu Arg Val Phe Arg Val Phe Arg Ile Phe Lys Phe Ser
        290                 295                 300

Arg His Ser Gln Gly Leu Arg Ile Leu Gly Tyr Thr Leu Lys Ser Cys
305                 310                 315                 320

Ala Ser Glu Leu Gly Phe Leu Leu Phe Ser Leu Thr Met Ala Ile Ile
                325                 330                 335

Ile Phe Ala Thr Val Met Phe Tyr Ala Glu Lys Gly Ser Ser Ala Ser
            340                 345                 350

Lys Phe Thr Ser Ile Pro Ala Ala Phe Trp Tyr Thr Ile Val Thr Met
            355                 360                 365

Thr Thr Leu Gly Tyr Gly Asp Met Val Pro Lys Thr Ile Ala Gly Lys
        370                 375                 380

Ile Phe Gly Ser Ile Cys Ser Leu Ser Gly Val Leu Val Ile Ala Leu
385                 390                 395                 400

Pro Val Pro Val Ile Val Ser Asn Phe Ser Arg Ile Tyr His Gln Asn
                405                 410                 415

Gln Arg Ala Asp Lys Arg Arg Ala Gln Lys Lys Ala Arg Leu Ala Arg
            420                 425                 430

Ile Arg Ala Ala Lys Ser Gly Ser Ala Asn Ala Tyr Met Gln Ser Lys
        435                 440                 445

Arg Asn Gly Leu Leu Ser Asn Gln Leu Gln Ser Ser Glu Asp Glu Gln
    450                 455                 460

Ala Phe Val Ser Lys Ser Gly Ser Ser Phe Glu Thr Gln His His His
465                 470                 475                 480

Leu Leu His Cys Leu Glu Lys Thr Thr Asn His Glu Phe Val Asp Glu
                485                 490                 495

Gln Val Phe Glu Glu Ser Cys Met Glu Val Ala Thr Val Asn Arg Pro
            500                 505                 510

Ser Ser His Ser Pro Ser Leu Ser Ser Gln Gln Gly Val Thr Ser Thr
        515                 520                 525
```

```
Cys Cys Ser Arg Arg His Lys Lys Thr Phe Arg Ile Pro Asn Ala Asn
        530                 535                 540

Val Ser Gly Ser His Gln Gly Ser Ile Gln Glu Leu Ser Thr Ile Gln
545                 550                 555                 560

Ile Arg Cys Val Glu Arg Thr Pro Leu Ser Asn Ser Arg Ser Ser Leu
                565                 570                 575

Asn Ala Lys Met Glu Glu Cys Val Lys Leu Asn Cys Glu Gln Pro Tyr
            580                 585                 590

Val Thr Thr Ala Ile Ile Ser Ile Pro Thr Pro Val Thr Thr Pro
        595                 600                 605

Glu Gly Asp Asp Arg Pro Glu Ser Pro Glu Tyr Ser Gly Gly Asn Ile
    610                 615                 620

Val Arg Val Ser Ala Leu
625                 630

<210> SEQ ID NO 262
<211> LENGTH: 2707
<212> TYPE: DNA
<213> ORGANISM: Homo sapiens

<400> SEQUENCE: 262
ggcaggccga gccagccgtg cgccgcgctc cagggcccag ggcgccgcac acgcacccac      60
ccacccaccc agcctcgcag cgccatgggc aagaacaagc agccacgcgg ccagcagagg     120
caggggggcc cgccggccgc ggacgccgct gggcccgacg acatggagcc gaagaagggc     180
acggggcccc ccaaggagtg cggggaggag gagccccgga cctgctgcgg ctgccggttc     240
ccgctgctgc tcgccctgct gcagctggcc ctgggcatcg ccgtgaccgt ggtgggcttc     300
ctcatggcga gcatcagctc ctccctgcta gtcaggaca ctccattttg gctgggatc      360 attgtctgct tagtggccta tcttggcttg tttatgcttt gtgtctcata tcaggttgac     420
gaacggacat gtattcaatt ttctatgaaa ctgttatact ttctgctgag tgccctgggc     480
ctgacggtct gtgtgctggc cgtggccttt gccgcccacc actatcgca gctcacacag     540 tttacctgtg agaccacact cgactcttgc agtgcaaac tgccctcctc ggagccgctc     600
agcaggacct tgtttaccg ggatgtgacg gactgtacca gcgtcactgg cactttcaaa     660
ctgttcttac tcatccagat gattcttaat ttggtctgcg ccttgtgtg cttgttggcc     720 tgctttgtga tgtggaaaca taggtaccag gtcttctatg tgggtgtcag gatatgctcc     780
ctcacggctt ccgaaggccc ccagcaaaag atctaacatt cttgctcaaa gttgcgagag     840
aaagtagcac atggagtagc tgaggttaaa caaacaaaaa aaattttaa acaaagaaag     900 gaaaaaatt gacaataaaa gtcactcttc taattgaata ttttttatatt tttatgaaac     960 aaaagagcat tcttcaggt ttctattgta ttttttttaa cattcttgca gagaaagcaa    1020
gatccaaatt gattttggga tattaaaagt taacagaaca ctgaacaagg aaagaatggc    1080
atagatctat ctttacagtc tggagttaat tcctgttaac tcattttatc cattccttac    1140
ataatcttct ttcctgttag tccagtttga tggtgtgaat ggtgaattc aggcccagtt    1200 gctaaatttt gtggcatctt cctctagtcc ttcccacctc cagtcatcag ccccactctg    1260
tcttggagac aggcaggagg tggggaaga gctgaatctc tttattttcc ctggtagaga    1320
catcttcaag gcatgaaata gcttaaagag cagagtagaa atggaagagg ctttgcaaaa    1380
ggctagataa ctaacaacac ctgggttggg gcggcggcct cttctcttca gctcccttag    1440
cttggctccg taagtggatc acttgccaaa tgctttagat gattgcctct caataattga    1500
```

```
aaggtggtgg tagttgtatt ctaaatgatg tagaaggttt aaaaataatt acattatgct    1560
tctattctat catctaaaac aaatcattaa aactaatttc tagctaattg ttaattataa    1620
ttatgctcag aagtctattt aatgagctct gactgtactt acgctgcact gtcggtgtta    1680
agagaaatta ctctcacaag agcagaggcc tgaagattct ttcttctgaa agccaagcac    1740
cacaaggaaa aaaaaattat taatagctca ggttaaaaac acccatttaa acaaaaacaa    1800
gagcatttgt aataggaagt gtttatacaa acagcacatt tgtgatatgt tgaaaagcat    1860
ctctcttggc aaccaatcta tgtttgagga agattgggta atgctgatgt gttccattca    1920
tgaaactgta tttgatacat aatcctatta ttaattcgta tgcttagtca acctaggaaa    1980
tcaaaataat gttttgaagt tcttatttga gcaatatggc cttgacttgg agggtagttt    2040
tagttgtttt gtttttaagt gactgtggtt taaagcacaa atgccccaag gtggggagac    2100
ttctctctgt gattattgtt gctattaaat tctgaactgt atccatattt taaggaagga    2160
gctaaaaatg gaaattcatg aaacataaat ggtatcaaga actttatcag tatgctttgt    2220
tgaaagcaga aattaagata taattgagt tcaattcgcc tctccgcatt gcctattgat     2280
acactttact aatcatgaaa ttctaaccta aaggaaaaac attttcctgc ttgtcttaga    2340
agaaagtgga ataattccac tgattgtgat aatggtttca atttctacac aatataaata    2400
tccagtataa aggaaagcgt taagtcggta agctagagga ttgtaaatat cttttatgtc    2460
ctctagataa acacccgat taacagatgt taaaccttt aatgtttga tttgctttaa       2520 aaatggcctt cctacacatt agctccagct aaaaagacac attggagagc ttagaggata    2580
agtctctgga gcagaattta tcacacacaa aagttacacc aacagaatac caagcagaat    2640
gatgaggacc tgtaaaatac cttgtgccct attaaaaaaa aaaaaaaaaa aaaaaaaaa     2700 aaaaaaa                                                              2707

<210> SEQ ID NO 263
<211> LENGTH: 2707
<212> TYPE: DNA
<213> ORGANISM: Homo sapiens

<400> SEQUENCE: 263
ggcaggccga ccagccgtg cgccgcgctc cagggcccag ggcgccgcac acgcacccac       60
ccacccaccc agcctcgcag cgccatgggc aagaacaagc agccacgcgg ccagcagagg      120
caggggggcc cgccggccgc ggacgccgct gggcccgacg acatggagcc gaagaagggc      180
acggggcccc ccaaggagtg cggggaggag gagccccgga cctgctgcgg ctgccggttc      240
ccgctgctgc tcgccctgct gcagctggcc ctgggcatcg ccgtgaccgt ggtgggcttc     300
ctcatggcga gcatcagctc ctccctgcta gtcaggaca ctccattttg ggctgggatc      360
attgtctgct tagtggccta tcttggcttg tttatgcttt gtgtctcata tcaggttgac     420
gaacggacat gtattcaatt ttctatgaaa ctgttatact ttctgctgag tgccctgggc     480
ctgacggtct gtgtgctggc cgtggccttt gccgcccacc actattcgca gctcacacag     540
tttacctgtg agaccacact cgactcttgc cagtgcaaac tgccctcctc ggagccgctc     600
agcaggacct tgtttaccg ggatgtgacg gactgtacca gcgtcactgg cactttcaaa      660
ctgttcttac tcatccagat gattcttaat ttggtctgcg gccttgtgtg cttgttggcc     720
tgctttgtga tgtggaaaca taggtaccag gtcttctatg tgggtgtcag gatatgctcc     780
ctcacggctt ccgaaggccc ccagcaaaag atctaacatt cttgctcaaa gttgcgagag     840
aaagtagcac atggagtagc tgaggttaaa caaacaaaaa aaaattttaa acaaagaaag     900
```

```
gaaaaaaatt gacaataaaa gtcactcttc taattgaata ttttttatatt tttatgaaac    960 aaaagagcat tcttcaggt ttctattgta ttttttttaa cattcttgca gagaaagcaa     1020
gatccaaatt gattttggga tattaaaagt taacagaaca ctgaacaagg aaagaatggc    1080
atagatctat ctttacagtc tggagttaat tcctgttaac tcattttatc cattccttac    1140
ataatcttct ttcctgttag tccagtttga tggtgtgaat ggtgaatttc aggcccagtt    1200
gctaaatttt gtggcatctt cctctagtcc ttcccacctc cagtcatcag ccccactctg    1260
tcttggagac aggcaggagg tgggggaaga gctgaatctc tttattttcc ctggtagaga    1320
catcttcaag gcatgaaata gcttaaagag cagagtagaa atggaagagg ctttgcaaaa    1380
ggctagataa ctaacaacac ctgggttggg gcggcggcct cttctcttca gctcccttag    1440
cttggctccg taagtggatc acttgccaaa tgctttagat gattgcctct caataattga    1500
aaggtggtgg tagttgtatt ctaaatgatg tagaaggttt aaaaataatt acattatgct    1560
tctattctat catctaaaac aaatcattaa aactaatttc tagctaattg ttaattataa    1620
ttatgctcag aagtctattt aatgagctct gactgtactt acgctgcact gtcggtgtta    1680
agagaaatta ctctcacaag agcagaggcc tgaagattct ttcttctgaa agccaagcac    1740
cacaaggaaa aaaaaattat taatagctca ggttaaaaac acccatttaa acaaaaacaa    1800
gagcatttgt aataggaagt gttttatacaa acagcacatt tgtgatatgt tgaaaagcat    1860
ctctcttggc aaccaatcta tgtttgagga agattgggta atgctgatgt gttccattca    1920
tgaaactgta tttgatacat aatcctatta ttaattcgta tgcttagtca acctaggaaa    1980
tcaaaataat gttttgaagt tcttatttga gcaatatggc cttgacttgg agggtagttt    2040
tagttgtttt gtttttaagt gactgtggtt taaagcacaa atgcccccaag gtggggagac    2100 ttctctctgt gattattgtt gctattaaat tctgaactgt atccatattt taaggaagga    2160
gctaaaaatg gaaattcatg aaacataaat ggtatcaaga actttatcag tatgctttgt    2220
tgaaagcaga aattaagata ataattgagt tcaattcgcc tctccgcatt gcctattgat    2280
acactttact aatcatgaaa ttctaaccta aaaggaaaac attttcctgc ttgtcttaga    2340
agaaagtgga ataattccac tgattgtgat aatggtttca atttctacac aatataaata    2400
tccagtataa aggaaagcgt taagtcggta agctagagga ttgtaaatat cttttatgtc    2460
ctctagataa aacacccgat taacagatgt taaaccttt aatgtttga tttgctttaa     2520 aaatggccctt cctacacatt agctccagct aaaaagacac attggagagc ttagaggata   2580
agtctctgga gcagaattta tcacacacaa aagttacacc aacagaatac caagcagaat    2640
gatgaggacc tgtaaaatac cttgtgccct attaaaaaaa aaaaaaaaa aaaaaaaaa      2700 aaaaaaa                                                              2707

<210> SEQ ID NO 264
<211> LENGTH: 732
<212> TYPE: DNA
<213> ORGANISM: Homo sapiens

<400> SEQUENCE: 264
atgggcaaga caagcagcc acgcggccag cagaggcagg ggggcccgcc ggccgcggac      60
gccgctgggc ccgacgacat ggagccgaag aagggcacgg ggggcccccaa ggagtgcggg   120 gaggaggagc cccggacctg ctgcggctgc cggttcccgc tgctgctcgc cctgctgcag    180
ctggccctgg gcatcgccgt gaccgtggtg ggcttcctca tggcgagcat cagctcctcc    240
```

| | |
|---|---|
| ctgctagtca gggacactcc attttgggct gggatcattg tctgcttagt ggcctatctt | 300 |
| ggcttgttta tgctttgtgt ctcatatcag gttgacgaac ggacatgtat tcaatttct | 360 |
| atgaaactgt tatactttct gctgagtgcc ctgggcctga cggtctgtgt gctggccgtg | 420 |
| gcctttgccg cccaccacta ttcgcagctc acacagttta cctgtgagac cacactcgac | 480 |
| tcttgccagt gcaaactgcc ctcctcggag ccgctcagca ggaccttgt ttaccgggat | 540 |
| gtgacggact gtaccagcgt cactggcact ttcaaactgt tcttactcat ccagatgatt | 600 |
| cttaatttgg tctgcggcct tgtgtgcttg ttggcctgct tgtgatgtg aaacatagg | 660 |
| taccaggtct ctatgtgggg tgtcaggata tgctccctca cggcttccga aggcccccag | 720 |
| caaaagatct aa | 732 |

<210> SEQ ID NO 265
<211> LENGTH: 681
<212> TYPE: DNA
<213> ORGANISM: Homo sapiens

<400> SEQUENCE: 265

| | |
|---|---|
| atggagccga agaagggcac gggggccccc aaggagtgcg gggaggagga gccccggacc | 60 |
| tgctgcggct gccggttccc gctgctgctc gccctgctgc agctggccct gggcatcgcc | 120 |
| gtgaccgtgg tgggcttcct catggcgagc atcagctcct ccctgctagt cagggacact | 180 |
| ccattttggg ctgggatcat tgtctgctta gtggcctatc ttggcttgtt tatgctttgt | 240 |
| gtctcatatc aggttgacga acggacatgt attcaatttt ctatgaaact gttatacttt | 300 |
| ctgctgagtg ccctgggcct gacggtctgt gtgctggccg tggcctttgc cgcccaccac | 360 |
| tattcgcagc tcacacagtt tacctgtgag accacactcg actcttgcca gtgcaaactg | 420 |
| ccctcctcgg agccgctcag caggaccttt gtttaccggg atgtgacgga ctgtaccagc | 480 |
| gtcactggca ctttcaaact gttcttactc atccagatga ttcttaattt ggtctgcggc | 540 |
| cttgtgtgct tgttggcctg ctttgtgatg tggaaacata ggtaccaggt cttctatgtg | 600 |
| ggtgtcagga tatgctccct cacggcttcc gaaggccccc agcaaaagat ctaacattct | 660 |
| tgctcaaagt tgcgagagaa a | 681 |

<210> SEQ ID NO 266
<211> LENGTH: 1502
<212> TYPE: DNA
<213> ORGANISM: Homo sapiens

<400> SEQUENCE: 266

| | |
|---|---|
| gtgaatttca ggcccagttg ctaaattttg tggcatcttc ctctagtcct tcccacctcc | 60 |
| agtcatcagc cccactctgt cttggagaca ggcaggaggt gggggaagag ctgaatctct | 120 |
| ttatttcccc tggtagagac atcttcaagg catgaaatag cttaaagagc agagtagaaa | 180 |
| cggaagaggc tttgcaaaag gctagataac taacaacacc tgggttgggg cggcggcctc | 240 |
| ttctctcttcag ctcccttagc ttggctccgt aagtggatca cttgccaaat gctttagatg | 300 |
| attgcctctc aataattgaa aggtggtggt agttgtattc taaatgatgt agaaggttta | 360 |
| aaaataatta cattatgctt ctattctatc atctaaaaca aatcattaaa actaatttct | 420 |
| agctaattgt taattataat tatgctcaga agtctattta atgagctctg actgtactta | 480 |
| cgctgcactg tcggtgttaa gagaaattac tctcacaaga gcagaggcct gaagattctt | 540 |
| tcttctgaaa gccaagcacc acaaggaaaa acaaattatt aatagctcag gttaaaaaca | 600 |
| cccatttaaa caaaaacaag agcatttgta ataggaagtg tttatacaaa tagcacattt | 660 |

| | |
|---|---|
| gtgatatgtt gaaaagcatc tctcttggca accaatctat gtttgaggaa gattgggtaa | 720 |
| tgctgatgtg ttccattcat gaaactgtat ttgatacata atcctattat taattcgtat | 780 |
| gcttagtcaa cctaggaaat caaaataatg ttttgaagtt cttatttgag caatatggcc | 840 |
| ttgacttgga gggtagtttt agttgttttg tttttaagtg actgtggttt aaagcacaaa | 900 |
| tgccccaagg tggggagact tctctctgtg attattgttg ctattaaatt ctgaactgta | 960 |
| tccatatttt aaggaaggag ctaaaaatgg aaattcatga acataaatg gtatcaagaa | 1020 |
| ctttatcagt atgctttgtt gaaagcagaa attaagataa taattgagtt caattcgcct | 1080 |
| ctccgcattg cctattgata cactttacta atcatgaaat tctaacctaa aaggaaaaca | 1140 |
| ttttcctgct tgtcttagaa gaaagtggaa taattccact gattgtgata atggtttcaa | 1200 |
| tttctacaca atataaatat ccagtataaa ggaaagcgtt aagtcggtaa gctagaggat | 1260 |
| tgtaaatatc ttttatgtcc tctagataaa cacccgatt aacagatgtt aaaccttta | 1320 |
| atgttttgat ttgctttaaa aatggccttc ctacacatta gctccagcta aaaagacaca | 1380 |
| ttggagagct tagaggataa gtctctggag cagaatttat cacacacaaa agttacacca | 1440 |
| acagaatacc aagcagaatg atgaggacct gtaaaatacc ttgtgcccta ttaaaaaaaa | 1500 |
| aa | 1502 |

<210> SEQ ID NO 267
<211> LENGTH: 4013
<212> TYPE: DNA
<213> ORGANISM: Homo sapiens

<400> SEQUENCE: 267

| | |
|---|---|
| tgtgtggaac acactcattt ggaggacttt tgtacacata ttttgtagtg tcacatatat | 60 |
| gttttaattt tgaattatat ataagggaag gtgggggaag gcatcatct tctcagagct | 120 |
| actttcctct gaacctggaa atgactgaa ctaatattac tttgtgaagt gtccatttac | 180 |
| cagaattgtt ctctgtagag agcaactttt gactgtggta atgtaattct tgcactaaga | 240 |
| actatgtgta ctagtctcaa aagctgggga ctctgagcct tacctagagt ctcagcaggt | 300 |
| ggaccattaa gattaacatt tctagtaggt gagttcaatc acaaaaatat ttcttgttcc | 360 |
| atagatttta ttgtggccat gtcagtgaac acccacaagt tttgctcaga atattttagg | 420 |
| tgtaagctaa atccctaaat tgttcagagt tcccacagcc ctgtagcagc agagcgagaa | 480 |
| ctttaaccag actttttcaa tcccaaagct aatctggagg ccaacagtgt tcaaaacctt | 540 |
| ggtgactgag gaaccattta gagttttttc aggctcagga atcacatggt cgttgttggg | 600 |
| cttgggggtaa gtttcacagg cgatgaagct gacgttgagt cacttgactt ctggagccat | 660 |
| aatttatttt ctcccagcaa cctcctactg gggattctca tgtttatgga tacagtttgg | 720 |
| caatcactac attgaatgta gtcttttaaa aaaattaact tatgctatta gttgacccat | 780 |
| cattgctaat tttggcccac acagtgtttg cattacaaaa acctgttctt tacttcctag | 840 |
| tcttgtttca gtcttaatat cagaagttct tgagttcaaa ataagcacaa catgtcatcc | 900 |
| agggatggct agcttgtttg ggattcatct aaactgctgg caatatctag acaaaaacat | 960 |
| tccacagtcc agctaaatg gttgtcacaa ctcttgaaaa gggcccaaca tctgatggc | 1020 |
| aagtgaaaat gtgatcaggg tttaagaact acccactaat aaataaacat ggagctattt | 1080 |
| ccatgtcttg ggtgttgtgt ttctaagaag agacagcctt tccatcagaa aatttctggg | 1140 |
| agggaagaaa aagaacagtt ttgatgaatt cgctttgcaa atcatcatcc aatgttcttt | 1200 |

```
gtaaccagaa aggttttctt ctgctttctt gcagctgtta tactttctgc tgagtgccct    1260
gggcctgacg gtctgtgtgc tggccgtggc ctttgccgcc caccactatt cgcagctcac    1320
acagtttacc tgtgagacca cactcgactc ttgccagtgc aaactgccct cctcggagcc    1380
gctcagcagg acctttgttt accgggatgt gacggactgt accagcgtca ctggcacttt    1440
caaactgttc ttactcatcc agatgattct taatttggtc tgcggccttg tgtgcttgtt    1500
ggcctgcttt gtgatgtgga acataggta ccaggtcttc tatgtgggtg tcaggatatg    1560
ctccctcacg gcttccgaag gcccccagca aaagatctaa cattcttgct caaagttgcg    1620
agagaaagta gcacatggag tagctgaggt taaacaaaca aaaaaaaatt ttaaacaaag    1680
aaaggaaaaa aattgacaat aaaagtcact cttctaattg aatattttta tattttatg     1740 aaacaaaaga gcatttcttc aggtttctat tgtattttt ttaacattct tgcagagaaa    1800
gcaagatcca aattgatttt gggatattaa aagttaacag aacactgaac aaggaaagaa    1860
tggcatagat ctatctttac agtctggagt taattcctgt taactcattt tatccattcc    1920
ttacataatc ttcttccctg ttagtccagt ttgatggtgt gaatggtgaa tttcaggccc    1980
agttgctaaa ttttgtggca tcttcctcta gtccttccca cctccagtca tcagccccac    2040
tctgtcttgg agacaggcag gaggtggggg aagagctgaa tctctttatt ttccctggta    2100
gagacatctt caaggcatga aatagcttaa agagcagagt agaaacggaa gaggctttgc    2160
aaaaggctag ataactaaca acacctgggt tggggcggcg gcctcttctc ttcagctccc    2220
ttagcttggc tccgtaagtg gatcacttgc caaatgcttt agatgattgc ctctcaataa    2280
ttgaaaggtg gtggtagttg tattctaaat gatgtagaag gtttaaaaat aattacatta    2340
tgcttctatt ctatcatcta aaacaaatca ttaaaactaa tttctagcta attgttaatt    2400
ataattatgc tcagaagtct atttaatgag ctctgactgt acttacgctg cactgtcggt    2460
gttaagagaa attactctca caagagcaga ggcctgaaga ttctttcttc tgaaagccaa    2520
gcaccacaag gaaaaaaaaa attattaata gctcaggtta aaaacaccca tttaaacaaa    2580
aacaagagca tttgtaatag gaagtgttta tacaaacagc acatttgtga tatgttgaaa    2640
agcatctctc ttggcaacca atctatgttt gaggaagatt gggtaatgct gatgtgttcc    2700
attcatgaaa ctgtatttga tacataatcc tattattaat tcgtatgctt agtcaaccta    2760
ggaaatcaaa ataatgtttt gaagttctta tttgagcaat atggccttga cttggagggt    2820
agttttagtt gttttgtttt taagtgactg tggtttaaag cacaaatgcc ccaaggtggg    2880
gagacttctc tctgtgatta ttgttgctat taaattctga actgtatcca tatttttaagg   2940 aaggagctaa aaatgaaat tcatgaaaca taaatggtat caagaacttt atcagtatgc    3000
tttgttgaaa gcagaaatta agataataat tgagttcaat tcgcctctcc gcattgccta    3060
ttgatacact ttactaatca tgaaattcta acctaaaagg aaaacatttt cctgcttgtc    3120
ttagaagaaa gtggaataat tccactgatt gtgataatgt ttcaatttc tacacaatat    3180 aaatatccag tataaaggaa agcgttaagt cggtaagcta gaggattgta aatatctttt    3240
atgtcctcta gataaaacac ccgattaaca gatgttaaac cttttaatgt tttgatttgc    3300
tttaaaaatg gccttcctac acattagctc cagctaaaaa gacacattgg agagcttaga    3360
ggataagtct ctggagcaga atttatcaca cacaaaagtt acaccaacag aataccaagc    3420
agaatgatga ggacctgtaa aataccttgt gccctattaa aaaaaaaaaa aaaaaaaag    3480 ccagtaactg aatccatttt gattttggt tgagtttcct acacaaagaa gaaaataact    3540
gagaatctgg aatgttgtag tccatccttt aaagagtaag aaagtagcag ttaatgctag    3600
```

```
taaccgtgaa ttaggcacca ctgaaagcac atcccgaatt tctttaacaa caacatttta    3660
tagtgaacac tacaagtttt tatatttaaa aattaagact ctgtatatcc ttaaggtgct    3720
ctatgcttta ccagtaattc acagggtatt tcaaatggta gaatcatttt agcttctgtg    3780
cttccttttt ctaaataatg caacttgtaa gagttgacat tgtaataagc tttataatag    3840
tataaccgtc aggagatata tatatatata tatacacata cacacacaca cacacatata    3900
tactatacat atataaaatg gggatattac tattgtatga ttaaatcatt cttaagtccc    3960
caaggaaaaa aaatcataaa caaatagaaa gaactaaaca gaaaagaaag aaa           4013

<210> SEQ ID NO 268
<211> LENGTH: 4003
<212> TYPE: DNA
<213> ORGANISM: Homo sapiens
<220> FEATURE:
<221> NAME/KEY: misc_feature
<222> LOCATION: 1,2,3,4,6,7,8,9,10,11,
      12,13,14,16,17,266,764,769,773,774,
      777,781,783,784,788,789,790,791,792,796,
      797,802,808,809,813,814,815,819,820,821,
      825,826,830,831,832,833,835,836,839,842,
      845,855,856,857,860,861,862,863,867,868,
      870,871,877,879,880,881,882,887,892,893,
      899,903,904,907,908,910,911,912,913,917,
      918,920,921,924,925,926,929,931,933,935,
      1011,1012,1015,1023,1026,1081,1098,1133,1136,1137,
      3472,3996,4000
<223> OTHER INFORMATION: n = A,T,C or G

<400> SEQUENCE: 268
yswktkkwwy wywytywttt ggaggacttt tgtacacata ttttgtagtg tcacatatat      60
gttttaattt tgaattatac ataagggaag gtggggaag ggcatcatct tctcagagct     120
actttcctct gaacctggaa atgactggaa ctaatattac tttgtgaagt gtccatttac    180
cagaattgtt ctctgtagag agcaactttt gactgtggta atgtaattct tgcactaaga    240
actatgtgta ctagtctcaa aagctkgggg actctgagcc ttacctagag tctcagcagg    300
tggaccatta agattaacat ttctagtagg tgagttcaat cacaaaaata tttcttgttc    360
catagatttt attgtggcca tgtcagtgaa cacccacaag ttttgctcag aatatttag     420 gtgtaagcta aatccctaaa ttgttcagag ttcccacagc cctgtagcag cagagcgaga    480
actttaacca gacttttca atcccaaagc taatctggag gccaacagtg ttcaaaacct    540
tggtgactga ggaaccattt agagttttt caggctcagg aatcacatgg tcgttgttgg     600
gcttggggta agtttcacag gcgatgaagc tgacgttgag tcacttgact tctggagcca    660
taatttattt tctcccagca acctcctact ggggattctc atgttatgg atacagtttg    720 gcaatcacta cattgaatgt agtctttaa aaaaattaac ttakgctakt agyygascca    780
kcmktgckmm kyttgsycca cmcagtgkyt gcmkyacamr maccyrttcy ywmcywccya    840
gyctygtttc agtckymatr ksmaagwwcw wgcagcmamr yrgccarcag akscagggrg    900
gcymgcykgy yksggaykcm kctrrrccyg rcrayatgga gccgaagaag ggcacggggg    960
cccccaagga gtgcggggag gaggagcccc ggacctgctg cggctgccgg kkccmgctgc   1020
tgmtcmgccc tgctgcagct ggccctgggc atcgccgtga ccgtggtggg cttcctcatg   1080
kcgagcatca gctcctcyct gctagtcagg gacactccat tttgggctgg gartcwytgt   1140
ctgcttagtg gcctatcttg gcttgtttat gctttgtgtc tcatatcagg ttgacgaacg   1200
gacatgtatt caatttttcta tgaaactgtt atactttctg ctgagtgccc tgggcctgac   1260
```

```
ggtctgtgtg ctggccgtgg cctttgccgc ccaccactat tcgcagctca cacagtttac    1320
ctgtgagacc acactcgact cttgccagtg caaactgccc tcctcggagc cgctcagcag    1380
gacctttgtt taccgggatg tgacggactg taccagcgtc actggcactt tcaaactgtt    1440
cttactcatc cagatgattc ttaatttggt ctgcggcctt gtgtgcttgt tggcctgctt    1500
tgtgatgtgg aaacataggt accaggtctt ctatgtgggt gtcaggatat gctccctcac    1560
ggcttccgaa ggcccccagc aaaagatcta acattcttgc tcaaagttgc gagagaaagt    1620
agcacatgga gtagctgagg ttaaacaaac aaaaaaaaat tttaaacaaa gaaaggaaaa    1680
aaattgacaa taaaagtcac tcttctaatt gaatatttt atatttttat gaaacaaaag    1740
agcatttctt caggtttcta ttgtattttt tttaacattc ttgcagagaa agcaagatcc    1800
aaattgattt tgggatatta aaagttaaca gaacactgaa caaggaaaga atggcataga    1860
tctatcttta cagtctggag ttaattcctg ttaactcatt ttatccattc cttacataat    1920
cttctttcct gttagtccag tttgatggtg tgaatggtga atttcaggcc cagttgctaa    1980
attttgtggc atcttcctct agtccttccc acctccagtc atcagcccca ctctgtcttg    2040
gagacaggca ggaggtgggg gaagagctga atctctttat tttccctggt agagacatct    2100
tcaaggcatg aaatagctta agagcagag tagaaatgga agaggctttg caaaaggcta    2160
gataactaac aacacctggg ttggggcggc ggcctcttct cttcagctcc cttagcttgg    2220
ctccgtaagt ggatcacttg ccaaatgctt tagatgattg cctctcaata attgaaaggt    2280
ggtggtagtt gtattctaaa tgatgtagaa ggtttaaaaa taattacatt atgcttctat    2340
tctatcatct aaaacaaatc attaaaacta atttctagct aattgttaat tataattatg    2400
ctcagaagtc tatttaatga gctctgactg tacttacgct gcactgtcgg tgttaagaga    2460
aattactctc acaagagcag aggcctgaag attctttctt ctgaaagcca agcaccacaa    2520
ggaaaaaaaa attattaata gctcaggtta aaaacaccca tttaaacaaa aacaagagca    2580
tttgtaatag gaagtgttta tacaaacagc acatttgtga tatgttgaaa agcatctctc    2640
ttggcaacca atctatgttt gaggaagatt gggtaatgct gatgtgttcc attcatgaaa    2700
ctgtatttga tacataatcc tattattaat tcgtatgctt agtcaaccta ggaaatcaaa    2760
ataatgtttt gaagttctta tttgagcaat atggccttga cttggagggt agttttagtt    2820
gttttgtttt taagtgactg tggtttaaag cacaaatgcc ccaaggtggg gagacttctc    2880
tctgtgatta ttgttgctat taaattctga actgtatccc atattttaag gaaggagcta    2940
aaaatggaaa ttcatgaaac ataaatggta tcaagaactt tatcagtatg ctttgttgaa    3000
agcagaaatt aagataataa ttgagttcaa ttcgcctctc cgcattgcct attgatacac    3060
tttactaatc atgaaattct aacctaaaag gaaaacattt tcctgcttgt cttagaagaa    3120
agtggaataa ttccactgat tgtgataatg gtttcaattt ctacacaata taaatatcca    3180
gtataaagga aagcgttaag tcggtaagct agaggattga aaatatcttt tatgtcctct    3240
agataaaaca cccgattaac agatgttaaa cctttaatg ttttgatttg ctttaaaaat    3300
ggccttccta cacattagct ccagctaaaa agacacattg gagagcttag aggataagtc    3360
tctggagcag aatttatcac acacaaaagt tacaccaaca gaataccaag cagaatgatg    3420
aggacctgta aaataccttg tgccctatta aaaaaaaaaa aaaaaaaaa arccagtaac    3480 tgaatccatt ttgatttttg gttgagtttc ctacacaaag aagaaaataa ctgagaatct    3540
ggaatgttgt agtccatcct ttaaagagta agaaagtagc agttaatgct agtaaccgtg    3600
aattaggcac cactgaaagc acatcccgaa tttcttaac aacaacattt tatagtgaac    3660
```

```
actacaagtt tttatattta aaaattaaga ctctgtatat ccttaaggtg ctctatgctt    3720
taccagtaat tcacagggta tttcaaatgg tagaatcatt ttagcttctg tgcttccttt    3780
ttctaaataa tgcaacttgt aagagttgac attgtaataa gctttataat agtataaccg    3840
tcaggagata tatatatata tatacacata cacacacaca cacacatata tactatacat    3900
atataaaatg gggatattac tattgtatga ttaaatcatt cttaagtccc caaggaaaaa    3960
aaatcataaa caaatagaaa gaactaaaca aaaaaraaar aaa                     4003
```

<210> SEQ ID NO 269
<211> LENGTH: 243
<212> TYPE: PRT
<213> ORGANISM: Homo sapiens
<400> SEQUENCE: 269

```
Met Gly Lys Asn Lys Gln Pro Arg Gly Gln Gln Arg Gln Gly Gly Pro
                 5                  10                  15

Pro Ala Ala Asp Ala Ala Gly Pro Asp Asp Met Glu Pro Lys Lys Gly
             20                  25                  30

Thr Gly Ala Pro Lys Glu Cys Gly Glu Glu Pro Arg Thr Cys Cys
         35                  40                  45

Gly Cys Arg Phe Pro Leu Leu Leu Ala Leu Leu Gln Leu Ala Leu Gly
     50                  55                  60

Ile Ala Val Thr Val Val Gly Phe Leu Met Ala Ser Ile Ser Ser Ser
 65                  70                  75                  80

Leu Leu Val Arg Asp Thr Pro Phe Trp Ala Gly Ile Ile Val Cys Leu
                 85                  90                  95

Val Ala Tyr Leu Gly Leu Phe Met Leu Cys Val Ser Tyr Gln Val Asp
            100                 105                 110

Glu Arg Thr Cys Ile Gln Phe Ser Met Lys Leu Leu Tyr Phe Leu Leu
        115                 120                 125

Ser Ala Leu Gly Leu Thr Val Cys Val Leu Ala Val Ala Phe Ala Ala
    130                 135                 140

His His Tyr Ser Gln Leu Thr Gln Phe Thr Cys Glu Thr Thr Leu Asp
145                 150                 155                 160

Ser Cys Gln Cys Lys Leu Pro Ser Ser Glu Pro Leu Ser Arg Thr Phe
                165                 170                 175

Val Tyr Arg Asp Val Thr Asp Cys Thr Ser Val Thr Gly Thr Phe Lys
            180                 185                 190

Leu Phe Leu Leu Ile Gln Met Ile Leu Asn Leu Val Cys Gly Leu Val
        195                 200                 205

Cys Leu Leu Ala Cys Phe Val Met Trp Lys His Arg Tyr Gln Val Phe
    210                 215                 220

Tyr Val Gly Val Arg Ile Cys Ser Leu Thr Ala Ser Glu Gly Pro Gln
225                 230                 235                 240

Gln Lys Ile
```

<210> SEQ ID NO 270
<211> LENGTH: 243
<212> TYPE: PRT
<213> ORGANISM: Homo sapiens
<400> SEQUENCE: 270

```
Met Gly Lys Asn Lys Gln Pro Arg Gly Gln Gln Arg Gln Gly Gly Pro
                 5                  10                  15
```

```
Pro Ala Ala Asp Ala Ala Gly Pro Asp Asp Met Glu Pro Lys Lys Gly
                20                  25                  30

Thr Gly Ala Pro Lys Glu Cys Gly Glu Glu Pro Arg Thr Cys Cys
            35                  40                  45

Gly Cys Arg Phe Pro Leu Leu Leu Ala Leu Leu Gln Leu Ala Leu Gly
    50                  55                  60

Ile Ala Val Thr Val Val Gly Phe Leu Met Ala Ser Ile Ser Ser Ser
65                  70                  75                  80

Leu Leu Val Arg Asp Thr Pro Phe Trp Ala Gly Ile Ile Val Cys Leu
                85                  90                  95

Val Ala Tyr Leu Gly Leu Phe Met Leu Cys Val Ser Tyr Gln Val Asp
            100                 105                 110

Glu Arg Thr Cys Ile Gln Phe Ser Met Lys Leu Leu Tyr Phe Leu Leu
            115                 120                 125

Ser Ala Leu Gly Leu Thr Val Cys Val Leu Ala Val Ala Phe Ala Ala
130                 135                 140

His His Tyr Ser Gln Leu Thr Gln Phe Thr Cys Glu Thr Thr Leu Asp
145                 150                 155                 160

Ser Cys Gln Cys Lys Leu Pro Ser Ser Glu Pro Leu Ser Arg Thr Phe
                165                 170                 175

Val Tyr Arg Asp Val Thr Asp Cys Thr Ser Val Thr Gly Thr Phe Lys
            180                 185                 190

Leu Phe Leu Leu Ile Gln Met Ile Leu Asn Leu Val Cys Gly Leu Val
                195                 200                 205

Cys Leu Leu Ala Cys Phe Val Met Trp Lys His Arg Tyr Gln Val Phe
            210                 215                 220

Tyr Val Gly Val Arg Ile Cys Ser Leu Thr Ala Ser Glu Gly Pro Gln
225                 230                 235                 240

Gln Lys Ile

<210> SEQ ID NO 271
<211> LENGTH: 243
<212> TYPE: PRT
<213> ORGANISM: Homo sapiens

<400> SEQUENCE: 271

Met Gly Lys Asn Lys Gln Pro Arg Gly Gln Arg Gln Gly Gly Pro
                5                   10                  15

Pro Ala Ala Asp Ala Ala Gly Pro Asp Asp Met Glu Pro Lys Lys Gly
                20                  25                  30

Thr Gly Ala Pro Lys Glu Cys Gly Glu Glu Pro Arg Thr Cys Cys
            35                  40                  45

Gly Cys Arg Phe Pro Leu Leu Leu Ala Leu Leu Gln Leu Ala Leu Gly
    50                  55                  60

Ile Ala Val Thr Val Val Gly Phe Leu Met Ala Ser Ile Ser Ser Ser
65                  70                  75                  80

Leu Leu Val Arg Asp Thr Pro Phe Trp Ala Gly Ile Ile Val Cys Leu
                85                  90                  95

Val Ala Tyr Leu Gly Leu Phe Met Leu Cys Val Ser Tyr Gln Val Asp
            100                 105                 110

Glu Arg Thr Cys Ile Gln Phe Ser Met Lys Leu Leu Tyr Phe Leu Leu
            115                 120                 125

Ser Ala Leu Gly Leu Thr Val Cys Val Leu Ala Val Ala Phe Ala Ala
130                 135                 140
```

```
His His Tyr Ser Gln Leu Thr Gln Phe Thr Cys Glu Thr Thr Leu Asp
145                 150                 155                 160

Ser Cys Gln Cys Lys Leu Pro Ser Ser Glu Pro Leu Ser Arg Thr Phe
                165                 170                 175

Val Tyr Arg Asp Val Thr Asp Cys Thr Ser Val Thr Gly Thr Phe Lys
            180                 185                 190

Leu Phe Leu Leu Ile Gln Met Ile Leu Asn Leu Val Cys Gly Leu Val
        195                 200                 205

Cys Leu Leu Ala Cys Phe Val Met Trp Lys His Arg Tyr Gln Val Phe
    210                 215                 220

Tyr Val Gly Val Arg Ile Cys Ser Leu Thr Ala Ser Glu Gly Pro Gln
225                 230                 235                 240

Gln Lys Ile

<210> SEQ ID NO 272
<211> LENGTH: 217
<212> TYPE: PRT
<213> ORGANISM: Homo sapiens

<400> SEQUENCE: 272

Met Glu Pro Lys Lys Gly Thr Gly Ala Pro Lys Glu Cys Gly Glu Glu
                5                   10                  15

Glu Pro Arg Thr Cys Cys Gly Cys Arg Phe Pro Leu Leu Leu Ala Leu
            20                  25                  30

Leu Gln Leu Ala Leu Gly Ile Ala Val Thr Val Val Gly Phe Leu Met
        35                  40                  45

Ala Ser Ile Ser Ser Ser Leu Leu Val Arg Asp Thr Pro Phe Trp Ala
    50                  55                  60

Gly Ile Ile Val Cys Leu Val Ala Tyr Leu Gly Leu Phe Met Leu Cys
65                  70                  75                  80

Val Ser Tyr Gln Val Asp Glu Arg Thr Cys Ile Gln Phe Ser Met Lys
                85                  90                  95

Leu Leu Tyr Phe Leu Leu Ser Ala Leu Gly Leu Thr Val Cys Val Leu
            100                 105                 110

Ala Val Ala Phe Ala Ala His His Tyr Ser Gln Leu Thr Gln Phe Thr
        115                 120                 125

Cys Glu Thr Thr Leu Asp Ser Cys Gln Cys Lys Leu Pro Ser Ser Glu
    130                 135                 140

Pro Leu Ser Arg Thr Phe Val Tyr Arg Asp Val Thr Asp Cys Thr Ser
145                 150                 155                 160

Val Thr Gly Thr Phe Lys Leu Phe Leu Leu Ile Gln Met Ile Leu Asn
                165                 170                 175

Leu Val Cys Gly Leu Val Cys Leu Leu Ala Cys Phe Val Met Trp Lys
            180                 185                 190

His Arg Tyr Gln Val Phe Tyr Val Gly Val Arg Ile Cys Ser Leu Thr
        195                 200                 205

Ala Ser Glu Gly Pro Gln Gln Lys Ile
    210                 215

<210> SEQ ID NO 273
<211> LENGTH: 5738
<212> TYPE: DNA
<213> ORGANISM: Homo sapiens
<220> FEATURE:
<221> NAME/KEY: misc_feature
<222> LOCATION: 356,357,358,396,627,691,1719,1722,1731,1739,
      3019,3228,3702,3946,3960,4004,4014,4015,4019,4024,
```

4026,4038,4039,4044,4046,4047,4048,4050,4053,4083,
4085,4087,4089,4090,4092,4094,4097,4098,4100,4105,
4108,4322,4935,4937,5401,5514,5519,5531,5532,5534
<223> OTHER INFORMATION: n = A,T,C or G

<400> SEQUENCE: 273

```
atgttgccag aaatatccac cacaagaaaa atcattaagt tccctacttc ccccatcctg      60
gcagaatcat cagaaatgac catcaagacc caaacaagtc ctcctgggtc tacatcagag     120
agtaccttta cattagacac atcaaccact ccctccttgg taatacccca ttcgactatg     180
actcagagat tgccacactc agagataacc actcttgtga gtagaggtgc tggggatgtg     240
ccacggccca gctctctccc tgtggaagaa acaagccctc catcttccca gctgtcttta     300
tctgccatga tctcaccttc tcctgtttct tccacattac cagcaagtag ccactmskct     360
tctgcttctg tgacttcact tctcacacca ggccamgtga agactactga ggtgttggac     420
gcaagtgcag aacctgaaac cagttcacct ccagtttga gcagcacctc agttgaaata     480
ctggccacct ctgaagtcac cacagatacg gagaaaattc atcctttctc aaacacggca     540
gtaaccaaag ttggaacttc cagttctgga catgaatccc cttcctctgt cctacctgac     600
tcagagacaa ccaaagccac atcggcwatg ggtaccatct ccattatggg ggatacaagt     660
gtttctacat taactcctgc cttatctaac rctaggaaaa ttcagtcaga gccagcttcc     720
tcactgacca ccagattgag ggagaccagc acctctgaag agaccagctt agccacagaa     780
gcaaacactg ttcttttctaa agtgtccact ggtgctacta ctgaggtctc caggacagaa     840
gccatctcct ttagcagaac atccatgtca ggccctgagc agtccacaat gtcacaagac     900
atctccatag gaaccatccc caggatttct gcctcctctg tcctgacaga atctgcaaaa     960
atgaccatca caacccaaac aggtccttcg gagtctacac tagaaagtac ccttaatttg    1020
aacacagcaa ccacaccctc ttgggtggaa acccactcta tagtaattca gggatttcca    1080
cacccagaga tgaccacttc catgggcaga ggtcctggag tgtgtcatg cctagccct    1140
cccttttgtga aagaaaccag ccctccatcc tcccgctgt ctttacctgc cgtgacctca    1200
cctcatcctg tttccaccac attcctagca catatccccc cctctcccct tcctgtgact    1260
tcactttctc acctctggcc cggcgacaac cacagatatc ttgggtacaa gcacagaacc    1320
tggaaccagt tcatcttcaa gtttgagcac cacctcccat gagagactga ccacttacaa    1380
agacactgca catacagaag ccgtgcatcc ttccacaaac acaggaggga ccaatgtggc    1440
aaccaccagc tctggatata atcacagtc ctctgtccta gctgactcat ctccaatgtg    1500
taccacctcc accatggggg atacaagtgt tctcacatca actcctgcct tccttgagac    1560
taggaggatt cagacagagc tagcttcctc cctgaccct ggattgaggg agtccagcgg    1620
ctctgaaggg accagctcag gcaccaagat gagcactgtc ctctctaaag tgcccactgg    1680
tgctactact gagatctcca aggaagacgt cacctcggrg arcatccatc hcaggtccyg    1740
ctcaatccac aatatcacca gacatctcca caagaaccgt cagctggttc tctacatccc    1800
ctgtcatgac agaatcagca gaaataacca tgaacaccca tacaagtcct ttaggggcca    1860
caacacaagg caccagtact ttggccacgt caagcacaac ctctttgaca atgacacact    1920
caactatatc tcaaggattt tcacactcac agatgagcac tcttatgagg aggggtcctg    1980
aggatgtatc atggatgagc cctccccttc tggaaaaaac tagaccttcc ttttctctga    2040
tgtcttcacc agccacaact tcaccttctc ctgtttcctc cacattacca gagagcatct    2100
cttcctctcc tcttcctgtg acttcactcc tcacgtctgg cttggcaaaa actacagata    2160
```

```
tgttgcacaa aagctcagaa cctgtaacca actcacctgc aaatttgagc agcacctcag    2220
ttgaaatact ggccacctct gaagtcacca cagatacaga gaaaactcat ccttcttcaa    2280
acagaacagt gaccgatgtg gggacctcca gttctggaca tgaatccact tcctttgtcc    2340
tagctgactc acagacatcc aaagtcacat ctccaatggt tattacctcc accatggagg    2400
atacgagtgt ctccacatca actcctggct tttttgagac tagcagaatt cagacagaac    2460
caacatcctc cctgaccctt ggactgagaa agaccagcag ctctgagggg accagcttag    2520
ccacagagat gagcactgtc ctttctggag tgcccactgg tgccactgct gaagtctcca    2580
ggacagaagt cacctcctct agcagaacat ccatctcagg ctttgctcag ctcacagtgt    2640
caccagagac ttccacagaa accatcacca gactccctac ctccagcata atgacagaat    2700
cagcagaaat gatgatcaag acacaaacag atcctcctgg gtctacacca gagagtactc    2760
atactgtgga catatcaaca cacccaact gggtagaaac ccactcgact gtgactcaga    2820
gattttcaca ctcagagatg accactcttg tgagcagaag ccctggtgat atgttatggc    2880
ctagtcaatc ctctgtggaa gaaaccagct ctgcctcttc cctgctgtct ctgcctgcca    2940
cgacctcacc ttctcctgtt tcctctacat tagtagagga tttcccttcc gcttctcttc    3000
ctgtgacttc tcttctcamc cctggcctgg tgataaccac agacaggatg gcataagca    3060 gagaacctgg aaccagttcc acttcaaatt tgagcagcac ctcccatgag agactgacca    3120 cttttggaaga cactgtagat acagaagaca tgcagccttc cacacacaca gcagtgacca    3180
acgtgaggac ctccatttct ggacatgaat cacaatcttc tgtcctakct gactcagaga    3240
cacccaaagc cacatctcca atgggtacca cctacaccat gggggaaacg agtgtttcca    3300
tatccacttc tgacttcttt gagaccagca gaattcagat agaaccaaca tcctccctga    3360
cttctggatt gagggagacc agcagctctg agaggatcag ctcagccaca gagggaagca    3420
ctgtcctttc tgaagtgccc agtggtgcta ccactgaggt ctccaggaca gaagtgtatat    3480 cctctagggg aacatccatg tcagggcctg atcagttcac catatcacca gacatctcta    3540
ctgaagcgat caccaggctt tctacttccc ccattatgac agaatcagca gaaagtgcca    3600
tcactattga gacaggttct cctggggcta catcagaggg taccctcacc ttggacacct    3660
caacaacaac cttttggtca gggacccact caactgcatc tycaggattt tcacactcag    3720
agatgaccac tcttatgagt agaactcctg gagatgtgcc atggccgagc cttccctctg    3780
tggaagaagc cagctctgtc tcttcctcac tgtcttcacc tgccatgacc tcaacttctt    3840
ttttctccac attaccagag agcatctcct cctctcctca tcctgtgact gcacttctca    3900
cccttggccc agtgaagacc acagacatgt tgcgcacaag ctcagracct gaaaccagty    3960
cacctccaaa tttgagcagc acctcagctg aaatattagc cacstctgaa gtcrscaarg    4020
atasakagaa aattcatmmc tccycmmmcr camctgtagt caatgtaggg actgtgattt    4080
atrawcwtmw aycmcckycm tctgwttygg ctgacttagt gacaacaaaa cccacatctc    4140
caatggctac cacctccact ctggggaata caagtgtttc cacatcaact cctgccttcc    4200
cagaaactat gatgacacag ccaacttcct ccctgacttc tggattaagg gagatcagta    4260
cctctcaaga gaccagctca gcaacagaga gaagtgcttc tctttctgga atgcccactg    4320
gygctactac taaggtctcc agaacagaag ccctctcctt aggcagaaca tccaccccag    4380
gtcctgctca atccacaata tcaccagaaa tctccacgga aaccatcact agaatttcta    4440
ctcccctcac cacgacagga tcagcagaaa tgaccatcac ccccaaaaca ggtcattctg    4500
gggcatcctc acaaggtacc tttaccttgg acacatcaag cagagcctcc tggccaggaa    4560
```

```
ctcactcagc tgcaactcac agatctccac actcagggat gaccactcct tatgagcaga    4620
ggtcctgagg atgtgtcatg gccaagccgc ccatcagtgg aaaaaactag ccctccatct    4680
tccctggtgt ctttatctgc agtaacctca ccttcgccac tttattccac accatctgag    4740
agtagccact catctcctct ccgggtgact tctcttttca cccctgtcat gatgaagacc    4800
acagacatgt tggacacaag cttggaacct gtgaccactt cacctcccag tatgaatatc    4860
acctcagatg agagtctggc cacttctaaa gccaccatgg agacagaggc aattcagctt    4920
tcagaaaaca cagcwgygac tcagatgggc accatcagtg ctagacaaga attctattcc    4980
tcttatccag gcctcccaga gccatccaaa gtgacatctc cagtggtcac ctcttccacc    5040
ataaaagaca ttgtttctac aaccatacct gcttcctctg agataacaag aattgagatg    5100
gagtcaacat ccaccctgac ccccacacca agggagacca gcacctccca ggagatccac    5160
tcagccacaa agccaagcac tgttccttac aaggcactca ctagtgccac gattgaggac    5220
tccatgacac aagtcatgtc ctctagcaga ggacctagcc ctgatcagtc cacaatgtca    5280
caagacatat ccactgaagt gatcaccagg ctctctacct cccccatcaa gacagaatct    5340
acagaaatga cattaccacc caaacaggtt ctcctggggc tacatcaagg ggtacccttn    5400
kccttggaca cttcaacaac ttttatgtca gggaccccact tcaactgcat ctcaaggatt    5460
ttcacactca cagatgaccg ctcttatgag tagactcctg gagatgtgcc atgrctaasc    5520
catccctctg skgmagagcc cgcctctgcc tctttctcac tggcttcacc tgtcttgacc    5580
tcattttttt cgttttttgc ccattcccaa aaacctccac cttttttggt tcctgggcaa    5640 acttttttccc tagggctggg gaaacccaaa atgtggggcc aacccagaac tgaaacattc    5700
cccccaatgg acaaccttttt tgaaaagggc cctttgc                             5738

<210> SEQ ID NO 274
<211> LENGTH: 1024
<212> TYPE: DNA
<213> ORGANISM: Homo sapiens

<400> SEQUENCE: 274
ccccacccga acacactca gcccttgcac tgacctgcct tctgattgga ggctggttgc     60
ttcggataat gacctccagg accccactgt tggttacagc ctgtttgtat tattcttact    120
gcaactcaag acacctgcag cagggcgtga gaaaaagtaa agaccagta ttttcacatt     180 gccaggtacc agaaacacag aagactgaca cccgccactt aagtggggcc agggctggtg    240
tctgcccatg ttgccatcct gatgggctgc ttgccacaat gagggatctt cttcaataca    300
tcgcttgctt ctttgccttt ttctctgctg ggttttttgat tgtggccacc tggactgact    360
gttggatggt gaatgctgat gactctctgg aggtgagcac aaaatgccga ggcctctggt    420
gggaatgcgt cacaaatgct tttgatggga ttcgcacctg tgatgagtac gattccatac    480
ttgcggagca tcccttgaag ctggtggtaa ctcgagcgtt gatgattact gcagatattc    540 tagctggggtt tggatttctc accctgctcc ttggtcttga ctgcgtgaaa ttcctccctg    600
atgagccgta cattaaagtc cgcatctgct tgttgctgg agccacgtta ctaatagcag    660
gtaccccagg aatcattggc tctgtgtggt atgctgttga tgtgtatgtg aacgttcta     720 ctttggtttt gcacaatata tttcttggta tccaatataa atttggttgg tcctgttggc    780
tcggaatggc tgggtctctg ggttgctttt ggctggagc tgttctcacc tgctgccttat    840 atcttttttaa agatgttgga cctgagagaa actatcctta ttccttgagg aaagcctatt    900
```

| | | |
|---|---|---|
| cagccgcggg tgtttccatg gccaagtcat actcagcccc tcgcacagag acggccaaaa | 960 | |
| tgtatgctgt agacacaagg gtgtaaaatg cacgtttcag ggtgtgtttg catatgattt | 1020 | |
| aatc | 1024 | |

<210> SEQ ID NO 275
<211> LENGTH: 1024
<212> TYPE: DNA
<213> ORGANISM: Homo sapiens

<400> SEQUENCE: 275

| | | |
|---|---|---|
| ccccacccga acacactca gcccttgcac tgacctgcct tctgattgga ggctggttgc | 60 | |
| ttcggataat gacctccagg accccactgt tggttacagc ctgtttgtat tattcttact | 120 | |
| gcaactcaag acacctgcag cagggcgtga gaaaaagtaa aagaccagta ttttcacatt | 180 | |
| gccaggtacc agaaacacag aagactgaca cccgccactt aagtggggcc agggctggtg | 240 | |
| tctgcccatg ttgccatcct gatgggctgc ttgccacaat gagggatctt cttcaataca | 300 | |
| tcgcttgctt cttttgccttt ttctctgctg ggttttttgat tgtggccacc tggactgact | 360 | |
| gttggatggt gaatgctgat gactctctgg aggtgagcac aaaatgccga ggcctctggt | 420 | |
| gggaatgcgt cacaaatgct tttgatggga ttcgcacctg tgatgagtac gattccatac | 480 | |
| ttgcggagca tcccttgaag ctggtggtaa ctcgagcgtt gatgattact gcagatattc | 540 | |
| tagctgggtt tggatttctc accctgctcc ttggtcttga ctgcgtgaaa ttcctccctg | 600 | |
| atgagccgta cattaaagtc cgcatctgct tgttgctgg agccacgtta ctaatagcag | 660 | |
| gtaccccagg aatcattggc tctgtgtggt atgctgttga tgtgtatgtg gaacgttcta | 720 | |
| ctttggtttt gcacaatata ttttcttggta tccaatataa atttggttgg tcctgttggc | 780 | |
| tcggaatggc tgggtctctg ggttgctttt tggctggagc tgttctcacc tgctgcttat | 840 | |
| atctttttaa agatgttgga cctgagagaa actatcctta ttccttgagg aaagcctatt | 900 | |
| cagccgcggg tgtttccatg gccaagtcat actcagcccc tcgcacagag acggccaaaa | 960 | |
| tgtatgctgt agacacaagg gtgtaaaatg cacgtttcag ggtgtgtttg catatgattt | 1020 | |
| aatc | 1024 | |

<210> SEQ ID NO 276
<211> LENGTH: 24110
<212> TYPE: DNA
<213> ORGANISM: Homo sapiens

<400> SEQUENCE: 276

| | | |
|---|---|---|
| ccccacccga acacactca gcccttgcac tgacctgcct tctgattgga ggctggttgc | 60 | |
| ttcggataat gacctccagg accccactgt tggttacagc ctgtttgtat tattcttact | 120 | |
| gcaactcaag acacctgcag cagggcgtga gaaaaagtaa aagaccagta ttttcacatt | 180 | |
| gccaggtacc agaaacacag aagactgaca cccgccactt aagtggggcc agggctggtg | 240 | |
| tctgcccatg ttgccatcct gatgggctgc ttgccacaat gagggatctt cttcaataca | 300 | |
| tcgcttgctt cttttgccttt ttctctgctg ggttttttgat tgtggccacc tggactgact | 360 | |
| gttggatggt gaatgctgat gactctctgg aggtaagaag atagcagctt cttttcatga | 420 | |
| tccaggccag cccaaatttt cgctaagtcc caactgccat gtacaacatt cagtatcttt | 480 | |
| actaaggcta atgataccaa aaataggcaa catggactat ttattgagtc tttacattat | 540 | |
| tagctcattt aatcctcata gttaatttat gaggtaggtc ttgttatccc attaaacaga | 600 | |
| tgaagttact aaatagttcc tccttttttc acaaggataa atttccacaa gggtaattaa | 660 | |

```
gtgatctctg ctactgagac ctccagaaat tcacgtcttc cattgctgca tatatcatat    720
tgagtaacat ttcagtacca ccctttttc  taagataaat tttttactct tgatgacagc    780
attaagaata gtgtgataga cttttttaa  ggagtgttaa taatctaaaa cgttgagaaa    840
gaaaatgcaa ggcatgcaaa acctacccaa ttaacatgca agaggaaaaa acattatctt    900
aatgatttcc aagtaaaaga aaaaatgttg agggagaaaa tgtctttcca gtgcatccca    960
atgtacgggg acaggcatg  gatttaaatc ctcccttaaa atgagttgct ctagggaact   1020
gactactatt caaagatga  gtgagtgggt tcacatttga ggattttatt tttctcgctg   1080
gagaagctca gaaagaagta attttgaagt tcaaaaccat tacctgtggc cataggaatc   1140
tgagagaggc agaactgagt aaaaaatcaa atcttcagaa ttagctgctg ttcattaatg   1200
aggcttagga aaacacaggt aagaaaaaga aacaatattt caagagctca aaaaaggag    1260
tatatagcaa aacaatttgc tttttaatgt gcatcctgaa gggaacaatt taccctagca   1320
aatgctataa tgtcacctct ataaagttta agaaagatac tcgactgagt ttatatattt   1380
ttcttctaat tttctttatt aaactctcaa attggagttc caatggaaa  gtaataatga   1440
ttctattttg ctgtgcatta ttttgctgc  tcgctttttc ttgcttttaa tttgcctctg   1500
acttgaacat ggcatttcaa aaccaatgga gttcttaat  cctctttaat gctagaaaat   1560
tacatttcca aaaattgtga tagaattgaa ctactgtaaa ggatgtctgc tataagtgag   1620
cccagtgatg catttatct  ggccatgaat atatgcaaag aatgaaataa atgcccttg    1680
aacagtgctc agggaaaagt gcagataaaa cgttctgctg tcattagttt gccattatct   1740
agatggccag tggtaggtga tgaatacaga aatatgttta acttgagcat aattataatt   1800
atgttttta  aaatacaaaa aaatgtaaaa tcccatctag gggcattgtt aaaatatttt   1860
ctaaaacaat ttaaaagtct ttctgcttaa gctgacataa ttgctaactt catttgataa   1920
gaaatagttt tagaaagggt caaaccttgc tgagagagag attgagagtc ctggaattta   1980
aagtgtcttc tttcatttta gtataaccaa ccaatttgcc atctgtccca tgaaagaata   2040
cttctagtta aaacgaatgg aatgagcagt ccaggttaca cacctcaagt aaaccccttgc  2100
taaccttgaa aaatagttaa tatttcttag cttccttctt atttcccata cttaaaatgt   2160
attgctataa tattcccaag aagccttcac atttaaagga agaggctggg catggtggct   2220
tatgcctgta atcccaatac tttggaaggc cgaggcgggc agatcacagg tcaagagatt   2280
gagaccatcc tggccgacat agtgaaaccc catctctaac aaaaatacaa aaattagctg   2340
ggtgtggtgg caggggcctg tagtcccagc tactaaggag gctgaggcag gagaatcgct   2400
tgaactaggg aggaggaggt tgcactgagc cgagattgtg ccactgcact ccagcctggc   2460
gacagagcga gactccatct taaaaaagaa gaagaagaag aagaaccctg taacaaatcc   2520
ggctcccttc tctttcaaca atctctttag ttgtcaatat ttttaaagag acaataatct   2580
cttataataa ttgctacttc aacaggccag gatagaaact tatattttcc acaaatttga   2640
aggttctgat gctagctcaa ttgctcttct cttttcttgc cgccatcctc atttatatat   2700
cacctttggt ccatataaca actcacttta tgttttatt  tttattttt  tatagatttg   2760
gtctcacgct gtcacccagg atagagtgta ctggtgtgat catatctcac tgcagattca   2820
aacttctagg ctcaagtcat cctcccacct cagcctccct agtagctagg cctacaggtg   2880
catgtcccca caactggcta attttaaaaa ttttttgtaa gaacaaggac tttctctgtt   2940
ctctaggctg gtctccaact ccaggcctca agtgatcctc ttgcctcggc ctcctaaagt   3000
```

```
actgggatta taggagtgaa ccaccacagc agctcacttt aatccattgt tggacaaaag   3060
tcaacgaaac aagtgttttg ttttgttttg atttttaag aaaaaaaagg aataccaata    3120
gacaatttaa ataagaagga gtattatact tttccagttt tttttttttt ttttagtata   3180
tttggatgat gttggcacgg gatttagaag aagagttttg tggttcaatt cagtataaaa   3240
atatatacaa ttatatcata taaaaggaat gatgctactc ctactagaag agacaaagat   3300
aaagcaaaaa ttgctcctgc ctctcaggag tgcacattta atgagggaaa aacaaagata   3360
cacatgaaac tataataaaa agcataaata aattcatatt ttgagcaaga aataaacgaa   3420
gtatcattgg ggaagaaaat atgcgatgat tacttcctat cagggccatc gaagcaggtc   3480
tcatgaaaga aaaggcattt gagcaaagcc ttgaaacgat gtaaagcatt tcaaattgta   3540
gaaatggcag caggggcctt tcagataagg ggacagagtg gcaaaagtgc aaagagagga   3600
gaagctcagg gcttgttaga ggactaaagt gggcaacaca aagaaggagg cagaaaaagc   3660
tcagatattc ttttgccta ccacactcta cctatctcaa atgaagttct tcgtattagg    3720
taaaaatgct aggaaagaaa atagcacaca gaattacgat gtgcacaacc ctacatcagt   3780
gactagaggc cctcagctac catcctgctc ttgtcattat tgattcattt gtgtctctga   3840
gaagactgat agggagaaga gaatttgggt tttgagattt tcaagcgta tgtttgcatc    3900
ttaacccta ttaactgcct tctattaagc aagtcacatt tcttgtcttt ggctcagttt    3960
tttcaattgt atagttgaac tcagttgttt ctaaggtcct tttcagtctt tttttttttt   4020
tttttaacat catgtctcca tgactgtctg aaacttcaga gagttggaca ctcactaatg   4080
gactggtggt gtctggcact tctccagaca tttccattgg gaatctagtg gaaggatcct   4140
ccatttttct gtagcttcat acactctccc ttccttcatt ccaacttctc ttttccttc    4200
atttccttgt tccttccttc ctcttcttta ttccccctct ctcttttcct cccttttctt   4260
aactctctct ctttccctcc tatatccttc ttttctttc tttctcttc ttcttcatct    4320
ctttacccct tcatttctct ctcttttctt tctacctttt gtcatttcac aaataatctc   4380
tgacaacttc tgtatacttg gcaccatggt gggtacatgg ttatgaagta ggatgagacc   4440
tggagcctcc ctaggctact gccagtgtag tgagtgggac aaataggtga accgacagtt   4500
atagcaccat gtagcacaca ctatgataat gaaaaccta agcgagtggc tcacttggtc    4560
ttggataacc agtgaaagct acccaaaaga agagatatct aaactaggac ttgaagaaca   4620
ggtgagtgaa gcaggagaag tagagagtat tccaagctca ggaaatggca ggaactgagg   4680
tcaaggtaca agagcgttgt atgtttgcgg tatttgtat atttcatcat agtaagaatt   4740
tccagtttag agaaaagaat acaggggttg ggtcattaag agttttgcat aacatgtaaa   4800
atatagatct tataccatag gcaagggttt gtcgctgtaa gcaatatgta catgtatttt   4860
agaaagatta atcattctgg ctatctgtgg ggagagattg gaagggtaaa atgaggtatg   4920
gggagaacaa ctaggagact tttgttatag accagaaggg agacaatagt ggtctgtact   4980
tcagtgacag caagcatgaa gaaatatgaa ataagggagg ctctaaaaat gtcaaattga   5040
tgagagttat aattgactgc atgtggggaa gtaggtgatg aagagacaca gtcaaagatg   5100
aaatctgcct ttctgatctg gggcaattgg agggtggtg atgttactca ccaagagttt    5160
aaatgaatga aaattagtat ctatacagaa accttcatgg agcaatgtcc ctgaaccatc   5220
ctactatttt tttctgctta gcttattata caatacttag aggtaggaac acaattcttt   5280
acaatggaga tgtttataga tttaacttta tatcagaggg acctgaggtt aaatcccacc   5340
ttaccaggca gtggctgtat gaatttagac agactcttaa atagctataa accacatttc   5400
```

```
ctattcagta atgagagaat aacaatacac acatcataag tttcttgtga gaattaaatg    5460
agcttgtgta tctaaagcat ttgccacagc agcaggcaga tatgaatcag ccaataaata    5520
ttagatacat tattgtctat ttgcagttta ttggtttgtt tttgttctgg agaaggagat    5580
gacattttgc ataatgttcg ctgaacagag aaatataagg tttaaattct attcctattt    5640
ttggtattgc ttctcttgga gaattttgt ttcctcctct aaagctgtca tttgccttt     5700 tttttttttt ttttttttaaa tcagaatctc tctctgtcgc ccaagctgga gtgcagtggc    5760
atgatcttgg ctcactgcag cctccacctc ctgagttcaa gcgattctcc tgcctcagcc    5820
tcctgagtag ccgggactac aggcaagcac caccacaccc ggctaatttt tttgtatttt    5880
ttgtagagac ggggtttcac catattggcc aggctcgtct tgaactcctg acctcaggtg    5940
atccgcccac ctcatcctcc caaagtgctg ggattacagg tgtgaaccag catggctggc    6000
cacccatttt tatatttaca tctatttcct ttttgtctga ccagggaaat aagcacagata    6060 ataagtcaaa tagtgaaggt tatttatcaa atgctcacat ttacaaagaa aataaattga    6120
gataatagca ttgttaatat gttaactaca agatatgcaa ttcttaatta tttcacactga    6180 aatagtttct tcacacagta gttactgatc tctcaattat aaaaaggaaa aagtgttttc    6240
acaagaagat ttcattttca gttcatcttt gttaattatt tattgagaac ctgctatgta    6300
ctgagcacta gtatgattaa aatttttatta cctcaaaaca aagttgctca cattagtatt    6360 tatttatct gtataatcag gttctcttct gggatttcta tttgcattaa tattacaatt    6420
cttttaaata taaagtaaat attaaaatta ttatatccag catgcccgtt gattatatcc    6480 attttaaac tttccaattg atttcaaact ctttcagcag atgtttgagg ctacaaatgt    6540
tctcttattt atctcatgat ttcctaagta cctagcactg atgtacatta atgtgaactc    6600
atgatgcatt tgctcacatg agttgataga gcgcctagta acacacttag catacctgtt    6660
gaaagaatga atatattaat gatatgaggt gattattgaa atctcacat tgaaccttaa    6720 ataagaagta tgtctgtaat gaaatgatca ttttttttaaa gcaagatttc gtatcttgct    6780
acaatttaaa tattttcagg atatgtattt ggttcatttt taaaaataaa attggaatac    6840
aaatctgatt cttgggatat ctaataaggt tgatgaagag tatattctgg actagagaat    6900 gtggctttt gcttagtgct ttaaagagag aaataaagaa aacagagaga aaaagaaat    6960 tgataatttg taataattta ctcaacataa attgtgatct ttatcactgg gcaataatca    7020
ttacaaagtt gtaatgccat acttttaaaa ggaagacatt ttaacgtatg taaccattta    7080
aaaatgttaa aatgaaaata tttagaaagt tcagatatat aacgtaggtc atatacctgt    7140
gaagagcaca aaattttatt tttctactaa gttggcatta cccatttctt atgatttata    7200
cctttagcca gtgctccaca aataaccaga actaaaacaa ataaattta gcaaataaag    7260 tcatgttttt ctttcgtatc ttataaatgt aagatataaa gtaaaagaa aaggcaacat    7320 tgattatgat tattttagtc ttgctccctc atctttatta aggcctgtat tgactccatt    7380
taggccctgg gatagtaaaa aatataatat aaaatgtaaa ggtaaaatgt tcagagtctt    7440
ggttggaaaa tttaaatgca ttttatgtta aaattgaaaa tgtttccaat tttagtagtc    7500
aaacgttatt tactacaata ttattaaaac ttttgcgtct taataaatat aagtaagtac    7560
taagtaggta tctaagtagg aaagtcacat cttcaaggtt aaaatatatt agcacatgga    7620
tagtaaagtg gtgtgaaaat tataaattct tacaatttgt atatgcaagg tggttttta    7680 aaataatata tcttaatagc ttattttctt ttagttgtct gtacatttat aatcttaatg    7740
```

```
catattgaca aaaaataatc ttgatagcgg ttaaccaaca ataaacattt acaaaatctg    7800
ctgtgtatat ttactctctc tctctctctg tagatagata catagataga tagatagata    7860
gacacacaca cagacataat ttcctatgtt actagagaag agataaatgc cgaacattgt    7920
tgaatgtctc taattctcaa gtattttta gtgtttctaa ttctcaaaag atacataaaa     7980
agacaaggca ggcaaaattg ttgctgctta tatttcaaga ttgataacaa aagagaaact    8040
gggaaaaact aggttagaga agtcttaatg ggagactgct atagagtcca gaataagaaa    8100
tcccaggatt aaggaactaa tttatgtcac tgtaactcaa gttggaagag tcatcatctc    8160 tatggttttcc taacactttt aagtgacatc ctactcattt ttagtactgt ggtaaacact    8220
ttccagagcc agttgagtaa acaaggtcca gaatgacacc aaatcaatgt aagctcttca    8280
gtctaaatca taatttttg gcttctggat ttagctgttt tgttatt agtcaagtag         8340 aaattgcact tattaagtag caactgtgca tataataacc attttctgct ccaaacttcc    8400
aatgagagta tatgaattga ttgacaaatt gagattttct tatcctcact aaacatttat    8460
taagcaccta ttatgtatca agagtaagag actgtatgct ccttgaagcc agctgccatg    8520
tttgtcttta ttatcgctgt atctccagca ttaatatagt cggcatgttg actagtaaat    8580
gacaggcatt taataaatat agtttgaaga ataacagatg acctataatt gcacatacaa    8640
aagataatgc aatattttaa atgctataat aatatgaca aattcctgtg ggatttcagg     8700
atagaaagtg ataaatgcca gctagagaga cttgggtggt gggaggctaa tgaaaaaaca    8760
gaagtcttta aaatggggct tgaataataa gtagaagttt gacaggttga gagcaaggag    8820
ttattctcat tagtataatt agtatatacc aggaagagaa aactcaaatg ccttaaggaa    8880
ccaagtagcc agcgttcacg agagaggcag gttgggtagg atctgtgggg aacctggtga    8940
gcctgagctc cacctaaatg ggagcagcca ctcctttctt gccagttgtt gctttgtgag    9000
actggtgagt tcaggtaccc agaatgacca agtttctaag ggaaccctga aatctgaact    9060
gttctgtaaa atctctacac attttttggca actaattaag agatttttttg ctttcctcat   9120 gcttgtgact tctactttat tattgtacct taaataaacc tacctctctc catttagcag    9180
gtaatccact cttcactttt gggaacaata gatattcatt gaaacaatac aaattagcat    9240
tgttttaacg ttatttatca atatataagt tgcatgttag aaggagaaat tttaaattta    9300
taatcctcta tttcagacaa ctctgtcaga ttaaaagtta ttacttaaca tttgcatttt    9360
ttacccttta agaaaggtta actatgatat ttgaaacatc agtctgcttt tttaagaacc    9420
ctgtcttaaa attttcaaga atttagattt gcttgctttt tagtttctaa taagccattt    9480
tacaacagag gaataagtaa atgaagatga taaatcatac cagagagcat tcctaaaatat   9540 aataaaaaac atgaaaaatt gtaaccttgt cttttgtgca caaaggcacc tttaagggtg    9600
tctccagtga gtgctacatt aacacagaag tttagttaat tacagccact attctcacgt    9660
accttaactg agtgtgaata ccaagccatc taatagtgtg cccctgagca ttaataccta    9720
atgaaattgg attccttgtt ttctctaatg agctcattgc ttttctaaat atggtcattg    9780
caggtaaatg atcaatagcc ttgaaactga taccactact gaattatttt ggcaagatgg    9840
aaatactctt atttgtgtaa aataagaatt tttgaatatg catttcagat cactttctaa    9900
ataatgtcat gtatgacagg aatgaccata gtaggctagt ttgtttcagt ggctggctta    9960
tacagtaaga aattgtggag agtcgctgtc tgatttacag cacagtgcct tcaaacttgt    10020
atcacctagc ttgagctaaa gtgaactgga tgcagcgtgt tcctgttcat taagacacta    10080
cagggcagtc agctttgaga agatctgttt tctgttatga tatagcagtt ctgtacaaac    10140
```

```
tgtctctaat atactaattt cctatagttg ccgtaacaaa tgaccataaa ctcggtggct    10200
taacaaaaga taactttatt ctctcacagt tctggaggct ggaagcttat aatcaagaag    10260
ttggcaaggc tgcgctgccc ctgaaagttc tggaagaatc cgttcttagc ctcttccagc    10320
ttctggtggc tgtaggcatt ccttgacttg tagctttatc cctccaatgt ctctgcctca    10380
gaggtcacat tgcatctttc ttttgtctgt ttctctcctg catgtgtctc ttataatgaa    10440
atttgtcagc ccacctgtat aacccaatat gatctcaagg tcctcagtta cattttcaaa    10500
gatccttttt ccaaataagg tcatatactg gtggtaagaa tgtggacata tctttctgag    10560
ggcctccatc tttctccacc ttcactgtgg ttagttagta aagcctaaca cagccactac    10620
tcaagtcatt atgatgttta agcactttac taccactatt tttatttatt gagcatatca    10680
tttatattgc gtgtgtattt gtaattttta attcttataa ccatcctatg attatctccc    10740
gtatacagat aaggagattg aggatcaaaa aaggtaagat cttccccaag gttacaacat    10800
agatagtaag agtttcaatc tatatttaat atttaatgca tatataaatt taatttacgt    10860
gtaatgcaca tataaattta gacgtccaca ttatttagaa atttatatgt tgaatttcac    10920
aagatagctg tttatcatta gattttttga tctctgtgtt acacaggatg agataatcct    10980
ccagaaagtc caagaattgt ttccaactta aacctaagga ggagcatgcc aaggtgaagt    11040
tcgcagaata atagccttgg gatgagatcc aagttagggc ttacttcacc caaagctatc    11100
atccaatacc caattctgga ttactttatt ttaaaatgga tttggaattc tttttaaaaa    11160
aatgtttta ggctgggcac ggtgcctcac gcctgtaatc ccagcacttt gggaggccga    11220
ggtgggcgga tcacctgagg tcaggagttc gagatcagcc tgaccaacat ggggaaaccc    11280
cgtctctact aaaaatactt aaaaaaaaaa agtagcctgg cgtggtggcg catgcctgta    11340
atcccatcta ctcgggaggc tgaggcagga gaatcgcttg aacccagaag gtggaggttg    11400
ccgtgagccg atcgcgccat gcactccag cctggggaaa acagcgagac tctgcctcaa    11460
aaaaaattgt ttttaaacat ttgtaactgt ttaaacaatt ttttagcaca tatgcatctt    11520
cttaaatggg gtacctagtg atgttttgat acatataatg tatagtgatc ccattagggt    11580
aattagcata cccatcatct caaacattta tttttgttg gaaacattaa atatccttt    11640
ttctagctat ttgaaattat atcattatta acaatagcca tcctagagtg ctatagaaca    11700
ggggtccaca accccaggc cacagaccag tactagtccg tggcctgtta gtaactgggc    11760
tgtgcagtgg gaggtgagca gtgagcaagt gagcattacc gcctaatggt ggacagaagc    11820
tccaccttct gtcggatcag cggcagtatt cgattctcat aggagtgcaa accctgttgt    11880
gaactgcaca tgcgagggtt ctgagttgca tgctccttac aagcacctaa tgcctgatga    11940
tctgagctgg aacagtttca tccaaaagca tccccaaccc cctacccact ggttccatgg    12000
aaaaattgtc ttgcacgaaa ccggtccctg gtgccaaaaa ggttgaagac cactggtata    12060
gaacactgga acttattcct cttatctagc tgcaattttg tatctcttaa caaatctctc    12120
cttgttcctt ggcccctacc cttcccagcc ttcagtatcc tctgtcttat ttttacctc    12180
gaggtttttt tttctgtttg tttgtttaga cggaatctcg ctctgtcgcc aggctgcagt    12240
gcagtggcgc gatctcggct cactgcaaca tccgactcag tggttcaagc gatgctcctg    12300
cctcccgagt ggctgggatt acaggcacgc accaccacgc ctagctaatt tttgtatttt    12360
tagtagagac ggggtttcac catgttagcc aggatgatcc cgatctcctg acctcttgat    12420
ccgtccgcct cagcctccca aagtgctggg attacaggcg tgagccaccg tgcccgaccg    12480
```

```
agatcaactt cttatagctt ccacatatga gtaaaaatat gcaatgttta actttctatt    12540
cctggcttat ttcatttaac attattcagt tccatccatg ctgacttaaa taaaagaatt    12600 tcattttta aattgttaaa tagtattcca ttgtgtagat ataccatatt gtatttaccc     12660
attgctctgt ggttggatat ctaggttgat tccatgtctt ggctattgtg aatagtgtca    12720
caaagagcat ggaggtgcgc acatactgat ttcctttcct ttgaataaat gcccagtagt    12780
gagatttgtt ggatcataaa gaatgggttt taaacacact gcaatgctca ggagcacacc    12840
cacacactgc tgtgtttgag tcctatctcc tccattaact atgctttctt ggggttactt    12900
aactttcctg tgccccaatt tcctcatttg taaaatggat gataaataat atctcttaac    12960
gtcccttaag aaataagaaa ataataata tgctaaatag taactgcttt atggtataga    13020
ctctgtattg aataattatt accaactata agtattttac atataaagta gtaatagagg    13080
taaaacattc agaatcgcga tgaagttgca agcagtagaa ttttatttgg cacataacac    13140
ggcctcaaaa aatagcatgg ggcagagagt ttcatagtgc atgtattcct gaatattatt    13200
ttattttcca aagcaaagtg ttcttatgtt tttttttctc cccacagcaa tttaaccccc    13260
tcctttgcat tcctcatccc accctgctct gttattatt cttcttggg gaaaaaatta     13320 agttttatt ttccaagata attcatagtt aaactttact aaactattcc cagatacaga    13380
aggtaatttg aatccataac tgggtcagag gaaacaattg tattagctct gttccatatg    13440
cgtgagctct atcaagaaca cctgaaacta ttttctgttg gcatgtttac gattctaaga    13500
aatctattgt gacttacggt ttgtagataa agtatgagaa ggttcaggga actggtacct    13560
tctagctcta agtggattct tagagtcatc tgcacatcat ttccaagtaa aaatggatta    13620
cagtcgtcaa gttgtatgaa attaatgctc aatctgctta catcctttac atagcttaag    13680
catttataat atatcattgg agcaataaat aagacttggg gcctttatat attttattta    13740
ttggcatctt ttcatttatt ggttttcttt gctaattatt ttatatttat aaacttcata    13800
tataaagata atattttctt tcatggaact cagtattcgt gataaagaaa caatatatat    13860
ttttaataga ctcaaggtgt caacagttat catctattgt tatatatata tatatttttt    13920
ggtgagtaaa tgtcagcaca gtgacatgaa atgatgtttt tccataacca taactcaatg    13980
gtggaagcag ccacagatat ttaaatatat ttagctctgg ttttatctct tccagacgtg    14040
acttatttct ctaccccac ccttcatgag gaagtggatt catttcctgg cccagaaagg     14100
cttcaattgt cagtgcttaa gggaaaatat tctaatacgc attgtttgtt gtaaatgaag    14160
ttctgatcac atgtgtaacc acttactttg ctatcaaaca caaccaccaa cttctctttt    14220
tgatcaaggg gaactgaact gtgcctgcat gaattgtttc acacggtgtc ttctctaaca    14280
tctaggtgag cacaaaatgc cgaggcctct ggtgggaatg cgtcacaaat gcttttgatg    14340
ggattcgcac ctgtgatgag tacgattcca tacttgcgga gcatccctgt acgtatgcct    14400
tagagctcac tgcttgccag gaagggaaag ggacagaaaa ctgagttcag gtttccattt    14460
tgtgctttgt tttctattgt actatattaa ggttcggtcc agtttgtaat ggttagaaat    14520
tgagctcatc tcgaaatgt gaattgaaat atatacttca gcacattttc tctttctca     14580 tatatttgta aattcattga gggaaaaata ttatcttatt aatctctgct gtccctcaga    14640
gggccaggca tagtgcttca tactcagcag gcttacagta aatggttttt taatcgaaat    14700
aaactcttta gggtgctgta atttcattat taaactggac gggttagggg gaaagcattt    14760
cagagatgtt ttaagctatg acttagttca aatagaaagt ttacagttat ttcagttgaa    14820
ggttagctaa gaaagagaga gtggcagagg cagaaagagg cagacagcca gagagagaga    14880
```

```
catagactat ggggatcagt ggaagaaaaa accaacacat gtgacgcact gttacaggca    14940
atattgaagc tggctcccct atcttcctta cttttagctt taaattatag ttaaagccag    15000
gtgcagtggc tcacacttgt aatcctagca ctttgggagg ccaaggcggg tggatcactg    15060
gaggtcagga gttcgaaacc agcctggcca acatggtgaa accccatccc taataaaatt    15120
accaaaaaaa gttagctcat catggtggtg ggagcctgta gttccagcta gtcaggagac    15180
tgaggcagga gaatcacttg aacccagaag gcagaggtta cagtgagccg agatcacacc    15240
actgcactcc agcctgggag acagagcaag acttcatctc aaaaataaaa taataaataa    15300
ataaattata gttacatgtc agcagagccc atgttgctat gaataaagaa atgtcttaaa    15360
tttaaaaatc ttactgttga ttctctcaat ccttctccat agtgtttatt tgtttatttta   15420 taagaacatc gaaccctgct aagaaacatc tgttctgtta tgaaagcaaa gtggttttag    15480
tctctttcaa agcaaatgat gggtgatggc accataaggc aacttctttt ctcaagataa    15540
ataaaaaatt aagcccttgg aatgtgactt ttcccctgaa cctctatttc agtccagagg    15600
aaagcactta aaaacagcag cactctaaaa ttcttcatct gctatttaaa agttgggtgc    15660
gtggaacatt tttaaaaaca tagttcataa ggtctttgtt ttattttgt taaaaaggat     15720 tttcttaatt ctttttcttt tcccctctct gtgctaacct agttctacct acaaagaaac    15780
actatttgct gaataggaat ggacattttg tctattctaa aaattcatta aaatggattt    15840
taattcataa gctgataaga aaatgaaaaa ttaaaaaaaa tttaaaactt ttaaatactg    15900
ttatatacat ttatgcaaga agaaaatata atcactcata agctcactac gtagagaaaa    15960
ccactgttta tatttaatat gttccttttt catctttgac ctatgtaacc tattaacata    16020
tgggggtaga gaaataagtc acgtctggaa gagataaaac ccatatggcc taatatgtaa    16080
tattggccaa gaagagtcat gatttaaata gctgaaagag aaaatgatct aatttccaga    16140
aattaccttc tacttaatag cacaaactaa ctctccttct tctaaagatc tccttatggc    16200
ttcttctatc ctgaactggc aaaaagaagt cttgaaatat tttattctgc ttccctgtgt    16260
caaattttag ccaattatta ttttttaaata aaaaaaaatt aaagtgatta tttattcaat    16320
atttattaag aaattttgt aggacagata tgctaccttc gattcagcaa tcggctacaa     16380
tatttgtgaa tgagacattt tccagagtag gaggcaaaaa ggaaaacatt tatttagttt    16440
ccactatcta ccaggatgct ctctgctagc ataccaacaa caaaactaag tagtgaactg    16500
tggttaaaca agcaataatg tcaataatct catattttt agttttatga aaacattagg     16560
ggtacttatg ttcaagttca tacaaagtct gacttttacc ggaggggtgt gttaatgtta    16620
cctacttgtc tgttttttt gctatgtctc tgtgagttaa tatggttcct tcttctgact     16680
ctgctttaac catatgccct ggtcttccag tgaagctggt ggtaactcga gcgttgatga    16740
ttactgcaga tattctagct gggttttggat ttctcaccct gctccttggt cttgactgcg   16800
tgaaattcct ccctgatgag ccgtacatta agtccgcat ctgctttgtt gctggagcca     16860
cgttactaat agcaggtacc ggtctggctg gactagcaac aggggtaggg agactctgct    16920
aagggcttga ggtgaaggag agagttgtgc tgaagctgct cattttcgga ttatatgtgg    16980 cttcccttc tagattgaaa aactaaaggt cacttctacc agcctgcat actttagctt      17040 tgaagtcagc taattagtct tttgttaata tctcagaaca aaatatgaag ctctcaggcc    17100
gggtgtggtg gctatgcct atattcccag cactttggga ggccaaggca ggcagatcac     17160
ttgaggccag gagtttgaaa ccagctggcc atcatggtga aaccctatcc ccactaaaaa    17220
```

```
tacaaatcca ggcatggtgg tgcacacctg tagtcccagc tactcggcgg ggctgaggca   17280
ggagaatcgc tcgacccag gaggcggagg ttgcagtgag cagagatcgc gccactgcac    17340
tccagcctgg gcaacagagc aagactccgt ctcacggaaa aaaaaaaaaa aaaaaaggaa   17400
ataaagaaaa aaaaaagctc taaaactatg ttttggccat ttaaaaagtt acataacttc   17460
aatttttaaa ataatttatc ttgtgattat tactgaagtt aaaatcctaa agtaagcccc   17520
aaacttctac ctccttacct atacccacca ccaccaactc caccaattct ttttaacaat   17580
aaactaacaa ttgtgccaag tcctatgtta aacttgtccc acgtactaac ccatttgttc   17640
ataaatgtaa caataaacag atcatattgt tatcctcact taagatgcag ataaataatt   17700
gaagttctga ggactggtca agcatattta ttagtcaagc atgactaata aacaacatat   17760
caaaaagcac tttaagtagt atttattagt gaaacagcaa aaatgatact ttattcaggt   17820
ctgtcttcaa cttcaaagct tagtcctctt cttttgcaac ataatgtctt cttcttgtct   17880
gttagcagga aaaatcttgt ctgctaacaa agcgaatata agtggcagcc tgaccaggca   17940
gtgtggggta gtacatcgat atggagtttg gaactagaaa cacttgtaga tatgtatgtg   18000
tgatatattc acccgtgtct ctgtttcctg atctgcaaag aggcatgagg ctaaggtagt   18060
aacatgtagc ctgaattgct atggtgaaga tgcaatgtgg gcacagcaaa ctgttagctg   18120
actgcctaac cctttgtatg ctcagaactt gggcctccct gacttttgac acagaaatgt   18180
taagtcaacg tcctaataat cctcagattg tattataaag ttacaaaaat ttagaattct   18240
tcccttctgt aagtcattta tttaattatc ccacctactg acagcataga acttttttaat  18300 atacaatgta attcatttaa cagatttaaa cattatttaa tctaattatt tacggctata   18360
taattttgtt cgagaatatt tttgagctat catcagtaaa taacccatct tatgtaaaac   18420
aacaaaacaa atagcattta aaaaataagt cactgaagaa aatcctgata ggaatgactg   18480
aagaaataac taaattgaaa gacaaagcat gtcctaagct ttggaaactt tagaattagt   18540
gtgctataaa atttattttt aaagtctata atctgttttg aaggtttaga aagggaattt   18600
ctaactgaaa actgcagata atggcattat agcaatgcta ttgcaatata tactgcgttt   18660
tctaaaggtt atgtgtttat tatctggctt ttttttttt ttttttttga gatggagtct   18720
cgctctgtcg cccaggctgg agtgcagtgg cgtgatctcg gctcactgca agctccacct   18780
cctgggttca cgccattctc ctgcctcagc ctcccaagta gctgggacta caggcgccca   18840
ccaccacgcc tggctacttt ttgtattttt agtagagaag gggtttcacc atgttggcca   18900
ggatggtctc aatctcttga cctcgtgatc cgcccgcctc ggcccccaa agcgctggga   18960 ttacaggtgt gagccaatgt gcccggccta tctgctcctt cttaaagttc ttacattaaa   19020
caattaggag aagaatacag ttaaatagtg atttaaatag atatcacaga ctatctaggg   19080
aaaaaaatgt aaaattttt ggagactaca tattttattt tattttttta gatttgggaa   19140
agacaaatat ttctctcatt agacagtaaa acaactctgg aaagtaatct gaagagattg   19200
tttgtgaaca catgcatcta acttagcaca gagtagcaga actttgaaat gaaggaaaag   19260
taggatccag ttatttgggt gttggtgggc aagatcttaa cactaacgtt gatacagctt   19320
caggatatca gtaagcatac atttacaagt aaataactga aaatccaact caagcagact   19380
tagacaacat atagagattact gatttcttgt aattgccttc tgctaggcat tgagcatgtg   19440
gagagtacat attttaaaaa cactcttta attcagtgtt ttgtcctcca actcaccaca   19500
tttcttattg catctaggct tcaacatgca atttatacct ttaaaataac aggacactag   19560
tggcgtcatt tcaaaccagt taattgtcag agaggctaag ctgtggagat gtatttaaag   19620
```

-continued

```
ggaataacat ttcttggtcc attcttatat ggtgtgaggg tagtagataa agatttattt   19680
gaaaataaaa acatttttta cttcaattat ttgtgtttga cctcaagaca ctgaaatcag   19740
tgactttaaa aacagttttc acatgggtgc tgattacgta gctggcatag cttcaaaagg   19800
gggtacaggg agcattaaat acaatgatat ttactcacaa tttaaaaatc attacagaat   19860
gaacatatgc tctatgttgt ttgtgttaga ctacattctt tttctgtttt gtttggtttt   19920
gttttagtat tttcctttat acaatactaa catggcattg gaaagacagg agaatcaaag   19980
aaaaccataa cgatgaattt cgatttacac agataagcac tgtgttattt cattttgca    20040
ttttctttat gtataaactg agataaaatt taaaaaagat acaagatgga aggcaaaagg   20100
aagagacaga agaagtgtcc gaagttcggg ttgcccatga atccatgtta ctgtttttac   20160
ctctctgaat cacgccagcc attttgtgta gtaagcaggt attttggat ttaaattcag    20220
aaaatgtccc ctattatttg tagcatcctc cctttctttc aggtaccca ggaatcattg     20280
gctctgtgtg gtatgctgtt gatgtgtatg tggaacgttc tactttggtt ttgcacaata   20340
tatttcttgg tatccaatat aaatttggtt ggtcctgttg gctcggaatg gctgggtctc   20400
tgggttgctt tttggctgga gctgttctca cctgctgctt atatcttttt aaaggtaaga   20460
ataaataaa atagcaaatt tccttgcctc cactatcgtt tttcccaatc cagtggaaac    20520
aaatttcaaa aggaaaaaaa tgttatttat ttgaattcct acctattgcc attaaaaatt   20580
ccaattgttc aagggcaatt gaattgtaat actcaaacat tattacccag ttagttctat   20640
attaattgaa aaataaaatc cacaactaca agcatgtcca atattcaaat gtataatagt   20700
tatcttgatg tattacaatt atacatatat acatatatac acacatatac ataccgtata   20760
tatactatat atgtatatat actatataca tatatataca catatagtat atatactata   20820
tatacatact gtatatatac ccttgtatat atacgtatac atagtacata tgtatacaca   20880
tatacacata tgtatatgca tatatgtata tgtatacata tatgtataat tgtaatacat   20940
caaaataact attgtacatt tgaatattgg acatagttgt agttgtggat tttttcaatt   21000
aatgtaacac taacttggta ataatgtttg agtattgtaa ttcagttgcc cttgaacaat   21060
tggaattttt aatggtaatt ggaattttta atggtaacag gtaggaatac acccatgtat   21120
atgcatgtat atatacacac acgtatatgc atgtatatat gcacacacgt atatgcatgt   21180
atatatgcac acacgtatat gcatgtatat atgcacacat gtatatgtat gtatatatgc   21240
acacatgtat atgtatgtat atgcacacat gtatatgta atattagaat tatacatata   21300
tgtgtgtcta tatatacaat tatacctttta taattgtatg catatatgta gatatacata   21360
taattgtaat acattaaaat aactattata catttgaata ttggacatgg ttgtagttgt   21420
gaattttcta tatatatata ttttgatgta ttacaattat acatgcatat atatcttcac   21480
ccactcaact aaatgtatat ttagtgttaa actgagaagt ggactaagat ccagccaaat   21540
acttcttttt aaagaattta acatgttatg ttgggtttct aaaaatatca cctaaaaaac   21600
taagggaata cctctcctga tgaagaaaaa aaaaataaca ggaaatctac ttggctgaat   21660
tttaaaccta aagaaacttt tcagaatgaa aatcttaaat tgtcttctag gattcttctt   21720
agagttccaa aatgataccct tctttgagta tctatattct tgttccttt gaggaagaac     21780
atataaaatg gtattttata attttcccaa gttcactgag ttctacttat ttttatattt   21840
ctttcaaaca gatgttggac ctgagagaaa ctatccttat tccttgagga aagcctattc   21900
agccgcgggt gtttccatgg ccaagtcata ctcagcccct cgcacagaga cggccaaaat   21960
```

```
gtatgctgta gacacaaggg tgtaaaatgc acgtttcagg gtgtgtttgc atatgattta   22020
atcaatcagt atggttacat tgataaaata gtaagtcaat ccaggaacag ttatttagaa   22080
ttcatattga attaaattaa ttgctagctt aatcaaaatg tttgattctc ctatactttt   22140
tctttctatt actcttatat tttcccgtca ttctctctgc taaccttcca ccttatgcac   22200
acactttccc tatattttaa gataagtctg ctaggatgta gaaatatttg tttgtgattt   22260
ctatatagct attagagatt atgacatagt aatattaaaa tgaaatgata cttaaacaga   22320
aagcaatttc caaagaggcc agggacccta atctttgaag agatgaagaa acttactttt   22380
ctccctggct tttggttcac ttttttgtact tttaacaagt gggtgaatta tttgataatt   22440
ttgaggaaga ttattctttt aaattcaaac tagtatgtca atgcctacca ttactctgat   22500
tatattaaaa cagaaaaagg aaataacaac ttcgtatacc agccactggt gagagttaaa   22560
gacaagagct gcccccccac ccccaaatgt caaaggcaaa tgctaaattg atactggagc   22620
tcgtggtgac tttctacctc actaacaaca taagggatct ccatattatt tcaccactat   22680
tctagctttg ctgatatatt gccaaatgat tagactacag aatagttcaa ccagagaatt   22740
tactcattta ttgattaaac atccaaatac tattgtaata tactatgtta aaattcatca   22800
attcaagtgc ccacacacca ctgaatcatc agcaccaagc aatatattag acatatggca   22860
aaattcaaca atatatttt gatataaata aataaacgtt cacgacttta cttaaaaaat   22920
caatgttgcg gctgggcacg gtagctcgcg tctgtaatcc ccgcactttg ggaggccaag   22980
gcgggtggat cacgaggtca agagacggag accatcctgg ctaacatggt gaaaccctgt   23040
ctctactaaa aatacaaaaa ttagccgggc gtggtggcgg tgcctgtagt cccagctact   23100
cgggaggctg aggcaggaga atcgtttgaa cccaggaggt ggaggttgca gtgagcggag   23160
atcgcaccat tgcactccag tctggcaaca gagcgagact ccatctcaaa aacaaaaat   23220 aaataaataa ataaatattc ttcataaaat gtgggttttg gggaaaatat agaattacat   23280
atacatttaa cgaagtcgct aatgacattt cattcatatt cataatgtaa ccatcttgaa   23340
tttttttaat tgtagcgatt ttaaaaatgt ttgtaaaatt taatttccag ttttctaatt   23400
acttgtcagt cacattaata acattagtac ctttatggta cccttgcagt acctgaaaag   23460
aatatcaacc tgaaaagaat atcaactcac ccagaaatta gttctttgaa aaaaagaaa   23520 ttaagttgtg aatttctaaa gaccttgaaa taagtgtttc aaatttaaag aacaaagaat   23580
gatgtgaaaa tgagattatg attcctacta catgaattaa cgtttcgaga ttgctgttta   23640
ttacttccca gagtatcttt aacagtattc tctgaagcag ttccaatcta gttggagaat   23700
taacagcaat tgatttaact atctcatttt tattaactgt aatttacttt aaaaatattt   23760
gcaaatcata ctcattagtt atttgatcat tgttctatgc attttaaaat taattttgtg   23820
ttgttcctct caatatttgt ttttaacatt tattcccatt tttatttat actattgtct   23880 gtcatgcttt atgtattcca ataagtgtct tgaaatcctt gtggggaaag gcaggacaaa   23940 ataattagt taattagatt tgaaaaatgt aattttcca ttttaaatat ttcatttgta   24000
taagaaaata tttcagagaa ccatgatgat aatggatatg tgtgactgtt ttgaatttt   24060 ttctcaatta aaacattttg tatgtaatgg gaggaatgtc aagatttgtt           24110
```

<210> SEQ ID NO 277
<211> LENGTH: 3111
<212> TYPE: DNA
<213> ORGANISM: Homo sapiens
<220> FEATURE:
<221> NAME/KEY: misc_feature
<222> LOCATION: 2411,3089,3090,3091,3092,3094,3095,3098,3099,3100,
    3101
<223> OTHER INFORMATION: n = A,T,C or G

<400> SEQUENCE: 277

| | | | | | |
|---|---|---|---|---|---|
| ccccacccga | aacacactca | gcccttgcac | tgacctgcct | tctgattgga | ggctggttgc | 60 |
| ttcggataat | gacctccagg | accccactgt | tggttacagc | ctgtttgtat | tattcttact | 120 |
| gcaactcaag | acacctgcag | cagggcgtga | aaaaagtaa | aagaccagta | ttttcacatt | 180 |
| gccaggtacc | agaaacacag | aagactgaca | cccgccactt | aagtggggcc | agggctggtg | 240 |
| tctgcccatg | ttgccatcct | gatgggctgc | ttgccacaat | gagggatctt | cttcaataca | 300 |
| tcgcttgctt | ctttgccttt | ttctctgctg | ggttttgat | tgtggccacc | tggactgact | 360 |
| gttggatggt | gaatgctgat | gactctctgg | aggtgagcac | aaaatgccga | ggcctctggt | 420 |
| gggaatgcgt | cacaaatgct | tttgatggga | ttcgcacctg | tgatgagtac | gattccatac | 480 |
| ttgcggagca | tcccttgaag | ctggtggtaa | ctcgagcgtt | gatgattact | gcagatattc | 540 |
| tagctgggtt | tggatttctc | accctgctcc | ttggtcttga | ctgcgtgaaa | ttcctccctg | 600 |
| atgagccgta | cattaaagtc | cgcatctgct | tgttgctgg | agccacgtta | ctaatagcag | 660 |
| gtaccccagg | aatcattggc | tctgtgtggt | atgctgttga | tgtgtatgtg | aacgttcta | 720 |
| ctttggtttt | gcacaatata | ttcttggta | tccaatataa | atttggttgg | tcctgttggc | 780 |
| tcggaatggc | tgggtctctg | ggttgctttt | tggctggagc | tgttctcacc | tgctgcttat | 840 |
| atctttttaa | agatgttgga | cctgagagaa | actatcctta | ttccttgagg | aaagcctatt | 900 |
| cagccgcggg | tgtttccatg | gccaagtcat | actcagcccc | tcgcacagag | acggccaaaa | 960 |
| tgtatgctgt | agacacaagg | gtgtaaaatg | cacgtttcag | ggtgtgtttg | catatgattt | 1020 |
| aatcaatcag | tatggttaca | ttgataaaat | agtaagtcaa | tccaggaaca | gttatttaga | 1080 |
| attcatattg | aattaaatta | attgctagct | taatcaaaat | gtttgattct | cctatacttt | 1140 |
| ttctttctat | tactcttata | ttttcccgtc | attctctctg | ctaaccttcc | accttatgca | 1200 |
| cacactttcc | ctatatttta | agataagtct | gctaggatgt | agaaatattt | gtttgtgatt | 1260 |
| tctatatagc | tattagagat | tatgacatag | taatattaaa | atgaaatgat | acttaaacag | 1320 |
| aaagcaattt | ccaaagaggc | cagggaccct | aatctttgaa | gagatgaaga | aacttacttt | 1380 |
| tctccctggc | ttttggttca | cttttttgtac | ttttaacaag | tgggtgaatt | atttgataat | 1440 |
| tttgaggaag | attattcttt | taaattcaaa | ctagtatgtc | aatgcctacc | attactctga | 1500 |
| ttatattaaa | acagaaaaag | gaaataacaa | cttcgtatac | cagccactgg | tgagagttaa | 1560 |
| agacaagagc | tgcccccca | ccccaaatg | tcaaaggcaa | atgctaaatt | gatactggag | 1620 |
| ctcgtggtga | ctttctacct | cactaacaac | ataagggatc | tccatattat | ttcaccacta | 1680 |
| ttctagcttt | gctgatatat | tgccaaatga | ttagactaca | gaatagttca | accagagaat | 1740 |
| ttactcattt | attgattaaa | catccaaata | ctattgtaat | atactatgtt | aaaattcatc | 1800 |
| aattcaagtg | cccacacacc | actgaatcat | cagcaccaag | caatatatta | gacatatggc | 1860 |
| aaaattcaac | aaatatattt | tgatataaat | aaataaacgt | tcacgacttt | acttaaaaaa | 1920 |
| tcaatgttgc | ggctgggcac | ggtagctcgc | gtctgtaatc | ccgcactttt | gggaggccaa | 1980 |
| ggcgggtgga | tcacgaggtc | aagagacgga | gaccatcctg | gctaacatgg | tgaaaccctg | 2040 |
| tctctactaa | aaatacaaaa | attagccggg | cgtggtggcg | gtgcctgtag | tcccagctac | 2100 |
| tcggaggct | gaggcaggag | aatcgtttga | acccaggagg | tggaggttgc | agtgagcgga | 2160 |
| gatcgcacca | ttgcactcca | gtctggcaac | agagcgagac | tccatctcaa | aaacaaaaa | 2220 |

-continued

```
taaataaata aataaatatt cttcataaaa tgtgggtttt ggggaaaata tagaattaca    2280
tatacattta acgaagtcgc taatgacatt tcattcatat tcataatgta accatcttga    2340
atttttttaa ttgtagcgat tttaaaaatg tttgtaaaat ttaatttcca gttttctaat    2400
tacttgtcag ycacattaat aacattagta cctttatggt acccttgcag tacctgaaaa    2460
gaatatcaac ctgaaaagaa tatcaactca cccagaaatt agttctttga aaaaaaagaa    2520
attaagttgt gaatttctaa agaccttgaa ataagtgttt caaatttaaa gaacaaagaa    2580
tgatgtgaaa atgagattat gattcctact acatgaatta acgtttcgag attgctgttt    2640
attacttccc agagtatctt taacagtatt ctctgaagca gttccaatct agttggagaa    2700
ttaacagcaa ttgatttaac tatctcattt ttattaactg taatttactt taaaaatatt    2760
tgcaaatcat actcattagt tatttgatca ttgttctatg cattttaaaa ttaattttgt    2820
gttgttcctc tcaatatttg tttttaacat ttattcccat tttattttta tactattgtc    2880
tgtcatgctt tatgtattcc aataagtgtc ttgaaatcct tgtggggaaa ggcaggacaa    2940
aaataattag ttaattagat ttgaaaaatg taatttttcc attttaaata tttcatttgt    3000
ataagaaaat atttcagaga accatgatga taatggatat gtgtgactgt tttgaatttt    3060
tttctcaatt aaaacatttt gtatgtaawr rrarraawrw maagatttgt t             3111
```

<210> SEQ ID NO 278
<211> LENGTH: 305
<212> TYPE: PRT
<213> ORGANISM: Homo sapiens

<400> SEQUENCE: 278

Met Thr Ser Arg Thr Pro Leu Leu Val Thr Ala Cys Leu Tyr Tyr Ser
              5                  10                  15

Tyr Cys Asn Ser Arg His Leu Gln Gln Gly Val Arg Lys Ser Lys Arg
          20                  25                  30

Pro Val Phe Ser His Cys Gln Val Pro Glu Thr Gln Lys Thr Asp Thr
      35                  40                  45

Arg His Leu Ser Gly Ala Arg Ala Gly Val Cys Pro Cys Cys His Pro
  50                  55                  60

Asp Gly Leu Leu Ala Thr Met Arg Asp Leu Leu Gln Tyr Ile Ala Cys
65                  70                  75                  80

Phe Phe Ala Phe Phe Ser Ala Gly Phe Leu Ile Val Ala Thr Trp Thr
                  85                  90                  95

Asp Cys Trp Met Val Asn Ala Asp Asp Ser Leu Glu Val Ser Thr Lys
              100                 105                 110

Cys Arg Gly Leu Trp Trp Glu Cys Val Thr Asn Ala Phe Asp Gly Ile
          115                 120                 125

Arg Thr Cys Asp Glu Tyr Asp Ser Ile Leu Ala Glu His Pro Leu Lys
      130                 135                 140

Leu Val Val Thr Arg Ala Leu Met Ile Thr Ala Asp Ile Leu Ala Gly
145                 150                 155                 160

Phe Gly Phe Leu Thr Leu Leu Gly Leu Asp Cys Val Lys Phe Leu
                  165                 170                 175

Pro Asp Glu Pro Tyr Ile Lys Val Arg Ile Cys Phe Val Ala Gly Ala
              180                 185                 190

Thr Leu Leu Ile Ala Gly Thr Pro Gly Ile Ile Gly Ser Val Trp Tyr
          195                 200                 205

Ala Val Asp Val Tyr Val Glu Arg Ser Thr Leu Val Leu His Asn Ile

-continued

```
            210                 215                 220
Phe Leu Gly Ile Gln Tyr Lys Phe Gly Trp Ser Cys Trp Leu Gly Met
225                 230                 235                 240

Ala Gly Ser Leu Gly Cys Phe Leu Ala Gly Ala Val Leu Thr Cys Cys
                245                 250                 255

Leu Tyr Leu Phe Lys Asp Val Gly Pro Glu Arg Asn Tyr Pro Tyr Ser
                260                 265                 270

Leu Arg Lys Ala Tyr Ser Ala Gly Val Ser Met Ala Lys Ser Tyr
            275                 280                 285

Ser Ala Pro Arg Thr Glu Thr Ala Lys Met Tyr Ala Val Asp Thr Arg
            290                 295                 300

Val
305

<210> SEQ ID NO 279
<211> LENGTH: 305
<212> TYPE: PRT
<213> ORGANISM: Homo sapiens

<400> SEQUENCE: 279

Met Thr Ser Arg Thr Pro Leu Leu Val Thr Ala Cys Leu Tyr Tyr Ser
                5                   10                  15

Tyr Cys Asn Ser Arg His Leu Gln Gln Gly Val Arg Lys Ser Lys Arg
                20                  25                  30

Pro Val Phe Ser His Cys Gln Val Pro Glu Thr Gln Lys Thr Asp Thr
                35                  40                  45

Arg His Leu Ser Gly Ala Arg Ala Gly Val Cys Pro Cys Cys His Pro
            50                  55                  60

Asp Gly Leu Leu Ala Thr Met Arg Asp Leu Leu Gln Tyr Ile Ala Cys
65                  70                  75                  80

Phe Phe Ala Phe Ser Ala Gly Phe Leu Ile Val Ala Thr Trp Thr
                85                  90                  95

Asp Cys Trp Met Val Asn Ala Asp Asp Ser Leu Glu Val Ser Thr Lys
                100                 105                 110

Cys Arg Gly Leu Trp Trp Glu Cys Val Thr Asn Ala Phe Asp Gly Ile
            115                 120                 125

Arg Thr Cys Asp Glu Tyr Asp Ser Ile Leu Ala Glu His Pro Leu Lys
            130                 135                 140

Leu Val Val Thr Arg Ala Leu Met Ile Thr Ala Asp Ile Leu Ala Gly
145                 150                 155                 160

Phe Gly Phe Leu Thr Leu Leu Gly Leu Asp Cys Val Lys Phe Leu
                165                 170                 175

Pro Asp Glu Pro Tyr Ile Lys Val Arg Ile Cys Phe Val Ala Gly Ala
                180                 185                 190

Thr Leu Leu Ile Ala Gly Thr Pro Gly Ile Ile Gly Ser Val Trp Tyr
            195                 200                 205

Ala Val Asp Val Tyr Val Glu Arg Ser Thr Leu Val Leu His Asn Ile
            210                 215                 220

Phe Leu Gly Ile Gln Tyr Lys Phe Gly Trp Ser Cys Trp Leu Gly Met
225                 230                 235                 240

Ala Gly Ser Leu Gly Cys Phe Leu Ala Gly Ala Val Leu Thr Cys Cys
                245                 250                 255

Leu Tyr Leu Phe Lys Asp Val Gly Pro Glu Arg Asn Tyr Pro Tyr Ser
                260                 265                 270
```

```
Leu Arg Lys Ala Tyr Ser Ala Ala Gly Val Ser Met Ala Lys Ser Tyr
        275                 280                 285

Ser Ala Pro Arg Thr Glu Thr Ala Lys Met Tyr Ala Val Asp Thr Arg
        290                 295                 300

Val
305

<210> SEQ ID NO 280
<211> LENGTH: 305
<212> TYPE: PRT
<213> ORGANISM: Homo sapiens

<400> SEQUENCE: 280

Met Thr Ser Arg Thr Pro Leu Leu Val Thr Ala Cys Leu Tyr Tyr Ser
  1               5                  10                  15

Tyr Cys Asn Ser Arg His Leu Gln Gln Gly Val Arg Lys Ser Lys Arg
                 20                  25                  30

Pro Val Phe Ser His Cys Gln Val Pro Glu Thr Gln Lys Thr Asp Thr
             35                  40                  45

Arg His Leu Ser Gly Ala Arg Ala Gly Val Cys Pro Cys His Pro
         50                  55                  60

Asp Gly Leu Leu Ala Thr Met Arg Asp Leu Leu Gln Tyr Ile Ala Cys
 65                  70                  75                  80

Phe Phe Ala Phe Phe Ser Ala Gly Phe Leu Ile Val Ala Thr Trp Thr
                 85                  90                  95

Asp Cys Trp Met Val Asn Ala Asp Asp Ser Leu Glu Val Ser Thr Lys
            100                 105                 110

Cys Arg Gly Leu Trp Trp Glu Cys Val Thr Asn Ala Phe Asp Gly Ile
        115                 120                 125

Arg Thr Cys Asp Glu Tyr Asp Ser Ile Leu Ala Glu His Pro Leu Lys
130                 135                 140

Leu Val Val Thr Arg Ala Leu Met Ile Thr Ala Asp Ile Leu Ala Gly
145                 150                 155                 160

Phe Gly Phe Leu Thr Leu Leu Gly Leu Asp Cys Val Lys Phe Leu
                165                 170                 175

Pro Asp Glu Pro Tyr Ile Lys Val Arg Ile Cys Phe Val Ala Gly Ala
            180                 185                 190

Thr Leu Leu Ile Ala Gly Thr Pro Gly Ile Ile Gly Ser Val Trp Tyr
        195                 200                 205

Ala Val Asp Val Tyr Val Glu Arg Ser Thr Leu Val Leu His Asn Ile
    210                 215                 220

Phe Leu Gly Ile Gln Tyr Lys Phe Gly Trp Ser Cys Trp Leu Gly Met
225                 230                 235                 240

Ala Gly Ser Leu Gly Cys Phe Leu Ala Gly Ala Val Leu Thr Cys Cys
                245                 250                 255

Leu Tyr Leu Phe Lys Asp Val Gly Pro Glu Arg Asn Tyr Pro Tyr Ser
            260                 265                 270

Leu Arg Lys Ala Tyr Ser Ala Ala Gly Val Ser Met Ala Lys Ser Tyr
        275                 280                 285

Ser Ala Pro Arg Thr Glu Thr Ala Lys Met Tyr Ala Val Asp Thr Arg
        290                 295                 300

Val
305

<210> SEQ ID NO 281
```

<211> LENGTH: 58
<212> TYPE: PRT
<213> ORGANISM: Homo sapiens

<400> SEQUENCE: 281

Met Ile Arg Leu Gln Asn Ser Ser Thr Arg Glu Phe Thr His Leu Leu
                5                   10                  15
Ile Lys His Pro Asn Thr Ile Val Ile Tyr Tyr Val Lys Ile His Gln
            20                  25                  30
Phe Lys Cys Pro His Thr Thr Glu Ser Ser Ala Pro Ser Asn Ile Leu
        35                  40                  45
Asp Ile Trp Gln Asn Ser Thr Asn Ile Phe
    50                  55

<210> SEQ ID NO 282
<211> LENGTH: 75
<212> TYPE: PRT
<213> ORGANISM: Homo sapiens

<400> SEQUENCE: 282

Met Asn Met Asn Glu Met Ser Leu Ala Thr Ser Leu Asn Val Tyr Val
                5                   10                  15
Ile Leu Tyr Phe Pro Gln Asn Pro His Phe Met Lys Asn Ile Tyr Leu
            20                  25                  30
Phe Ile Tyr Phe Cys Phe Leu Arg Trp Ser Leu Ala Leu Leu Pro Asp
        35                  40                  45
Trp Ser Ala Met Val Arg Ser Pro Leu Thr Ala Thr Ser Thr Ser Trp
    50                  55                  60
Val Gln Thr Ile Leu Leu Pro Gln Pro Pro Glu
65                  70                  75

<210> SEQ ID NO 283
<211> LENGTH: 414
<212> TYPE: DNA
<213> ORGANISM: Homo sapiens

<400> SEQUENCE: 283
atgcagcatc accaccatca ccaccacttc ttgcttccag gctttgcgct gcaaatccag      60
tgctaccagt gtgaagaatt ccagctgaac aacgactgct cctcccccga gttcattgtg     120
aattgcacgg tgaacgttca agacatgtgt cagaaagaag tgatggagca aagtgccggg     180
atcatgtacc gcaagtcctg tgcatcatca gcggcctgtc tcatcgcctc tgccgggtac     240
cagtccttct gctccccagg gaaactgaac tcagtttgca tcagctgctg caacacccct     300
ctttgtaacg ggccaaggcc caagaaaagg ggaagttctg cctcggccct caggccaggg     360
ctccgcacca ccatcctgtt cctcaaatta gccctcttct cggcacactg ctga            414

<210> SEQ ID NO 284
<211> LENGTH: 137
<212> TYPE: PRT
<213> ORGANISM: Homo sapiens

<400> SEQUENCE: 284

Met Gln His His His His His His Phe Leu Leu Pro Gly Phe Ala
                5                   10                  15
Leu Gln Ile Gln Cys Tyr Gln Cys Glu Glu Phe Gln Leu Asn Asn Asp
            20                  25                  30
Cys Ser Ser Pro Glu Phe Ile Val Asn Cys Thr Val Asn Val Gln Asp
        35                  40                  45

```
Met Cys Gln Lys Glu Val Met Glu Gln Ser Ala Gly Ile Met Tyr Arg
        50                  55                  60

Lys Ser Cys Ala Ser Ala Ala Cys Leu Ile Ala Ser Ala Gly Tyr
 65                  70                  75                  80

Gln Ser Phe Cys Ser Pro Gly Lys Leu Asn Ser Val Cys Ile Ser Cys
                 85                  90                  95

Cys Asn Thr Pro Leu Cys Asn Gly Pro Arg Pro Lys Lys Arg Gly Ser
            100                 105                 110

Ser Ala Ser Ala Leu Arg Pro Gly Leu Arg Thr Thr Ile Leu Phe Leu
        115                 120                 125

Lys Leu Ala Leu Phe Ser Ala His Cys
130                 135

<210> SEQ ID NO 285
<211> LENGTH: 1740
<212> TYPE: DNA
<213> ORGANISM: Homo sapiens
<220> FEATURE:
<221> NAME/KEY: misc_feature
<222> LOCATION: 755,756,757,758,759,760,761,762,763,764,
      765,766,767,768,769,770,771,772,773,774,
      775,776,777,778,779,780,781,782,783,784,
      785,786,787,788,789,790,791,792,793,794,
      795,796,797,798,799,800,801,802,803,804,
      805,806,807,808,809,810,811,812,813,814,
      815,816,817,818,819,820,821,822,823,824,
      825,826,827,828,829,830,831,832,833,834,
      835,1605,1606,1607,1608,1609,1610,1611,1612,1613,
      1614,1615,1616,1617,1618,1619,1620,1621,1622,1623,
      1624,1625,1626,1629
<223> OTHER INFORMATION: n = A,T,C or G

<400> SEQUENCE: 285
ggaaaattca tgaagagggg actgaaatcc acaactcaat cagcatagag cagaagtaag     60
ggggaagtgg taagaggtgc actatgaatg agctggagaa tttaaaggga ggctgaactc    120
agagtcgaag tgaccttgag aagataaacc ctctggaaat tctcagaatc tcaggatggg    180
ccccagagta tctaaagatg ctacagttca agggattgag ccaattgtat ataaatctta    240
atggataggt tgacctcagc ataaaacttg ggtggaaatt ttaaacaggt ttctttattt    300
cagcacttct cagagccact cattgtataa ggtactttgt gaatatccag atagtattct    360
tcaaactctc tttatttcc ccaggggca tcccatagga caagaagcat tctttgtgac     420
actctgtggg aagagctggt ttaaagggggt acctgtctgg gcaacactgt cccacagggg    480
cccccatgac caaactaact ctgcttctac ccagaaaggg tgcagagtag ccactagact    540
tttatgtggc aaatgggatg ttatgcccca gcctgaagcc aagatgccct ttctggttgc    600
cttgatttgt gttaacagc tccaaatgct taatgaggca gtaagagacg tctctcttgg    660
gcagtacttc ccaactaggg gtgagtttgc caccttacc cccatcccag tgaatatttg     720
caattcctaa agacgtgttt tgattgtcac actgnnnnnn nnnnnnnnnn nnnnnnnnnn    780
nnnnnnnnnn nnnnnnnnnn nnnnnnnnnn nnnnnnnnnn nnnnnnnnnn nnnnnacaaa    840
agagaattat ctagccccaa atgtccataa cactgctgtt gagaaaacct accgcaggat    900
cttactgggc ttcataggta agcttgccct tgttctggc ttctgtagat atataaaata    960
aagacactgc ccagtccctc cctcaacgtc ccgagccagg gctcaaggca aattccaata   1020
acagtagaat gaacactaaa tattgatttc aaaatctcag caactagaag aatgaccaac   1080
catcctggtt ggcctgggac tgtcctagtt ttagcattga aagtttcagg ttccaggaaa   1140
```

-continued

```
gccctcaggc ctgggctgct ggtcaccota gcagctgagg gactcttcaa tacagaatta    1200
gtctttgcgc actggagatg aatatacttt aatttgtaac atgtgaaaac atctataaac    1260
atctactgga agcctgttct gtctgcaccg acatttcat tgaagtacgg attcttcctg     1320
acctagatga cagctggctg ctgacaactt tgcgagggct cggtatataa actgagcttt    1380
gtacctattt ttaataatta catgatatag tatataactt ggattaaccc agtattcggg    1440
tattttcaat ttccttgggg agcttagagg gacggacaaa taaaaaagat tatttcaaca    1500
ttcaaatata tgccattggt ttacatatga agataaccac atatatgtat aaattcaccg    1560 ttactttta gcaatactat aaaatccaac agaaaaaaat agcannnnnn nnnnnnnnnn     1620
nnnnnngant tagtctttgt gggtttgggg caagcaactg cccttctcag ttaggatggg    1680
ggagttctgg acatttctag ctaaagccca ggggtcaagg gaatgataaa ctcctcggtc    1740
```

<210> SEQ ID NO 286
<211> LENGTH: 116
<212> TYPE: PRT
<213> ORGANISM: Homo sapiens

<400> SEQUENCE: 286

```
Met Phe Ile Asp Val Phe Thr Cys Tyr Lys Leu Lys Tyr Ile His Leu
            5                   10                  15

Gln Cys Ala Lys Thr Asn Ser Val Leu Lys Ser Pro Ser Ala Ala Arg
        20                  25                  30

Val Thr Ser Ser Pro Gly Leu Arg Ala Phe Leu Glu Pro Glu Thr Phe
    35                  40                  45

Asn Ala Lys Thr Arg Thr Val Pro Gly Gln Pro Gly Trp Leu Val Ile
50                  55                  60

Leu Leu Val Ala Glu Ile Leu Lys Ser Ile Phe Ser Val His Ser Thr
65                  70                  75                  80

Val Ile Gly Ile Cys Leu Glu Pro Trp Leu Gly Thr Leu Arg Glu Gly
            85                  90                  95

Leu Gly Ser Val Phe Ile Leu Tyr Ile Tyr Arg Ser Gln Asn Lys Gly
        100                 105                 110

Gln Ala Tyr Leu
    115
```

<210> SEQ ID NO 287
<211> LENGTH: 32
<212> TYPE: DNA
<213> ORGANISM: Artificial Sequence
<220> FEATURE:
<223> OTHER INFORMATION: PCR primer

<400> SEQUENCE: 287
cacttcttgc ttccaggctt tgcgctgcaa at                                    32

<210> SEQ ID NO 288
<211> LENGTH: 29
<212> TYPE: DNA
<213> ORGANISM: Artificial Sequence
<220> FEATURE:
<223> OTHER INFORMATION: PCR primer

<400> SEQUENCE: 288
actagctcga gtcagcagtg tgccgagaa                                        29

<210> SEQ ID NO 289
<211> LENGTH: 114

<212> TYPE: PRT
<213> ORGANISM: Homo sapiens

<400> SEQUENCE: 289

Met Trp Val Leu Gly Ile Ala Ala Thr Phe Cys Gly Leu Phe Leu Leu
1               5                   10                  15

Pro Gly Phe Ala Leu Gln Ile Gln Cys Tyr Gln Cys Glu Glu Phe Gln
            20                  25                  30

Leu Asn Asn Asp Cys Ser Ser Pro Glu Phe Ile Val Asn Cys Thr Val
        35                  40                  45

Asn Val Gln Asp Met Cys Gln Lys Glu Val Met Glu Gln Ser Ala Gly
    50                  55                  60

Ile Met Tyr Arg Lys Ser Cys Ala Ser Ser Ala Ala Cys Leu Ile Ala
65                  70                  75                  80

Ser Ala Gly Tyr Gln Ser Phe Cys Ser Pro Gly Lys Leu Asn Ser Val
                85                  90                  95

Cys Ile Ser Cys Cys Asn Thr Pro Leu Cys Asn Gly Pro Arg Pro Lys
            100                 105                 110

Lys Arg

<210> SEQ ID NO 290
<211> LENGTH: 115
<212> TYPE: PRT
<213> ORGANISM: Homo sapiens

<400> SEQUENCE: 290

Met Trp Val Leu Gly Ile Ala Ala Thr Phe Cys Gly Leu Phe Leu Leu
1               5                   10                  15

Pro Gly Phe Ala Leu Gln Ile Gln Cys Tyr Gln Cys Glu Glu Phe Gln
            20                  25                  30

Leu Asn Asn Asp Cys Ser Ser Pro Glu Phe Ile Val Asn Cys Thr Val
        35                  40                  45

Asn Val Gln Asp Met Cys Gln Lys Glu Val Met Glu Gln Ser Ala Gly
    50                  55                  60

Ile Met Tyr Arg Lys Ser Cys Ala Ser Ser Ala Ala Cys Leu Ile Ala
65                  70                  75                  80

Ser Ala Gly Tyr Gln Ser Phe Cys Ser Pro Gly Lys Leu Asn Ser Val
                85                  90                  95

Cys Ile Ser Cys Cys Asn Thr Pro Leu Cys Asn Gly Pro Arg Pro Lys
            100                 105                 110

Lys Arg Gly
        115

<210> SEQ ID NO 291
<211> LENGTH: 30
<212> TYPE: PRT
<213> ORGANISM: Artificial Sequence
<220> FEATURE:
<223> OTHER INFORMATION: Synthetic peptide used for generation of rabbit
      polyclonal anti-sera against O591s.

<400> SEQUENCE: 291

Tyr Gln Cys Glu Glu Phe Gln Leu Asn Asn Asp Cys Ser Ser Pro Glu
1               5                   10                  15

Phe Ile Val Asn Cys Thr Val Asn Val Gln Asp Met Cys Gln
            20                  25                  30

<210> SEQ ID NO 292

```
<211> LENGTH: 25
<212> TYPE: PRT
<213> ORGANISM: Artificial Sequence
<220> FEATURE:
<223> OTHER INFORMATION: Synthetic peptide used for generation of rabbit
      polyclonal anti-sera against O591s.

<400> SEQUENCE: 292

Cys Gln Lys Glu Val Met Glu Gln Ser Ala Gly Ile Met Tyr Arg Lys
 1               5                  10                  15

Ser Cys Ala Ser Ser Ala Ala Cys Leu
             20                  25

<210> SEQ ID NO 293
<211> LENGTH: 30
<212> TYPE: PRT
<213> ORGANISM: Artificial Sequence
<220> FEATURE:
<223> OTHER INFORMATION: Synthetic peptide used for generation of rabbit
      polyclonal anti-sera against O591s.

<400> SEQUENCE: 293

Thr Pro Leu Cys Asn Gly Pro Arg Pro Lys Lys Arg Gly Ser Ser Ala
 1               5                  10                  15

Ser Ala Leu Arg Pro Gly Leu Arg Thr Thr Ile Gly Cys Gly
             20                  25                  30
```